United States Patent
Rothberg et al.

(10) Patent No.: US 11,879,841 B2
(45) Date of Patent: Jan. 23, 2024

(54) OPTICAL SYSTEM AND ASSAY CHIP FOR PROBING, DETECTING AND ANALYZING MOLECULES

(71) Applicant: Quantum-Si Incorporated, Branford, CT (US)

(72) Inventors: Jonathan M. Rothberg, Miami Beach, FL (US); Ali Kabiri, Guilford, CT (US); Jason W. Sickler, Arlington, MA (US); Brett J. Gyarfas, Aptos, CA (US); Jeremy Lackey, Foster City, CA (US); Gerard Schmid, Guilford, CT (US); Paul E. Glenn, Wellesley, MA (US); Lawrence C. West, Las Vegas, NV (US); Benjamin Cipriany, Branford, CT (US); Keith G. Fife, Palo Alto, CA (US)

(73) Assignee: Quantum-Si Incorporated, Branford, CT (US)

( * ) Notice: Subject to any disclaimer, the term of this patent is extended or adjusted under 35 U.S.C. 154(b) by 0 days.

(21) Appl. No.: 17/497,827

(22) Filed: Oct. 8, 2021

(65) Prior Publication Data
US 2022/0120685 A1    Apr. 21, 2022

Related U.S. Application Data

(63) Continuation of application No. 16/442,861, filed on Jun. 17, 2019, now Pat. No. 11,175,227, which is a
(Continued)

(51) Int. Cl.
*G01N 21/64* (2006.01)
*C12Q 1/6874* (2018.01)

(52) U.S. Cl.
CPC ....... *G01N 21/6408* (2013.01); *C12Q 1/6874* (2013.01); *G01N 21/648* (2013.01);
(Continued)

(58) Field of Classification Search
CPC .......... G01N 21/6408; G01N 21/6452; G01N 21/648; G01N 21/6428; G01N 2021/6419;
(Continued)

(56) References Cited

U.S. PATENT DOCUMENTS

| 5,198,543 A | 3/1993 | Blanco et al. |
| 5,302,509 A | 4/1994 | Cheeseman |

(Continued)

FOREIGN PATENT DOCUMENTS

| EP | 1681356 A1 | 7/2006 |
| EP | 2182523 A1 | 5/2010 |

(Continued)

OTHER PUBLICATIONS

Honghua Hu, "Confocal epifluorescence detection for microspheres delivered on disposable microfluidic chip", 2005 (Year: 2005).*
(Continued)

*Primary Examiner* — Maurice C Smith
(74) *Attorney, Agent, or Firm* — Wolf, Greenfield & Sacks, P.C.

(57) ABSTRACT

Apparatus and methods for analyzing single molecule and performing nucleic acid sequencing. An apparatus can include an assay chip that includes multiple pixels with sample wells configured to receive a sample, which, when excited, emits emission energy; at least one element for directing the emission energy in a particular direction; and a light path along which the emission energy travels from the sample well toward a sensor. The apparatus also includes an instrument that interfaces with the assay chip. The instrument includes an excitation light source for exciting the sample in each sample well; a plurality of sensors corresponding the sample wells. Each sensor may detect emission energy from a sample in a respective sample well. The
(Continued)

instrument includes at least one optical element that directs the emission energy from each sample well towards a respective sensor of the plurality of sensors.

14 Claims, 103 Drawing Sheets

Related U.S. Application Data continuation of application No. 15/882,776, filed on Jan. 29, 2018, now Pat. No. 10,371,634, which is a continuation of application No. 14/821,686, filed on Aug. 7, 2015, now Pat. No. 9,921,157.

(60) Provisional application No. 62/035,242, filed on Aug. 8, 2014.

(52) U.S. Cl.
CPC ..... *G01N 21/6428* (2013.01); *G01N 21/6452* (2013.01); *G01N 2021/6419* (2013.01); *G01N 2021/6421* (2013.01); *G01N 2021/6439* (2013.01); *G01N 2201/0446* (2013.01); *G01N 2201/062* (2013.01)

(58) Field of Classification Search
CPC ... G01N 2021/6421; G01N 2021/6439; G01N 2201/062; G01N 2201/0446; G01N 21/6454; C12Q 1/6874
See application file for complete search history.

(56) References Cited

U.S. PATENT DOCUMENTS

| | | | |
|---|---|---|---|
| 5,471,515 A | 11/1995 | Fossum et al. | |
| 5,674,743 A | 10/1997 | Ulmer | |
| 5,822,472 A | 10/1998 | Danielzik et al. | |
| 5,912,155 A | 6/1999 | Chatterjee et al. | |
| 5,929,986 A * | 7/1999 | Slater | G01J 3/28 |
| | | | 356/326 |
| 5,961,924 A | 10/1999 | Reichert et al. | |
| 6,137,117 A | 10/2000 | Feldstein et al. | |
| 6,198,869 B1 | 3/2001 | Kraus et al. | |
| 6,210,896 B1 | 4/2001 | Chan | |
| 6,232,103 B1 | 5/2001 | Short | |
| 6,255,083 B1 | 7/2001 | Williams | |
| 6,261,797 B1 | 7/2001 | Sorge et al. | |
| 6,265,193 B1 | 7/2001 | Brandis et al. | |
| 6,280,939 B1 | 8/2001 | Allen | |
| 6,327,410 B1 | 12/2001 | Walt et al. | |
| 6,355,420 B1 | 3/2002 | Chan | |
| 6,399,320 B1 | 6/2002 | Markau et al. | |
| 6,399,335 B1 | 6/2002 | Kao et al. | |
| 6,437,345 B1 | 8/2002 | Bruno-Raimondi et al. | |
| 6,607,883 B1 | 8/2003 | Frey et al. | |
| 6,716,394 B2 | 4/2004 | Jensen et al. | |
| 6,787,308 B2 | 9/2004 | Balasubramanian et al. | |
| 6,825,921 B1 | 11/2004 | Modlin et al. | |
| 6,917,726 B2 | 7/2005 | Levene et al. | |
| 6,936,702 B2 | 8/2005 | Williams et al. | |
| 7,033,762 B2 | 4/2006 | Nelson et al. | |
| 7,052,847 B2 | 5/2006 | Korlach et al. | |
| 7,057,026 B2 | 6/2006 | Barnes et al. | |
| 7,153,672 B1 | 12/2006 | Eickbush et al. | |
| 7,158,224 B2 | 1/2007 | Montagu | |
| 7,170,050 B2 | 1/2007 | Turner et al. | |
| 7,175,811 B2 | 2/2007 | Bach et al. | |
| 7,179,654 B2 | 2/2007 | Verdonk et al. | |
| 7,270,951 B1 | 9/2007 | Stemple et al. | |
| 7,345,764 B2 * | 3/2008 | Bulovic | G01J 3/0259 |
| | | | 356/419 |
| 7,393,640 B2 | 7/2008 | Kumar et al. | |
| 7,405,281 B2 | 7/2008 | Xu et al. | |
| 7,426,322 B2 | 9/2008 | Hyde | |
| 7,462,452 B2 | 12/2008 | Williams et al. | |
| 7,595,883 B1 | 9/2009 | El Gamal et al. | |
| 7,630,073 B2 | 12/2009 | Lundquist et al. | |
| 7,738,086 B2 | 6/2010 | Shepard et al. | |
| 7,745,116 B2 | 6/2010 | Williams | |
| 7,820,983 B2 | 10/2010 | Lundquist et al. | |
| 7,834,329 B2 | 11/2010 | Lundquist et al. | |
| 7,838,847 B2 | 11/2010 | Lundquist et al. | |
| 7,871,777 B2 | 1/2011 | Schneider et al. | |
| 7,873,085 B2 | 1/2011 | Babushkin et al. | |
| 7,875,440 B2 | 1/2011 | Williams et al. | |
| 7,968,702 B2 | 6/2011 | Wegener et al. | |
| 7,973,146 B2 | 7/2011 | Shen et al. | |
| 7,981,604 B2 | 7/2011 | Quake | |
| 8,053,742 B2 | 11/2011 | Lundquist et al. | |
| 8,058,030 B2 | 11/2011 | Smith et al. | |
| 8,133,672 B2 | 3/2012 | Bjornson et al. | |
| 8,153,375 B2 | 4/2012 | Travers et al. | |
| 8,174,696 B2 | 5/2012 | Ebbesen et al. | |
| 8,207,509 B2 | 6/2012 | Lundquist et al. | |
| 8,274,034 B2 | 9/2012 | Vogel et al. | |
| 8,274,040 B2 | 9/2012 | Zhong et al. | |
| 8,278,728 B2 | 10/2012 | Murshid | |
| 8,323,939 B2 | 12/2012 | Hanzel et al. | |
| 8,343,746 B2 | 1/2013 | Rank et al. | |
| 8,465,699 B2 | 6/2013 | Fehr et al. | |
| 8,471,219 B2 | 6/2013 | Lundquist et al. | |
| 8,471,230 B2 | 6/2013 | Zhong et al. | |
| 8,481,264 B2 | 7/2013 | Bjornson et al. | |
| 8,501,406 B1 | 8/2013 | Gray et al. | |
| 8,501,922 B2 | 8/2013 | Otto et al. | |
| 8,502,169 B2 | 8/2013 | Rigneault et al. | |
| 8,525,982 B2 * | 9/2013 | Kato | G01M 11/0228 |
| | | | 356/124 |
| 8,580,539 B2 | 11/2013 | Korlach | |
| 8,618,507 B1 | 12/2013 | Lundquist et al. | |
| 8,773,665 B1 * | 7/2014 | Logan, Jr. | G01C 19/72 |
| | | | 356/460 |
| 8,865,077 B2 | 10/2014 | Chiou et al. | |
| 8,921,086 B2 | 12/2014 | Hanzel et al. | |
| 9,029,802 B2 | 5/2015 | Lundquist et al. | |
| 9,062,091 B2 | 6/2015 | Bjornson et al. | |
| 9,127,259 B2 | 9/2015 | Bjornson et al. | |
| 9,157,864 B2 | 10/2015 | Fehr et al. | |
| 9,222,123 B2 | 12/2015 | Zhong et al. | |
| 9,222,133 B2 | 12/2015 | Lundquist et al. | |
| 9,223,084 B2 | 12/2015 | Grot et al. | |
| 9,372,308 B1 | 6/2016 | Saxena et al. | |
| 9,587,276 B2 | 3/2017 | Lundquist et al. | |
| 9,606,060 B2 | 3/2017 | Chen et al. | |
| 9,658,161 B2 | 5/2017 | Saxena et al. | |
| 9,666,748 B2 | 5/2017 | Leobandung | |
| 9,719,138 B2 | 8/2017 | Zhong et al. | |
| 9,765,395 B2 | 9/2017 | Goldsmith | |
| 9,921,157 B2 * | 3/2018 | Rothberg | G01N 21/6408 |
| 9,946,017 B2 | 4/2018 | Saxena et al. | |
| 10,018,764 B2 | 7/2018 | Grot et al. | |
| 10,090,429 B2 | 10/2018 | Leobandung | |
| 10,138,515 B2 | 11/2018 | Fehr et al. | |
| 10,280,457 B2 | 5/2019 | Zhong et al. | |
| 10,310,178 B2 | 6/2019 | Saxena et al. | |
| 10,371,634 B2 * | 8/2019 | Rothberg | G01N 21/6428 |
| 10,487,356 B2 | 11/2019 | Lundquist et al. | |
| 10,578,788 B2 | 3/2020 | Grot et al. | |
| 10,655,172 B2 | 5/2020 | Rank et al. | |
| 10,724,090 B2 | 7/2020 | McCaffrey et al. | |
| 11,175,227 B2 * | 11/2021 | Rothberg | G01N 21/6452 |
| 2002/0031836 A1 | 3/2002 | Feldstein | |
| 2002/0182716 A1 | 12/2002 | Weisbuch et al. | |
| 2003/0174992 A1 | 9/2003 | Levene et al. | |
| 2003/0222222 A1 | 12/2003 | Dong et al. | |
| 2004/0169842 A1 | 9/2004 | Dosluoglu et al. | |
| 2005/0074784 A1 | 4/2005 | Vo-Dinh | |
| 2005/0083522 A1 * | 4/2005 | Aravanis | G01N 21/6408 |
| | | | 250/458.1 |
| 2005/0161669 A1 * | 7/2005 | Jovanovich | B01L 9/527 |
| | | | 257/727 |
| 2006/0240541 A1 | 10/2006 | Petruno et al. | |

(56) References Cited

U.S. PATENT DOCUMENTS

| | | | |
|---|---|---|---|
| 2007/0188736 A1* | 8/2007 | Fouquet | G01N 21/6428 356/39 |
| 2007/0281288 A1 | 12/2007 | Belkin et al. | |
| 2008/0030628 A1 | 2/2008 | Lundquist et al. | |
| 2008/0050747 A1 | 2/2008 | Korlach et al. | |
| 2010/0009872 A1 | 1/2010 | Eid et al. | |
| 2010/0065726 A1 | 3/2010 | Zhong et al. | |
| 2010/0173394 A1 | 7/2010 | Colston et al. | |
| 2010/0255487 A1 | 10/2010 | Beechem et al. | |
| 2010/0323406 A1 | 12/2010 | Vatta et al. | |
| 2010/0329929 A1* | 12/2010 | Goix | G01N 21/6428 422/69 |
| 2011/0136201 A1 | 6/2011 | Mao et al. | |
| 2011/0165652 A1 | 7/2011 | Hardin et al. | |
| 2011/0236983 A1 | 9/2011 | Beechem et al. | |
| 2012/0021525 A1 | 1/2012 | Fehr et al. | |
| 2012/0094332 A1 | 4/2012 | Lee et al. | |
| 2012/0322692 A1 | 12/2012 | Pham et al. | |
| 2013/0023039 A1 | 1/2013 | Zaccarin et al. | |
| 2013/0071849 A1* | 3/2013 | Kong | C12Q 1/6869 435/6.12 |
| 2013/0116153 A1 | 5/2013 | Bowen et al. | |
| 2013/0217007 A1 | 8/2013 | Kamtekar et al. | |
| 2014/0131593 A1* | 5/2014 | Nakata | G01N 21/6408 250/459.1 |
| 2014/0162378 A1* | 6/2014 | Hanashi | G02B 21/0032 436/501 |
| 2014/0199016 A1* | 7/2014 | Grot | G02B 6/12004 385/11 |
| 2015/0141267 A1 | 5/2015 | Rothberg et al. | |
| 2015/0141268 A1 | 5/2015 | Rothberg et al. | |
| 2015/0293021 A1* | 10/2015 | Finkelstein | G01N 21/6452 506/13 |
| 2016/0041095 A1 | 2/2016 | Rothberg et al. | |
| 2016/0084761 A1 | 3/2016 | Rothberg et al. | |
| 2016/0133668 A1 | 5/2016 | Rothberg et al. | |
| 2017/0146479 A1 | 5/2017 | Levine et al. | |
| 2019/0292590 A1 | 9/2019 | Zhong et al. | |
| 2019/0383739 A1 | 12/2019 | Rothberg et al. | |

FOREIGN PATENT DOCUMENTS

| | | |
|---|---|---|
| EP | 2339632 A1 | 6/2011 |
| EP | 2391639 | 12/2011 |
| EP | 2134871 B1 | 3/2012 |
| JP | H05-281041 A | 10/1993 |
| JP | H08-015590 A | 1/1996 |
| JP | 2003-515163 A | 4/2003 |
| JP | 2006-300950 A | 11/2006 |
| JP | 2007-248063 A | 9/2007 |
| JP | 2008-089346 A | 4/2008 |
| JP | 2008-520975 A | 6/2008 |
| JP | 2008-185585 A | 8/2008 |
| JP | 2010-511148 A | 4/2010 |
| JP | 2010-161629 A | 7/2010 |
| JP | 2012-047719 A | 3/2012 |
| KR | 10-2006-0024368 A | 3/2006 |
| KR | 10-2009-0060423 A | 6/2009 |
| KR | 10-2014-0067165 A | 6/2014 |
| WO | WO 91/06678 A1 | 5/1991 |
| WO | WO 2005/073407 A1 | 8/2005 |
| WO | WO 2006/055521 A2 | 5/2006 |
| WO | WO 2007/015168 A2 | 2/2007 |
| WO | WO 2011/0153962 A1 | 12/2011 |
| WO | WO 2013/171197 A1 | 11/2013 |
| WO | WO 2014/031157 A1 | 2/2014 |
| WO | WO 2014/065329 A1 | 5/2014 |
| WO | WO 2015/074001 A1 | 5/2015 |

OTHER PUBLICATIONS

Alberto Diaspro, "Two-photon microscopy and spectroscopy based on a compact confocal scanning head", 2011 (Year: 2011).*

IBiology Techniques, "Microscopy: Objectives and Eyepieces" https://www.youtube.com/watch?v=Y2tn7Prw1GA, Nov. 17, 2013 (Year: 2013).*

Olivier Y.F. Henry, "Fabrication of molecularly imprinted polymer microarray on a chip by mid-infrared laser pulse initiated polymerization", Feb. 16, 2008 (Year: 2008).*

Invitation to Pay Additional Fees for International Application No. PCT/US2014/066014 dated Jan. 28, 2015.

International Search Report and Written Opinion for International Application No. PCT/US2014/066014 dated Apr. 7, 2015.

International Preliminary Report on Patentability for International Application No. PCT/US2014/066014 dated May 26, 2016.

Invitation to Pay Additional Fees for International Application No. PCT/US2015/044360 dated Nov. 20, 2015.

International Search Report and Written Opinion for International Application No. PCT/US2015/044360 dated Feb. 3, 2016.

Invitation to Pay Additional Fees for International Application No. PCT/US2015/044378 dated Oct. 30, 2015.

International Search Report and Written Opinion for International Application No. PCT/US2015/044378 dated Jan. 15, 2016.

Invitation to Pay Additional Fees for International Application No. PCT/US2015/044379 dated Nov. 2, 2015.

International Search Report and Written Opinion for International Application No. PCT/US2015/044379 dated Jan. 15, 2016.

Invitation to Pay Additional Fees for International Application No. PCT/US2014/066013 dated Jan. 28, 2015.

International Search Report and Written Opinion for International Application No. PCT/US2014/066013 dated Apr. 7, 2015.

International Preliminary Report on Patentability for International Application No. PCT/US2014/066013 dated May 26, 2016.

Invitation to Pay Additional Fees for International Application No. PCT/US2014/066010 dated Jan. 28, 2015.

International Search Report and Written Opinion for International Application No. PCT/US2014/066010 dated Apr. 7, 2015.

International Preliminary Report on Patentability for International Application No. PCT/US2014/066010 dated May 26, 2016.

[No Author Listed] 5.2 Megapixels, 1-inch, 250fps, global-shutter CMOS image sensor, Anafocus, Oct. 2012, 4 pages, Sevilla, Spain.

[No Author Listed] Description of our technology, CrackerBio, 4 pages, Taiwan.

[No Author Listed] Detect Cancer with our 4 Picos ICCD camera, Stanford Computer Optics, 2013, 2 pages, http://www.stanfordcomputeroptics.com/applications/life-science/time-resolved-flim.html [last accessed May 9, 2014].

[No Author Listed] ICCD camera applications in the field of Life Science, Stanford Computer Optics, 2013, 2 pages, http://www.stanfordcomputeroptics.com/applications/life-science.html [last accessed May 9, 2014].

[No Author Listed] OLED-on-CMOS for Sensors and Microdisplays, IPMS Fraunhofer Institut Photonische Mikrosysteme, 2 pages, Dresden, Germany.

Achermann, Exciton—Plasmon Interactions in Metal—Semiconductor Nanostructures, The Journal Physical Chemistry Letters, Sep. 13, 2010, 1(19):2837-43.

Akselrod et al, Twenty-fold enhancement of molecular fluorescence by coupling to a J-aggregate critically coupled resonator. ACS Nano. Jan. 24, 2012;6(1):467-71. doi: 10.1021/nn203789t. Epub Dec. 1, 2011.

Algar et al., Interfacial Chemistry and the Design of Solid-Phase Nucleic Acid Hybridization Assays Using Immobilized Quantum Dots as Donors in Fluorescence Resonance Energy Transfer, Sensors, Jun. 2011, 11(6):6214-36.

Aouani et al., Bright unidirectional fluorescence emission of molecules in a nanoaperture with plasmonic corrugations. Nano Lett. Feb. 9, 2011;11(2):637-44. doi: 10.1021/nl103738d. Epub Jan. 19, 2011.

Aouani et al., Plasmonic Antennas for Directional Sorting of Fluorescence Emission, Nano Letters, May 18, 2011, 11(6):2400-6.

Aouani et al., Saturated excitation of fluorescence to quantify excitation enhancement in aperture antennas, Optics Express, Jul. 30, 2012, 20(16):18085-90.

(56) References Cited

OTHER PUBLICATIONS

Aouani et al., Supporting Information for Bright unidirectional fluorescence emission of molecules in a nanoaperture with plasmonic corrugations. Nano Lett. Feb. 9, 2011;11(2):19 pages.
Aouani et al., Supporting Information for Plasmonic Antennas for Directional Sorting of Fluorescence Emission, Nano Letters, May 18, 2011, 11(6):9 pages.
Bergman et al., Surface Plasmon Amplification by Stimulated Emission of Radiation: Quantum Generation of Coherent Surface Plasmons in Nanosystems, Physical Review Letters, Jan. 17, 2013, 90(2):027402-1-4.
Bogaerts et al., High speed 36 Gbps 12Mpixel global pipelined shutter CMOS image sensor with CDS, 2011 International Image Sensor Workshop, Jun. 8-11, 2011, 4 pages, Hokkaido, Japan.
Carretero-Palacious et al., Mechanisms for extraordinary optical transmission through bull's eye structures, Optics Express, May 23, 2011, 19(11):10429-42.
Chanyawadee et al., Nonradiative exciton energy transfer in hybrid organic-inorganic heterostructures, Phys. Rev. B., May 14, 2008, 77(19): 193402-1-4.
Daldosso et al., Fabrication and optical characterization of thin two-dimensional Si3N4 waveguides, Materials Science in Semiconductor Processing, Oct. 18, 2004, 7(4-6): 453-8.
Davies et al., Plasmonic Nanogap Tilings: Light-Concentrating Surfaces for Low-Loss Photonic Integration, ACS Nano, Jul. 4, 2013, 7(8):7093-100, arXiv:1305.2839v2, http://arxiv.org/abs/1305.2839v2.
Deshpande et al., Electrically driven polarized single-photon emission from an InGaN quantum dot in a GaN nanowire, Nature Communcations, Apr. 9, 2013, 8 pages.
Deutsch et al., Luminescence upconversion in colloidal double quantum dots, Nature Nanotechnology Letter, Sep. 2013, 8(9):649-53.
Edel et al., Accurate Single Molecule FRET Efficiency Determination for Surface Immobilized DNA Using Maximum Likelihood Calculated Lifetimes, J. Phys. Chem, Mar. 22, 2007, 111(11):2986-90.
Eid et al., Real-time DNA sequencing from single polymerase molecules. Science. Jan. 2, 2009;323(5910):133-8. doi:10.1126/science.1162986. Epub Nov. 20, 2008.
Eid et al., Supporting Online Material for Real-time DNA sequencing from single polymerase molecules. Science. Jan. 2, 2009;323(5910):21 pages.
Feldman et al., Wafer-Level Camera Technologies Shrink Camera Phone Handsets, Photonics.com, Aug. 1, 2007, 3 pages, http://www.photonics.com/Article.aspx?AID=30459 . [last accessed Dec. 17, 2013].
Fu et al., A microfabricated fluorescence-activated cell sorter. Nature Biotechnology. Nov. 1999; 17(11): 1109-1111.
Gorin et al., Fabrication of silicon nitride waveguides for visible-light using PECVD: a study of the effect of plasma frequency on optical properties, Optics Express, Sep. 1, 2008, 16(18):13509-16.
Gryczynski et al., Two-photon excitation by the evanescent wave from total internal reflection. Anal Biochem., Apr. 5, 1997;247(1):69-76.
Haase et al., Upconverting Nanoparticles, Angewandte Chemie International Edition, Jun. 20, 2011, 50(26):5808-29.
Hale, Fibre Optic Sensors using Adiabatically Tapered Single Mode Fibres. Dissertation submitted to the University of Cambridge. Feb. 1994. 209 pages.
Hallman et al., 3 nJ, 100 ps laser pulses generated with an asymmetric waveguide laser diode for a single-photon avalanche diode time-of-flight (SPAD TOF) rangefinder application, Measurement Science and Technology, Jan. 5, 2012, 23(2): 8 pages.
Hansard et al., Time-of-Flight Cameras: Principles, Methods and Applications, Nov. 2012, 102 pages, Springer-Verlag, London, UK.
He et al., DNA Sequencing by Capillary Electrophoresis with Four-Decay Fluorescence Detection, Anal. Chem., Dec. 15, 2000, 72(24):5865-73.

Herold et al., OLED-on-CMOS Integration for Augmented-Reality Systems, IEEE 2008 International Students and Young Scientists Workshop Photonics and Microsystems, Jun. 20-22, 2008, 19-22, Wroclaw—Szlarska Poreba, Poland.
Heucke et al., Placing Individual Molecules in the Center of Nanoapertures, Nano Letters, Feb. 12, 2014, 14(2):391-5.
Inoue et al., CMOS active pixel image sensor with in-pixel CDS for high-speed cameras, Proc. SPIE, Sensors and Camera Systems for Scientific, Industrial, and Digital Photography Applications V, 250, Jun. 7, 2004, 5301(4):8 pages.
Ishii et al., Self-matched high-voltage rectangular wave pulse generator, Rev. Sci. Instrum, Nov. 1985, 56(11):2116-8.
Jun et al., Plasmonic beaming and active control over fluorescent emission, Nature Communications, Apr. 19, 2011, 6 pages.
Juoda Wlkis et al., High-Power, Low-Noise Slab-Coupled Optical Waveguide (SCOW) Amplifiers and Lasers, IEEE Optical Society of America Optical Fiber Communication Conference and Exposition and the National FiberOptic Engineers Conference, Mar. 6-10, 2011, 3 pages, Los Angeles, CA.
Juodawlkis et al., High-Power, Ultralow-Noise Semiconductor External Cavity Lasers Based on Low-Confinement Optical Waveguide Gain Media, Proc. of SPIE Novel In-Plane Semiconductor Lasers IX, Feb. 12, 2010, vol. 7616:76160X-1-9.
Kano et al., Two-photon-excited fluorescence enhanced by a surface plasmon. Opt Lett. Nov. 15, 1996;21(22):1848-50.
Karow, PacBio Aims to Boost Throughput of SMRT Technology with Microchip Co-development Deal, In Sequence and Clinical Sequencing News, Jul. 24, 2012, 3 pages, GenomeWeb.
Klein et al., Controlling plasmonic hot spots by interfering Airy beams, Optics Letters, Aug. 15, 2012, 37(16): 3402-4.
Korlach et al., Real-time DNA sequencing from single polymerase molecules. Methods Enzymol. May 2010;472:431-55. doi:10.1016/S0076-6879(10)72001-2.
Kreye et al, P-200: Evaluation of different OLED-Stacks for Active-Matrix OLED Microdisplays on CMOS-Substrates, SID 06 Digest, Jun. 2006, 37(1); 979-81.
Kumar et al., Terminal phosphate labeled nucleotides: synthesis, applications, and linker effect on incorporation by DNA polymerases. Nucleosides Nucleotides Nucleic Acids. Nov. 2005;24(5-7):401-8.
Lenne et al., Fluorescence fluctuations analysis in nanoapertures: physical concepts and biological applications, Histochem Cell Biol, Sep. 2008, 130:795-805.
Leslie et al., Convex Lens-Induced Confinement for Imaging Single Molecules, Anal. Chem., Jul. 15, 2010, 82(14):6224-9.
Levy et al., An 852×600 Pixel OLED-on-Silicon Color Microdisplay Using CMOS Subthreshold-Voltage-Scaling Current Drivers, IEEE Journal of Solid-State Circuits, Dec. 2002, 37(12): 1879-89.
Lezec et al., Beaming Light from a Subwavelength Aperture, Science, Aug. 2, 2002, 297(5582):820-2.
Li et al., Employing ~ 100% Excitons in OLEDs by Utilizing a Fluorescent Molecule with Hybridized Local and Charge-Transfer Excited State, Advanced Functional Materials, Mar. 19, 2014, 24(11):1609-14.
Lin et al., Cosine-Gauss Plasmon Beam: A Localized Long-Range Nondiffracting Surface Wave, Physical Review Letters, Aug. 31, 2012, 109(9):093904-1-5.
Mcginty et al., Wide-field fluorescence lifetime imaging of cancer, Biomedical Optics Express, Sep. 1, 2010, 1(2): 627-40.
Misra et al., White organic LEDs and their recent advancements, Semiconductor Science and Technology, Apr. 25, 2006, 21(7):R35-47.
Mitchell et al., Nanosecond Fluorescence Lifetime Imaging with gated CCD detection and pulsed laser excitation, Photonic Research Systems Ltd., May 1, 2013, 13 pages, Newhaven East Sussex UK.
Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.
Murshid et al., Array of concentric CMOS photodiodes for detection and de-multiplexing of spatially modulated optical channels, Optics & Laser Technology, Sep. 2009, 41(6):764-9.
Murshid et al., CMOS Detectors: Concentric photodiode array enables spatial-domain multiplexing, Laser Focus World, Apr. 1,

(56) References Cited

OTHER PUBLICATIONS 2009, 10 pages, http://www.laserfocusworld.com/articles/print/volume-45/issue-4/features/cmos-detectors-concentric-photodiode-array-enables-spatial-domain-multiplexing.html, [last accessed Dec. 12, 2013].

Murshid et al., Concentric octagonal CMOS photodiodes for direct detection of spatially multiplexed optical fiber channels, Optical Society of America, Oct. 2008, 1 page.

Nozik, Multiple exciton generation in semiconductor quantum dots, Chemical Physics Letters, May 20, 2008, 457(1-3):3-11.

Park et al., A dual-modality optical coherence tomography and fluorescence lifetime imaging microscopy system for simultaneous morphological and biochemical tissue characterization, Biochemical Optics Express, Aug. 2, 2010, 1(1):186-200.

Pfeifer et al., Improved optical outcoupling of OLED microdisplays by nanostructured substrates, IEEE Semiconductor Conference Dresden, Sep. 27-18, 2011, 4 pages, Dresden, Germany.

Poddubny et al., Photonic quasicrystalline and aperiodic structures, Physica E: Low-dimensional Systems and Nanostructures, May 2010, 42(7): 1871-95.

Pons et al., Solution-phase single quantum dot fluorescence resonance energy transfer. J Am Chem Soc., Nov. 29, 2006;128(47):15324-31.

Pudavar, Fluorescence Lifetime Imaging (FILM), Leica Microsystems Inc., Oct. 25, 2009, 60 pages, Exton, PA.

Punj et al., Plasmonic antennas and zero-mode waveguides to enhance single molecule fluorescence detection and fluorescence correlation spectroscopy toward physiological concentrations. Wiley Interdiscip Rev Nanomed Nanobiotechnol. May-Jun. 2014;6(3):268-82. doi: 10.1002/wnan.1261. Epub Feb. 24, 2014.

Ramuz et al., Coupling light from an organic light emitting diode (OLED) into a single-mode waveguide: Toward monolithically integrated optical sensors, Journal of Applied Physics, Apr. 2009, 105(8):084508-1-7.

Ran et al., Design of a 16 gray scales 320 × 240 pixels OLED-on-silicon driving circuit, Journal of Semiconductors, Jan. 2009, 30(1):015010-1-4.

Reckziegel et al., Optical sensors based on monlithic integrated organic light-emitting diodes (OLEDs), Proceedings of SPIE Optical Sensors, Apr. 28, 2008, vol. 7003: 8 pages.

Richter et al., Bidirectional OLED microdisplay: Combining display and image sensor functionality into a monolithic CMOS chip, 2011 IEEE International Solid-State Circuits Conference Digest of Technical Papers (ISSCC), Feb. 20-24, 2011, 3 pages, San Francisco, CA.

Richter et al., OLED-on-CMOS based bidirectional microdisplay for near-to-eye and sensor applications, IEEE Semiconductor Conference Dresden, Sep. 27-28, 2011, 3 pages, Dresden, Germany.

Rigneault et al., Enhancement of Single-Molecule Fluorescence Detection in Subwavelength Apertures, Physical Review Letters, Sep. 9, 2005, 95(11): 117401-1-4.

Romero-Garcia et al., Silicon nitride back-end optics for biosensor applications, Proc. of SPIE Integrated Optics: Physics and Simulations, May 7, 2013, vol. 8781: 87810W-1-11.

Romero-Garcia et al., Visible wavelength silicon nitride focusing grating coupler with AlCu/TiN reflector. Optics Letters. Jul. 15, 2013, 38(14):2521-3.

Rui et al., Demonstration of beam steering via dipole-coupled plasmonic spiral antenna, Scientific Reports, Jul. 19, 2013, 7 pages.

Sakadzic et al., Multi-photon microscopy with a low-cost and highly efficient Cr:LiCAF laser, Optics Express, Dec. 8, 2008, 16(25):20848-63.

Salthouse et al., Development of a Time Domain Fluorimeter for Fluorescent Lifetime Multiplexing Analysis, IEEE Biomed Circuits Syst., Sep. 1, 2008, 2(3): 204-11.

Schalberger et al., 60.4: Distinguished Paper: A Fully Integrated 1" AMOLED Display Using Current Feedback Based on a Five Mask LTPS CMOS Process, SID 10 Digest, May 2010, 41(1): 905-8.

Schmidt, Direct Encapsulation of OLED on CMOS, Bio and Nano Packaging Techniques for Electron Devices, Jul. 17, 2012, Chapter 29, 581-99, Springer-Verlag Berling Heidelberg.

Siegfried et al., Gap Plasmons and Near-Field Enhancement in Closely Packed Sub-10 nm Gap Resonators, Nano Lett., Oct. 10, 2013, 13(11):5449-53.

Sorokina et al., Fluorescent Lifetime Trajectories of a Single Fluorophore Reveal Reaction Intermediates During Transcription Initiation, J. Am. Chem. Soc., Jul. 22, 2009, 131(28):9630-31.

Sorokina et al., Supporting Information for Fluorescent Lifetime Trajectories of a Single Fluorophore Reveal Reaction Intermediates During Transcription Initiation, J. Am. Chem. Soc., Jul. 22, 2009, 131(28):4 pages.

Sun et al., Fluorescence lifetime imaging microscopy (FLIM) for image guided surgery, Stanford Computer Optics, 2013, 2 pages, http://www.stanfordcomputeroptics.com/applications/life-science/flim-guided-surgery.html, [last accessed May 9, 2014].

Taitt et al., Evanescent wave fluorescence biosensors. Biosens Bioelectron. Jun. 2005;20(12):2470-87. Epub Dec. 8, 2004.

Takkellapati et al., Synthesis of aminomethyl- and bis-aminomethyl-fluorescein energy transfer terminators. Nucleosides Nucleotides Nucleic Acids. Dec. 2007;26(10-12):1467-70.

Toerker et al., Integration of Top-Emitting Organic Light Emitting Diodes on CMOS Substrates, Proc. of SPIE Organic Optoelectronics and Photonics III, Apr. 16, 2008, vol. 6999, 4 pages.

Toma et al., Compact surface plasmon-enhanced fluorescence biochip, Opt. Express Apr. 22, 2013, 21(8): 10121-10132.

Toma et al., Surface plasmon-coupled emission on plasmonic Bragg gratings, Optics Express, Jun. 18, 2012, 20(13):14042-53.

Uhring et al., 200 ps FWHM and 100 MHz Repetition Rate Ultrafast Gated Camera for Optical Medical Functional Imaging, Proc. of SPIE Optical Sensing and Detection II, May 9, 2012, vol. 8439, 10 pages.

Unfricht et al., Grating-coupled surface plasmon resonance: a cell and protein microarray platform. Proteomics. Nov. 2005;5(17):4432-42.

Vogel et al., OLED-on-CMOS Integration for Optoelectronic Sensor Applications, Proc. of SPIE Silicon Photonics II, Mar. 1, 2007, vol. 6477:8 pages.

Vogel et al., Optoelectronic Sensors based on OLED-on-CMOS, 2008 2nd European Conference & Exhibition on Integration Issues of Minaturized Systems—MOMS, MOEMS, ICS, and Electronic Components (SSI), Apr. 9-10, 2008, 3 pages, Barcelona, Spain.

Von Ketteler et al., Fluorescence Lifetime-Based Glucose Sensing using NADH, Proc. of SPIE Optical Diagnostics and Sensing XII: Toward Point-of-Care Diagnostics; and Design and Performance Validation of Phantoms Used in Conjunction with Optical Measurement of Tissue IV, Feb. 1, 2012, vol. 8229, 8 pages.

Walpole, Slab-coupled optical waveguide lasers: a review, Proc. SPIE Novel In-Plane Semiconductor Lasers III, May 11, 2004, vol. 5365, 124-32.

Wenger et al., Emission and excitation contributions to enhanced single molecule fluorescence by gold nanometric apertures, Optics Express, Mar. 3, 2008, 16(5):3008-20.

Wenger et al., Enhanced fluorescence from metal nanoapertures: physical characterizations and biophotonic applications, Proc. SPIE Plasmonics in Biology and Medicine VII, Feb. 16, 2010, 8 pages.

Wenger, Aperture optical antennas, Optical Antennas, Feb. 2013, 25pages, Cambridge University Press, Cambridge, UK.

Willoughby, Elastically Averaged Precision Alignment, Massachusetts Institute of Technology, Jun. 2005, 158 pages, Cambridge, MA.

Xiong et al., Aluminum nitrade as a new material for chip-scale optomechanics and nonlinear optics, New Journal of Physics, Sep. 17, 2012, 14: 21 pages.

Yan-Yan et al., OLED-on-silicon chip with new pixel circuit, J. Cent. South Univ., May 2012 19(5):1276-82.

Yu et al., Light Propagation with Phase Discontinuities: Generalized Laws of Reflection and Refraction, Science, Oct. 21, 2011, 334 (6054):333-7.

(56) References Cited

OTHER PUBLICATIONS

Yuk et al. Analysis of immunoarrays using a gold grating-based dual mode surface plasmon-coupled emission (SPCE) sensor chip. Analyst. Jun. 7, 2012;137(11):2574-81. doi: 10.1039/c2an35143a. Epub Apr. 13, 2012.
Zhang et al., Continuous metal plasmonic frequency selective surfaces, Optics Express, Nov. 7, 2011, 19(23):23279-85.
Zhao et al., Plasmonic demultiplexer and guiding. ACS Nano. Nov. 23, 2010;4(11):6433-8. doi: 10.1021/nn101334a. Epub Oct. 6, 2010.
Zhu et al., Zero-Mode Waveguides for Single-Molecule Analysis, Annu. Rev. Biophys., Jun. 2012, 41:269-93.
Zong et al., Equivalent Circuit Model of Top-emitting OLED for the Designing of OLED-on-Silicon Microdisplay, Advanced Materials Research, Nov. 2011, 383-90:7037-42.
Benetti et al., Highly parallel SPAD detector for time-resolved lab-on-chip. Optics, Photonics, and Digital Technologies for Multimedia Applications. SPIE. Apr. 2010;7723. 11 pages.
U.S. Appl. No. 14/821,686, filed Aug. 7, 2015, Rothberg et al.
U.S. Appl. No. 15/882,776, filed Jan. 29, 2018, Rothberg et al.
U.S. Appl. No. 16/442,861, filed Jun. 17, 2019, Rothberg et al.
PCT/US2014/066014, Jan. 28, 2015, Invitation to Pay Additional Fee.
PCT/US2014/066014, Apr. 7, 2015, International Search Report and Written Opinion.
PCT/US2014/066014, May 26, 2016, International Preliminary Report on Patentability.
PCT/US2015/044360, Nov. 20, 2015, Invitation to Pay Additional Fees.
PCT/US2015/044360, Feb. 3, 2016, International Search Report and Written Opinion.
PCT/US2015/044378, Oct. 30, 2015, Invitation to Pay Additional Fees.
PCT/US2015/044378, Jan. 15, 2016, International Search Report and Written Opinion.
PCT/US2015/044379, Nov. 2, 2015, Invitation to Pay Additional Fees.
PCT/US2015/044379, Jan. 15, 2016, International Search Report and Written Opinion.
PCT/US2014/066013, Jan. 28, 2015, Invitation to Pay Additional Fees.
PCT/US2014/066013, Apr. 7, 2015, International Search Report and Written Opinion.
PCT/US2014/066013, May 26, 2016, International Preliminary Report on Patentability.
PCT/US2014/066010, Jan. 28, 2015, Invitation to Pay Additional Fees.
PCT/US2014/066010, Apr. 7, 2015, International Search Report and Written Opinion.
PCT/US2014/066010, May 26, 2016, International Preliminary Report on Patentability.

* cited by examiner

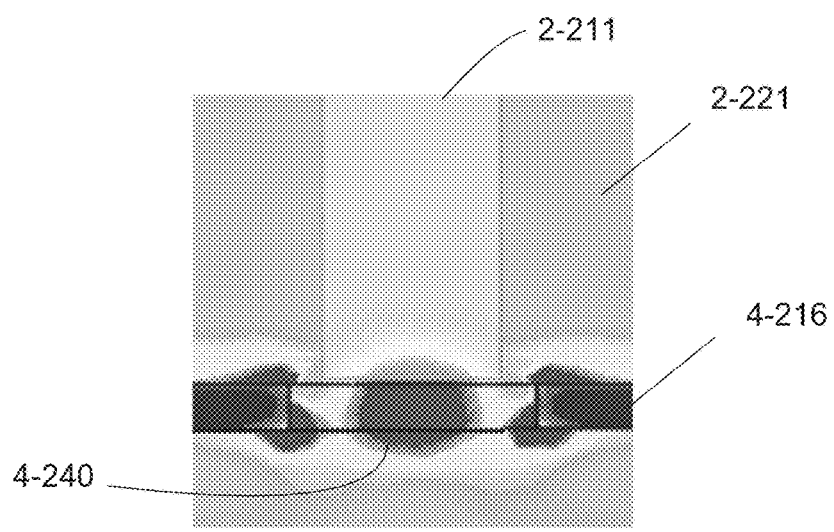
*FIG. 4-2D*
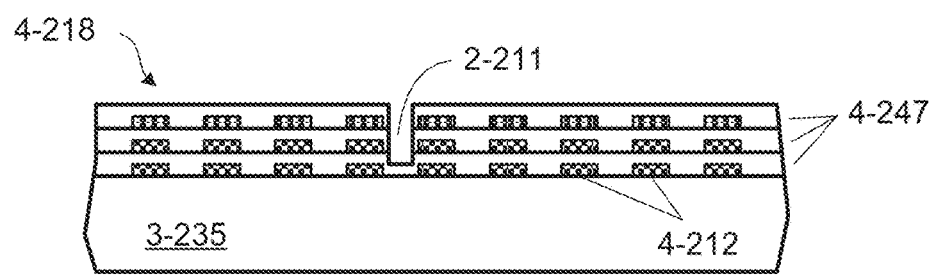
*FIG. 4-2E*
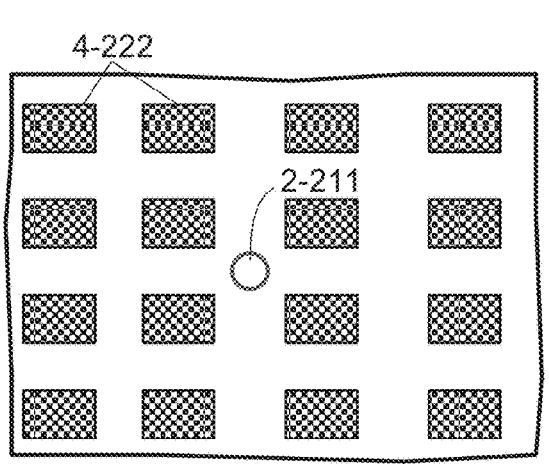 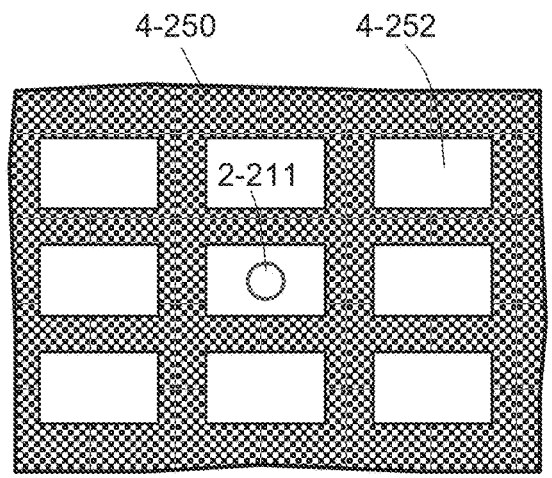
*FIG. 4-2F*  *FIG. 4-2G*

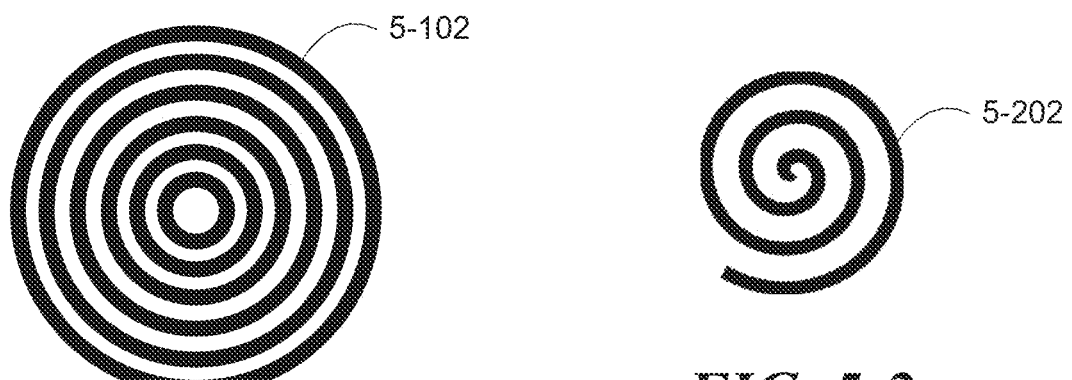
FIG. 5-1
FIG. 5-2
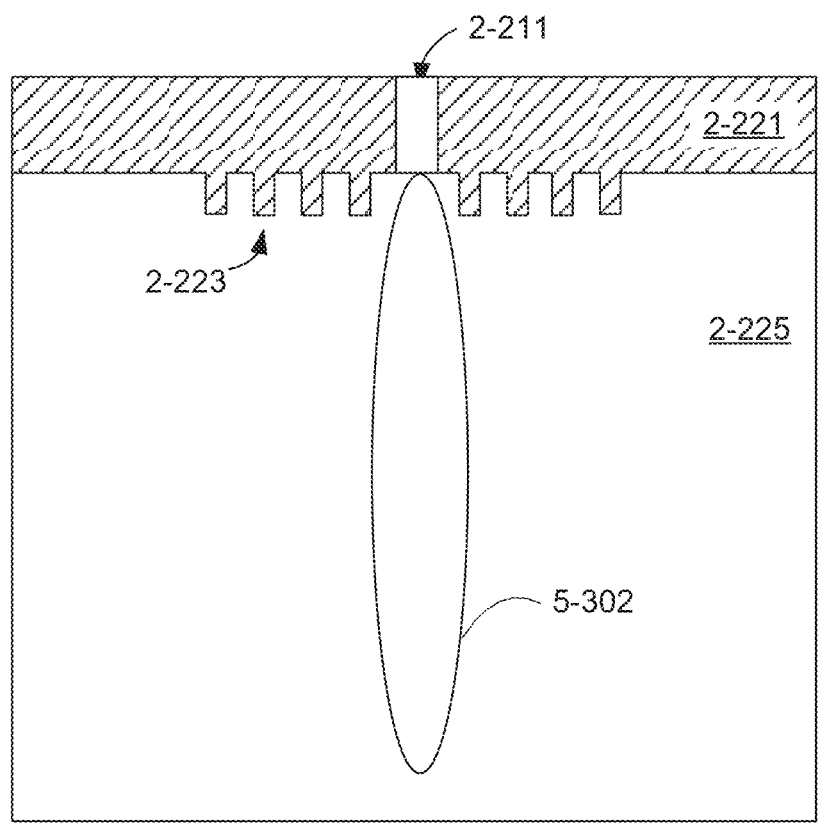
FIG. 5-3A

OPTICAL SYSTEM AND ASSAY CHIP FOR PROBING, DETECTING AND ANALYZING MOLECULES

RELATED APPLICATIONS

This application is a continuation and claims the benefit under 35 U.S.C. § 120 of U.S. application Ser. No. 16/442,861, filed on Jun. 17, 2019, which is hereby incorporated by reference in its entirety. Application Ser. No. 16/442,861 is a continuation and claims the benefit under 35 U.S.C. § 120 of U.S. application Ser. No. 15/882,776 filed on Jan. 29, 2018, which is hereby incorporated by reference in its entirety. Application Ser. No. 15/882,776 is a continuation and claims the benefit under 35 U.S.C. § 120 of U.S. application Ser. No. 14/821,686 filed on Aug. 7, 2015, which is hereby incorporated by reference in its entirety. Application Ser. No. 14/821,686 claims priority to U.S. Provisional Patent Application No. 62/035,242 filed Aug. 8, 2014, which is hereby incorporated by reference in its entirety.

This application is related to the following U.S. applications:

- U.S. Provisional Patent Application 62/164,506, entitled "INTEGRATED DEVICE FOR TEMPORAL BINNING OF RECEIVED PHOTONS", filed on May 20, 2015;
- U.S. Provisional Patent Application 62/164,485, entitled "PULSED LASER", filed on May 20, 2015;
- U.S. Provisional Patent Application 62/164,482, entitled "METHODS FOR NUCLEIC ACID SEQUENCING", filed on May 20, 2015;
- U.S. Provisional Patent Application 62/164,464, entitled "INTEGRATED DEVICE WITH EXTERNAL LIGHT SOURCE FOR PROBING DETECTING AND ANALYZING MOLECULES", filed on May 20, 2015;
- A U.S. non-provisional patent application Ser. No. 14/821,656, filed on Aug. 7, 2015, titled "INTEGRATED DEVICE FOR TEMPORAL BINNING OF RECEIVED PHOTONS;" and
- A U.S. non-provisional patent application Ser. No. 14/821,688 filed on Aug. 7, 2015, titled "INTEGRATED DEVICE WITH EXTERNAL LIGHT SOURCE FOR PROBING, DETECTING, AND ANALYZING MOLECULES."

Each of the above-listed related applications is hereby incorporated by reference in its entirety.

BACKGROUND

Field

The present application is directed generally to devices, methods and techniques for performing rapid, massively parallel, quantitative analysis of biological and/or chemical samples, and methods of fabricating said devices.

Related Art

Detection and analysis of biological samples may be performed using biological assays ("bioassays"). Bioassays conventionally involve large, expensive laboratory equipment requiring research scientists trained to operate the equipment and perform the bioassays. Moreover, bioassays are conventionally performed in bulk such that a large amount of a particular type of sample is necessary for detection and quantitation.

Some bioassays are performed by tagging samples with luminescent tags that emit light of a particular wavelength. The tags are illuminated with an excitation light source to cause luminescence, and the luminescent light is detected with a photodetector to quantify the amount of luminescent light emitted by the tags. Bioassays using luminescent tags conventionally involve expensive laser light sources to illuminate samples and complicated, bulky detection optics and electronics to collect the luminescence from the illuminated samples.

SUMMARY

Some embodiments relate to an instrument configured to interface with an assay chip that includes a plurality of sample wells. Each sample well of the plurality of sample wells may receive a sample. The instrument includes at least one pulsed excitation light source for exciting the sample of at least a portion of the plurality of sample wells. The instrument also includes a plurality of sensors, each sensor of the plurality of sensors corresponding to a sample well of the plurality of sample wells. Each sensor of the plurality of sensors is detects emission energy from the sample in a respective sample well. Also, each sensor of the plurality of sensors is capable of detecting the detection time of the emission energy. The instrument also includes at least one optical element configured to direct the emission energy from each sample well of the plurality of sample wells towards a respective sensor of the plurality of sensors.

Some embodiments relate to an apparatus that includes an assay chip and an instrument. The assay chip includes a plurality of pixels. Each pixel of the assay chip includes a sample well that receives a sample, which, when excited, emits emission energy. Each pixel of the assay chip also includes at least one element for directing the emission energy in a particular direction. The at least one element may be a refractive element, a diffractive element, a plasmonic element or a resonator. Each pixel of the assay chip also includes a light path along which the emission energy travels from the sample well toward a sensor of the instrument. The instrument interfaces with the assay chip and includes at least one pulsed excitation light source that excites the sample in each sample well. The instrument also includes a plurality of sensors, each sensor of the plurality of sensors corresponding to a respective sample well. Each sensor of the plurality of sensors is detects emission energy from the sample in the respective sample well and detects the detection time of the emission energy. The instrument also includes at least one optical element that directs the emission energy from each sample well towards a respective sensor of the plurality of sensors.

Some embodiments relate to a method of analyzing a specimen. The method includes providing the specimen on the top surface of an assay chip that includes a plurality of sample wells. The method also includes aligning the chip with an instrument that includes at least one excitation light source and at least one sensor. The method also includes exciting a sample from the specimen in at least one of the plurality of sample wells with pulsed excitation light from the at least one pulsed excitation light source. The method also includes detecting, with the at least one sensor, emission energy generated by the sample in the at least one sample well in response to excitation by the excitation light. The at least one sensor is capable of determining the lifetime of the emission energy generated by the sample.

Some embodiments relate to a method for sequencing a target nucleic acid molecule. The method includes providing a chip adjacent to an instrument that includes a pulsed excitation source and a sensor capable of detecting at least one temporal property of light. The chip includes at least one well that is operatively coupled to said excitation source and said sensor when said chip is at a sensing position of said instrument. The well contains said target nucleic acid molecule, a polymerizing enzyme and a plurality of types of nucleotides or nucleotide analogs. The method also includes, with said chip at said sensing position, performing an extension reaction at a priming location of said target nucleic acid molecule in the presence of said polymerizing enzyme to sequentially incorporate said nucleotides or nucleotide analogs into a growing strand that is complementary to said target nucleic acid molecule. Upon incorporation and excitation by excitation energy from said excitation source, said nucleotides or nucleotides analogs emit signals in said well. The method also includes using said sensor to detect spatial and/or temporal distribution patterns of said signals that are distinguishable for said plurality of types of nucleotides or nucleotide analogs. The method also includes identifying said nucleotides or nucleotide analogs based on said spatial and/or temporal distribution patterns of said signals, thereby sequencing said target nucleic acid molecule.

Some embodiments relate to a method for nucleic acid sequencing. The method includes providing a chip adjacent to an instrument. The chip includes a plurality of wells that are each operatively coupled to a pulsed excitation source and a sensor of said instrument when said chip is at a sensing position of said instrument. An individual well of said plurality of wells contains said target nucleic acid molecule, a polymerizing enzyme and a plurality of types of nucleotides or nucleotide analogs. The method also includes, with the chip at said sensing position, subjecting said target nucleic acid molecule to a polymerization reaction to yield a growing strand that is complementary to said target nucleic acid molecule in the presence of said nucleotides or nucleotide analogs and said polymerizing enzyme. The nucleotides or nucleotides analogs emit signals in said individual well upon excitation by excitation energy from said excitation source during incorporation. The method also includes using said sensor to detect temporal distribution patterns of said signals that are distinguishable for said plurality of types of nucleotides or nucleotide analogs. The method also includes identifying a sequence of said target nucleic acid molecule based on said spatial and/or temporal distribution patterns of said signals.

The foregoing and other aspects, embodiments, and features of the present teachings can be more fully understood from the following description in conjunction with the accompanying drawings.

The term "pixel" may be used in the present disclosure to refer to a unit cell of an integrated device. The unit cell may include a sample well and a sensor. The unit cell may further include an excitation source. The unit cell may further include at least one excitation-coupling optical structure (which may be referred to as a "first structure") that is configured to enhance coupling of excitation energy from the excitation source to the sample well. The unit cell may further include at least one emission-coupling structure that is configured to enhance coupling of emission from the sample well to the sensor. The unit cell may further include integrated electronic devices (e.g., CMOS devices). There may be a plurality of pixels arranged in an array on an integrated device.

The term "optical" may be used in the present disclosure to refer to visible, near infrared, and short-wavelength infrared spectral bands.

The term "tag" may be used in the present disclosure to refer to a tag, probe, marker, or reporter attached to a sample to be analyzed or attached to a reactant that may be reacted with a sample.

The phrase "excitation energy" may be used in the present disclosure to refer to any form of energy (e.g., radiative or non-radiative) delivered to a sample and/or tag within the sample well. Radiative excitation energy may comprise optical radiation at one or more characteristic wavelengths.

The phrase "characteristic wavelength" may be used in the present disclosure to refer to a central or predominant wavelength within a limited bandwidth of radiation. In some cases, it may refer to a peak wavelength of a bandwidth of radiation. Examples of characteristic wavelengths of fluorophores are 563 nm, 595 nm, 662 nm, and 687 nm.

The phrase "characteristic energy" may be used in the present disclosure to refer to an energy associated with a characteristic wavelength.

The term "emission" may be used in the present disclosure to refer to emission from a tag and/or sample. This may include radiative emission (e.g., optical emission) or non-radiative energy transfer (e.g., Dexter energy transfer or Förster resonant energy transfer). Emission results from excitation of a sample and/or tag within the sample well.

The phrase "emission from a sample well" or "emission from a sample" may be used in the present disclosure to refer to emission from a tag and/or sample within a sample well.

The term "self-aligned" may be used in the present disclosure to refer to a microfabrication process in which at least two distinct elements (e.g., a sample well and an emission-coupling structure, a sample well and an excitation-source) may be fabricated and aligned to each other without using two separate lithographic patterning steps in which a first lithographic patterning step (e.g., photolithography, ion-beam lithography, EUV lithography) prints a pattern of a first element and a second lithographic patterning step is aligned to the first lithographic patterning step and prints a pattern of the second element. A self-aligned process may comprise including the pattern of both the first and second element in a single lithographic patterning step, or may comprise forming the second element using features of a fabricated structure of the first element.

The term "sensor" may be used in the present disclosure to refer to one or more integrated circuit devices configured to sense emission from the sample well and produce at least one electrical signal representative of the sensed emission.

The term "nano-scale" may be used in the present disclosure to refer to a structure having at least one dimension or minimum feature size on the order of 150 nanometers (nm) or less, but not greater than approximately 500 nm.

The term "micro-scale" may be used in the present disclosure to refer to a structure having at least one dimension or minimum feature size between approximately 500 nm and approximately 100 microns.

The phrase "enhance excitation energy" may be used in the present disclosure to refer to increasing an intensity of excitation energy at an excitation region of a sample well. The intensity may be increased by concentrating and/or resonating excitation energy incident on the sample well, for example. In some cases, the intensity may be increased by anti-reflective coatings or lossy layers that allow the excitation energy to penetrate further into the excitation region of a sample well. An enhancement of excitation energy may be a comparative reference to an embodiment that does not include structures to enhance the excitation energy at an excitation region of a sample well.

The terms "about," "approximately," and "substantially" may be used in the present disclosure to refer to a value, and are intended to encompass the referenced value plus and minus acceptable variations. The amount of variation could be less than 5% in some embodiments, less than 10% in some embodiments, and yet less than 20% in some embodiments. In embodiments where an apparatus may function properly over a large range of values, e.g., a range including one or more orders of magnitude, the amount of variation could be a factor of two. For example, if an apparatus functions properly for a value ranging from 20 to 350, "approximately 80" may encompass values between 40 and 160.

The term "adjacent" may be used in the present disclosure to refer to two elements arranged within close proximity to one another (e.g., within a distance that is less than about one-fifth of a transverse or vertical dimension of a pixel). In some cases there may be intervening structures or layers between adjacent elements. In some cases adjacent elements may be immediately adjacent to one another with no intervening structures or elements.

The term "detect" may be used in the present disclosure to refer to receiving an emission at a sensor from a sample well and producing at least one electrical signal representative of or associated with the emission. The term "detect" may also be used in the present disclosure to refer to determining the presence of, or identifying a property of, a particular sample or tag in the sample well based upon emission from the sample well.

BRIEF DESCRIPTION

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

FIG. 1-2A depicts emission wavelength spectra, according to some embodiments.

FIG. 1-2B depicts absorption wavelength spectra, according to some embodiments.

FIG. 1-2C depicts emission wavelength spectra, according to some embodiments.

FIG. 1-3A depicts a phase space for emission wavelength and emission lifetime.

FIG. 1-3B depicts a phase space for absorption wavelength and emission lifetime.

FIG. 1-4 depicts a phase space for emission wavelength, absorption wavelength, and emission lifetime.

FIG. 2-1 is a block diagram representation of an apparatus that may be used for rapid, mobile analysis of biological and chemical specimens, according to some embodiments.

Figure 1:
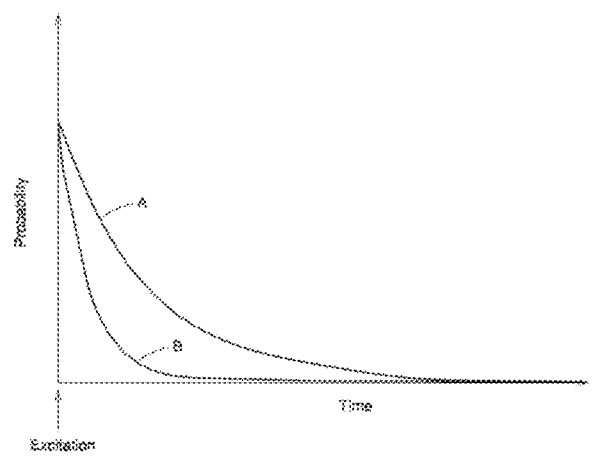
FIG. 1-1 depicts fluorescent lifetime curves for two different markers, according to some embodiments.
Figures 1, 2, 2A:
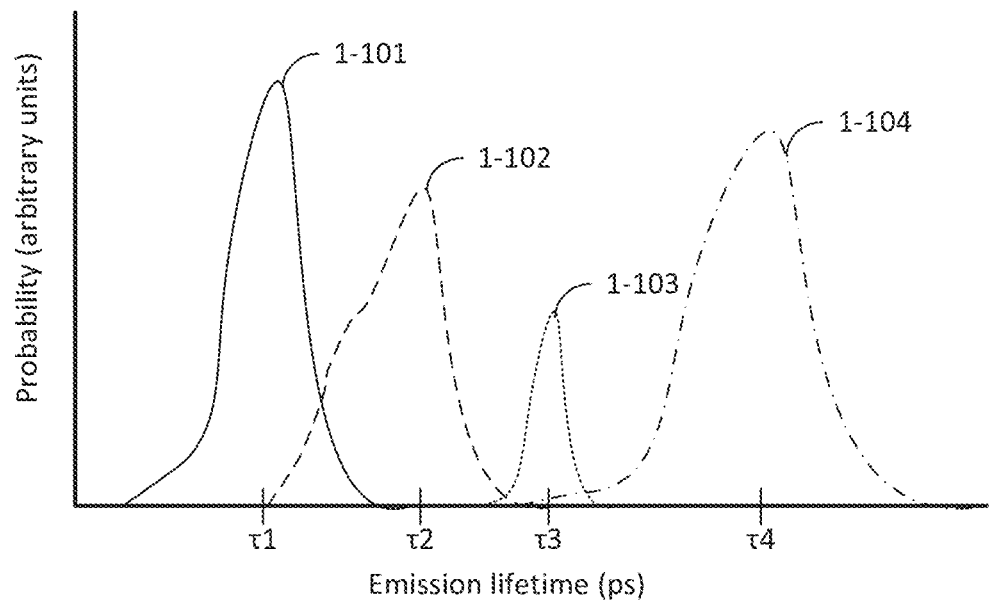

FIG. 2-2 a schematic diagram of the relationship between pixels of the sensor chip and pixels of the assay chip, according to some embodiments.

Figures 1, 2, 2B:
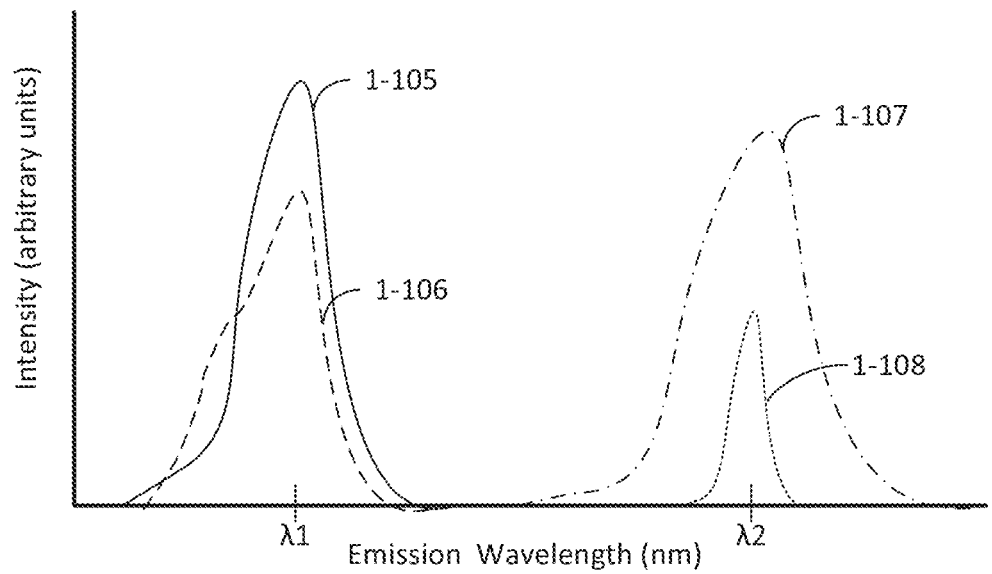
Figures 1, 2, 2C:
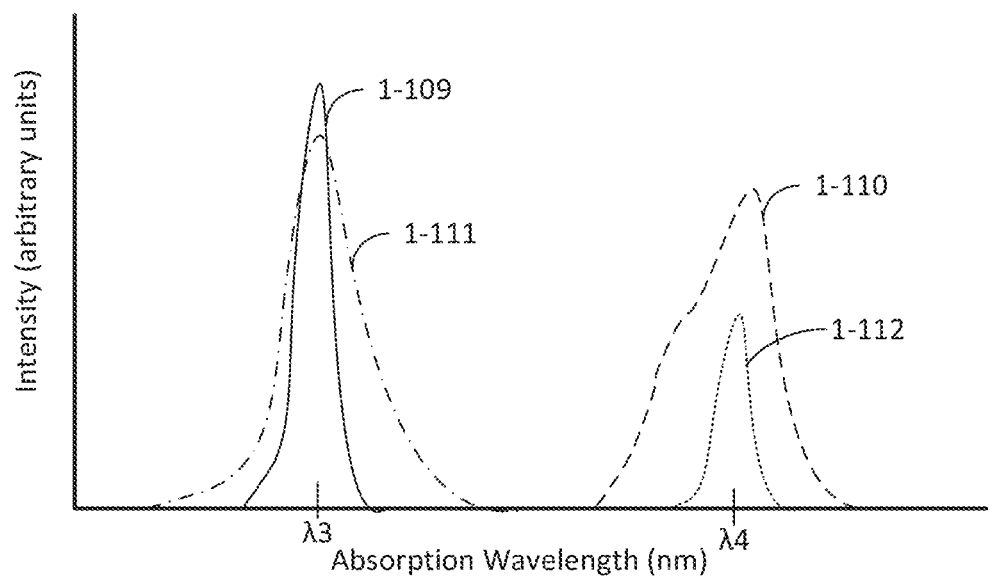
Figures 1, 2, 3, 3A:
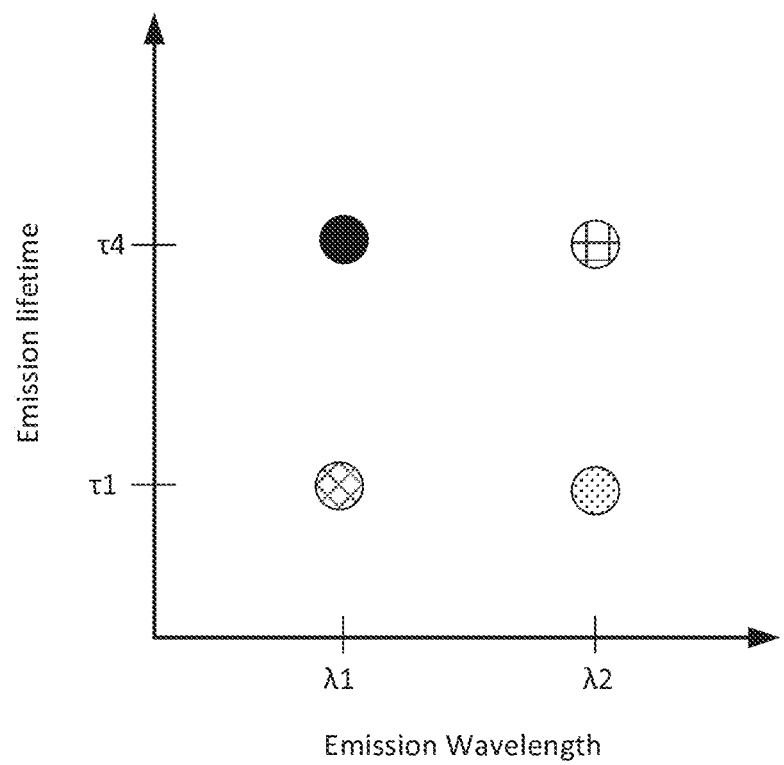

FIG. 2-3 depicts components associated with a single pixel of the assay chip and a single pixel of the sensor chip, according to some embodiments.

Figures 1, 2, 3, 3B:
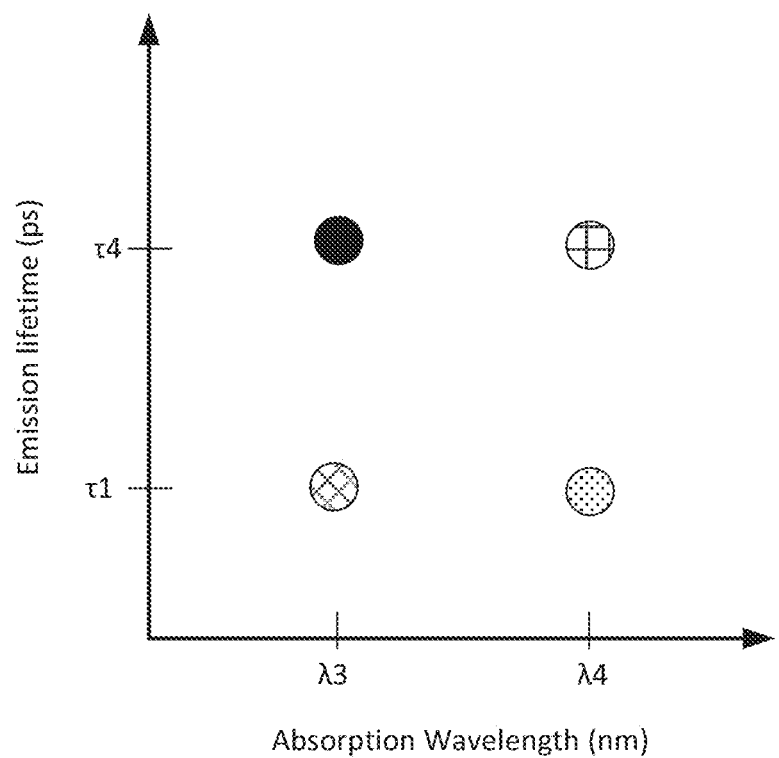
Figures 1, 2, 3, 4:
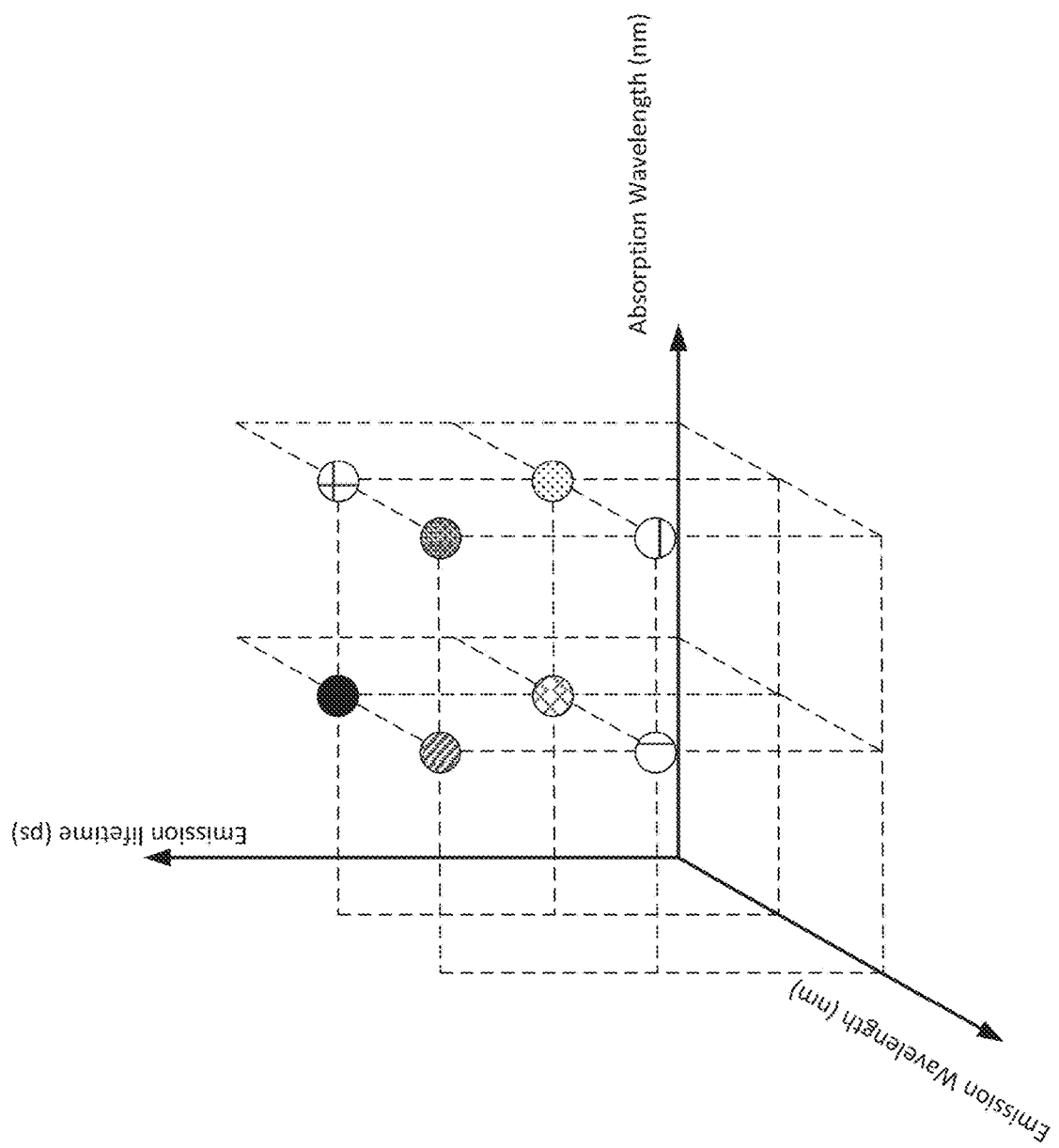
Figures 1, 2:
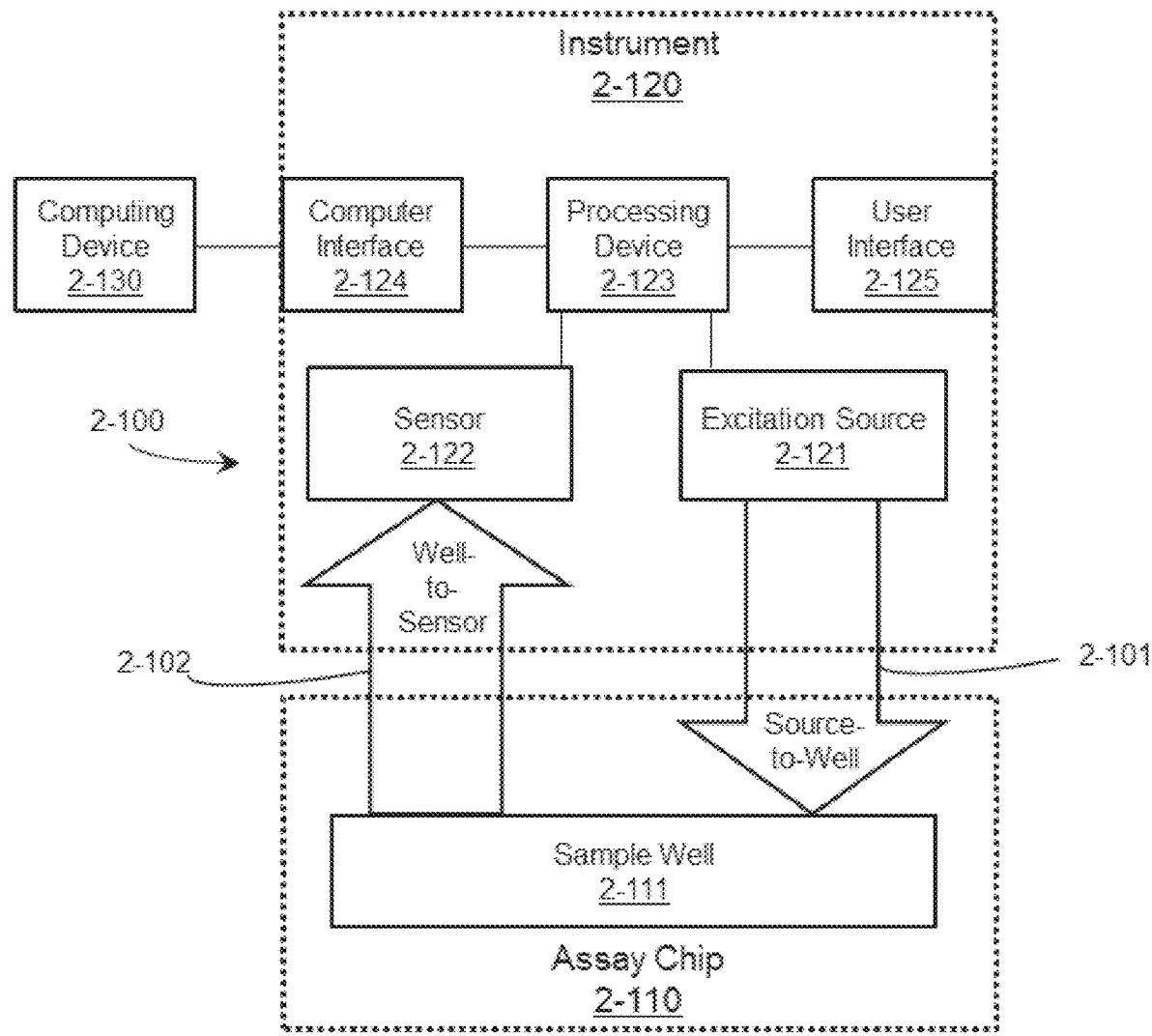
Figure 2:
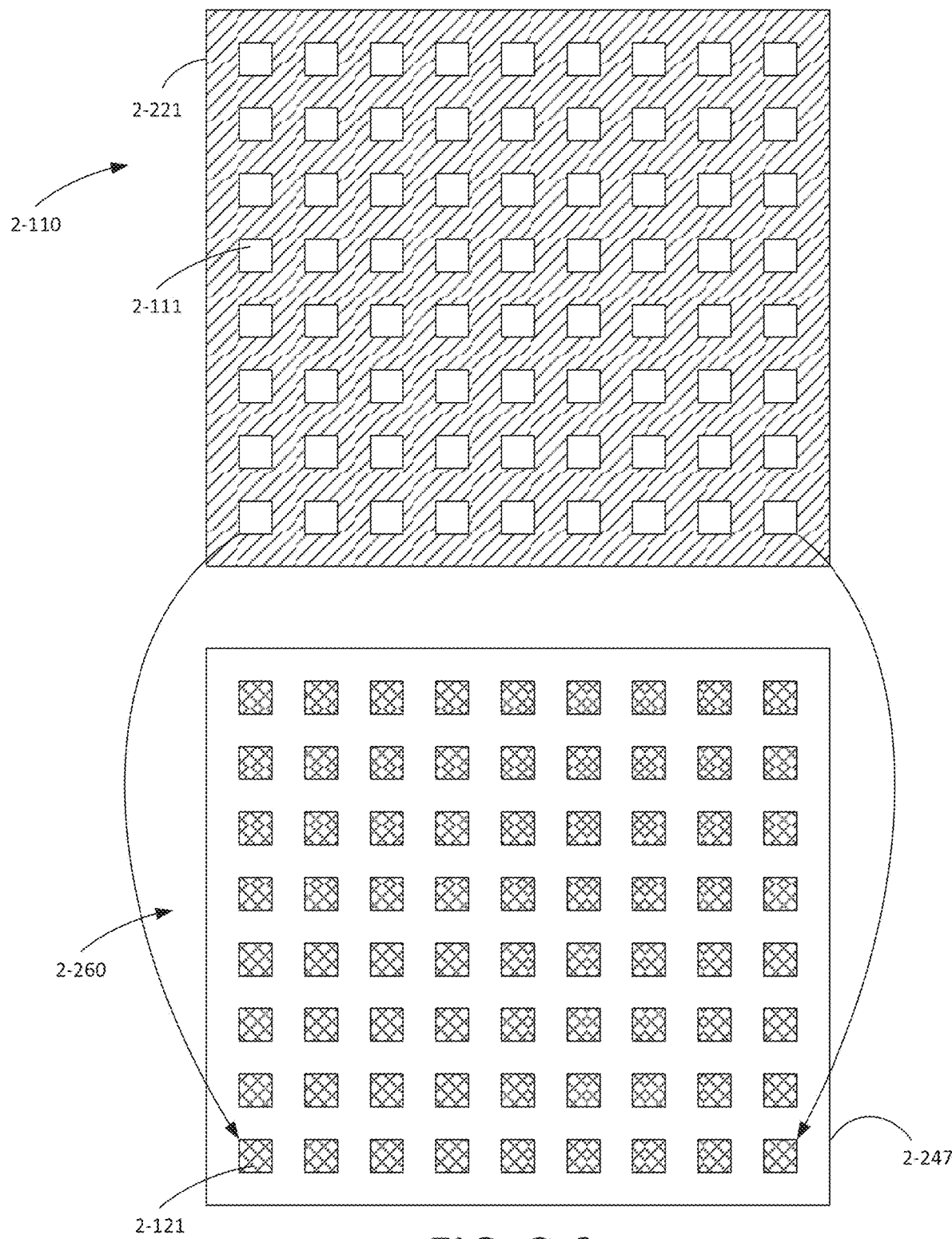
Figures 2, 3:
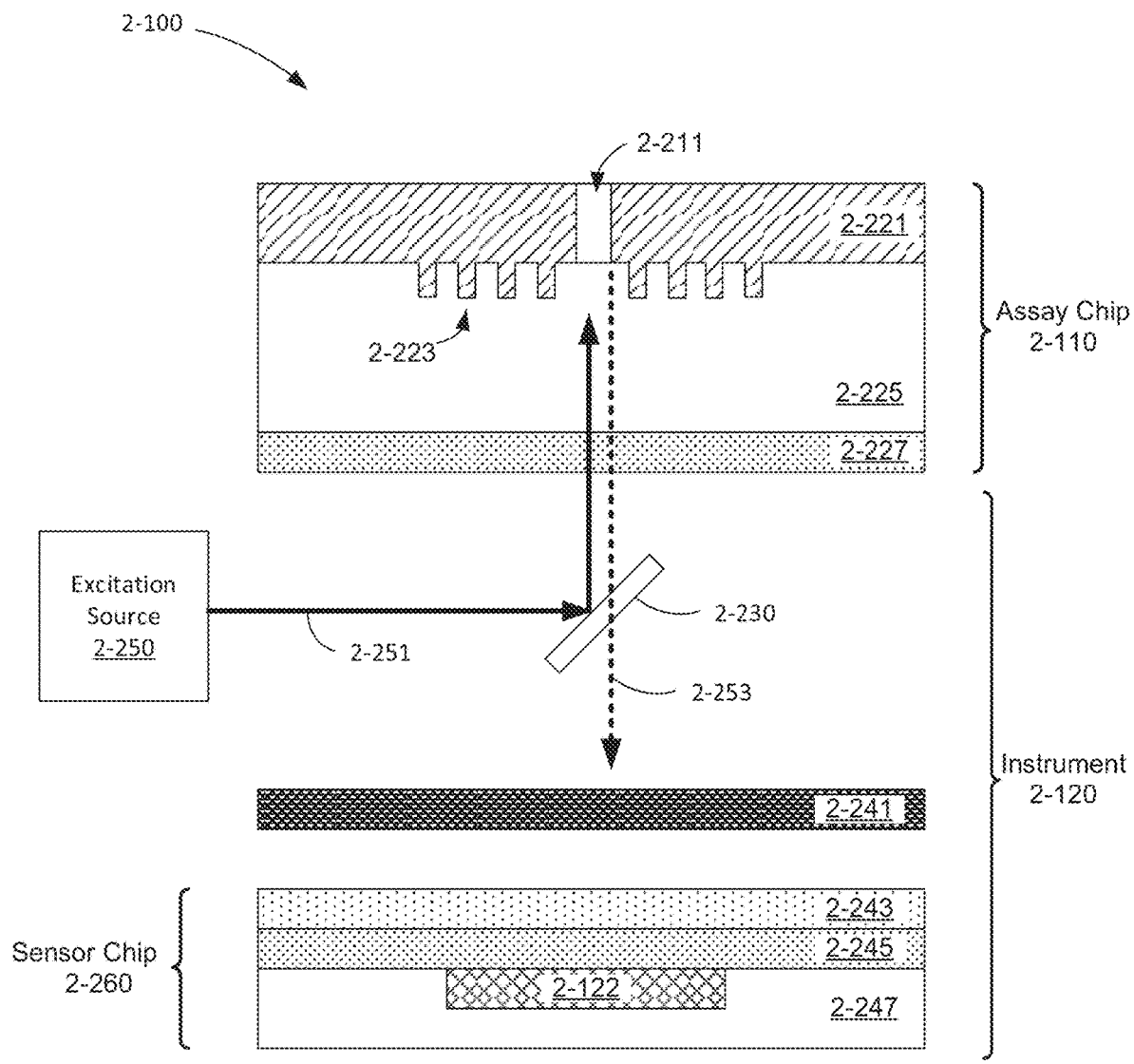
Figures 2, 3, 4:
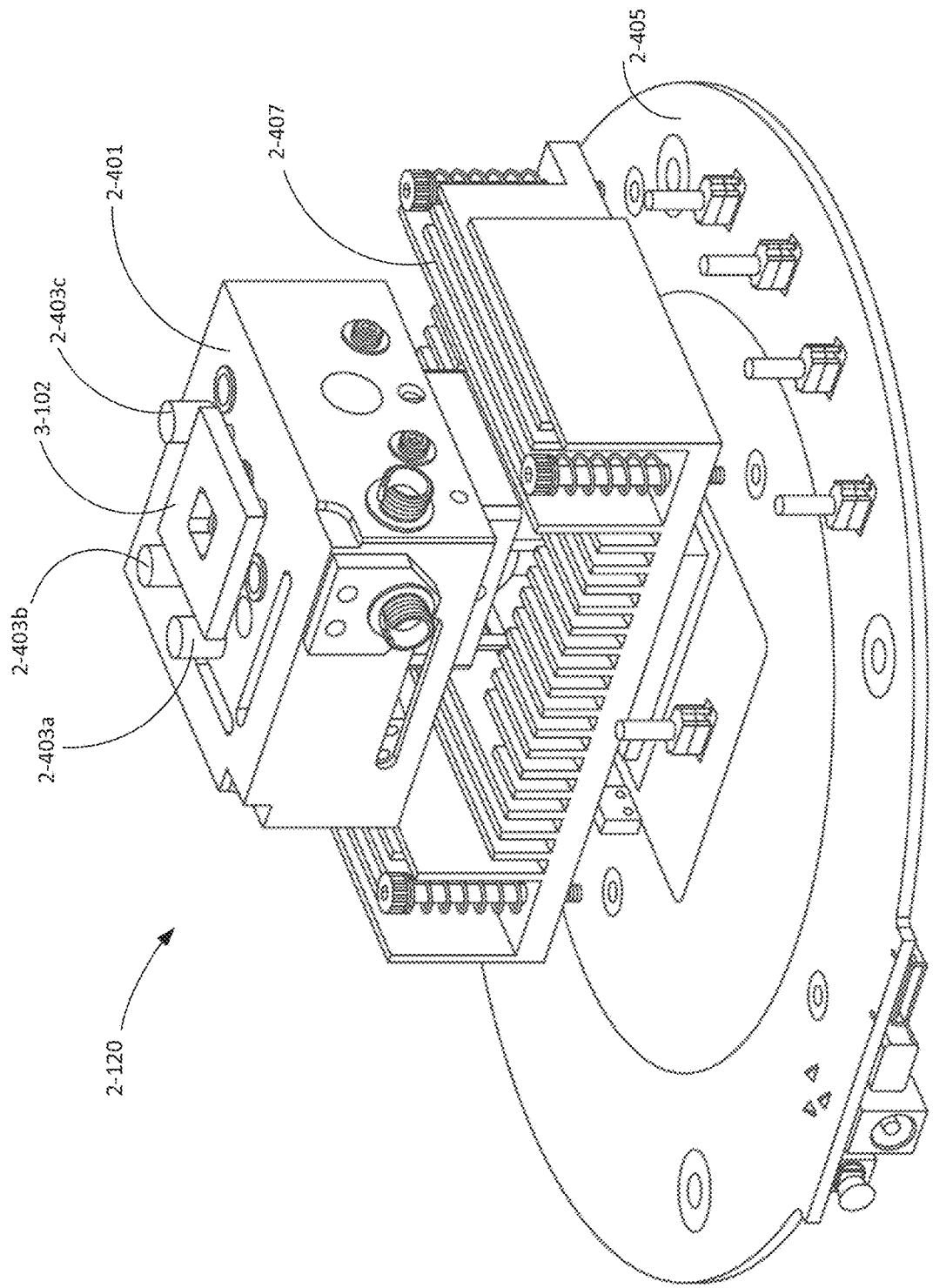

FIG. 2-4 depicts a portion of the components of the instrument, according to some embodiments.

Figures 1A, 3:
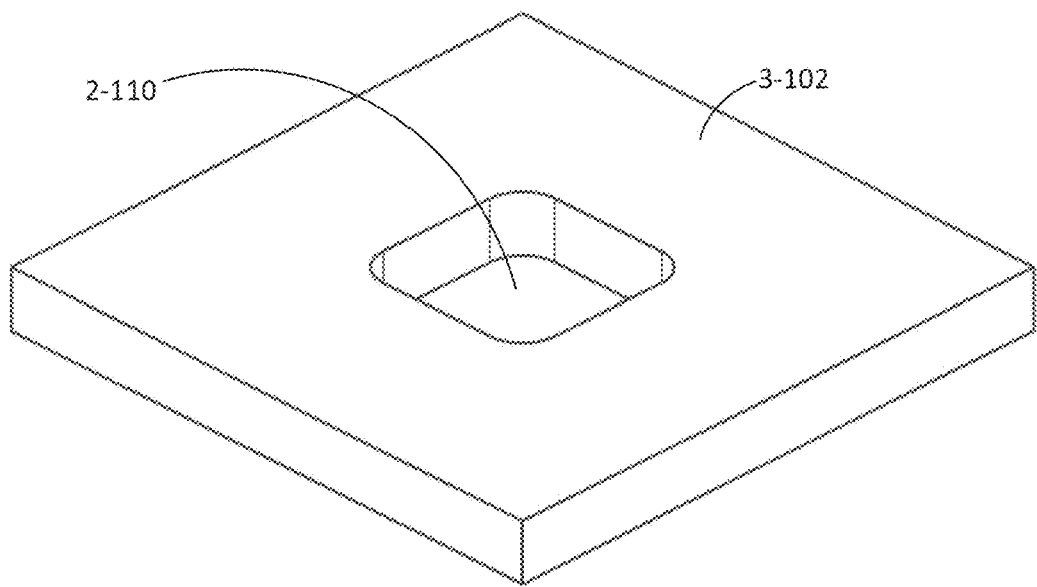

FIG. 3-1A is a top perspective view of the assay chip and a chip holder frame, according to some embodiments.

Figures 1B, 3:
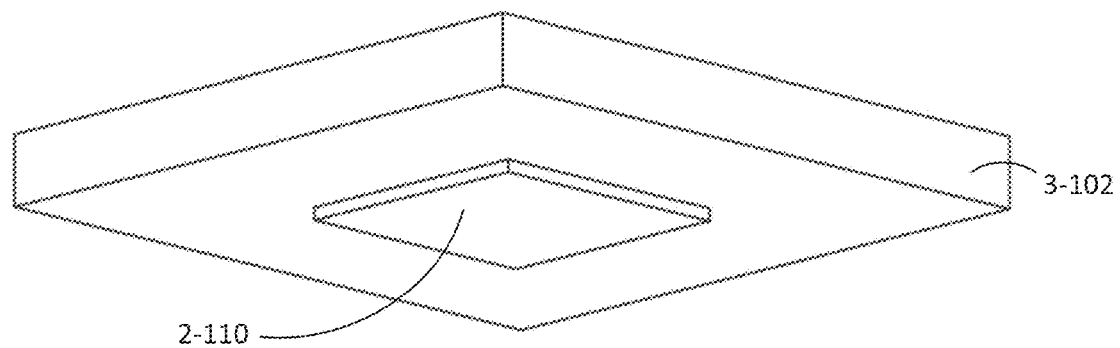

FIG. 3-1B is a bottom perspective view of the assay chip and the chip holder frame, according to some embodiments.

Figures 1C, 3:
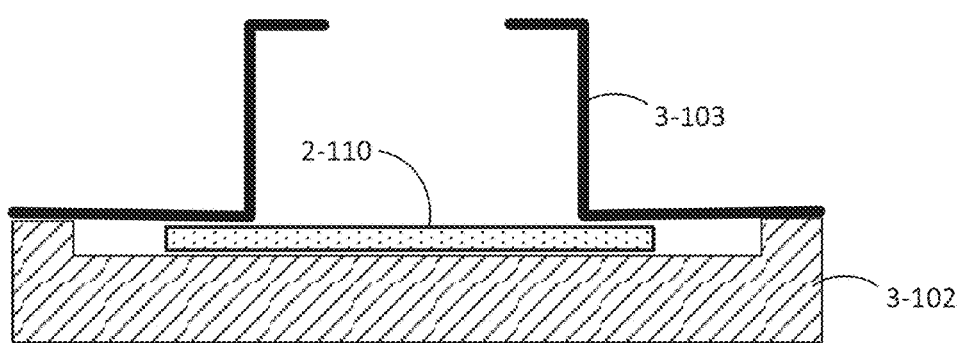
Figures 2, 3:
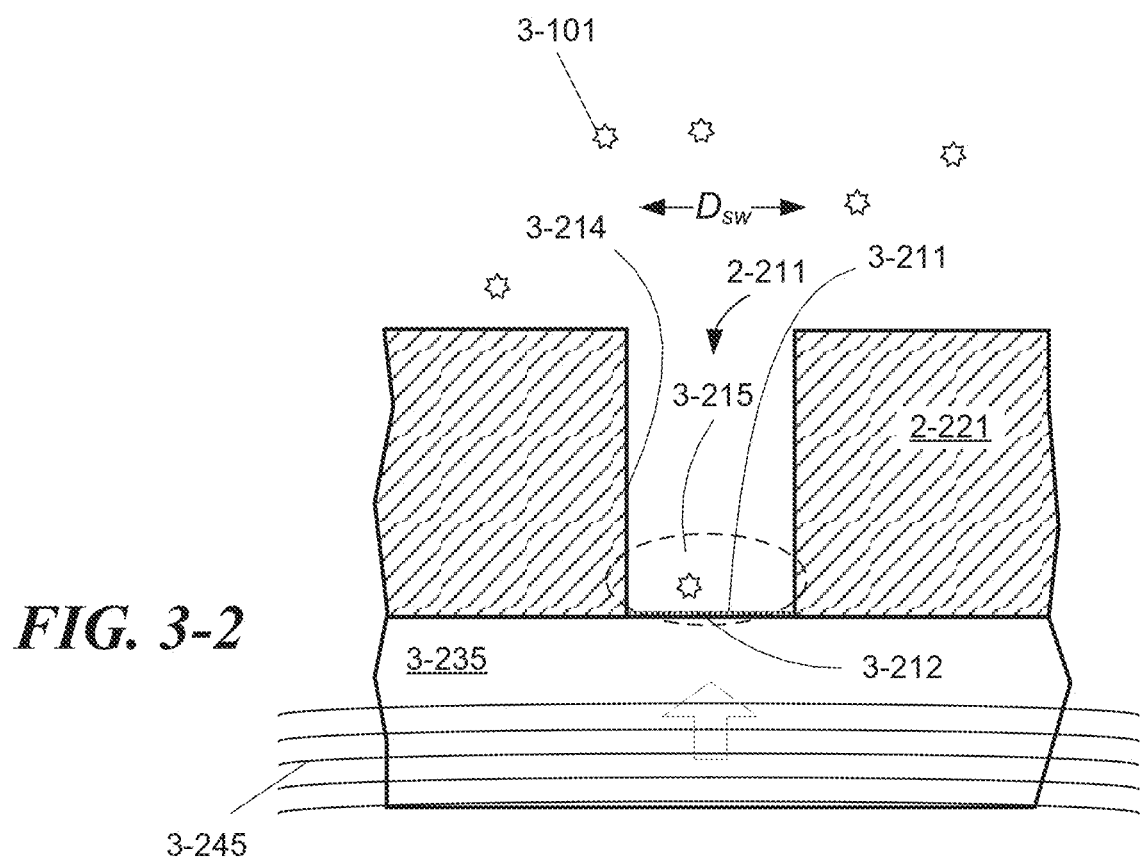
Figure 3:
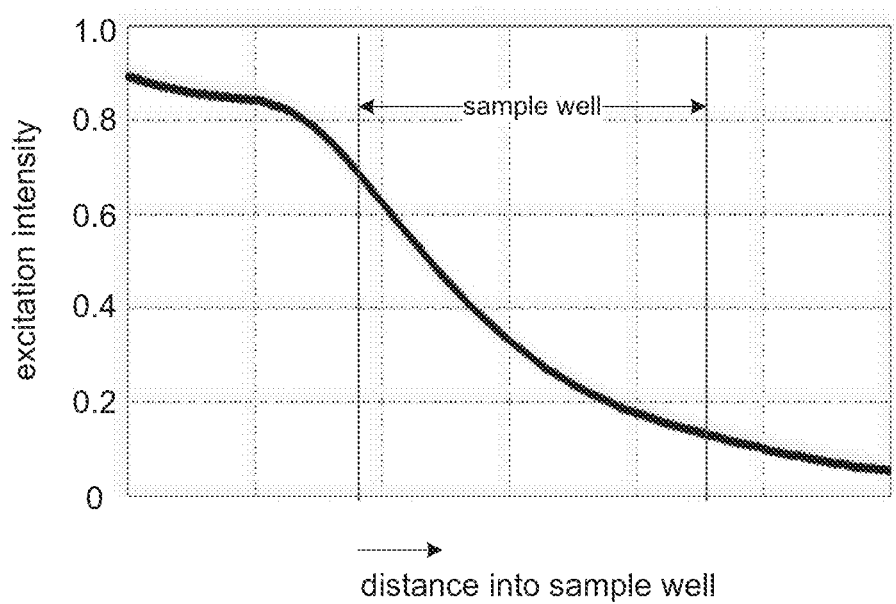
Figures 3, 4:
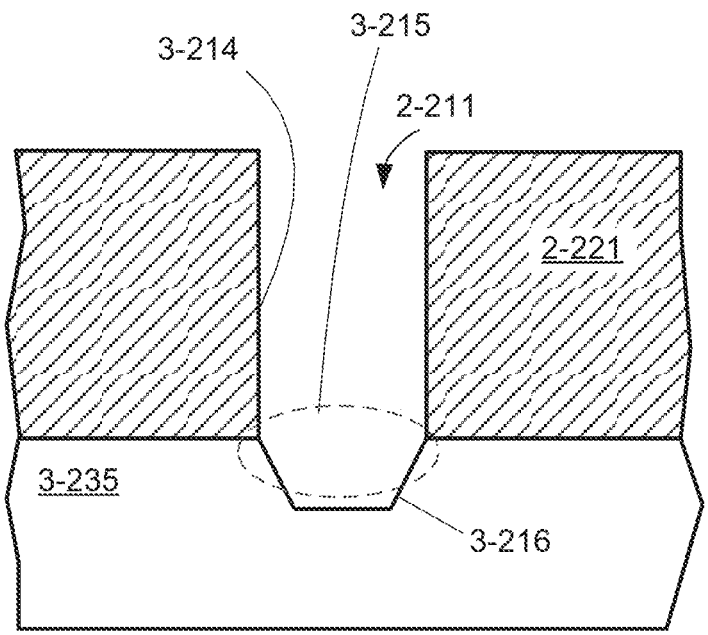

FIG. 3-1C is a cross-section view of the assay chip and the chip holder frame, according to some embodiments.

FIG. 3-2 depicts excitation energy incident on a sample well, according to some embodiments.

FIG. 3-3 illustrates attenuation of excitation energy along a sample well that is formed as a zero-mode waveguide, according to some embodiments.

FIG. 3-4 depicts a sample well that includes a divot, which increases excitation energy at an excitation region associated with the sample well in some embodiments.

Figures 3, 4, 5:
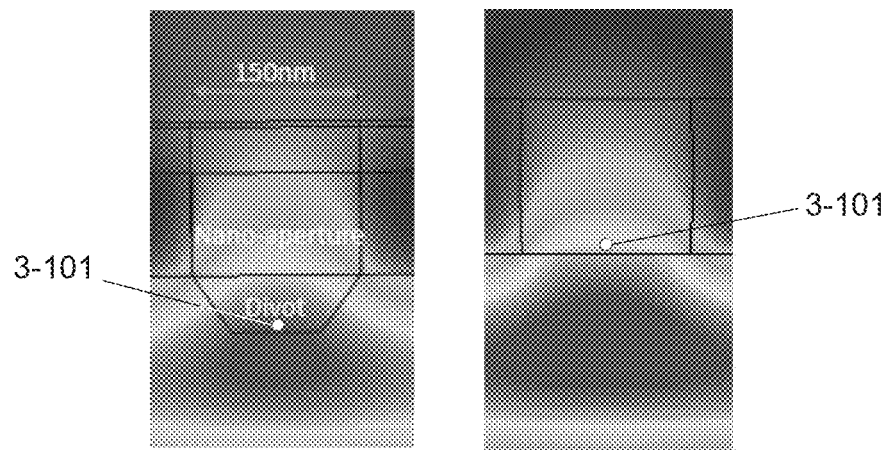

FIG. 3-5 compares excitation intensities for sample wells with and without a divot, according to one embodiment.

FIG. 3-6 depicts a sample well and divot formed at a protrusion, according to some embodiments.

FIG. 3-7A depicts a sample well having tapered sidewalls, according to some embodiments.

FIG. 3-7B depicts a sample well having curved sidewalls and a divot with a smaller transverse dimension, according to some embodiments.

FIG. 3-7C illustrates a side elevation view of a sample well formed from surface plasmonic structures.

FIG. 3-7D illustrates a plan view of a sample well formed from surface plasmonic structures.

FIG. 3-7E depicts a sample well that includes an excitation-energy-enhancing structure formed along sidewalls of the sample well, according to some embodiments.

FIG. 3-7F depicts a sample well formed in a multi-layer stack, according to some embodiments.

FIG. 3-8 illustrates surface coating formed on surfaces of a sample well, according to some embodiments.

FIG. 3-9A through FIG. 3-9E depict structures associated with a lift-off process of forming a sample well, according to some embodiments.

FIG. 3-9F depicts a structure associated with an alternative lift-off process of forming a sample well, according to some embodiments.

FIG. 3-10A through FIG. 3-10D depict structures associated with a direct etching process of forming a sample well, according to some embodiments.

FIG. 3-11 depicts a sample well that may be formed in multiple layers using a lift-off process or a direct etching process, according to some embodiments.

FIG. 3-12 depicts a structure associated with an etching process that may be used to form a divot, according to some embodiments.

FIG. 3-13A through FIG. 3-13C depict structures associated with an alternative process of forming a divot, according to some embodiments.

FIG. 3-14A through FIG. 3-14D depict structures associated with a process for depositing an adherent and passivating layers, according to some embodiments.

FIG. 3-15 depicts a structure associated with a process for depositing an adherent centrally within a sample well, according to some embodiments.

FIG. 4-1A and FIG. 4-1B depict a surface-plasmon structure, according to just one embodiment.

FIG. 4-1C depicts a surface-plasmon structure formed adjacent a sample well, according to some embodiments.

Figures 1A, 4:
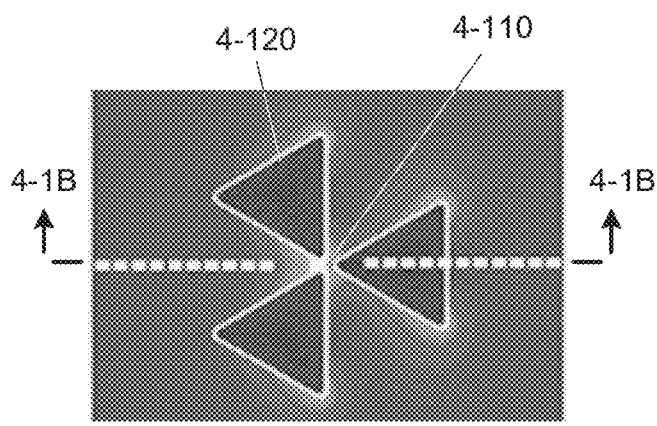
Figures 1B, 4:
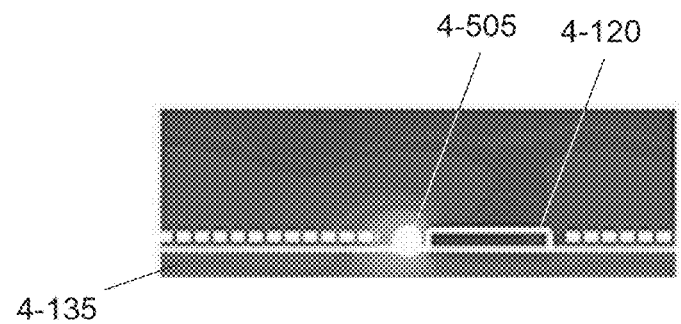
Figures 1C, 4:
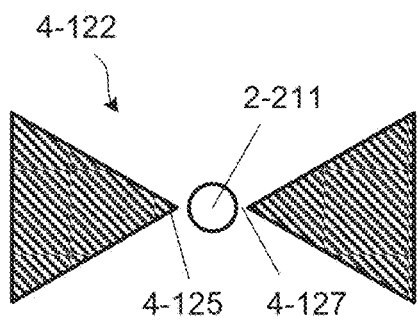
Figures 1D, 4:
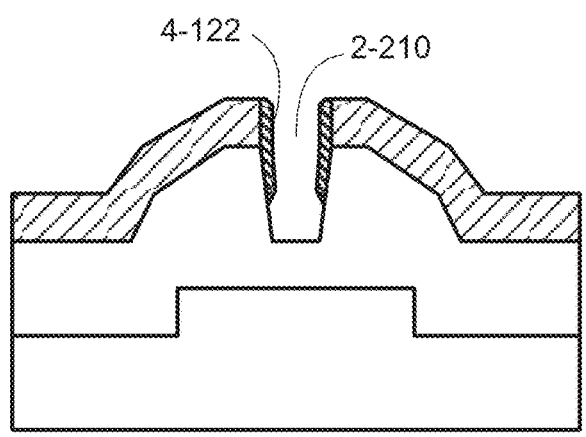
Figures 1E, 4:
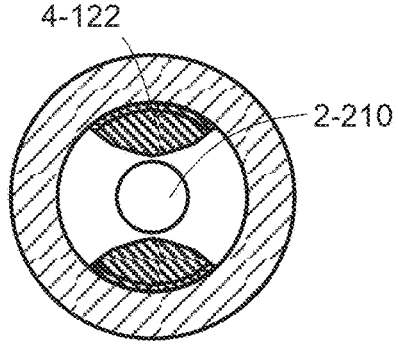
Figures 2A, 4:
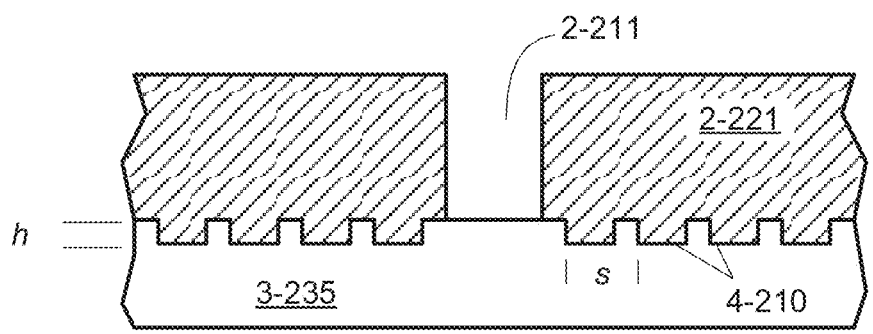
Figures 2B, 4:
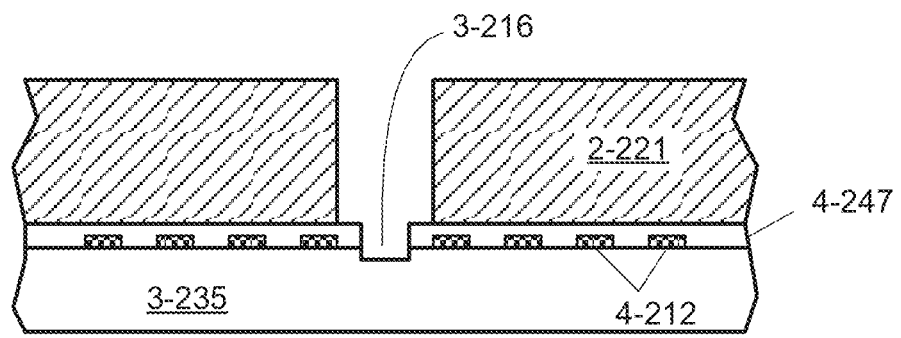
Figures 2C, 4:
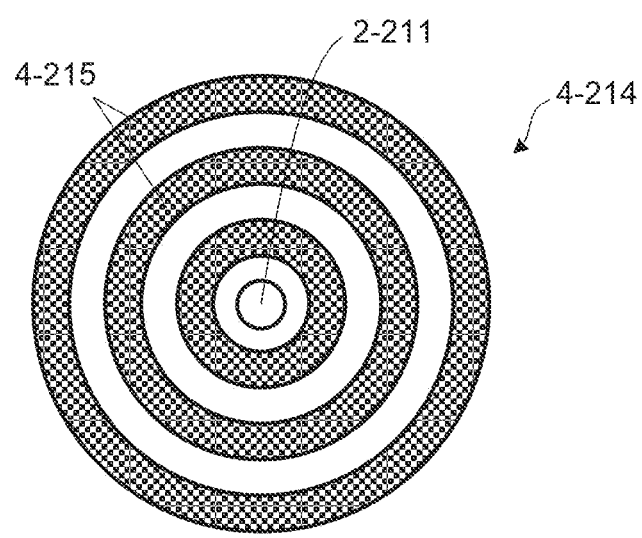

FIG. 4-1D and FIG. 4-1E depict surface-plasmon structures formed in a sample well, according to some embodiments.

FIG. 4-2A through FIG. 4-2C depict examples of periodic surface-plasmon structures, according to some embodiments.

Figures 1A, 7:
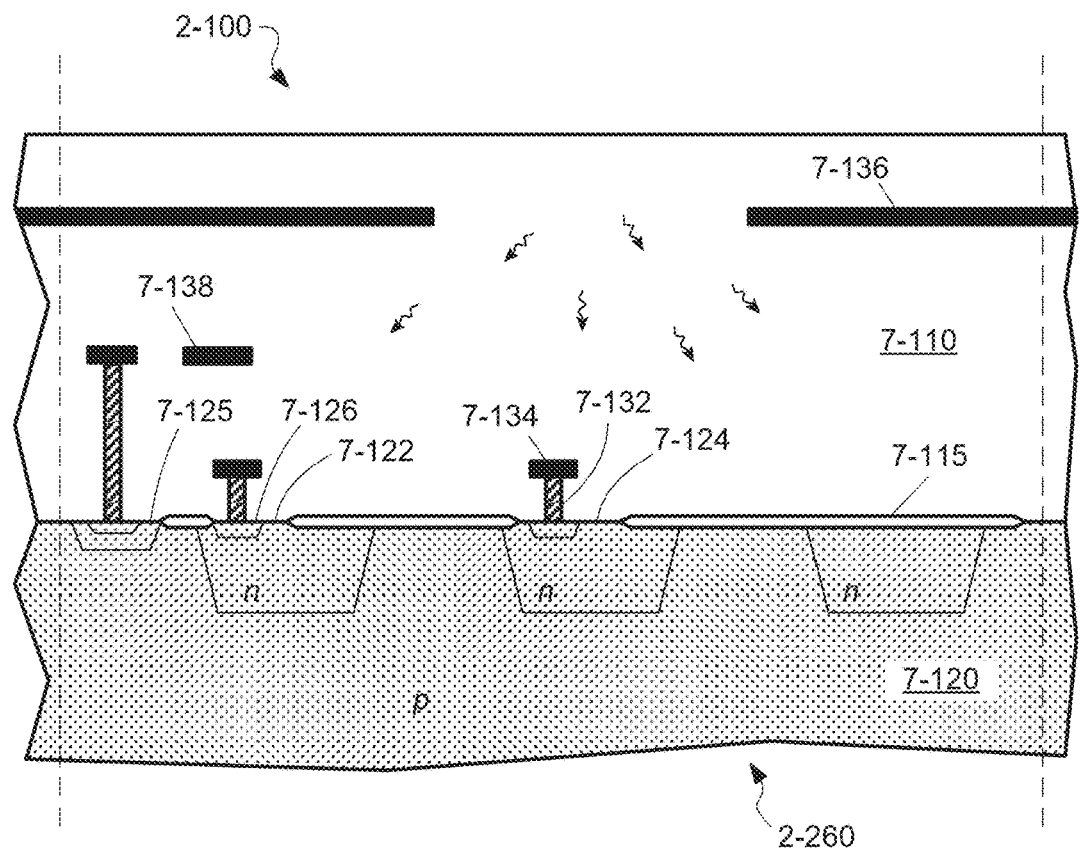
Figures 1B, 7:
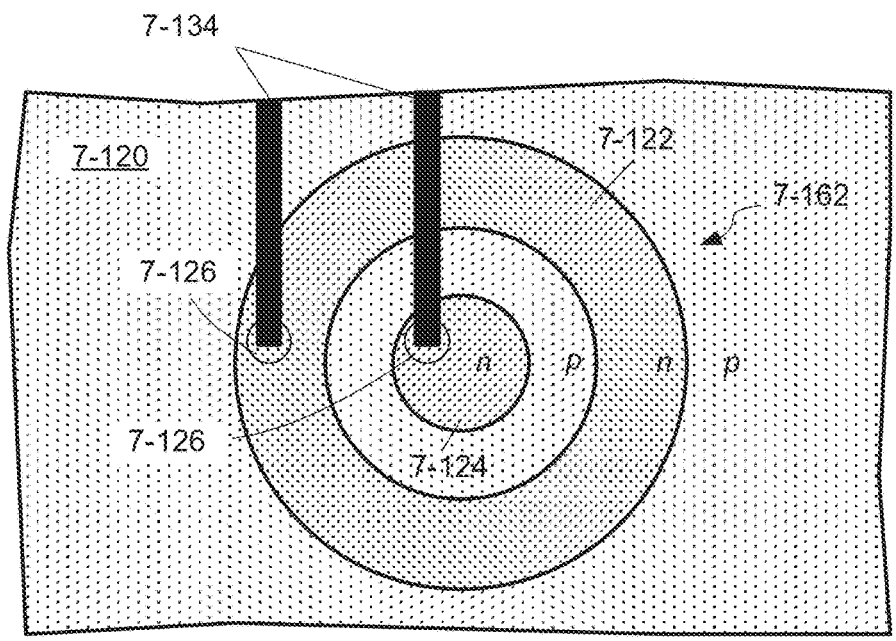
Figures 1C, 7:
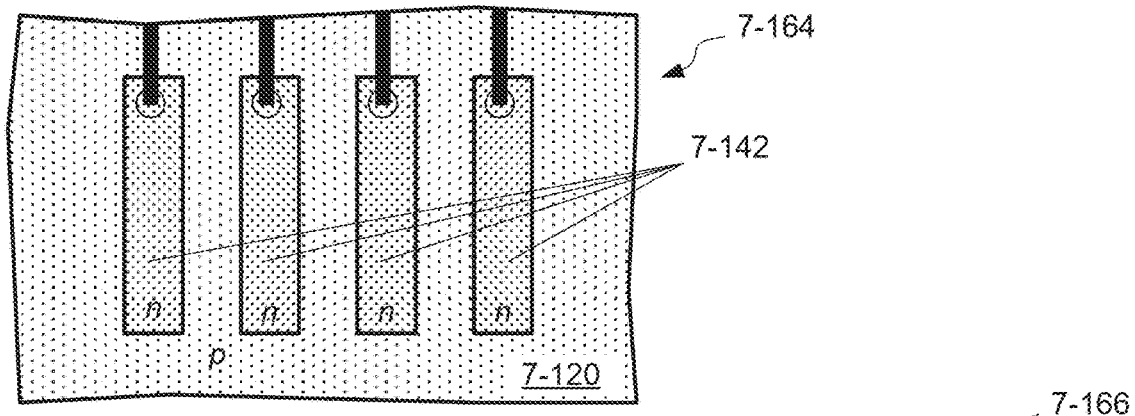
Figures 1D, 7:
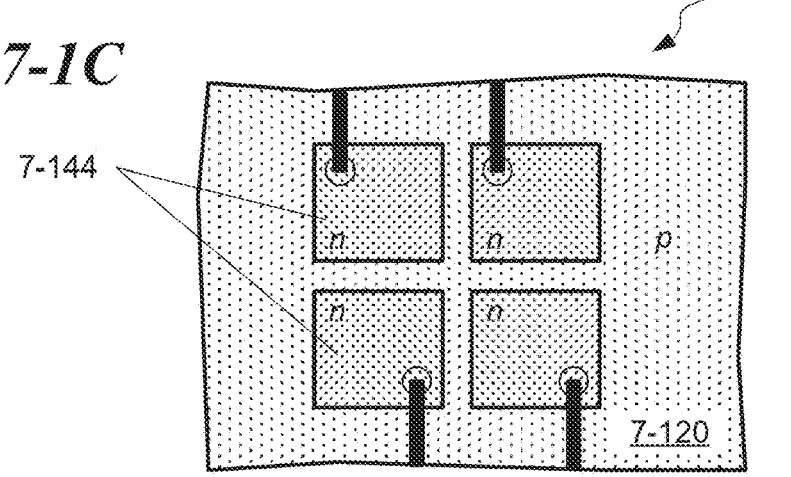
Figures 1E, 7:
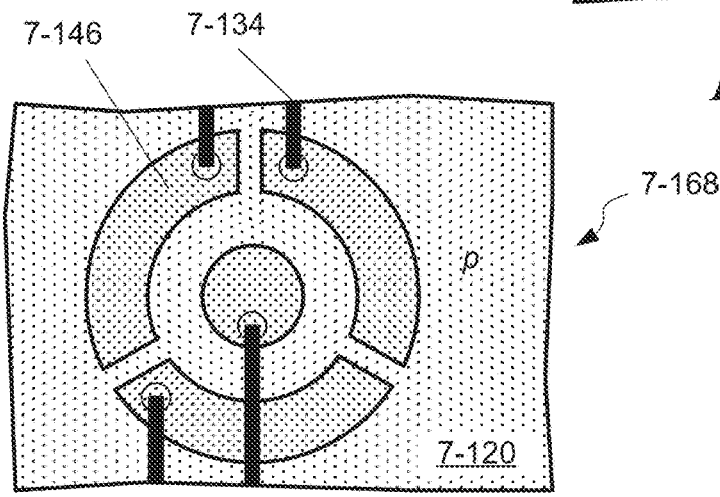
Figures 1F, 7:
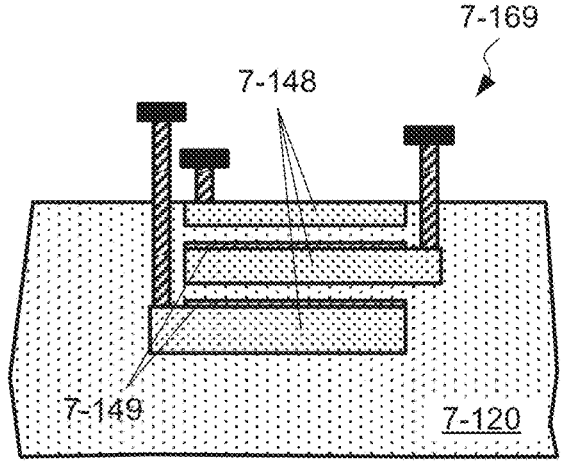
Figures 2A, 7:
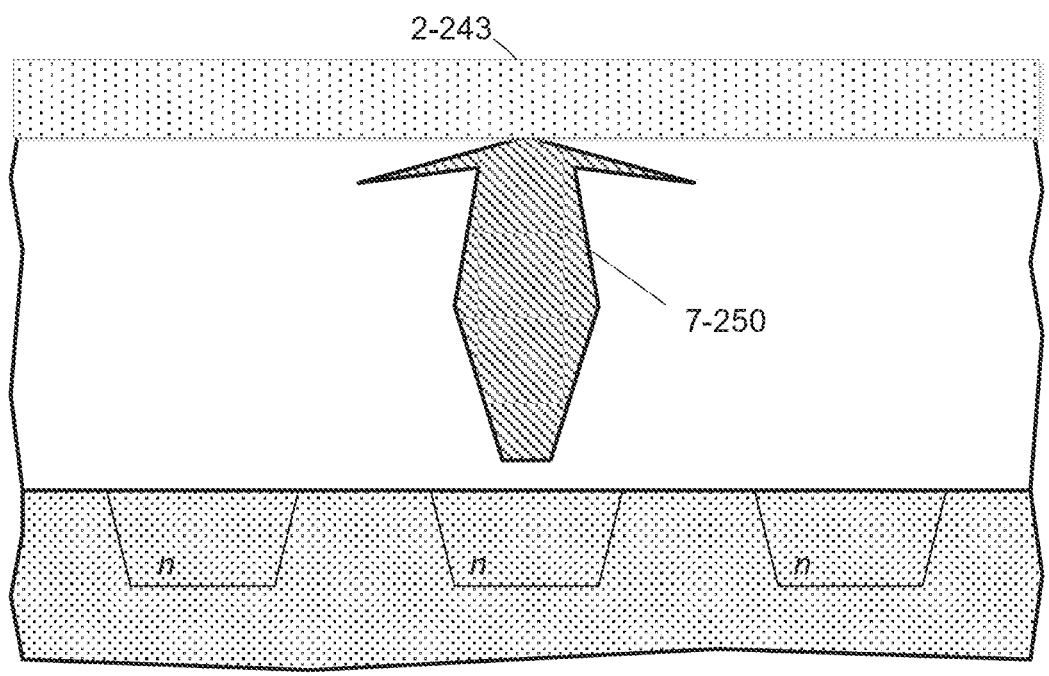
Figures 2B, 7:
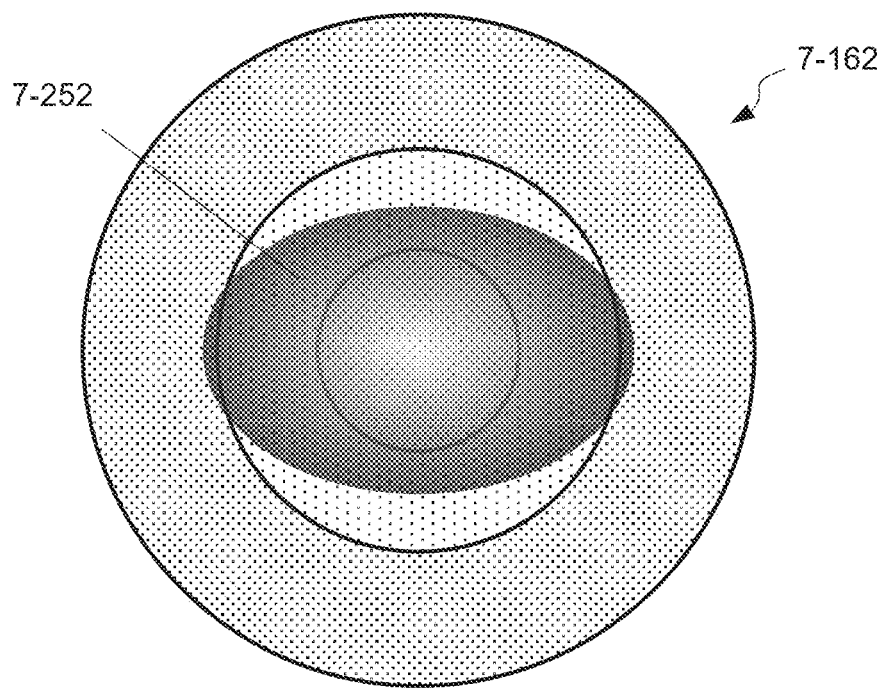
Figures 2C, 7:
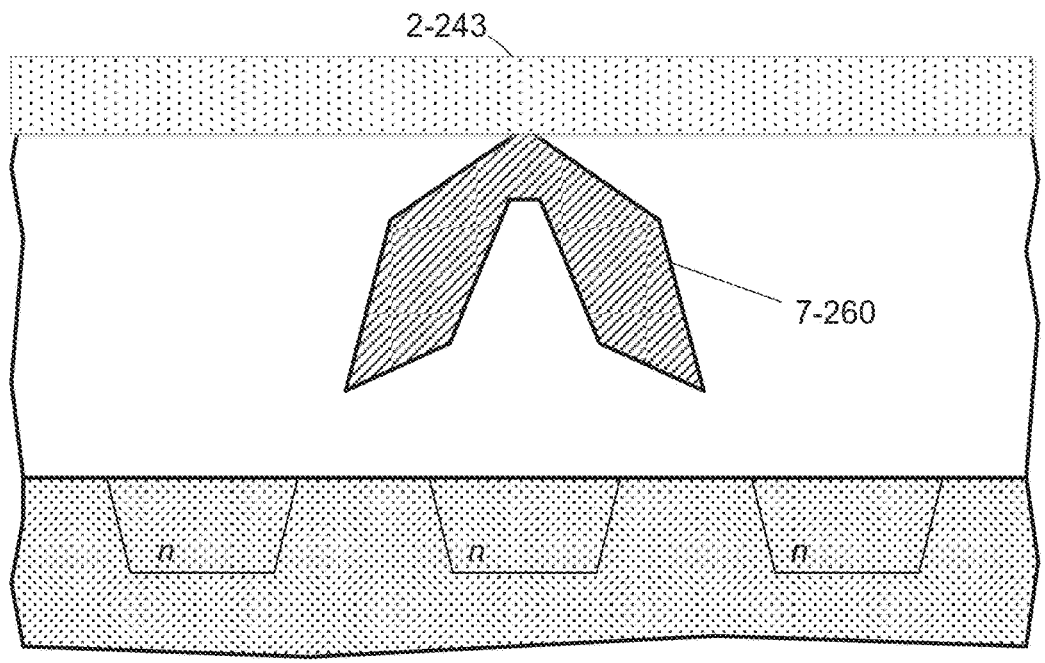
Figures 2D, 7:
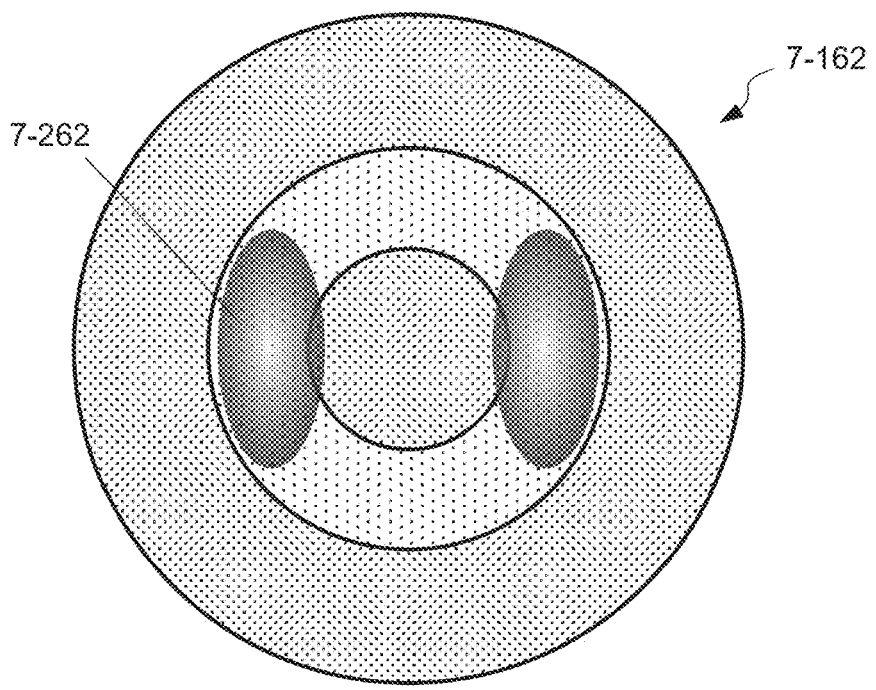

FIG. 4-2D depicts a numerical simulation of excitation energy at a sample well-formed adjacent a periodic surface-plasmon structure, according to some embodiments.

Figures 2E, 7:
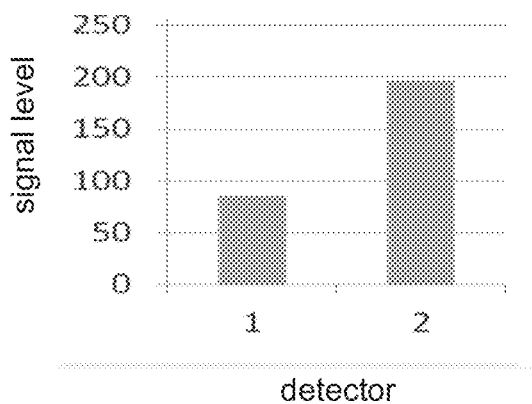
Figures 2F, 7:
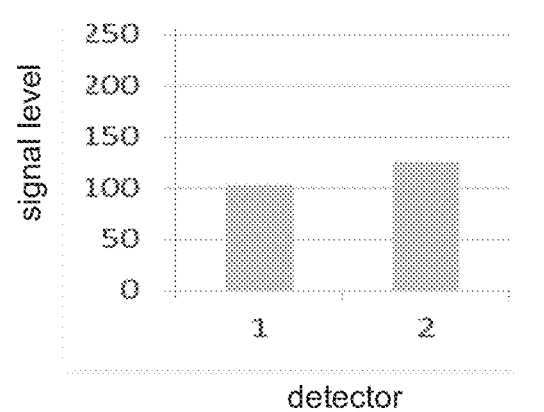
Figures 2G, 7:
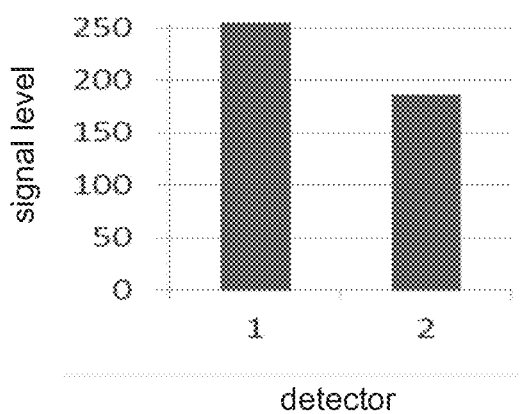
Figures 2H, 7:
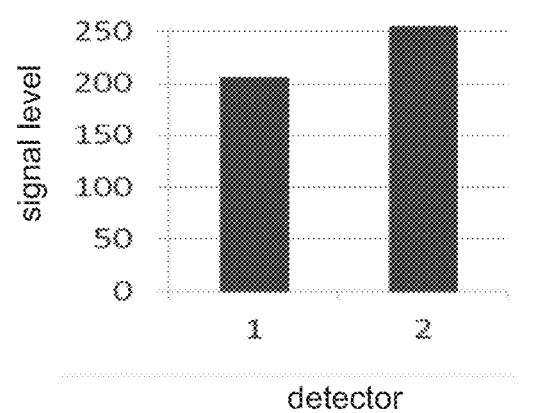
Figures 2I, 7:
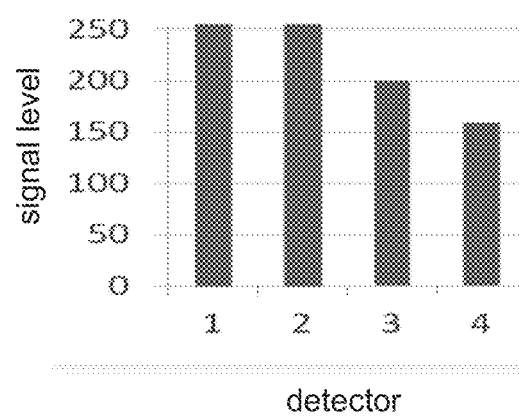

FIG. 4-2E through FIG. 4-2G depict periodic surface-plasmon structures, according to some embodiments.

Figures 2H, 4:
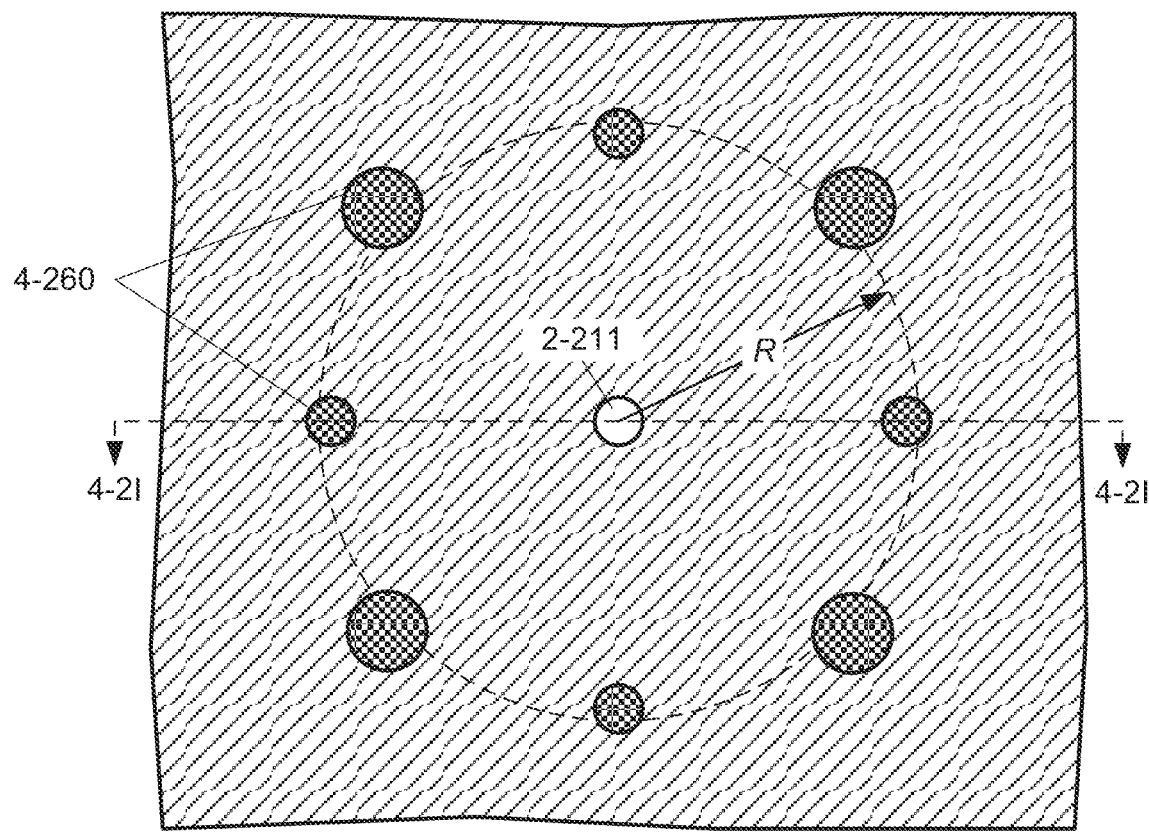
Figures 2I, 4:
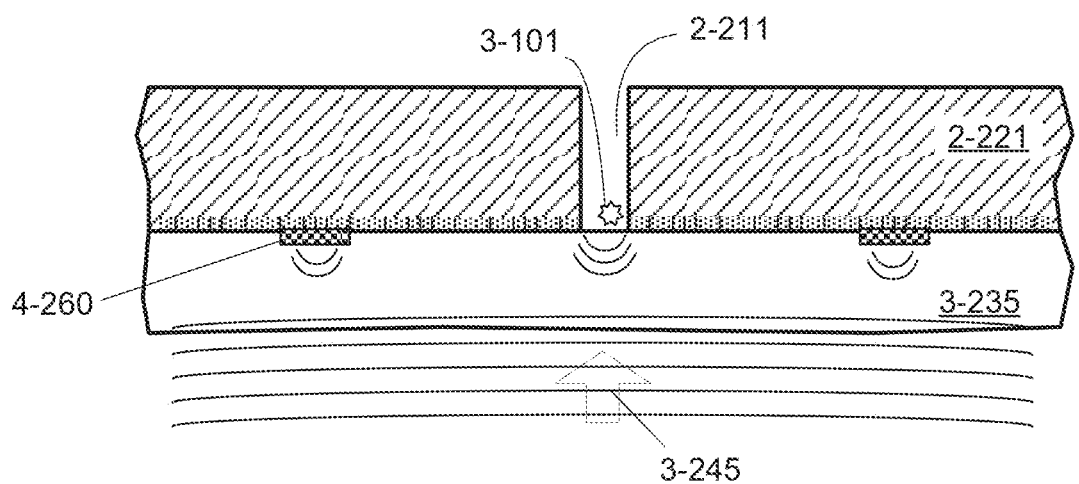
Figures 3A, 4:
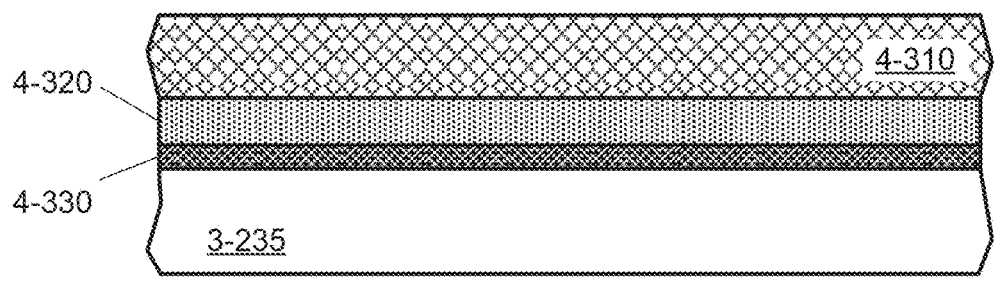
Figures 3B, 4:
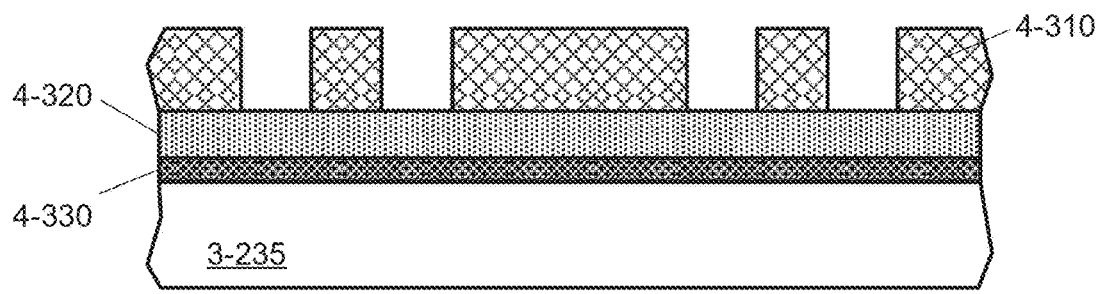

FIG. 4-2H and FIG. 4-2I depict a nano-antenna comprising surface-plasmon structures, according to some embodiments.

Figures 3C, 4:
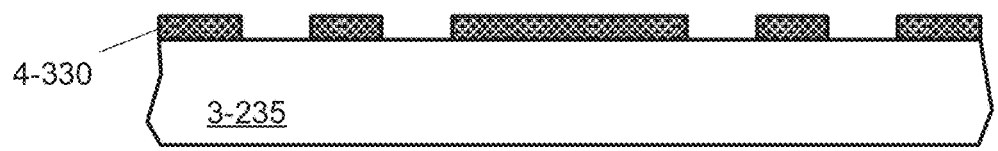
Figures 3D, 4:
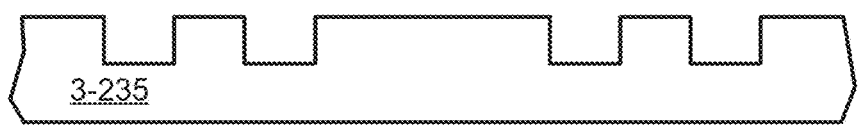
Figures 3E, 4:
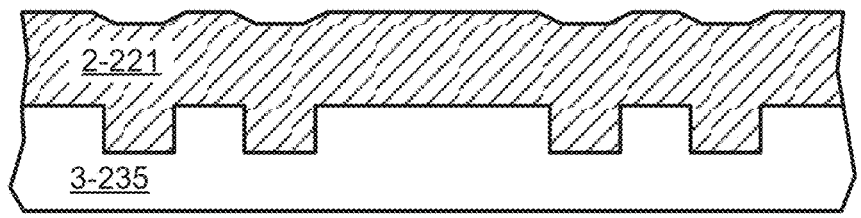

FIG. 4-3A through FIG. 4-3E depict structures associated with process steps for forming a surface-plasmon structure, according to some embodiments.

Figures 4, 4A:
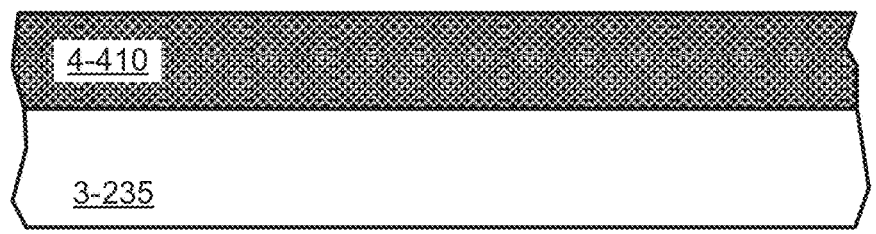
Figures 4, 4B:
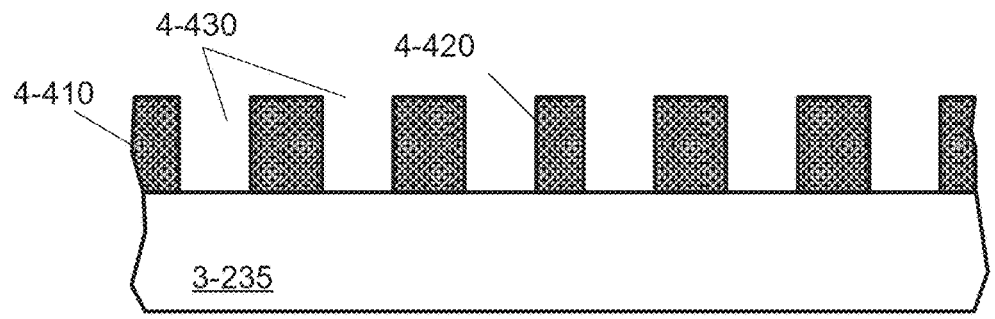
Figures 4, 4C:
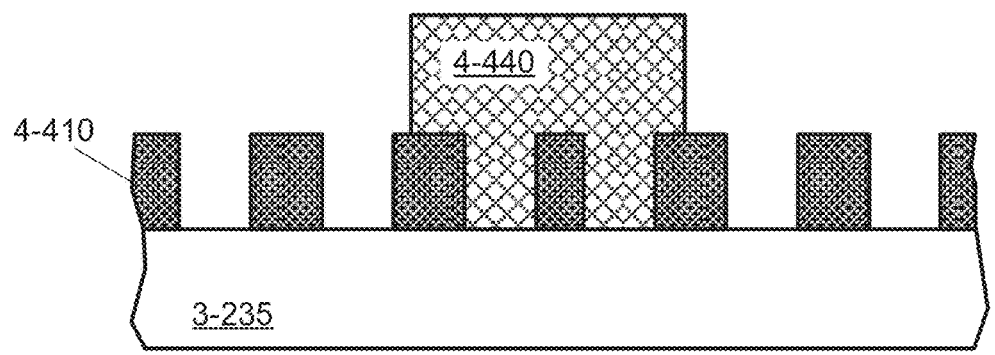
Figures 4, 4D:
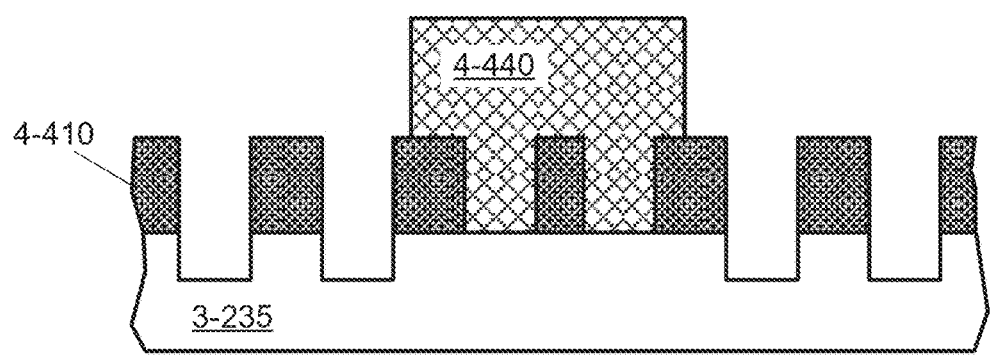
Figures 4, 4E:
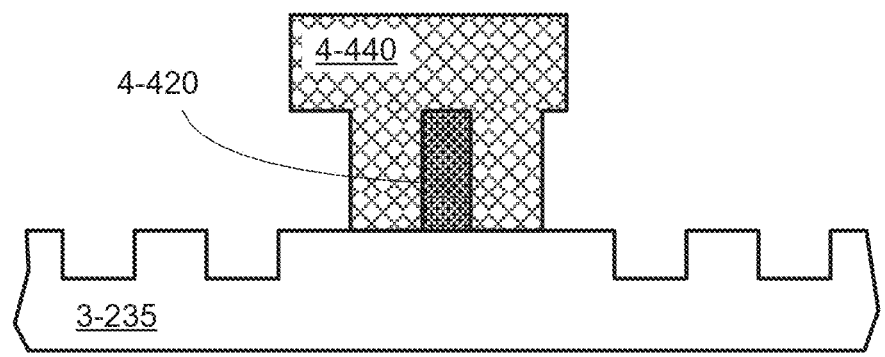
Figures 4, 4F:
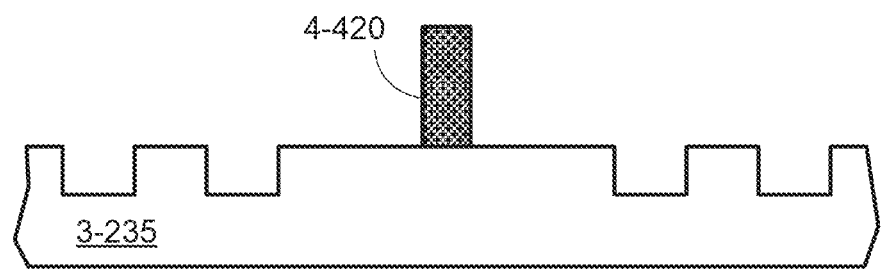
Figures 4, 4G:
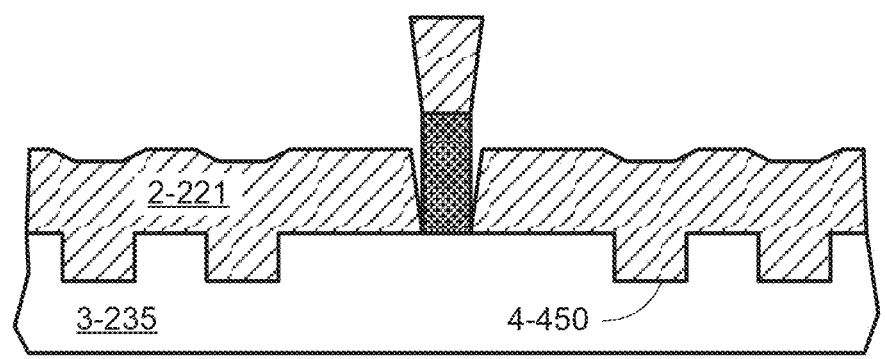

FIG. 4-4A through FIG. 4-4G depict structures associated with process steps for forming a surface-plasmon structure and self-aligned sample well, according to some embodiments.

FIG. 4-5A through FIG. 4-5E depict structures associated with process steps for forming a surface-plasmon structure and self-aligned sample well, according to some embodiments.

FIG. 4-6A depicts a thin lossy film formed adjacent a sample well, according to some embodiments.

FIG. 4-6B and FIG. 4-6C depict results from numerical simulations of excitation energy in the vicinity of a sample well and thin lossy film, according to some embodiments.

FIG. 4-6D depicts a thin lossy film spaced from a sample well, according to some embodiments.

FIG. 4-6E depicts a thin lossy film stack formed adjacent a sample well, according to some embodiments.

FIG. 4-7A illustrates a reflective stack that may be used to form a resonant cavity adjacent a sample well, according to some embodiments.

FIG. 4-7B depicts a dielectric structure that may be used to concentrate excitation energy at a sample well, according to some embodiments.

FIG. 4-7C and FIG. 4-7D depict a photonic bandgap structure that may be patterned adjacent a sample well, according to some embodiments.

FIG. 4-8A through FIG. 4-8G depict structures associated with process steps for forming dielectric structures and a self-aligned sample well, according to some embodiments.

FIG. 4-9A and FIG. 4-9B depict structures for coupling excitation energy to a sample via a non-radiative process, according to some embodiments.

FIG. 4-9C depicts a structure for coupling excitation energy to a sample by multiple non-radiative processes, according to some embodiments.

FIG. 4-9D depicts a structure that incorporates one or more energy-converting particles to couple excitation energy to a sample via a radiative or non-radiative process, according to some embodiments.

FIG. 4-9E depicts spectra associated with down conversion of excitation energy to a sample, according to some embodiments.

FIG. 4-9F depicts spectra associated with up conversion of excitation energy to a sample, according to some embodiments.

FIG. 5-1 depicts a concentric, plasmonic circular grating, according to some embodiments.

FIG. 5-2 depicts a spiral plasmonic grating, according to some embodiments.

FIG. 5-3A depicts emission spatial distribution patterns from a concentric, plasmonic circular grating, according to some embodiments.

FIG. 5-3B illustrates the directivity of aperiodic and periodic concentric, plasmonic circular gratings, according to some embodiments.

FIG. 5-4A through FIG. 5-4B depict plasmonic nano-antennas, according to some embodiments.

Figures 4, 5, 5A:
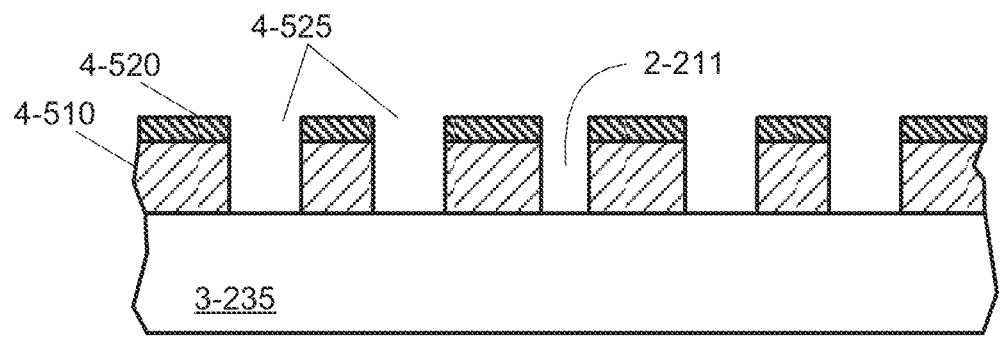
Figures 4, 5, 5B:
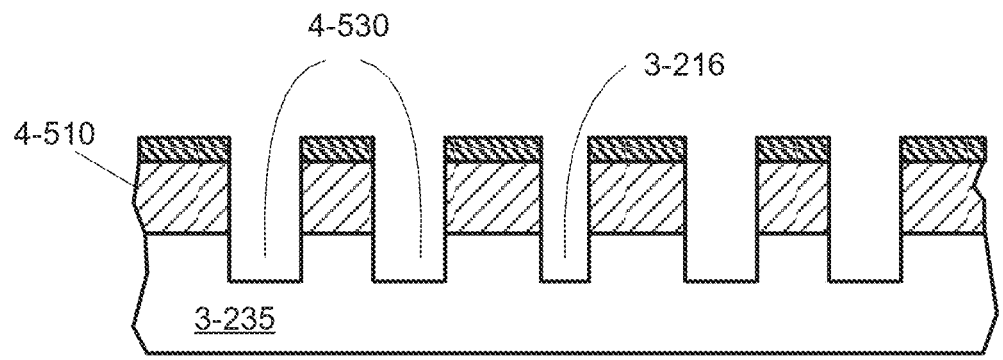

FIG. 5-5A through FIG. 5-5B depict plasmonic nano-antennas, according to some embodiments.

Figures 4, 5, 5C:
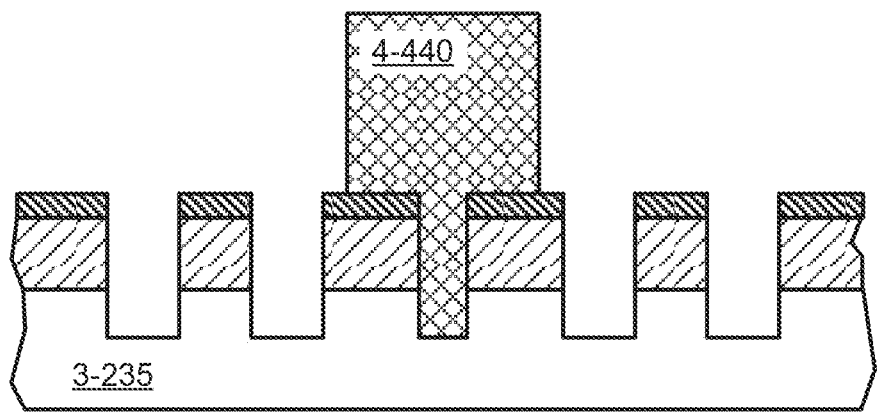

FIG. 5-5C depicts the radiation pattern of emission energy from a nano-antenna array, according to come embodiments.

Figures 3, 4, 5, 6:
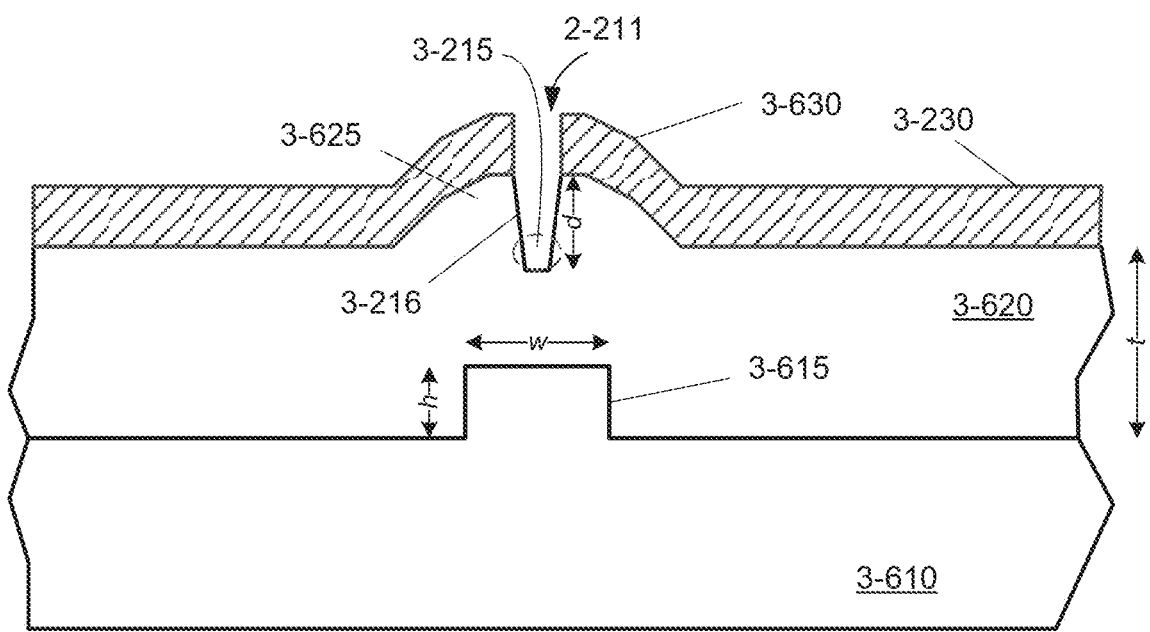
Figures 4, 5, 5D:
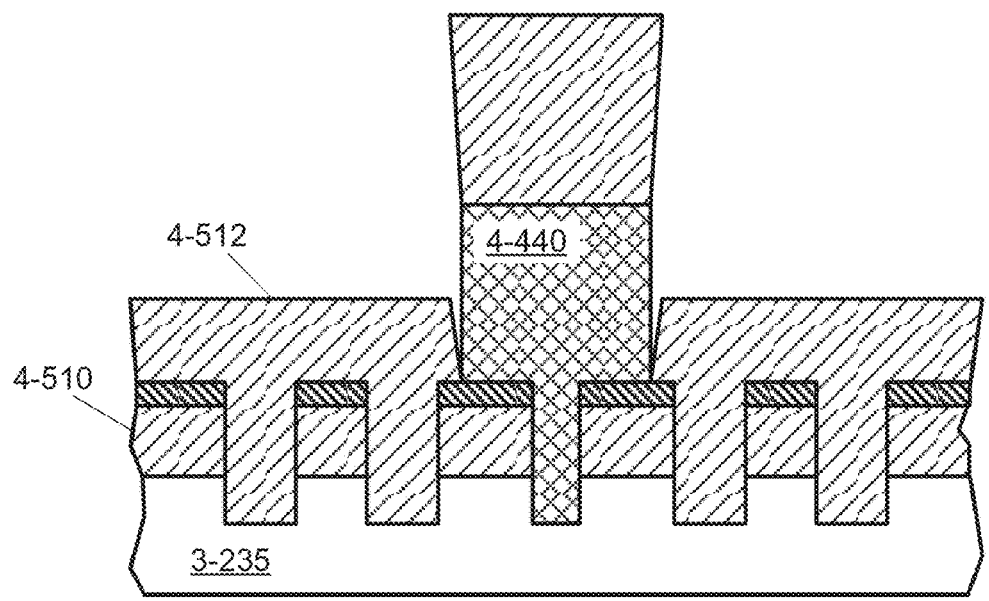
Figures 4, 5, 5E:
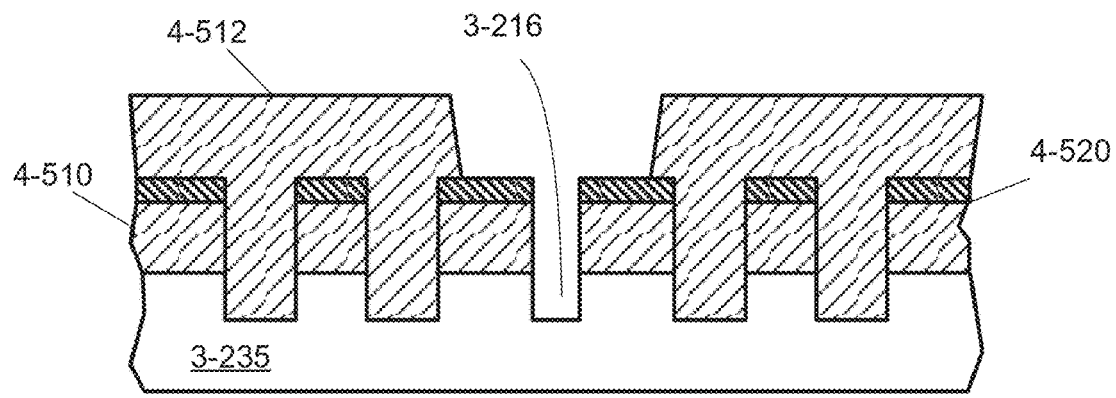
Figures 4, 5, 6, 6A:
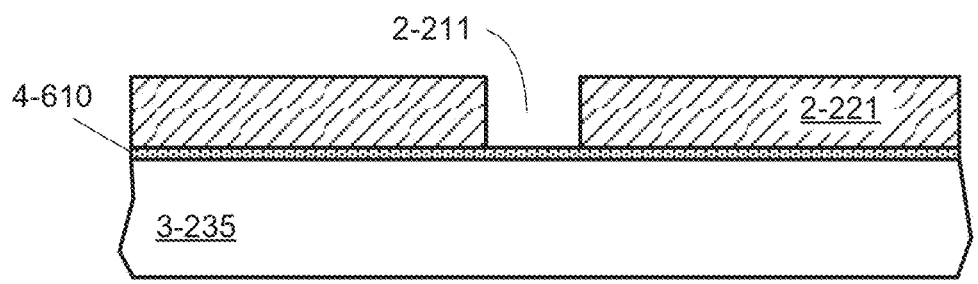

FIG. 5-6A depicts refractive optics of the assay chip, according to some embodiments.

Figures 4, 5, 6, 6B:
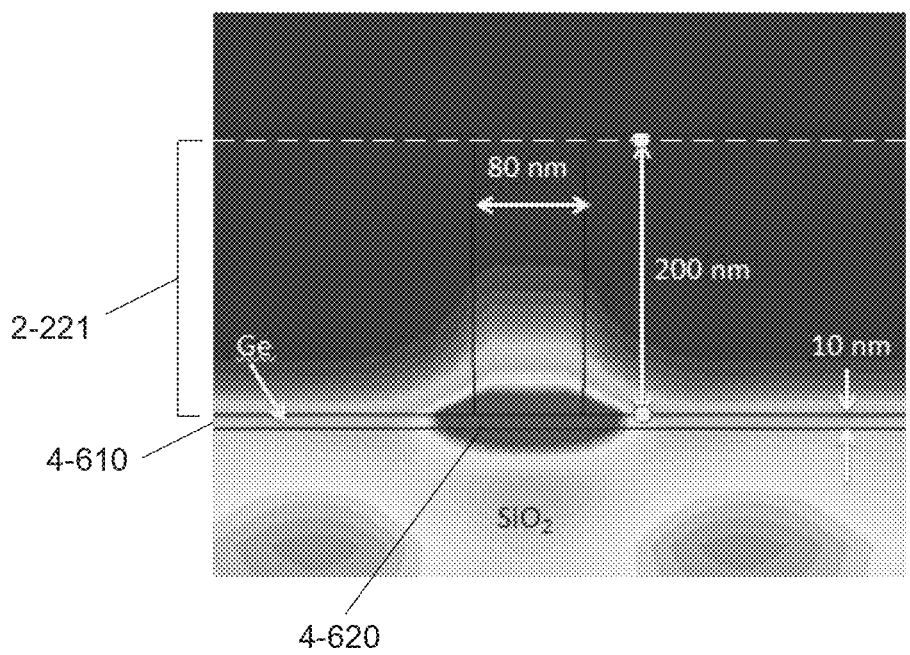
Figures 4, 5, 6, 6C:
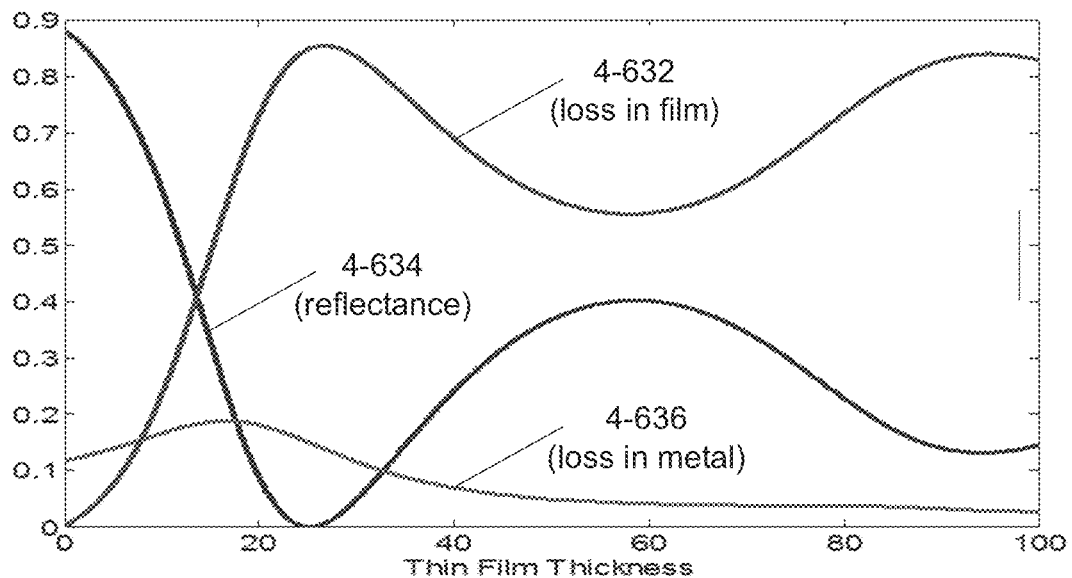
Figures 4, 5, 6, 6D:
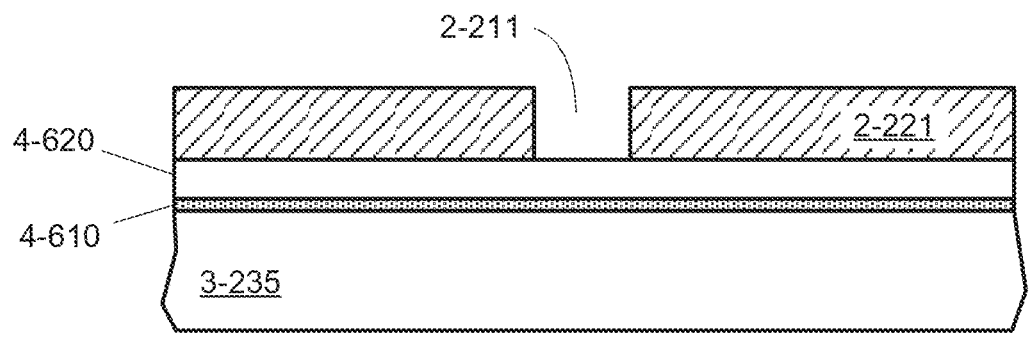
Figures 4, 5, 6, 6E:
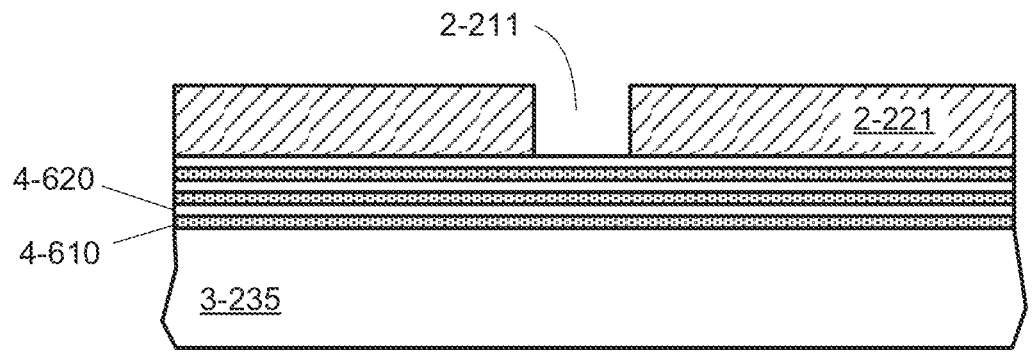
Figures 4, 5, 6, 7, 7A:
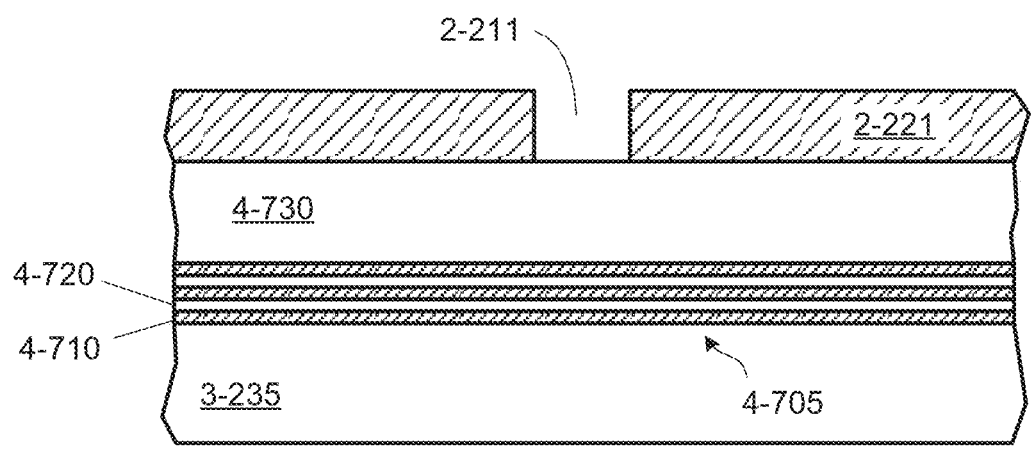
Figures 4, 5, 6, 7, 7B:
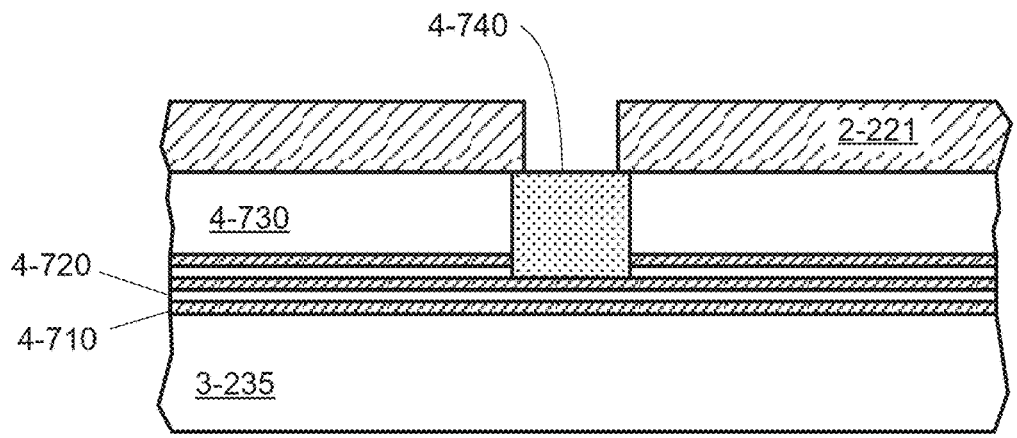
Figures 4, 5, 6, 7, 7C:
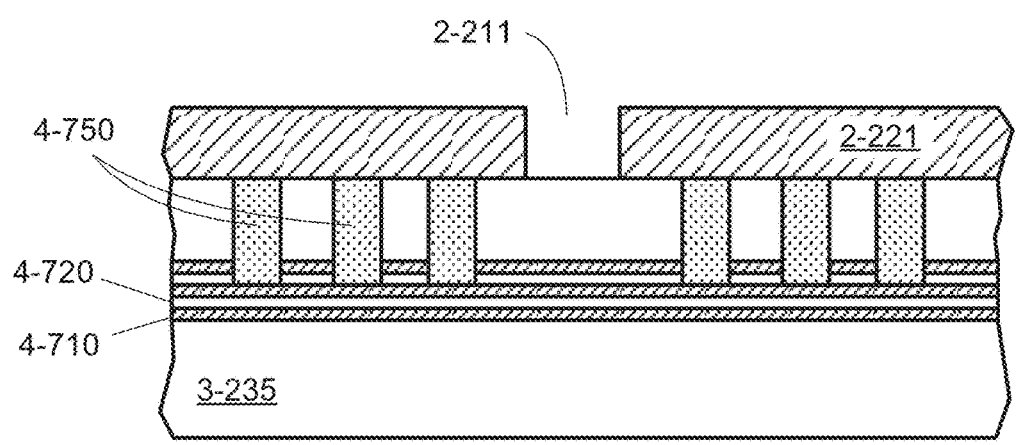
Figures 4, 5, 6, 7, 7D:
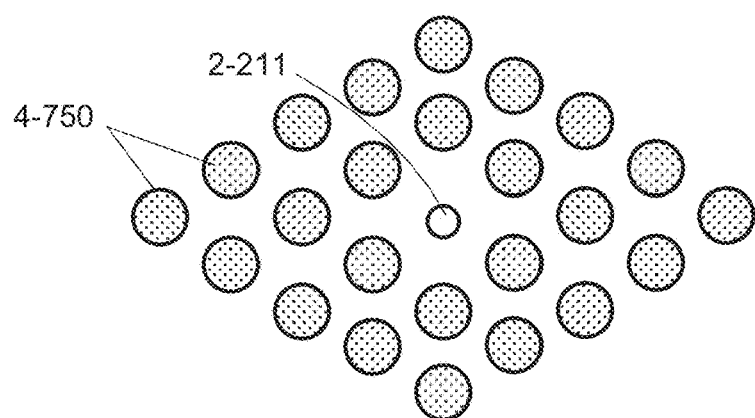

FIG. 5-6B depicts Fresnel lenses of the assay chip, according to some embodiments.

FIG. 6-1 depicts microscopy components of the instrument, according to some embodiments.

FIG. 6-2A depicts far-field spectral sorting elements of the sensor chip, according to some embodiments.

FIG. 6-2B depicts far-field filtering elements of the sensor chip, according to some embodiments.

FIG. 6-3A and FIG. 6-3B depict thin lossy films of the sensor chip, according to some embodiments.

FIG. 6-4A and FIG. 6-4B depict the optical block of the instrument, according to some embodiments.

FIG. 6-5 illustrates optical paths through the optical system, according to some embodiments.

Figures 3, 4, 5, 6, 7, 7A:
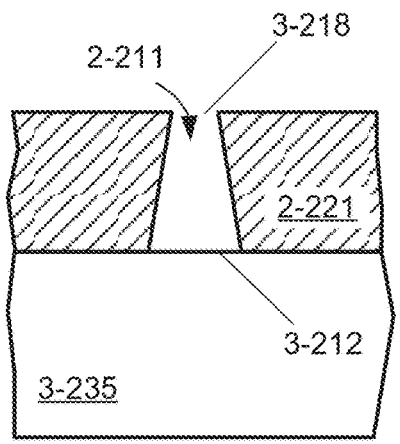
Figures 3, 4, 5, 6, 7, 7B:
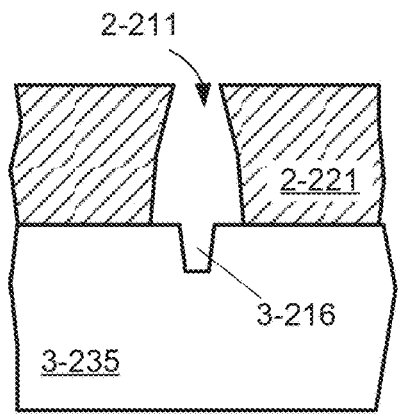
Figures 3, 4, 5, 6, 7, 7C:
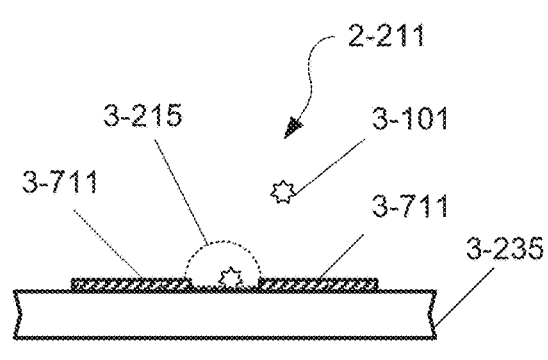
Figures 3, 4, 5, 6, 7, 7D:
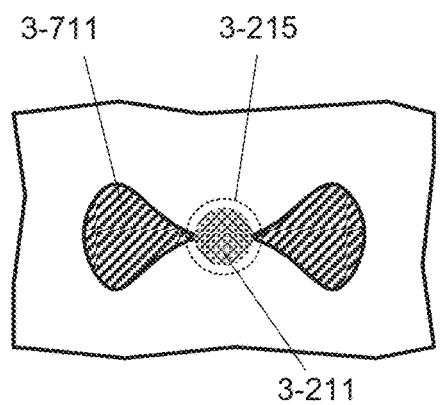
Figures 3, 4, 5, 6, 7, 7E:
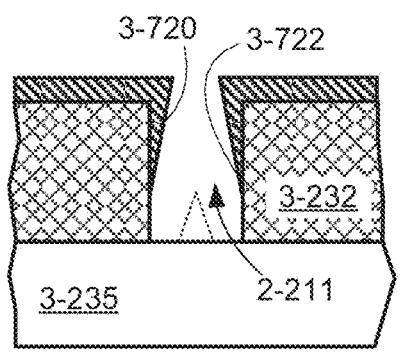
Figures 3, 4, 5, 6, 7, 7F:
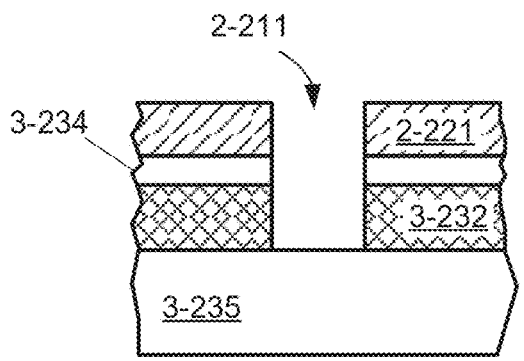

FIG. 7-1A depicts, in elevation view, a sensor within a pixel of a sensor chip, according to some embodiments.

FIG. 7-1B depicts a bulls-eye sensor having two separate and concentric active areas, according to some embodiments.

FIG. 7-1C depicts a stripe sensor having four separate active areas, according to some embodiments.

FIG. 7-1D depicts a quad sensor having four separate active areas, according to some embodiments.

FIG. 7-1E depicts an arc-segment sensor having four separate active areas, according to some embodiments.

FIG. 7-1F depicts a stacked-segment sensor, according to some embodiments.

FIG. 7-2A depicts an emission distribution from the sorting elements for energy emitted at a first wavelength, according to some embodiments.

FIG. 7-2B depicts a radiation pattern received by a bulls-eye sensor corresponding to the emission distribution depicted in FIG. 7-2A, according to some embodiments.

FIG. 7-2C depicts an emission distribution from the sorting elements for energy emitted at a second wavelength, according to some embodiments.

FIG. 7-2D depicts a radiation pattern received by a bulls-eye sensor corresponding to the emission distribution depicted in FIG. 7-2C, according to some embodiments.

FIG. 7-2E represents results from a numerical simulation of signal detection for a bulls-eye sensor having two active areas for a first emission wavelength from a sample, according to some embodiments.

FIG. 7-2F represents results from a numerical simulation of signal detection for the bulls-eye sensor associated with FIG. 7-2E for a second emission wavelength from a sample, according to some embodiments.

FIG. 7-2G represents results from a numerical simulation of signal detection for the bulls-eye sensor associated with FIG. 7-2E for a third emission wavelength from a sample, according to some embodiments.

FIG. 7-2H represents results from a numerical simulation of signal detection for the bulls-eye sensor associated with FIG. 7-2E for a fourth emission wavelength from a sample, according to some embodiments.

FIG. 7-2I represents results from a numerical simulation of signal detection for a bulls-eye sensor having four active areas for a first emission wavelength from a sample, according to some embodiments.

Figures 2J, 7:
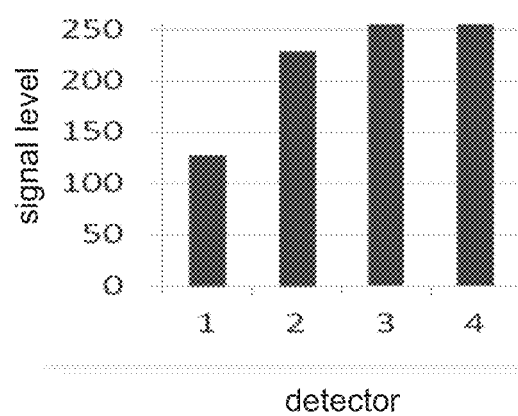
Figures 3A, 3B, 7:
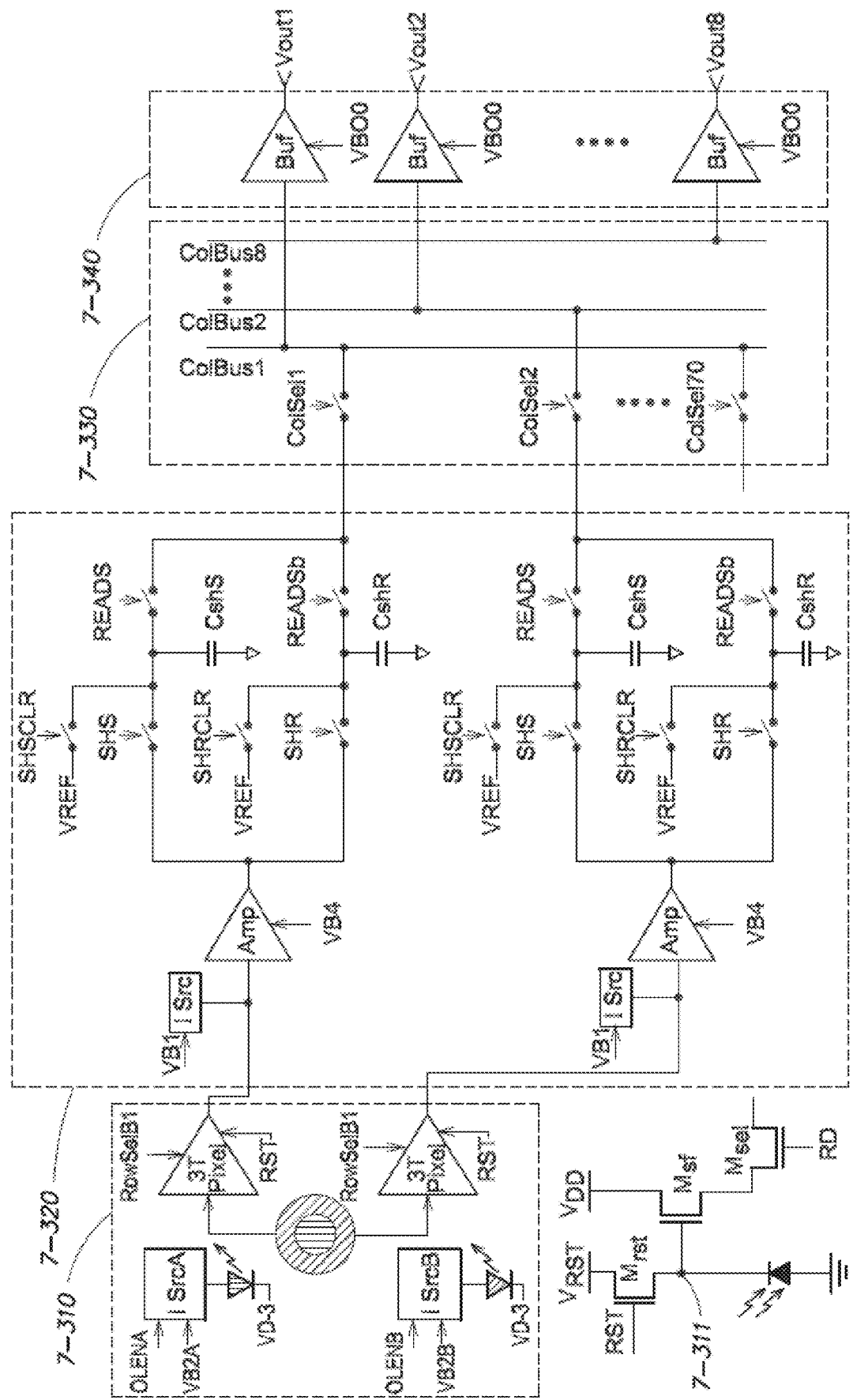
Figures 3C, 7:
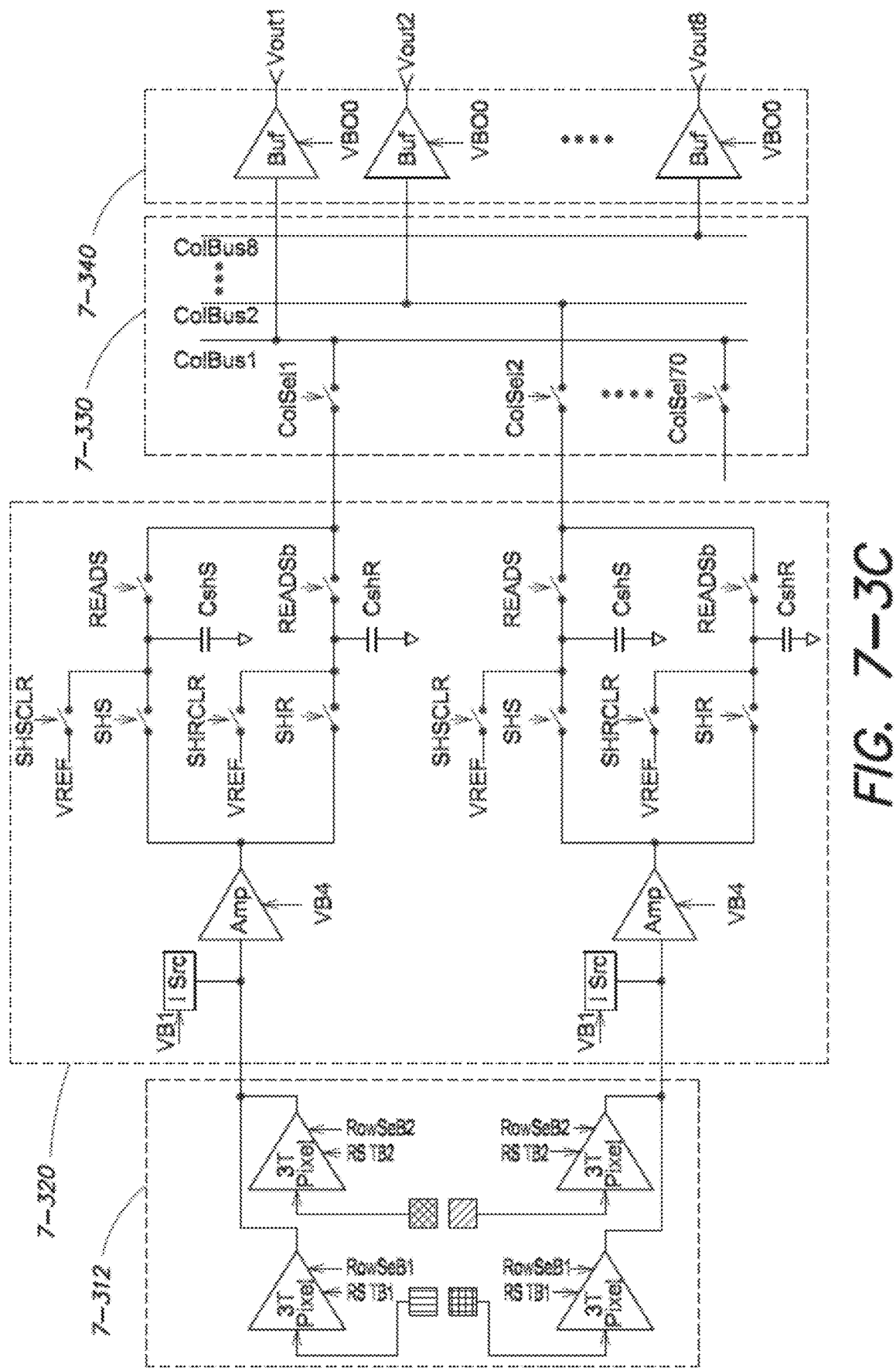
Figures 4A, 7:
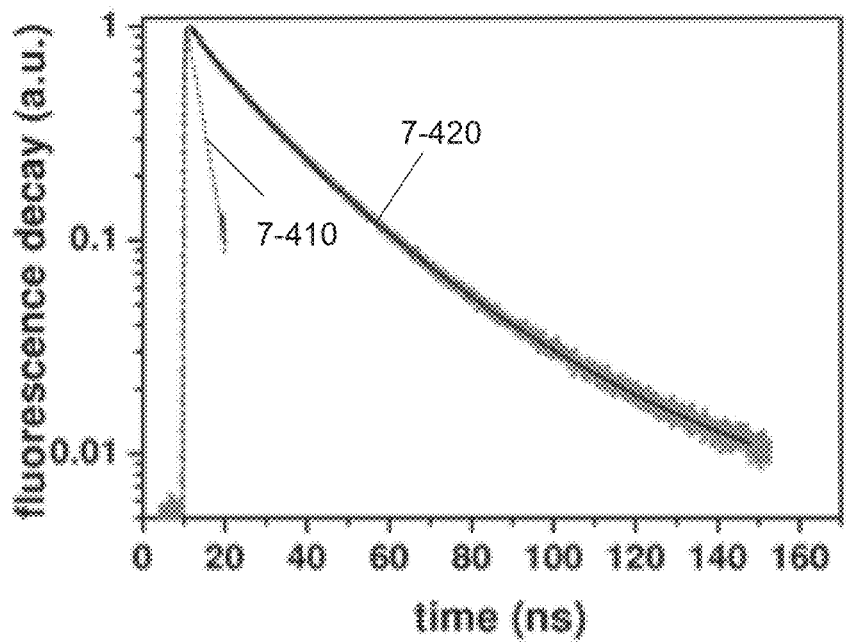
Figures 4B, 7:
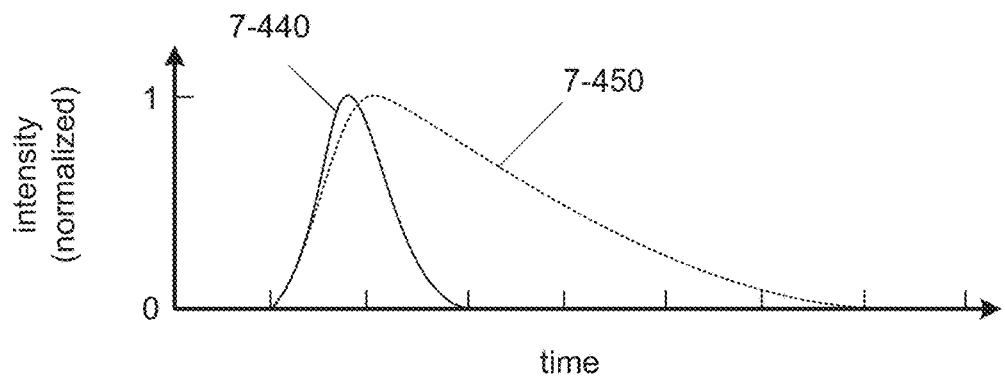
Figures 4C, 7:
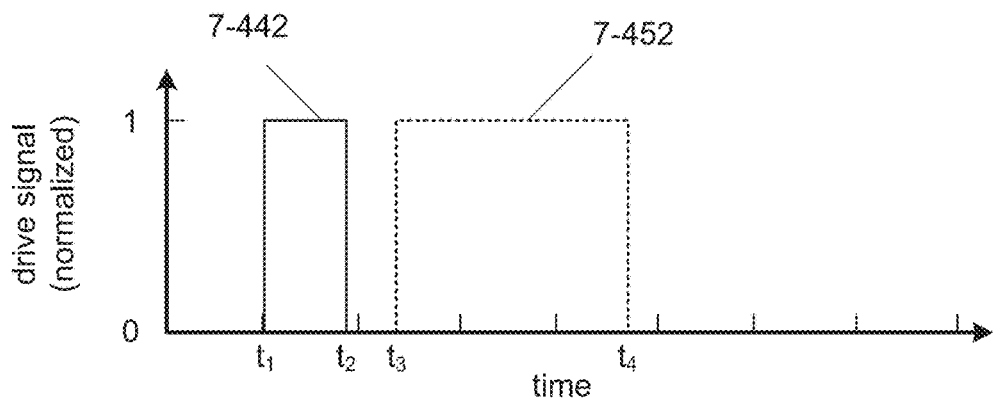
Figures 4D, 7:
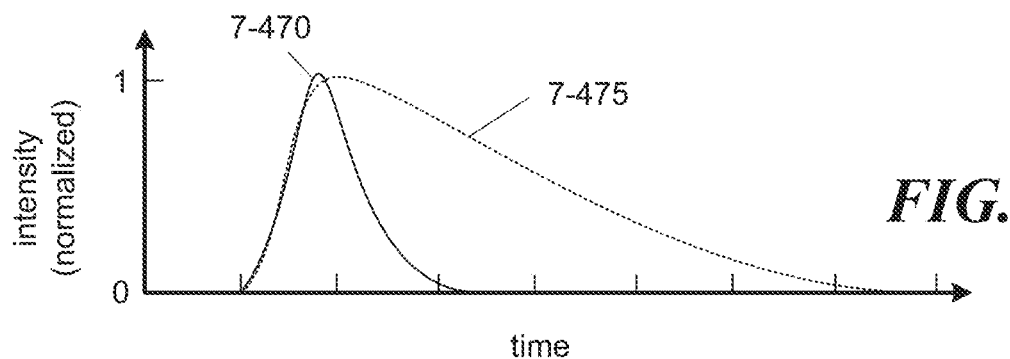
Figures 4E, 7:
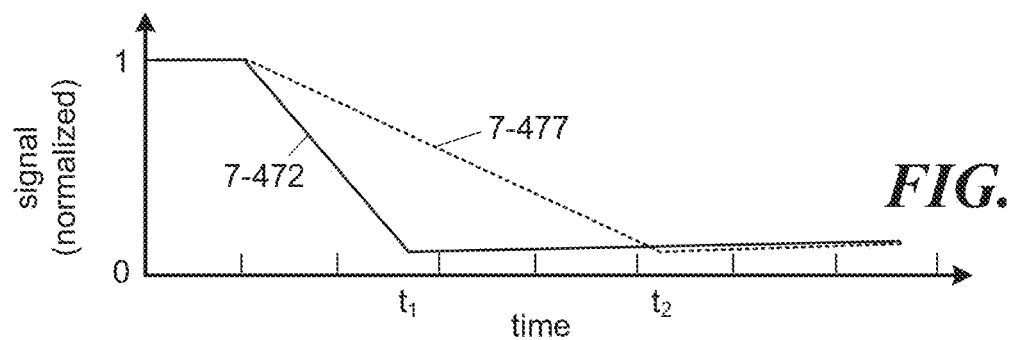
Figures 4F, 7:
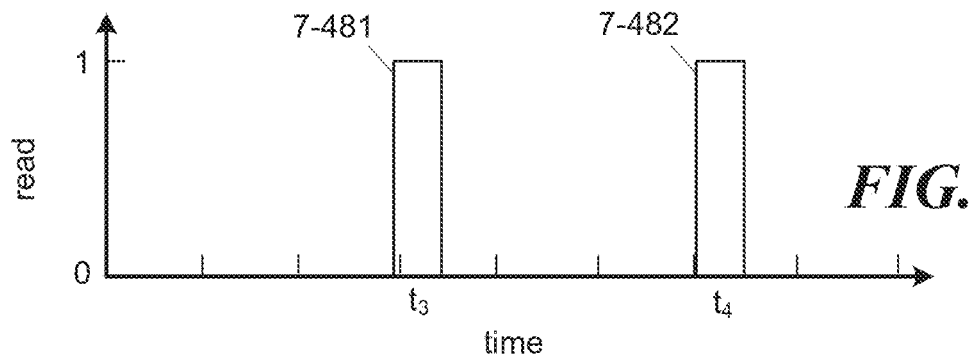
Figures 4G, 7:
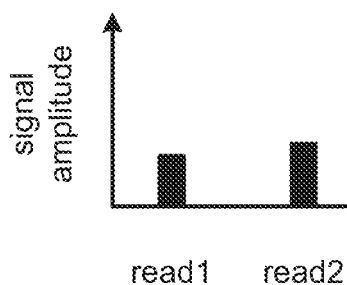

FIG. 7-2J represents results from a numerical simulation of signal detection for the bulls-eye sensor associated with FIG. 7-2I for a second emission wavelength from a sample, according to some embodiments.

FIG. 7-3A depicts circuitry on an instrument that may be used to read signals from a sensor comprising two active areas, according to some embodiments.

FIG. 7-3B depicts a three-transistor circuit that may be included at a sensor chip for signal accumulation and read-out, according to some embodiments.

FIG. 7-3C depicts circuitry on an instrument that may be used to read signals from a sensor comprising four active areas, according to some embodiments.

FIG. 7-4A depicts temporal emission characteristics for two different emitters that may be used for sample analysis, according to some embodiments.

FIG. 7-4B depicts temporal evolution of an excitation source and luminescence from a sample, according to some embodiments.

FIG. 7-4C illustrates time-delay sampling, according to some embodiments.

FIG. 7-4D depicts temporal emission characteristics for two different emitters, according to some embodiments.

FIG. 7-4E depicts voltage dynamics at a charge-accumulation node of a sensor, according to some embodiments.

FIG. 7-4F depicts a double read of a sensor segment without reset, according to some embodiments.

Figures 4H, 7:
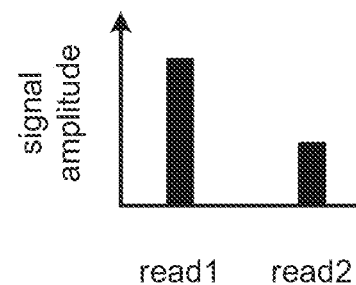
Figures 5, 7:
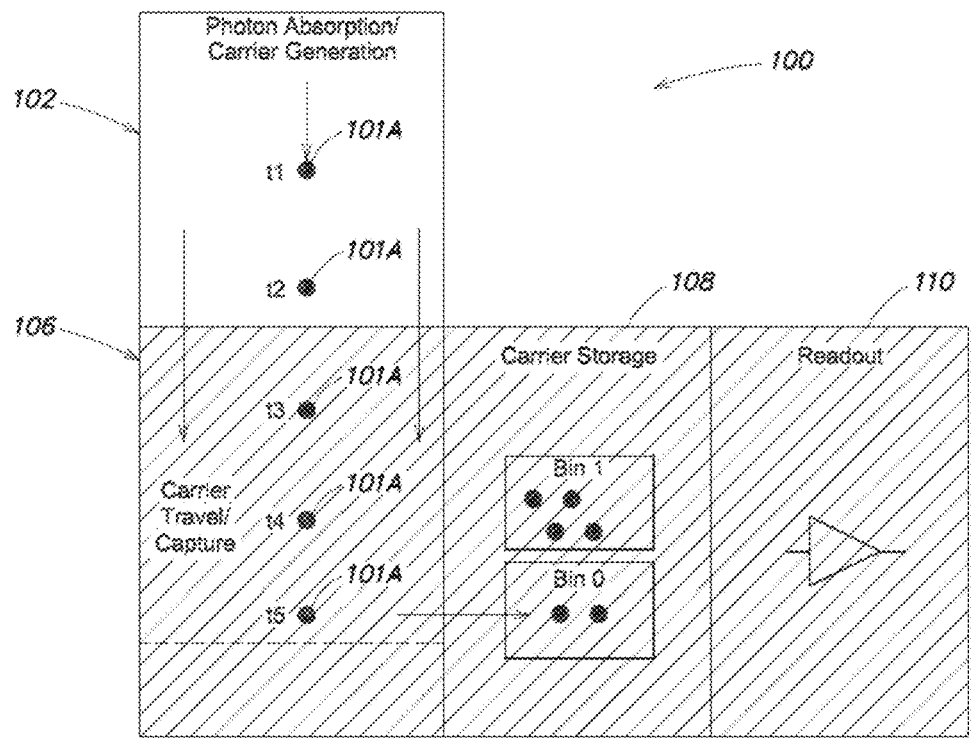
Figures 6, 7:
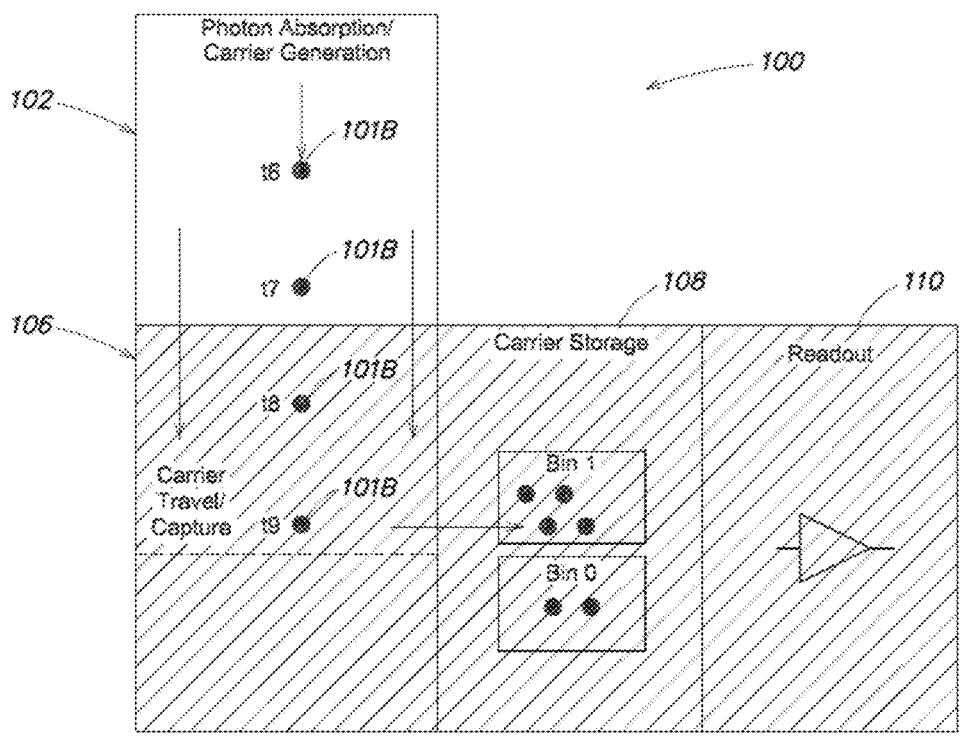
Figures 1A, 8:
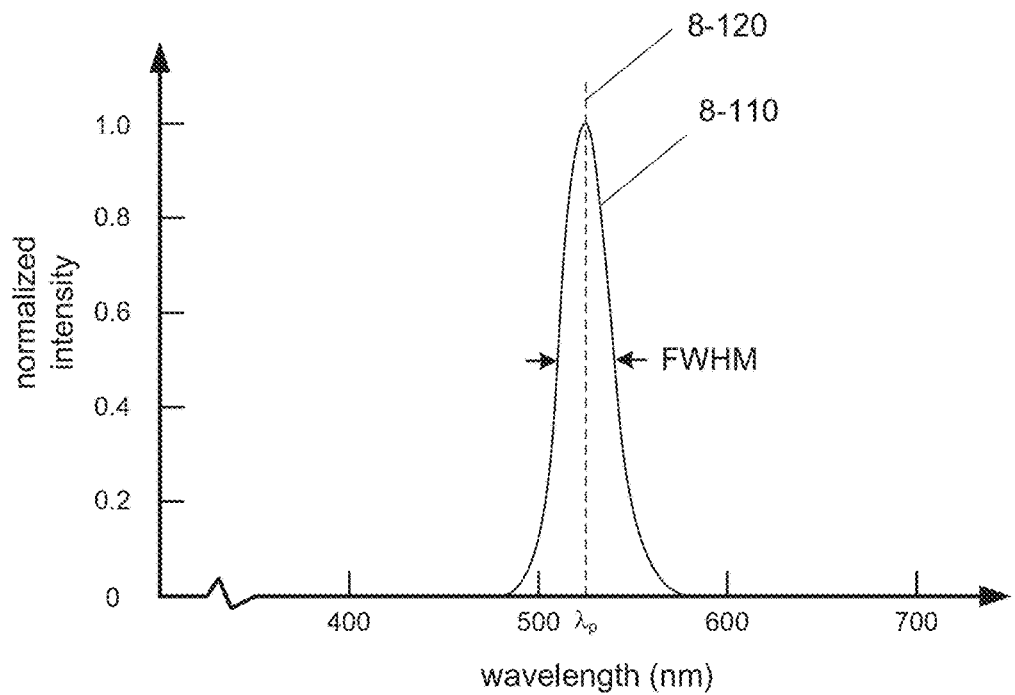
Figures 1B, 8:
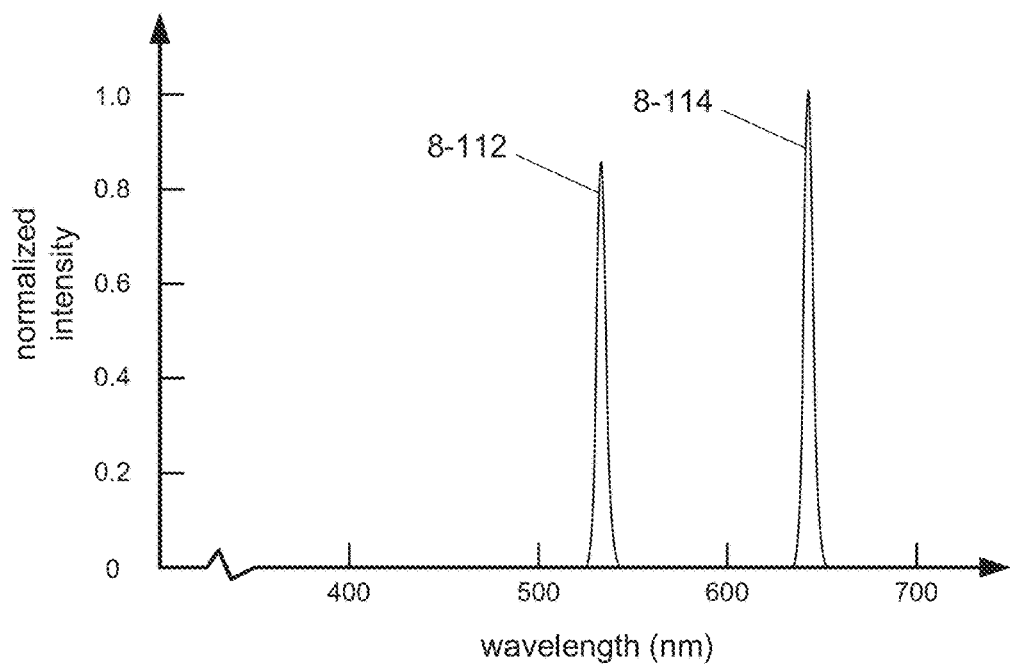
Figures 2A, 8:
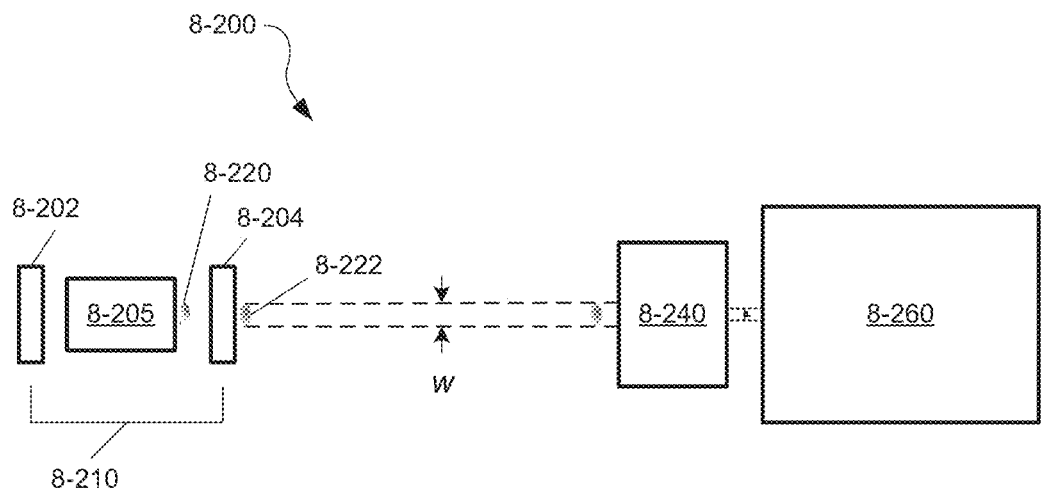
Figures 2B, 8:
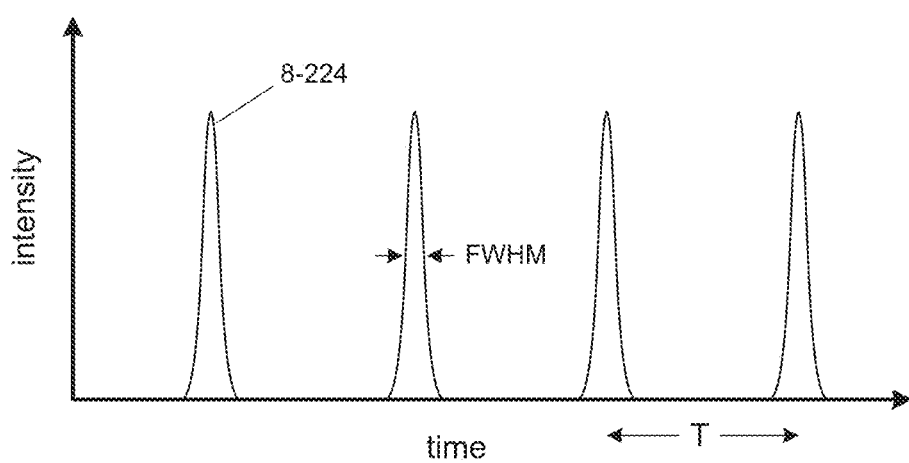
Figures 3, 8:
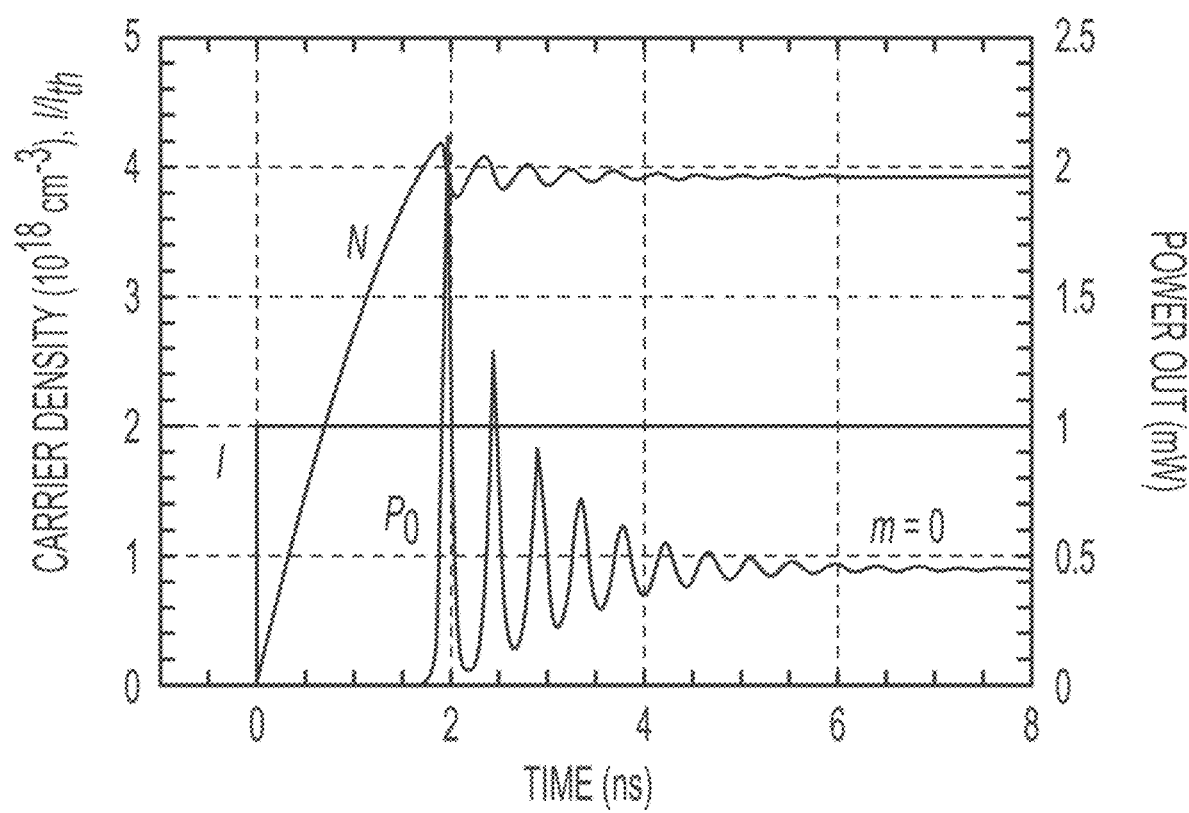
Figures 4, 8:
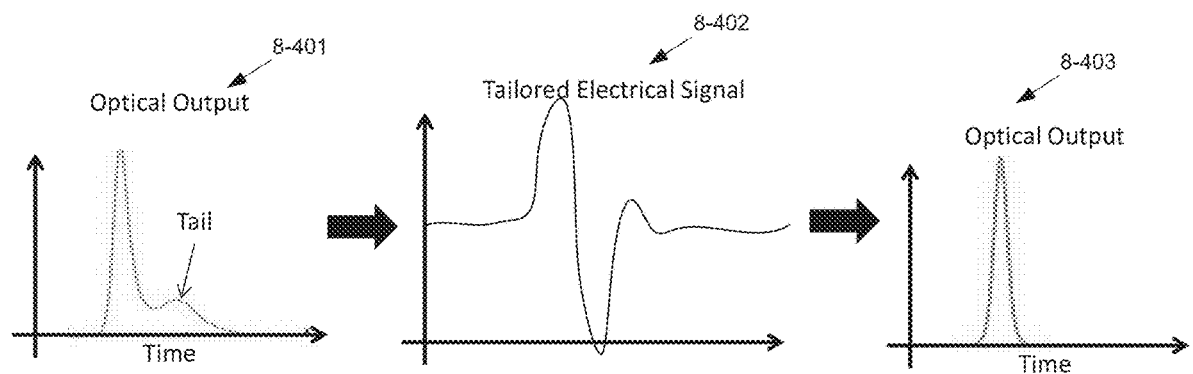
Figures 5, 8:
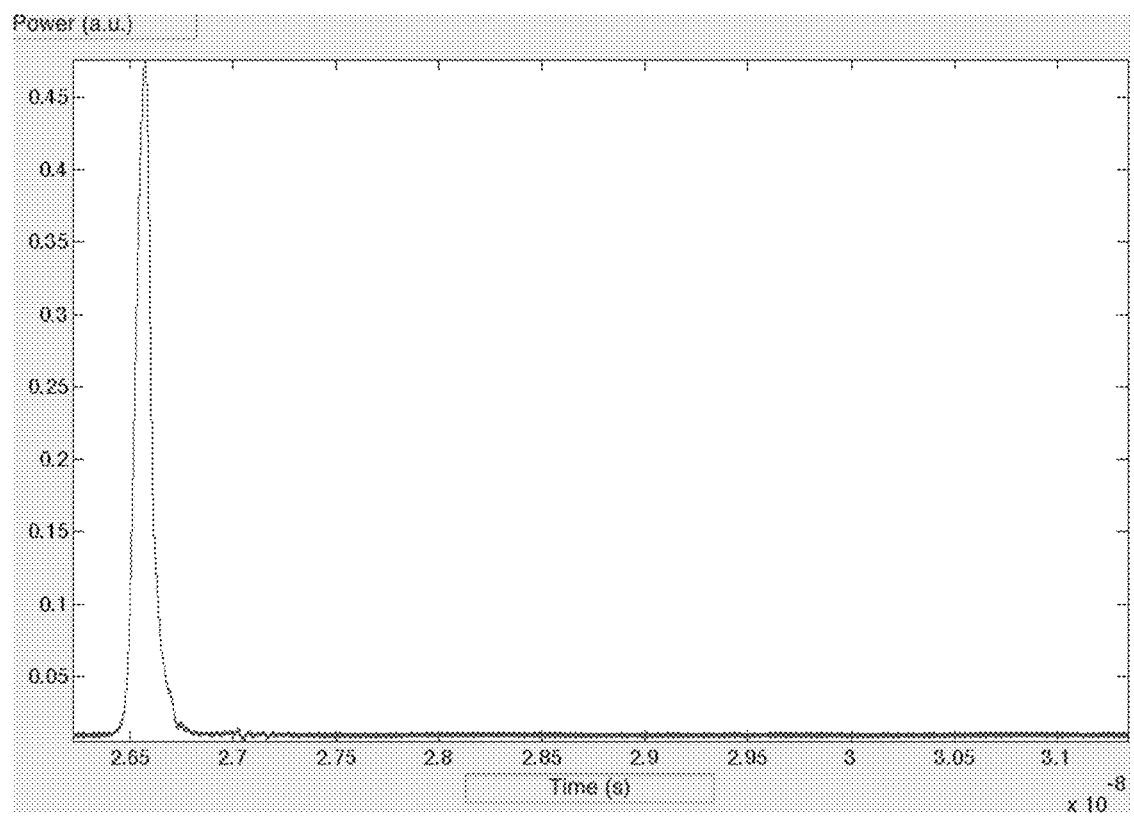
Figures 6, 8:
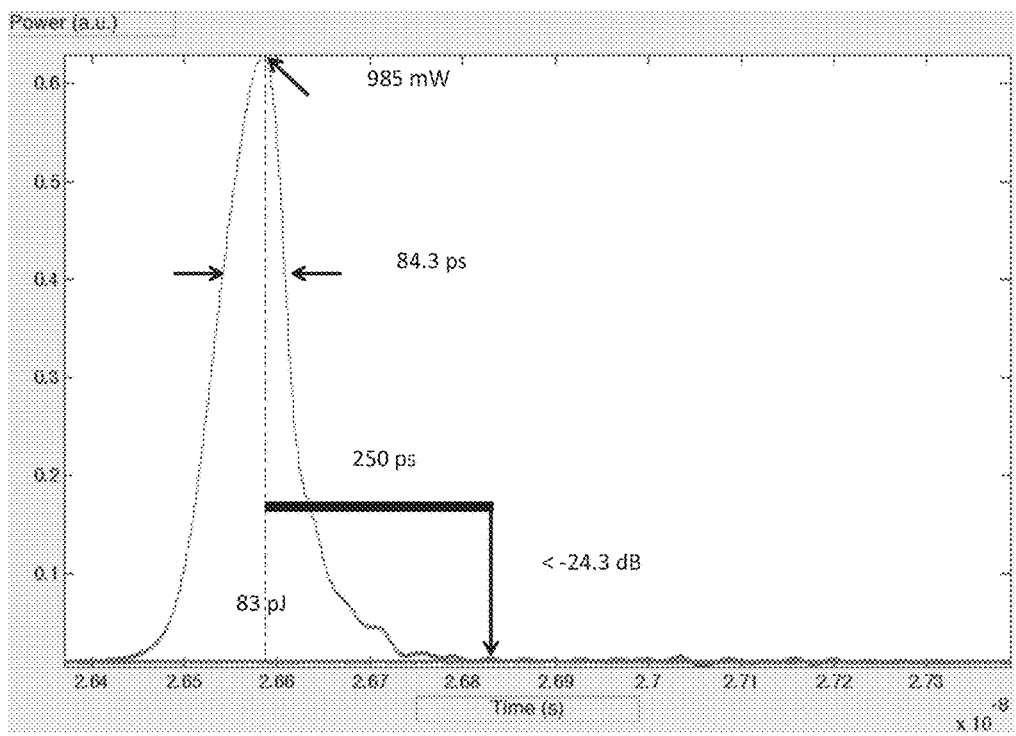
Figures 7, 8:
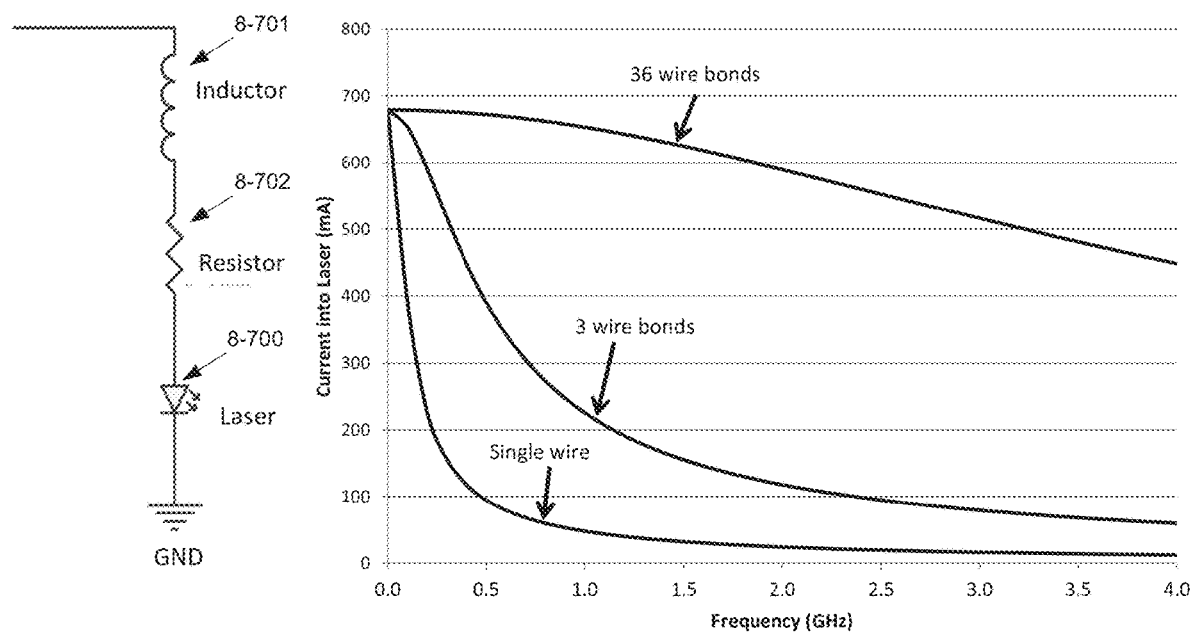
Figures 8, 8A:
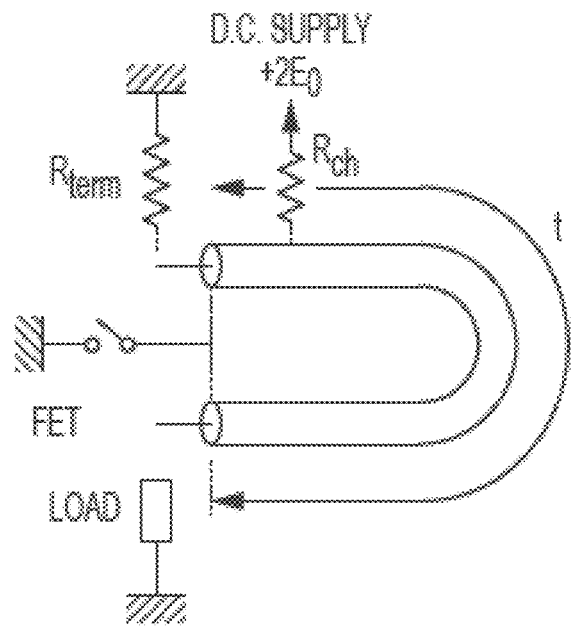
Figures 8, 8B:
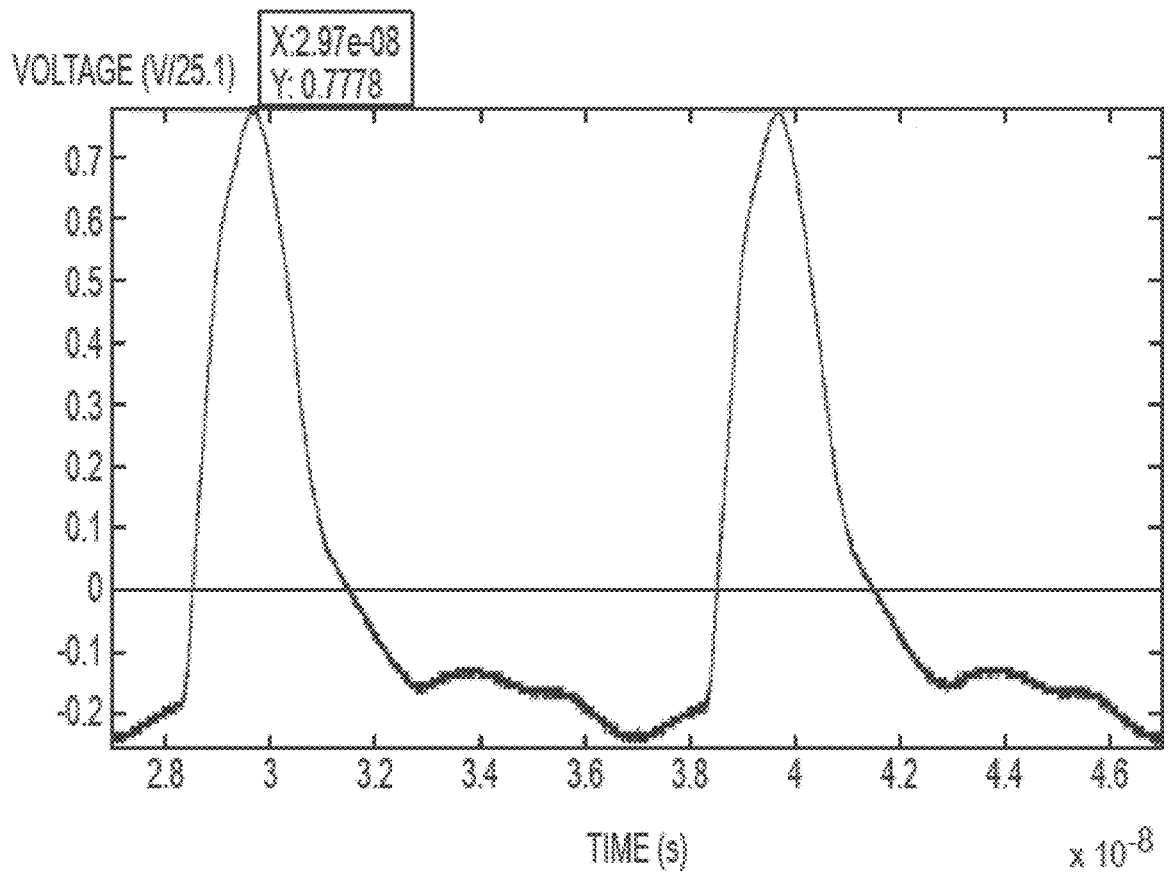
Figures 8, 9:
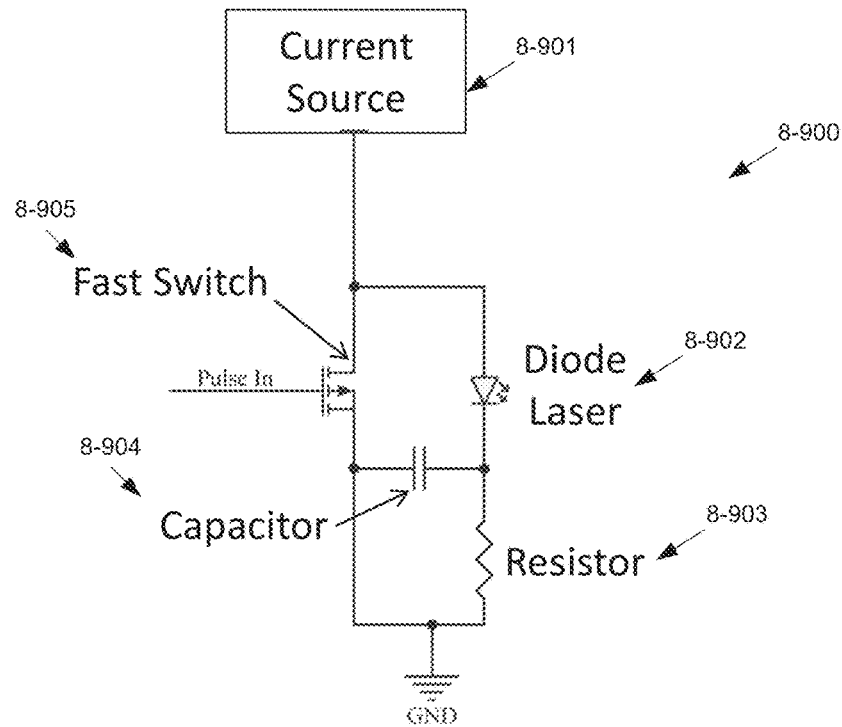
Figures 8, 9, 10:
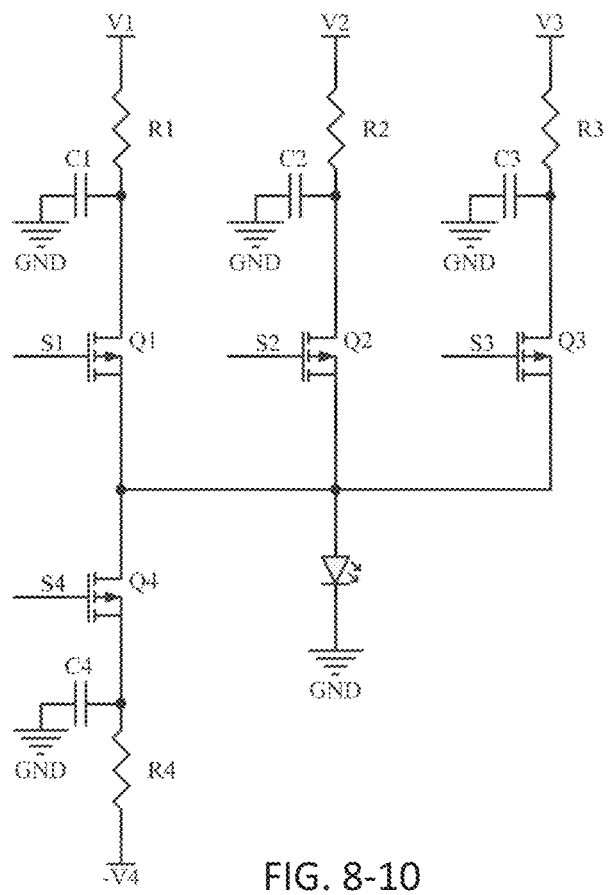
Figures 8, 9, 10, 11, 11A:
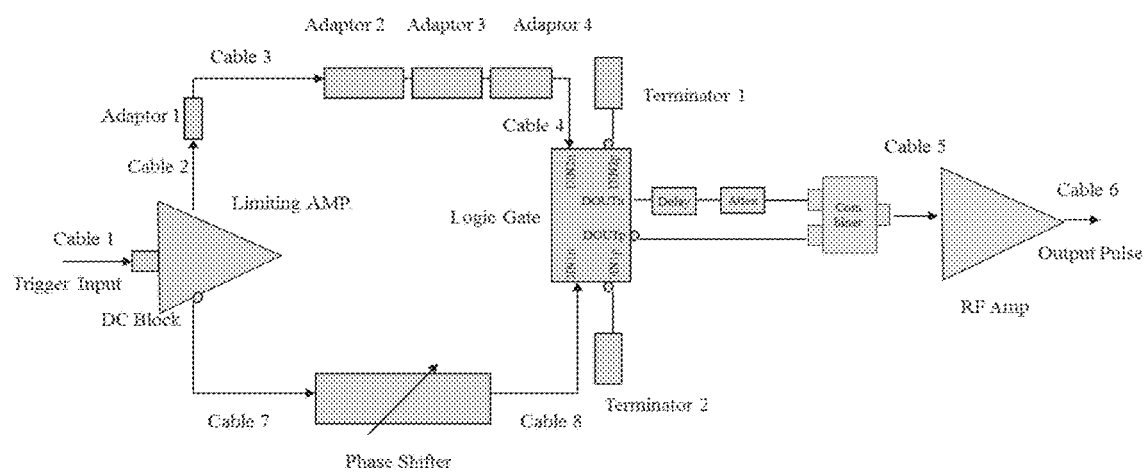
Figures 8, 9, 10, 11, 11B:
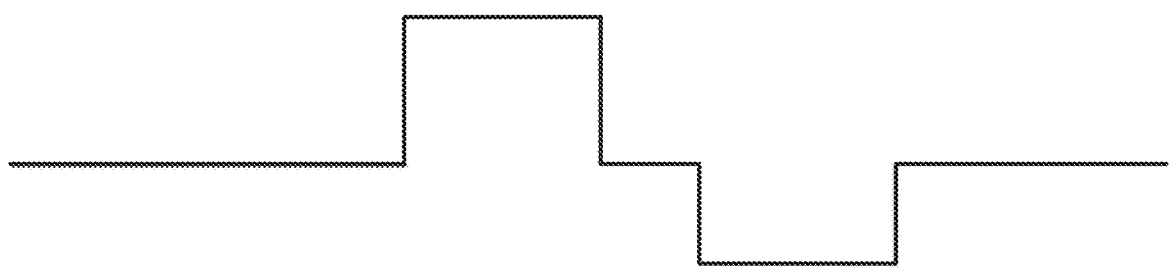
Figures 8, 9, 10, 11, 12, 12A:
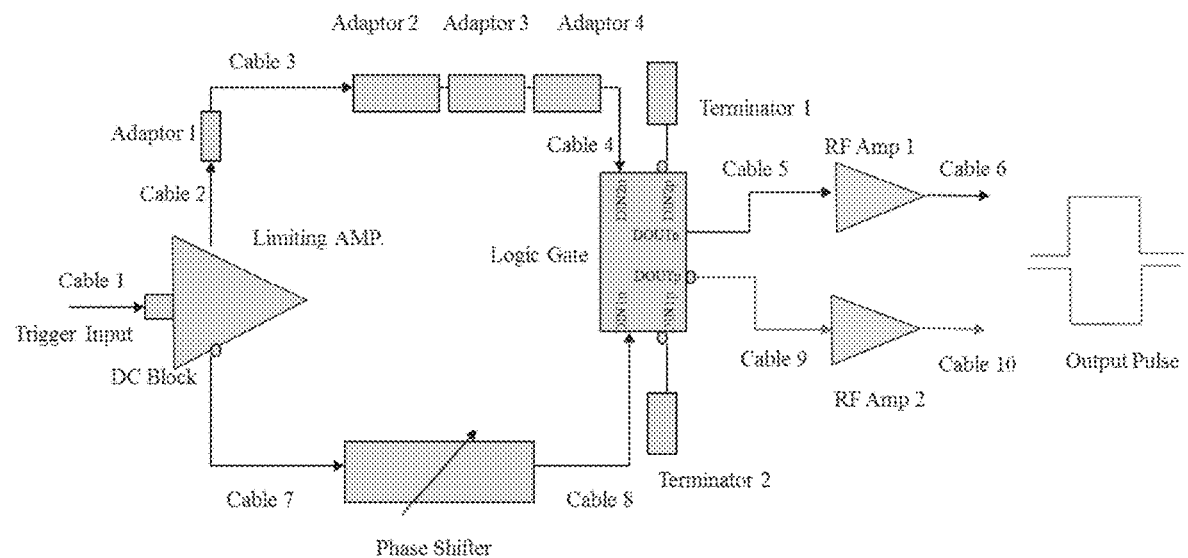
Figures 8, 9, 10, 11, 12, 12B:
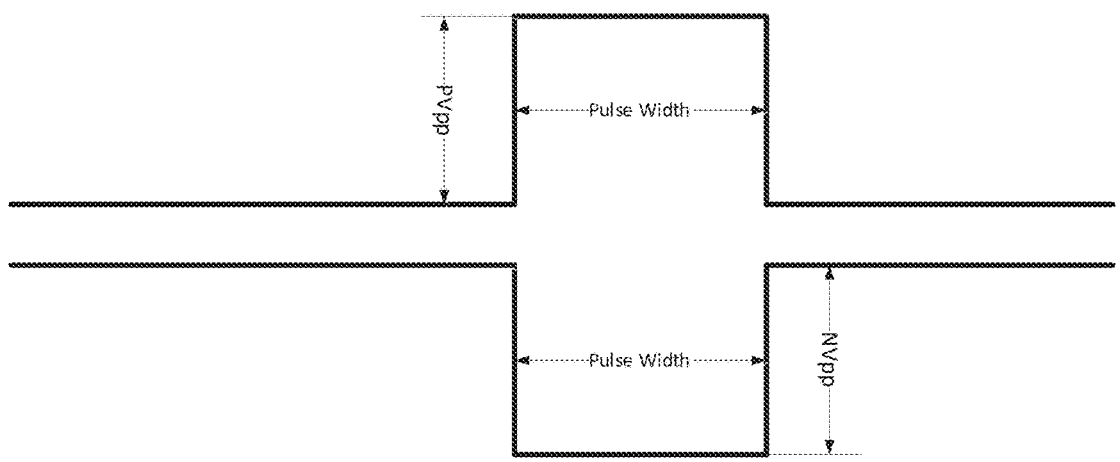
Figures 8, 9, 10, 11, 12, 13, 13A:
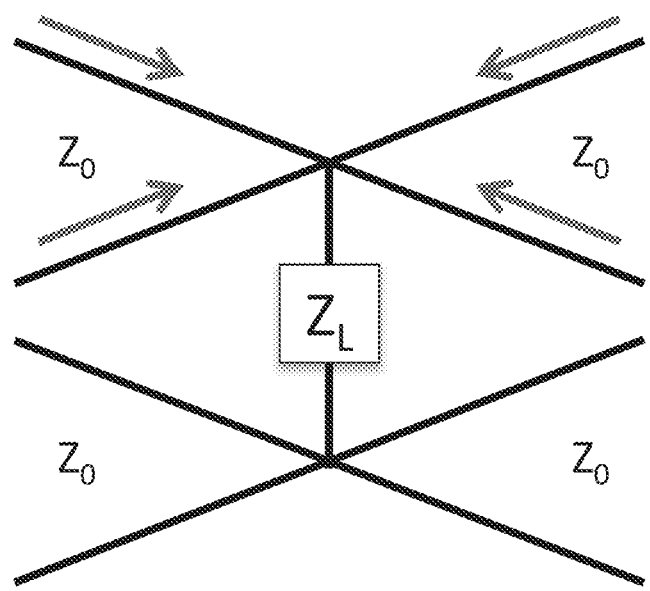
Figures 8, 9, 10, 11, 12, 13, 13B:
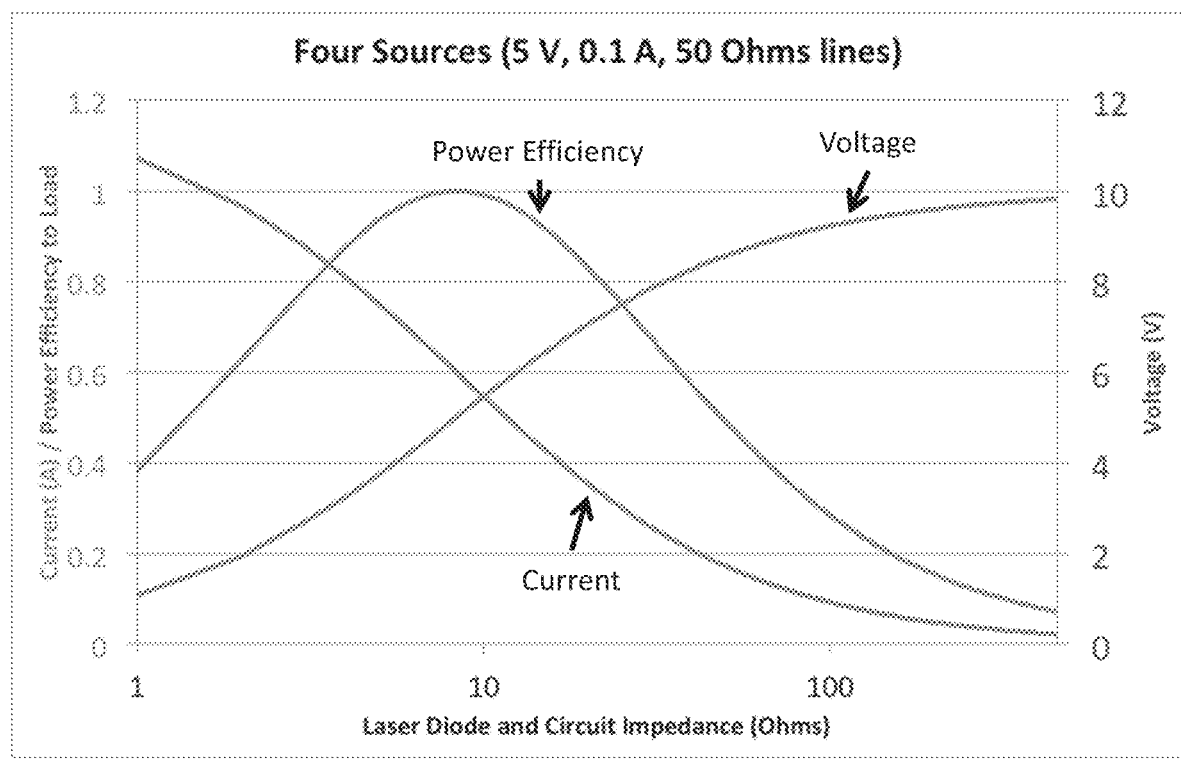
Figures 1, 9:
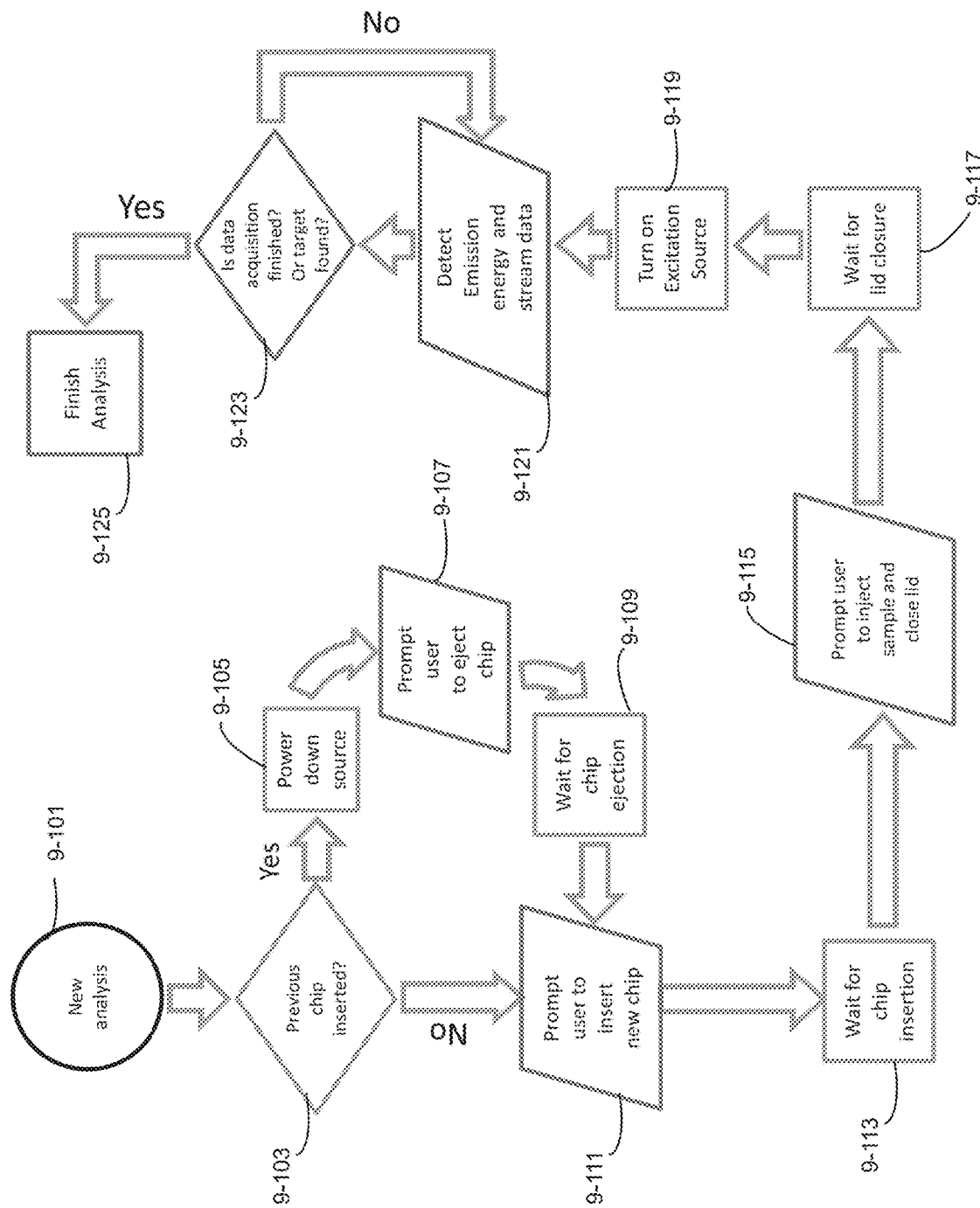
Figures 3, 9:
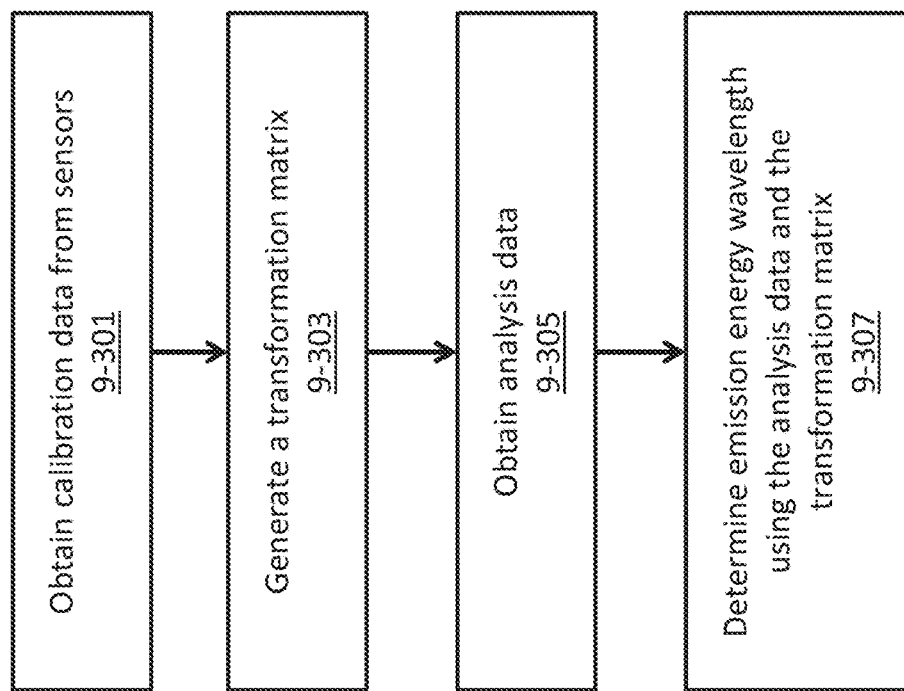
Figures 2, 9:
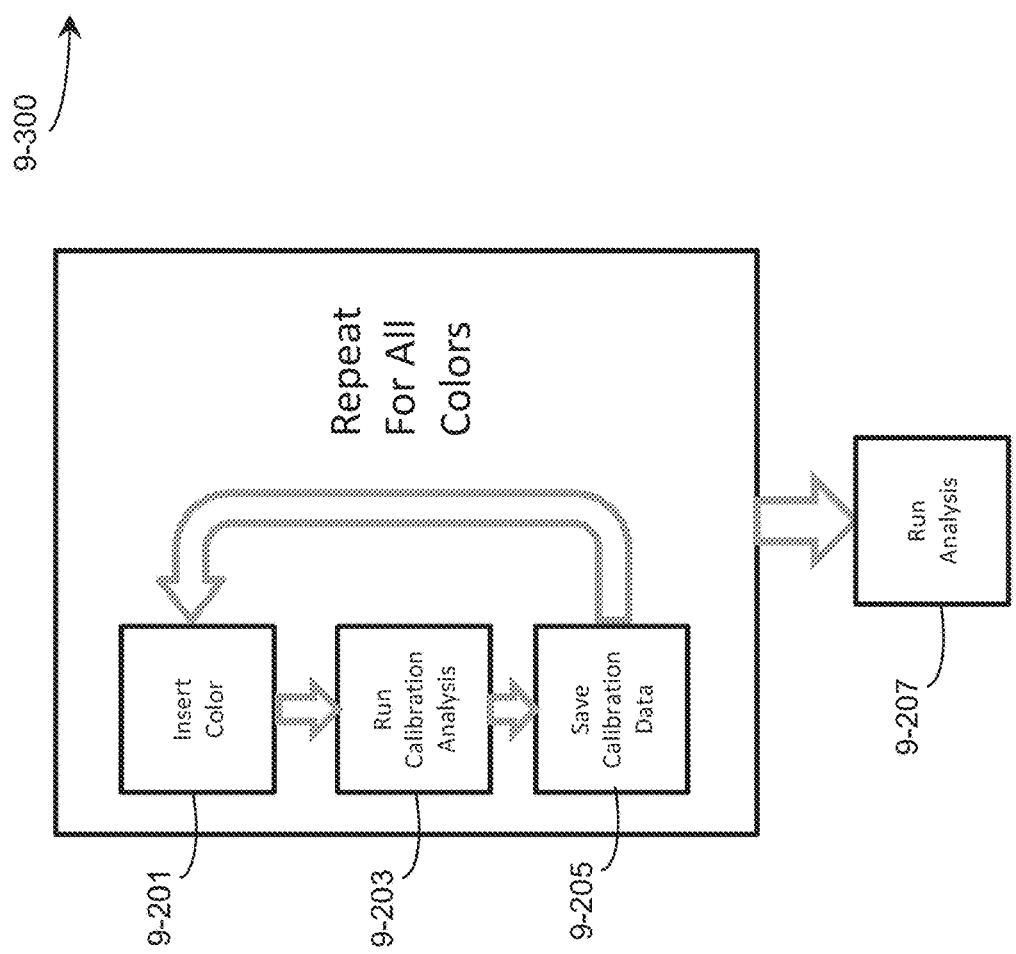
Figures 1, 10:
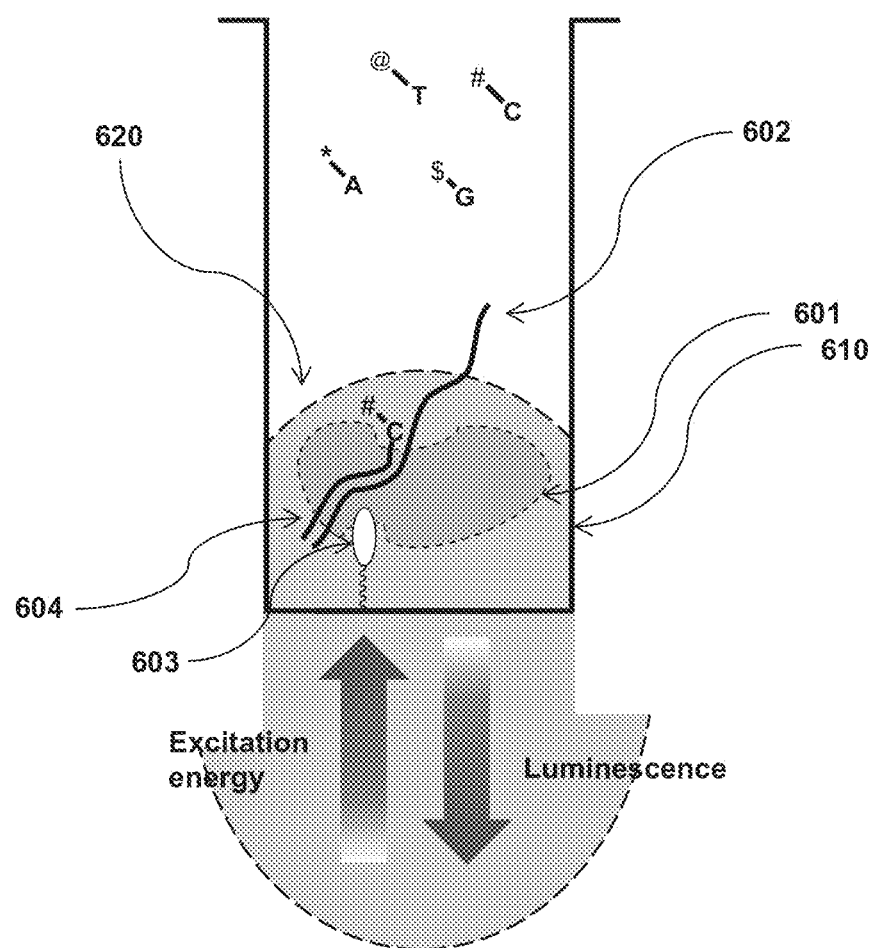
Figures 2, 10:
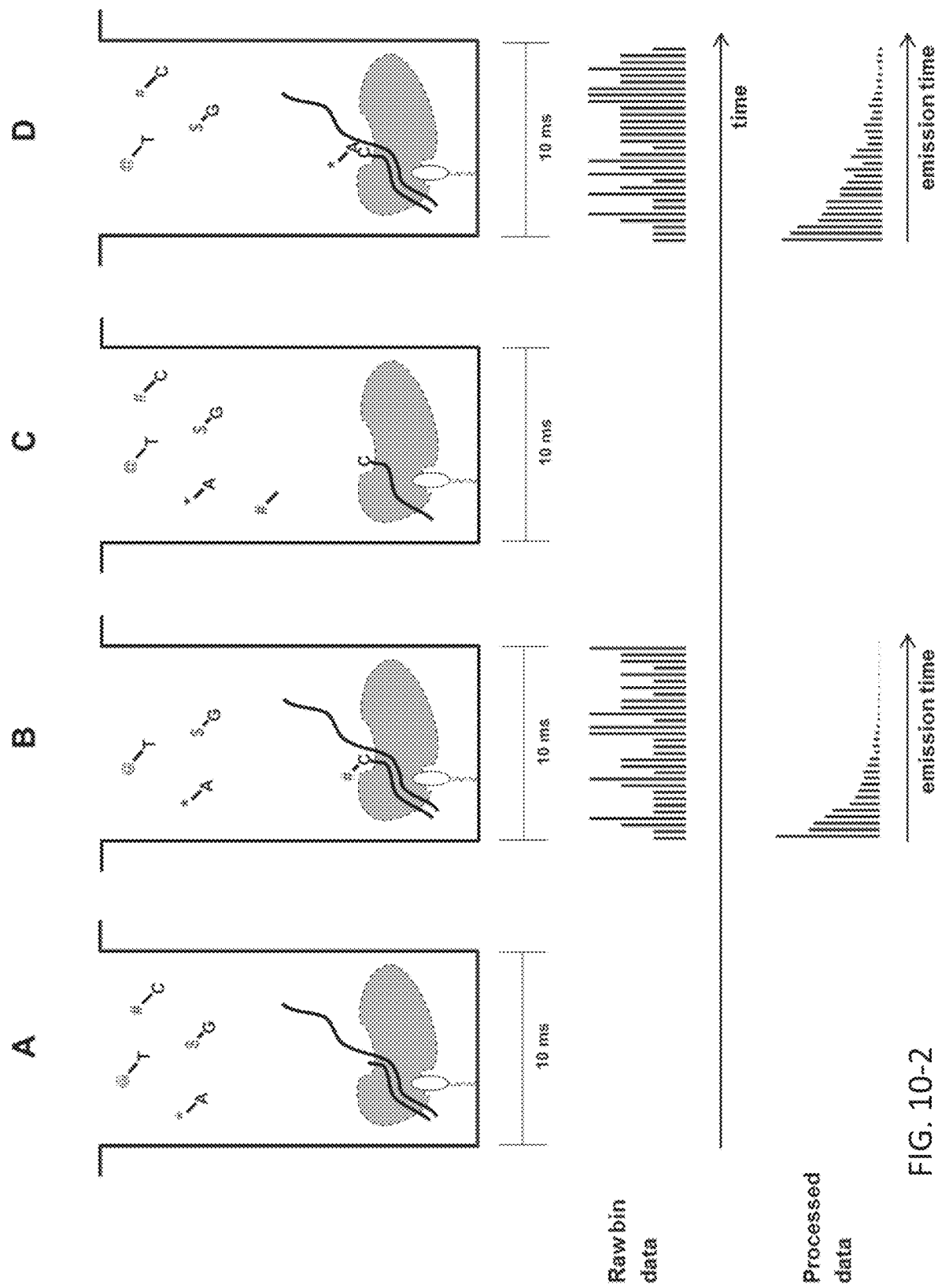
Figures 3, 10:
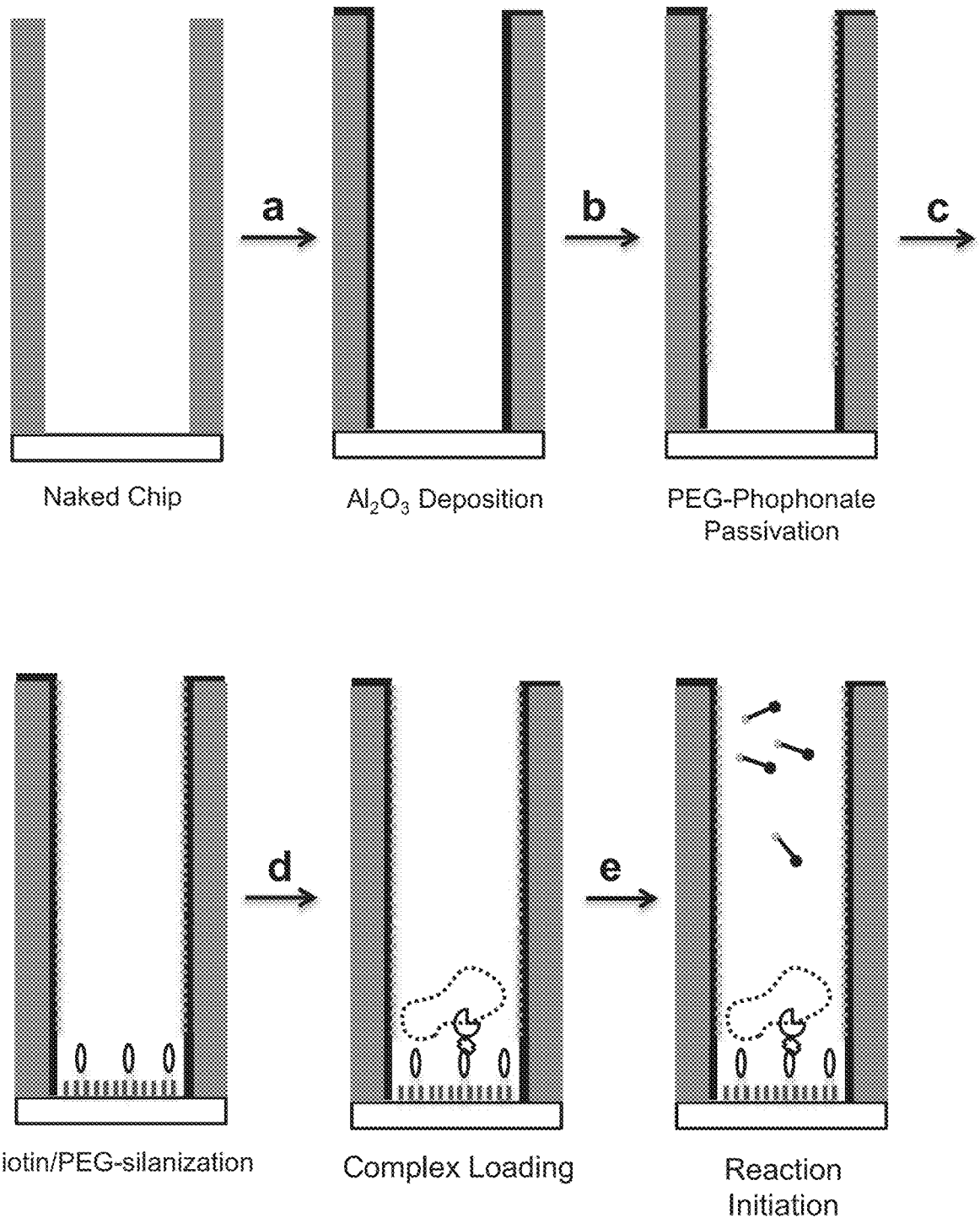
Figures 4, 10:
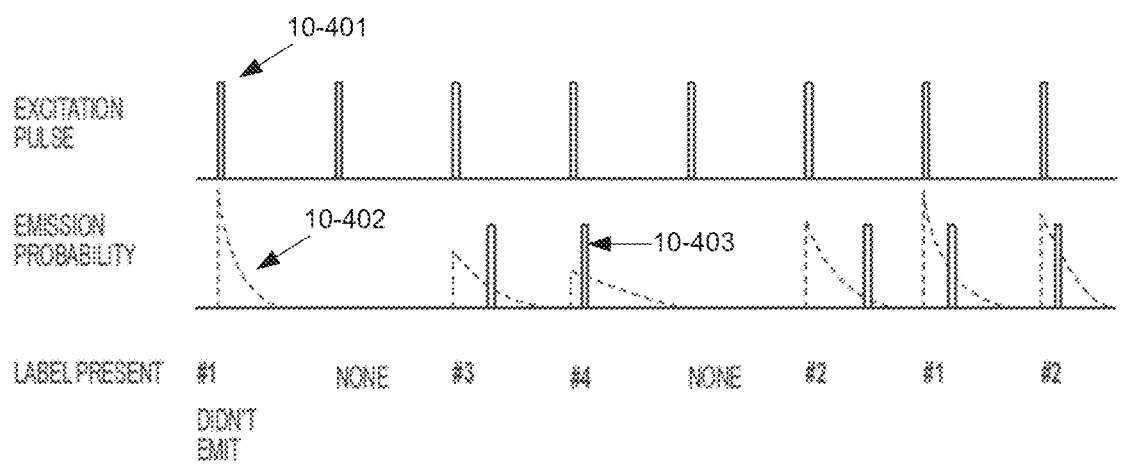
Figures 5, 10:
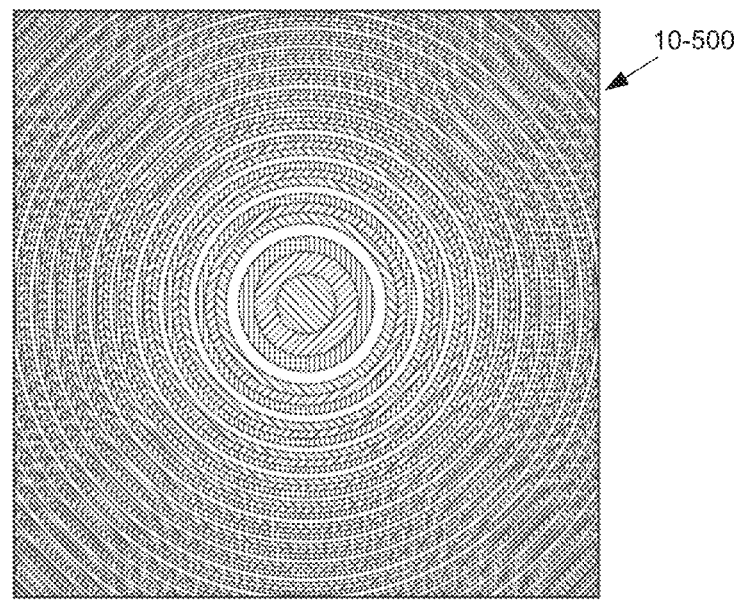
Figures 6, 10:
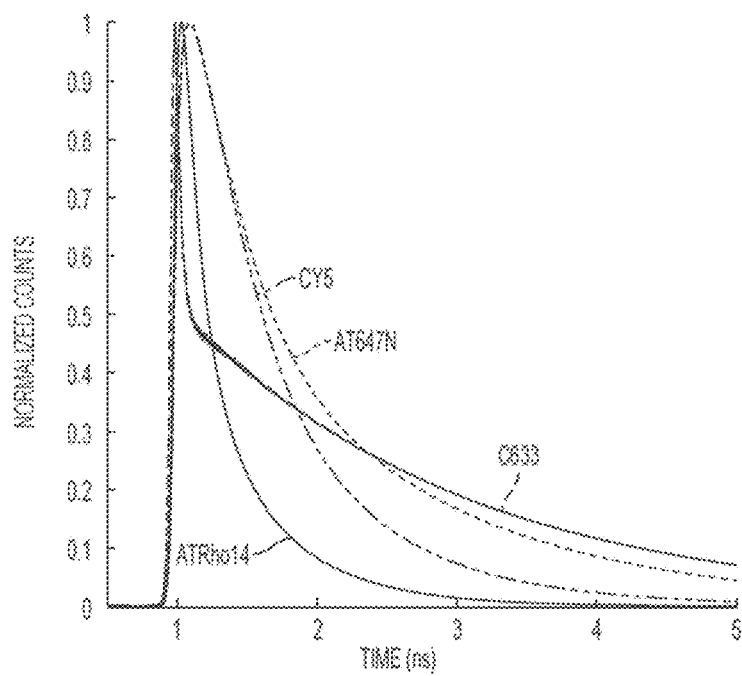
Figures 7, 10:
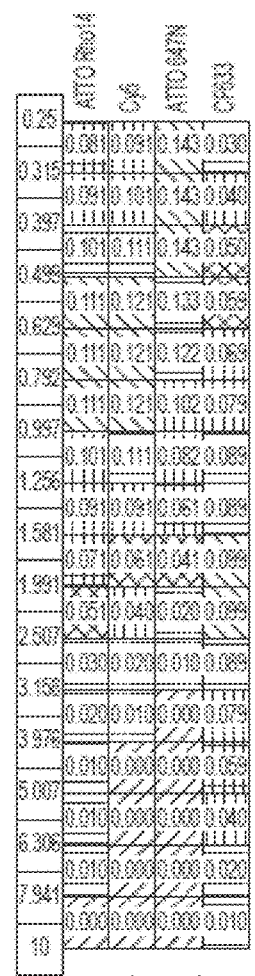
Figures 8, 9, 10:
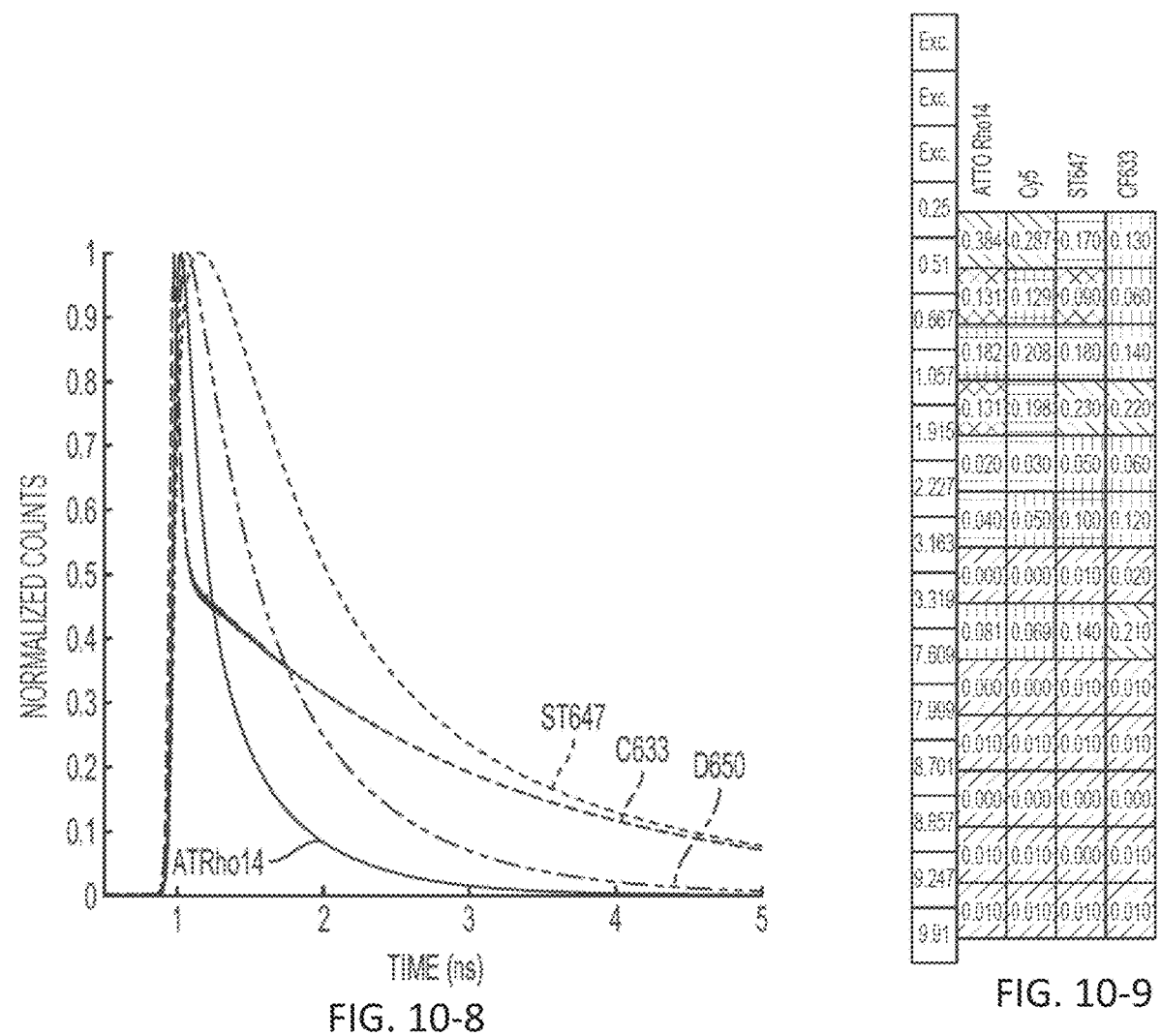
Figure 10:
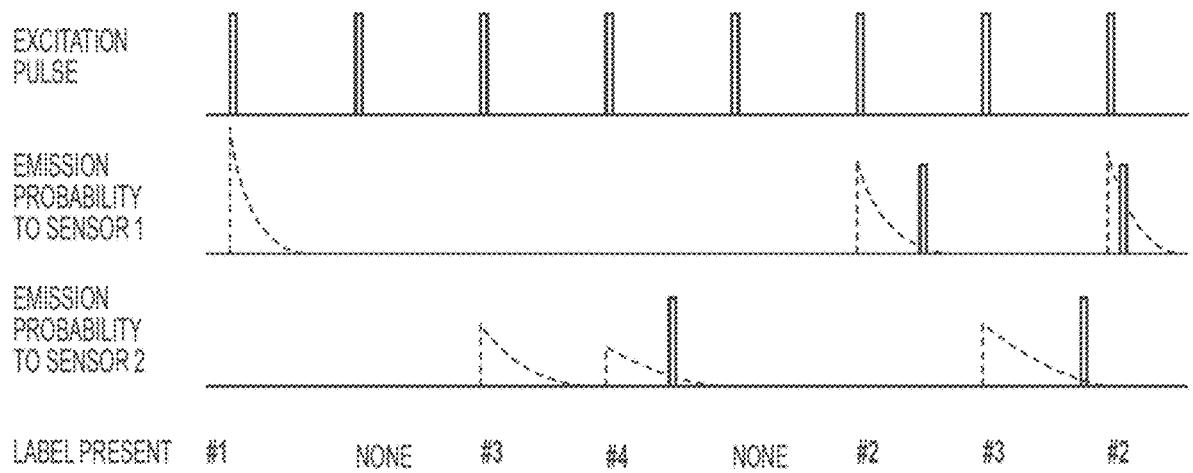
Figures 10, 11:
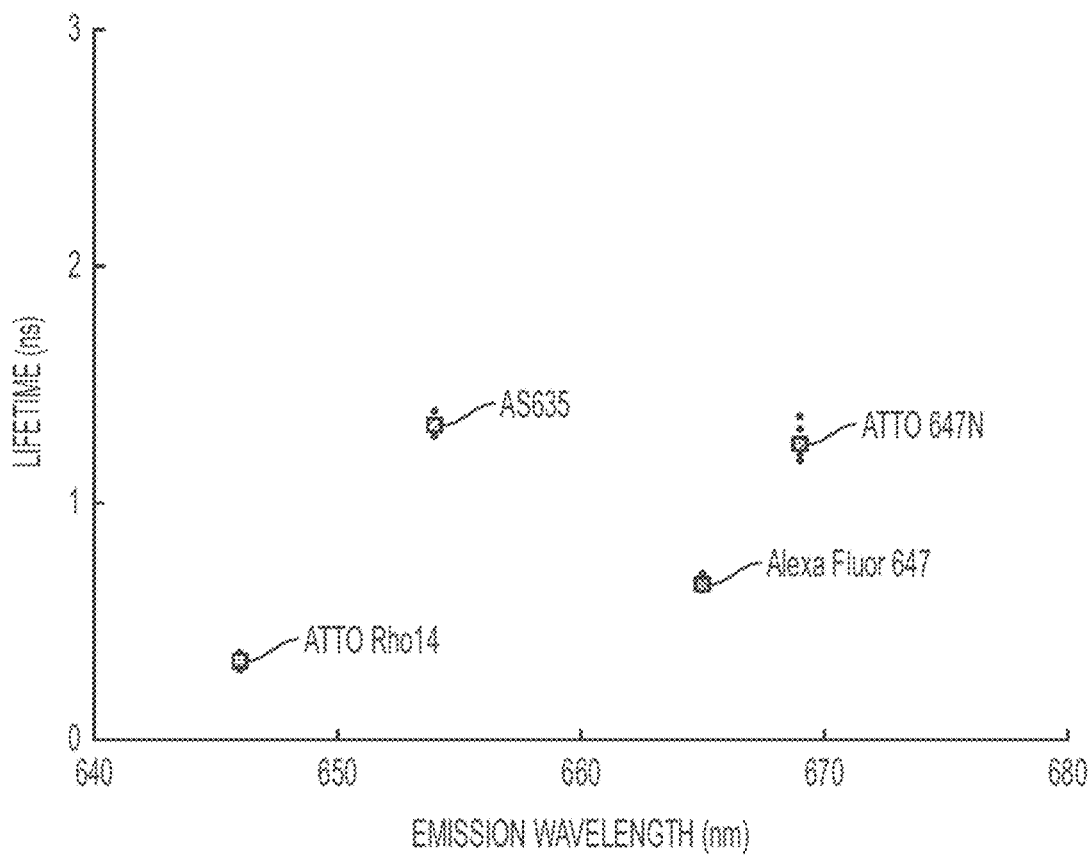
Figures 10, 11, 12:
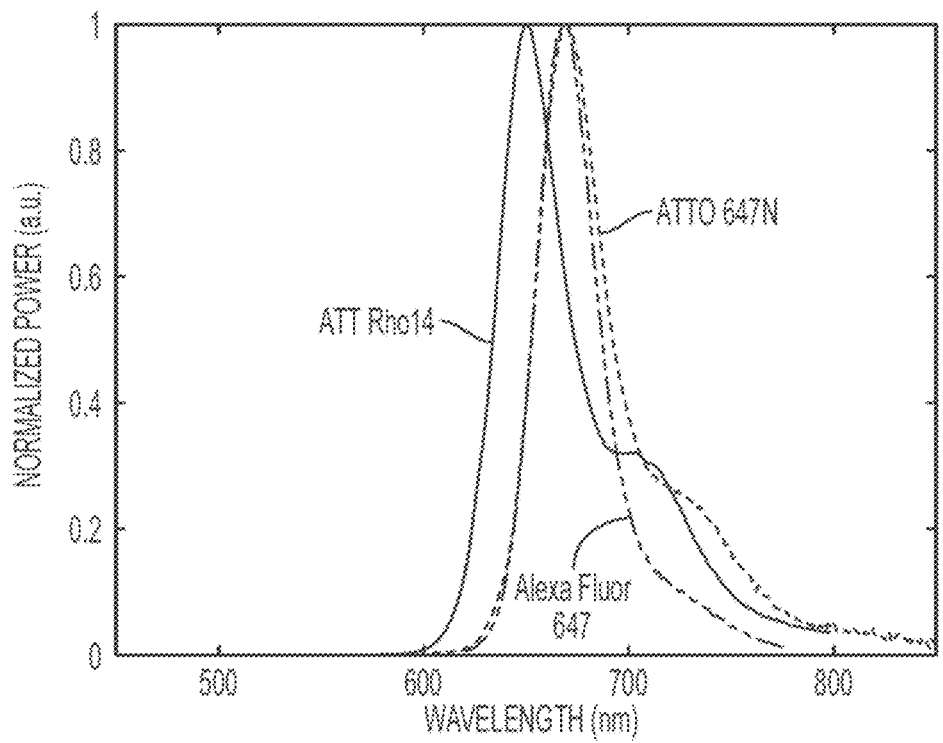
Figures 10, 11, 12, 13:
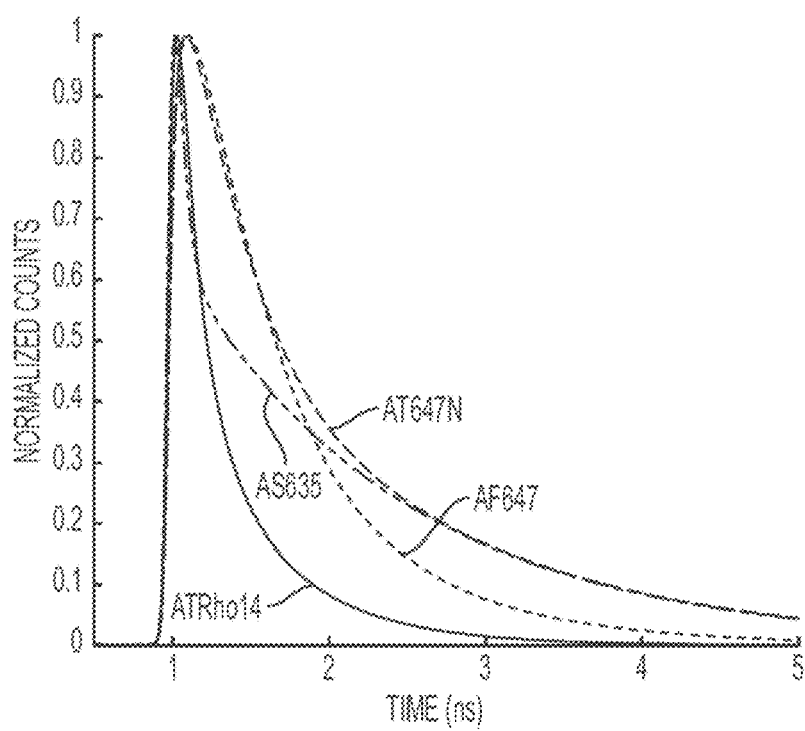
Figures 10, 11, 12, 13, 14:
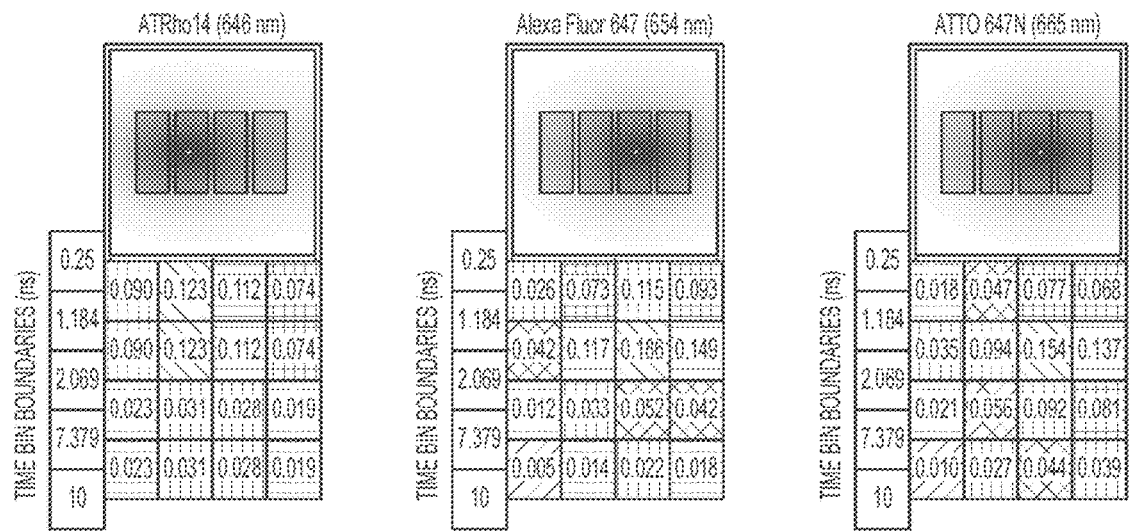
Figures 10, 11, 12, 13, 14, 15:
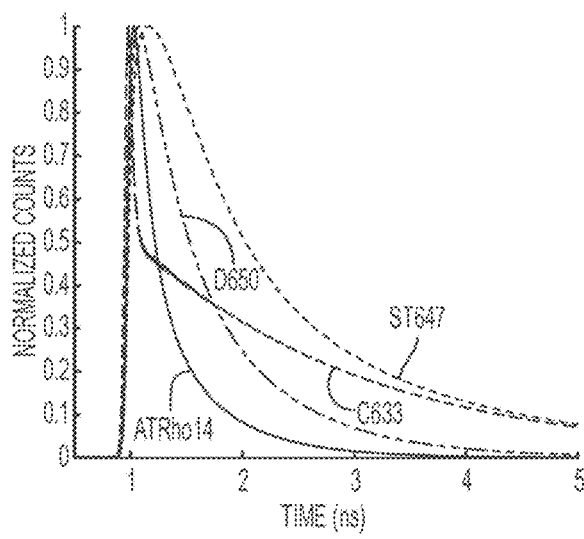
Figures 10, 11, 12, 13, 14, 15, 16:
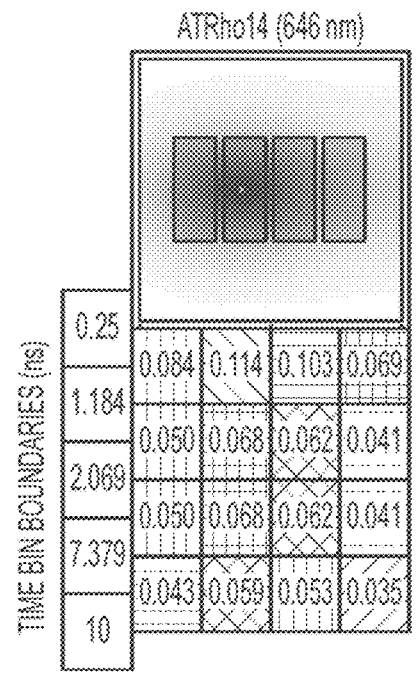
Figures 10, 11, 12, 13, 14, 15, 16, 17:
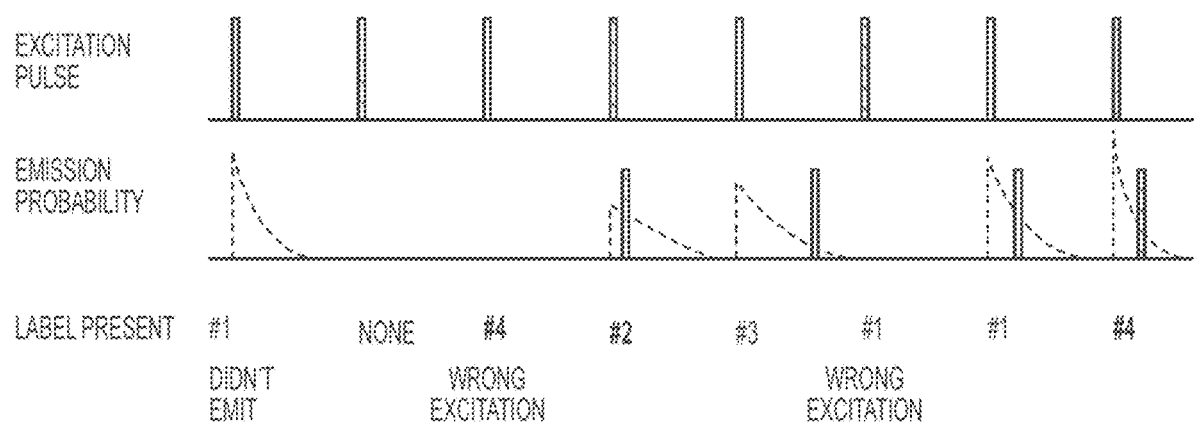
Figures 10, 11, 12, 13, 14, 15, 16, 17, 18:
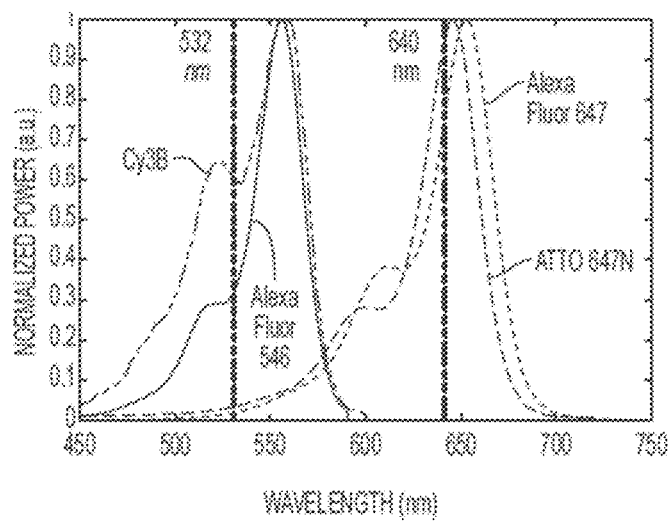
Figures 10, 11, 12, 13, 14, 15, 16, 17, 18, 19, 20:
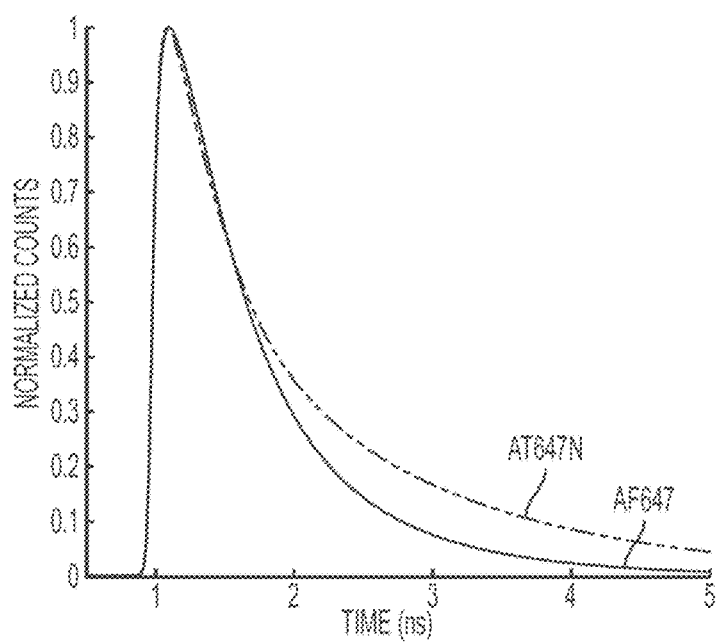
Figures 10, 11, 12, 13, 14, 15, 16, 17, 18, 19, 20, 21:
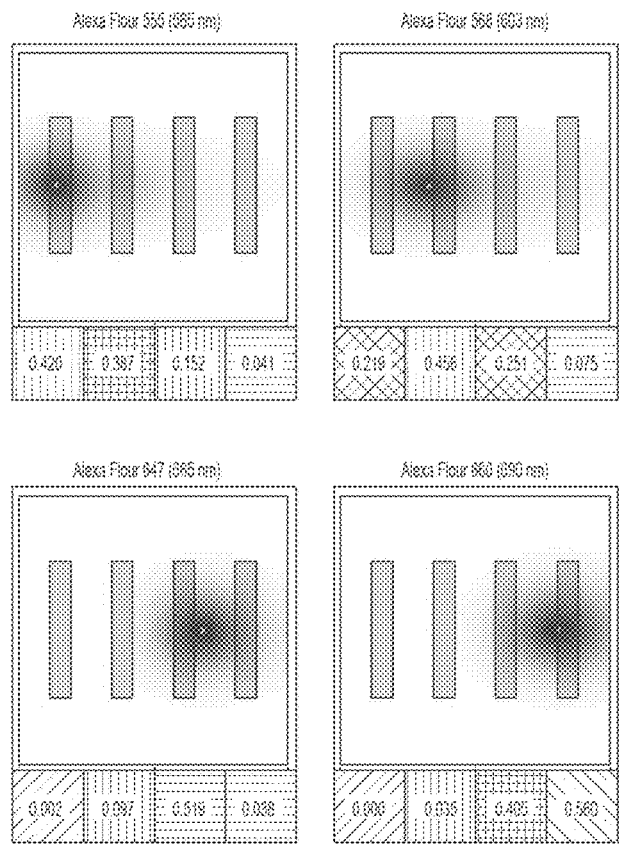
Figures 10, 11, 12, 13, 14, 15, 16, 17, 18, 19, 20, 21, 22:
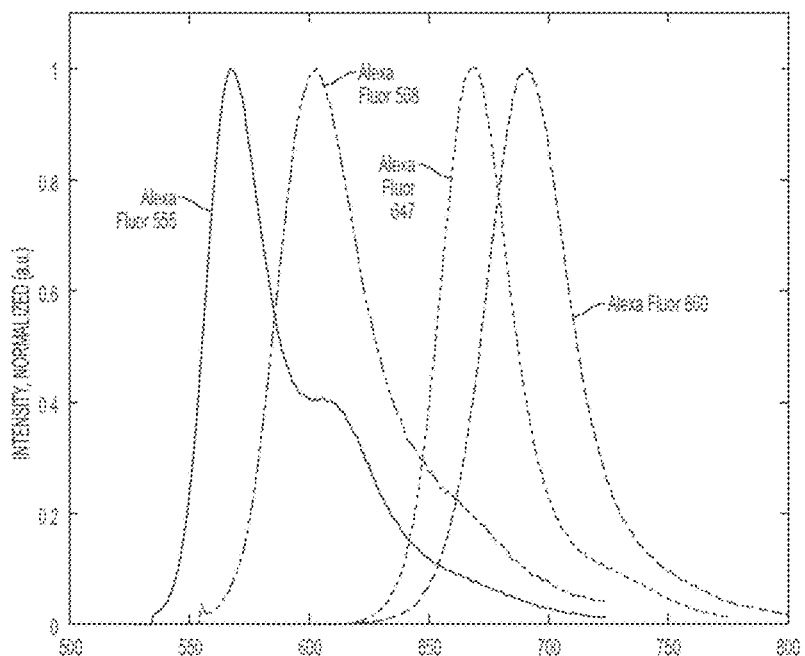
Figures 10, 11, 12, 13, 14, 15, 16, 17, 18, 19, 20, 21, 22, 23:
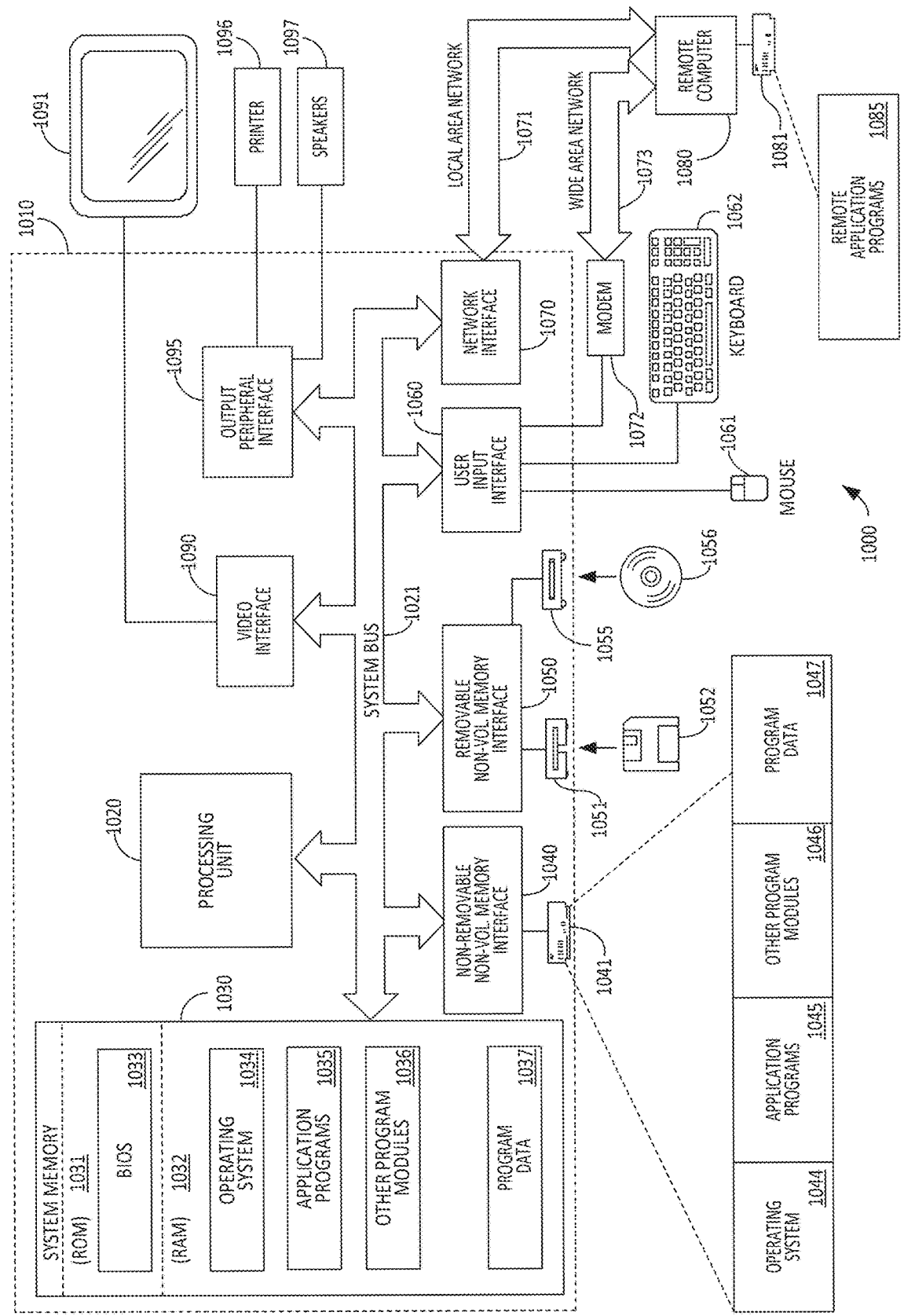
Figures 1, 11:
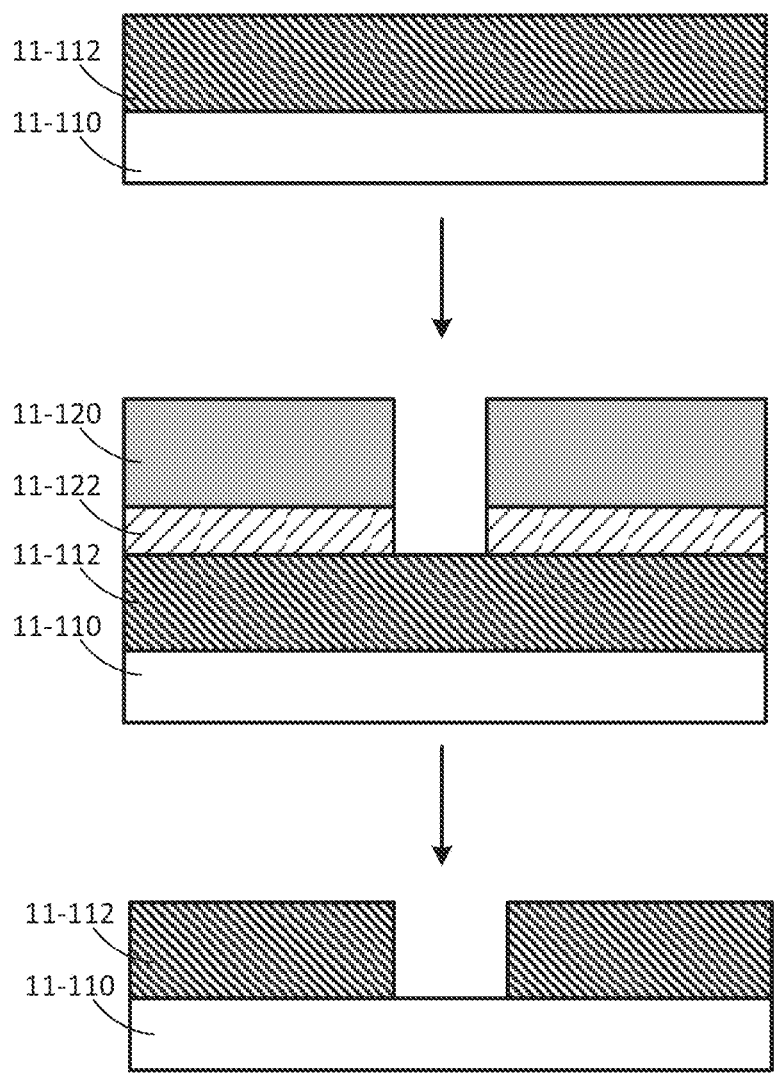
Figures 2, 11:
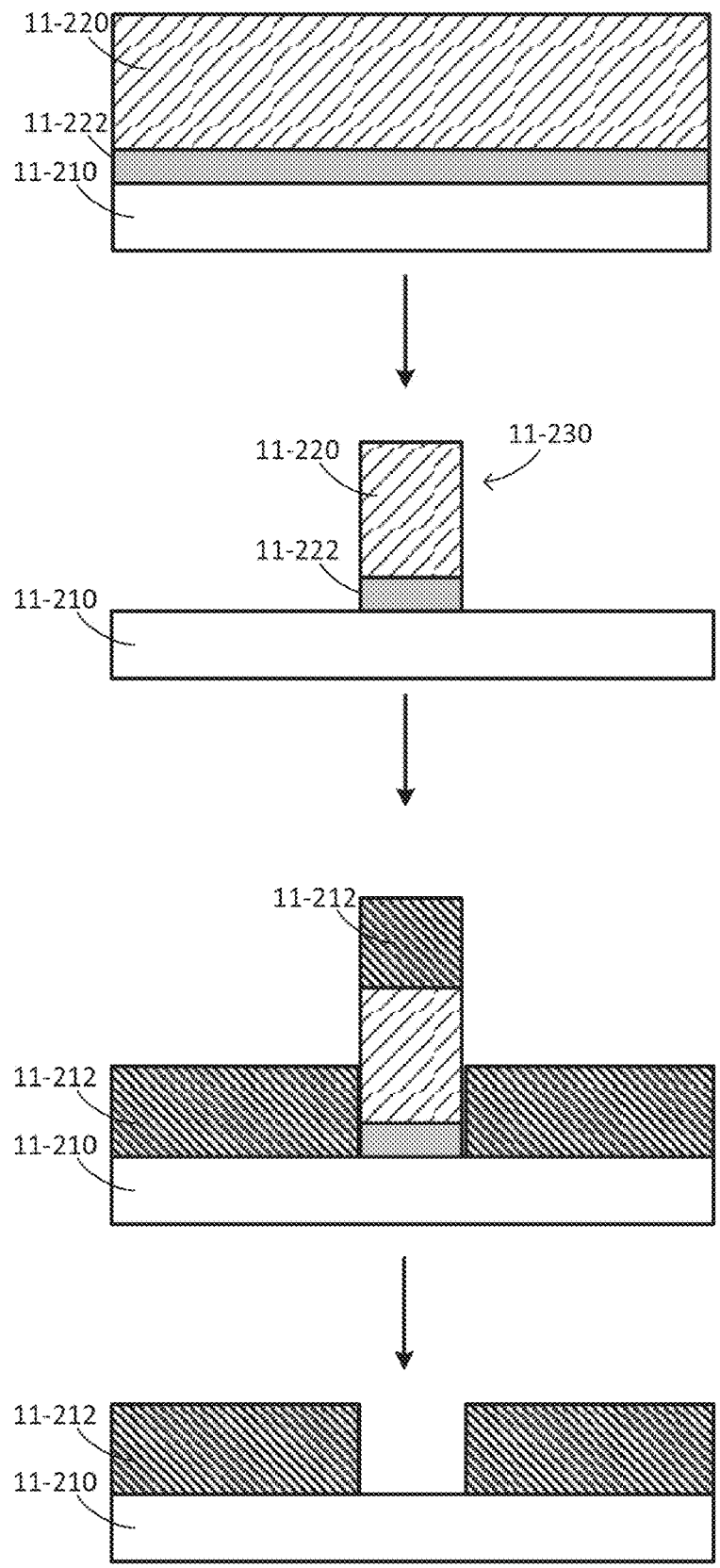
Figures 3, 11:
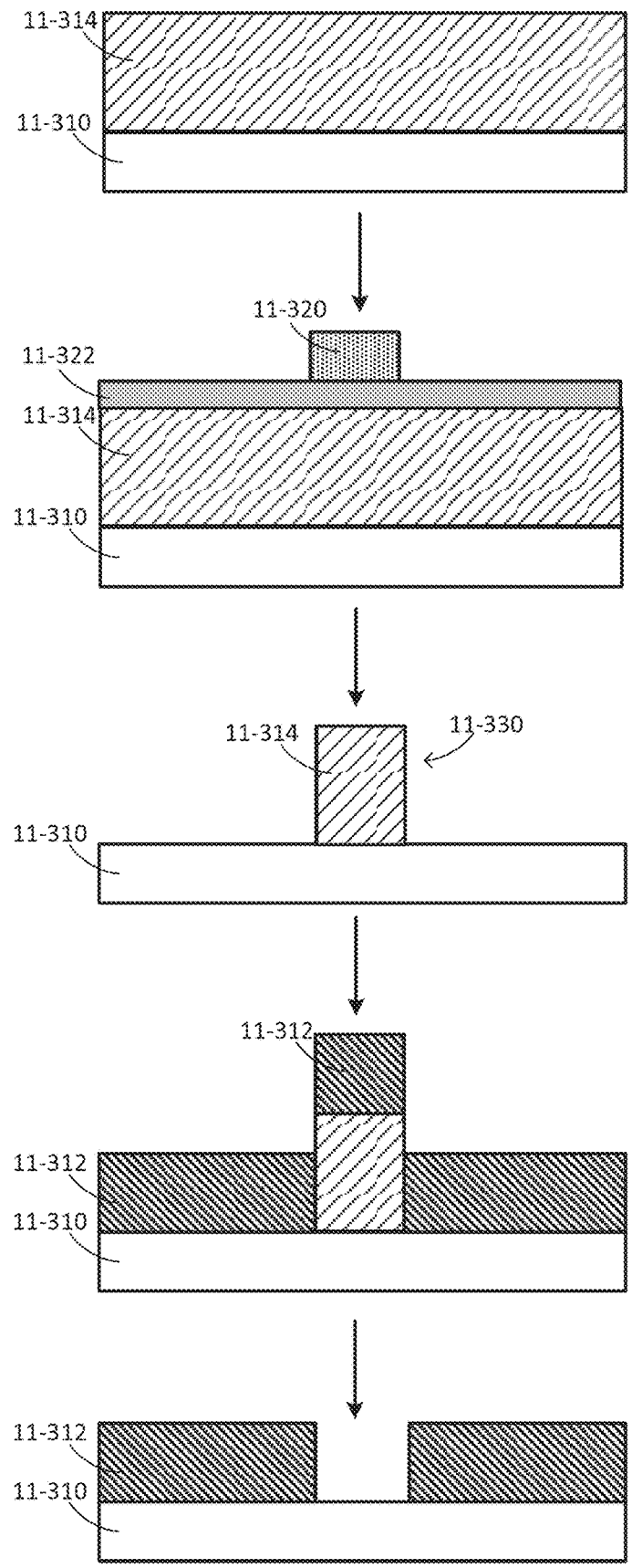
Figures 4, 11:
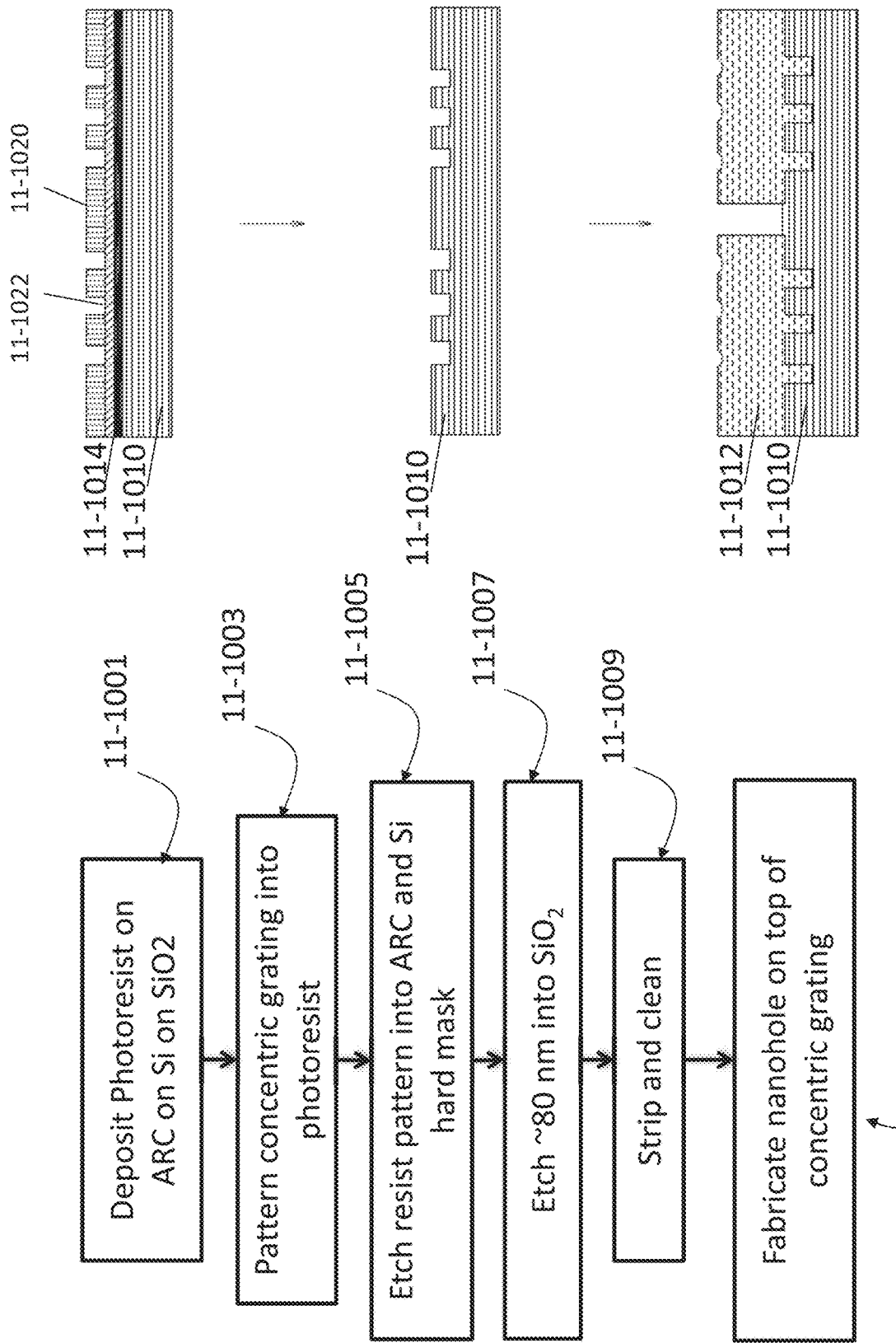
Figures 5, 11:
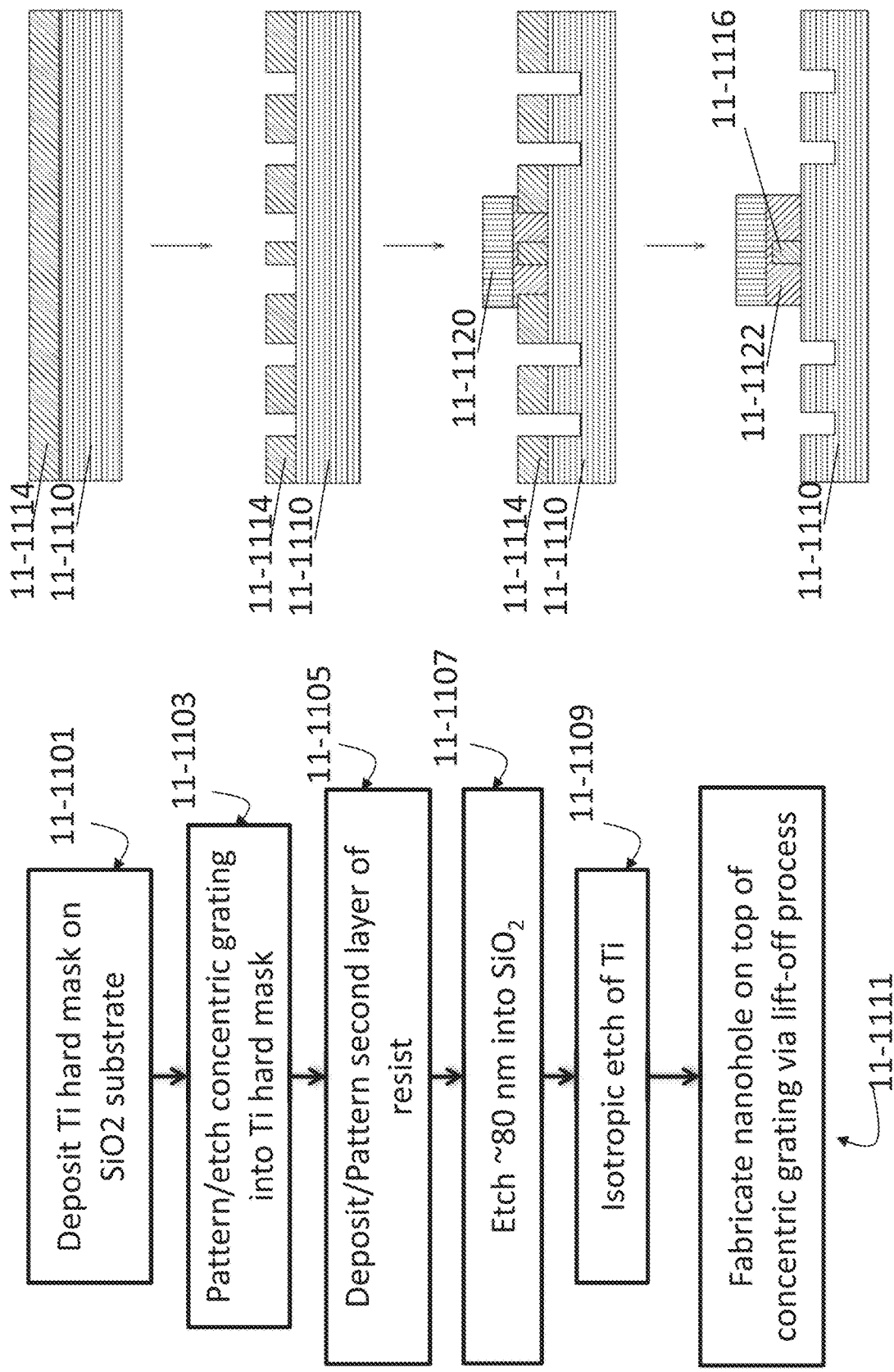
Figures 6, 11:
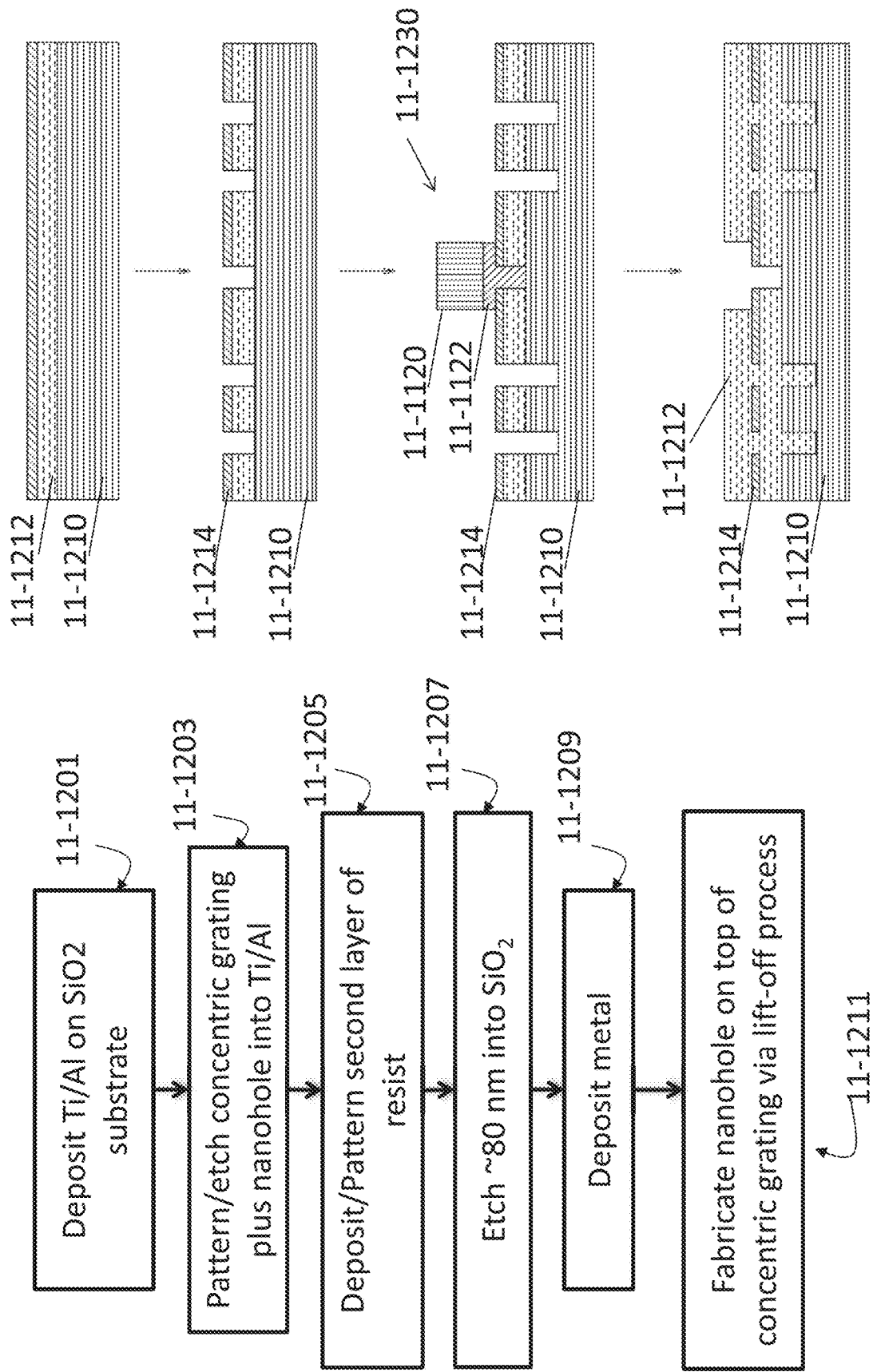
Figures 7, 11:
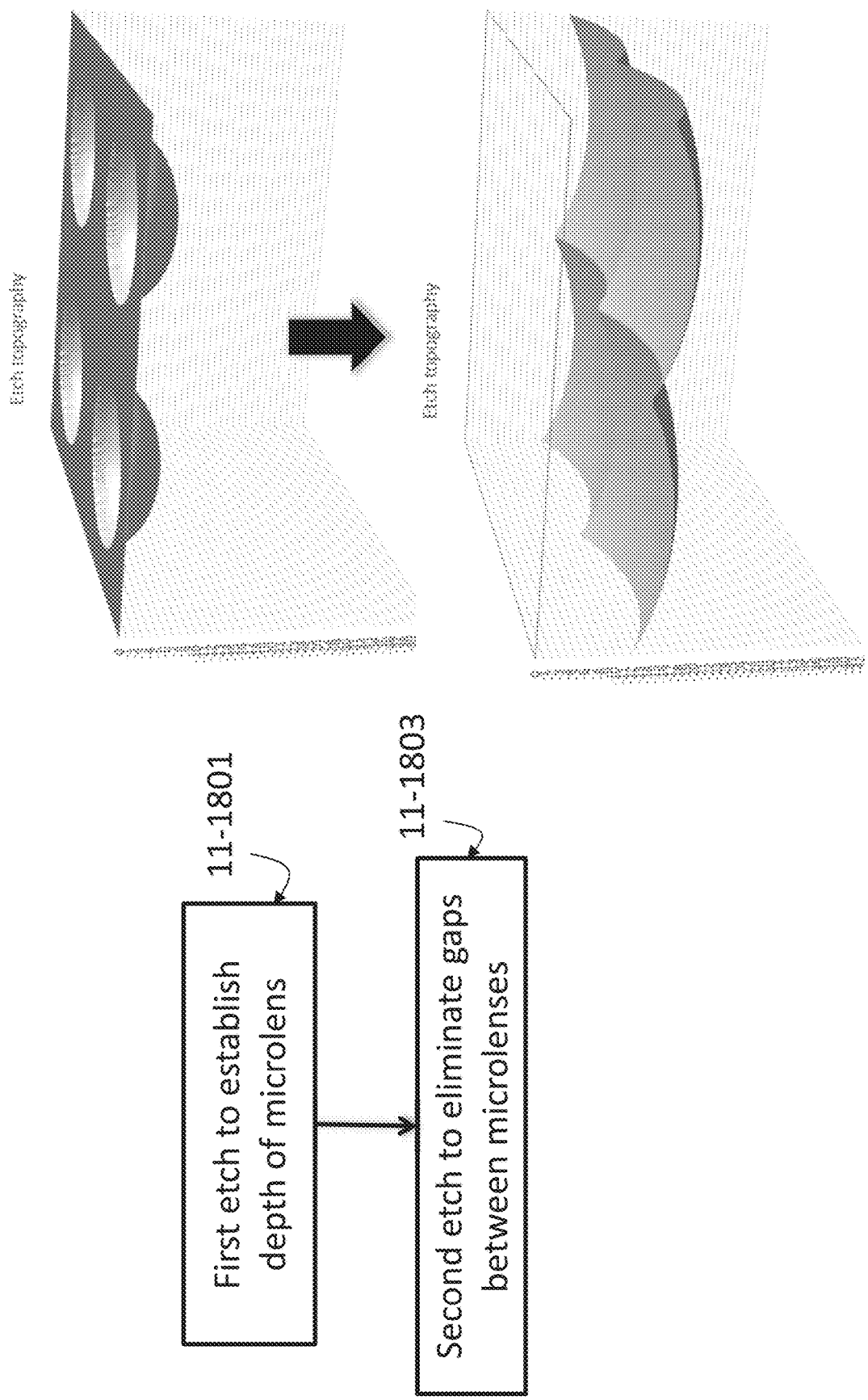
Figures 8, 11:
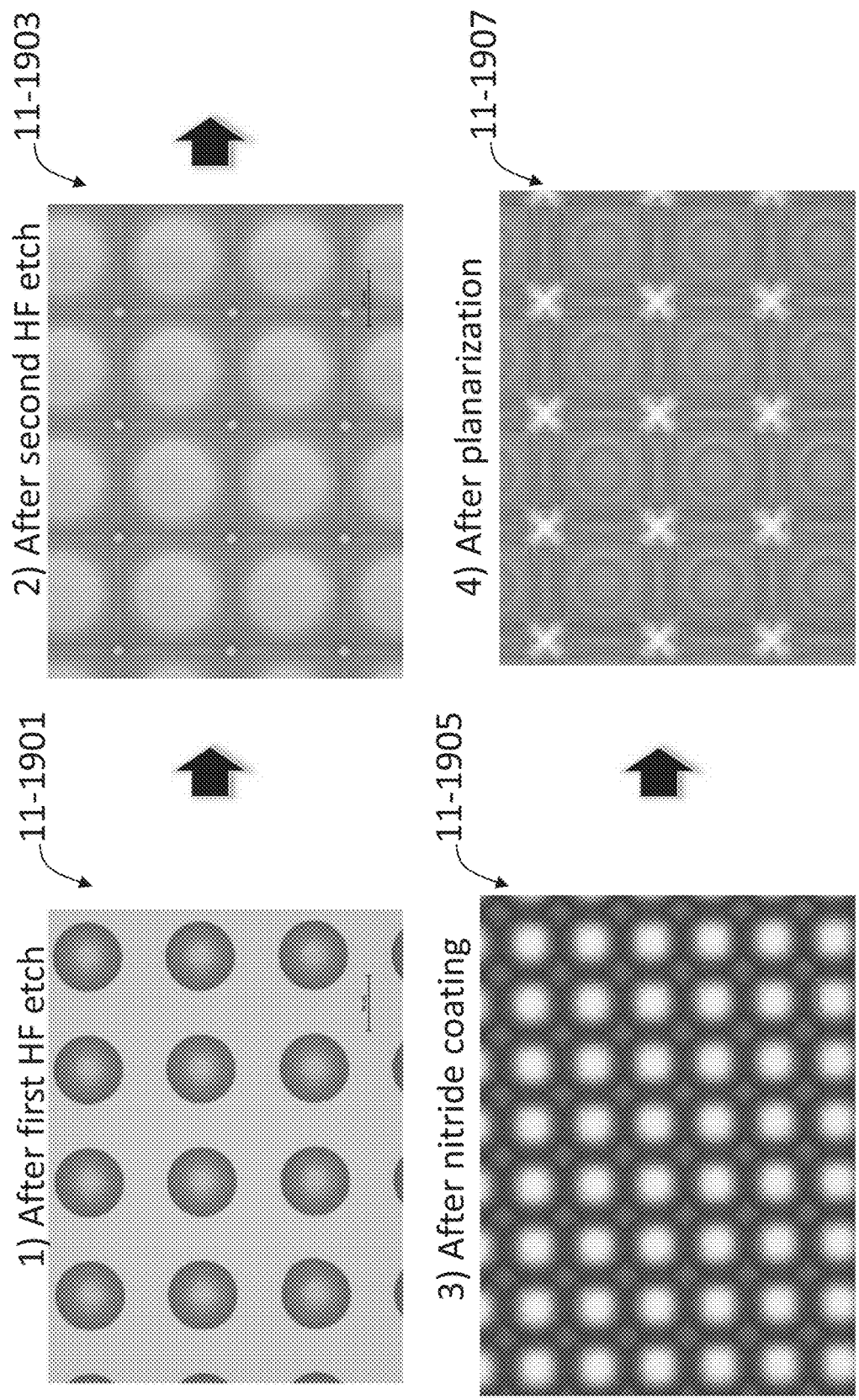
Figures 9, 11:
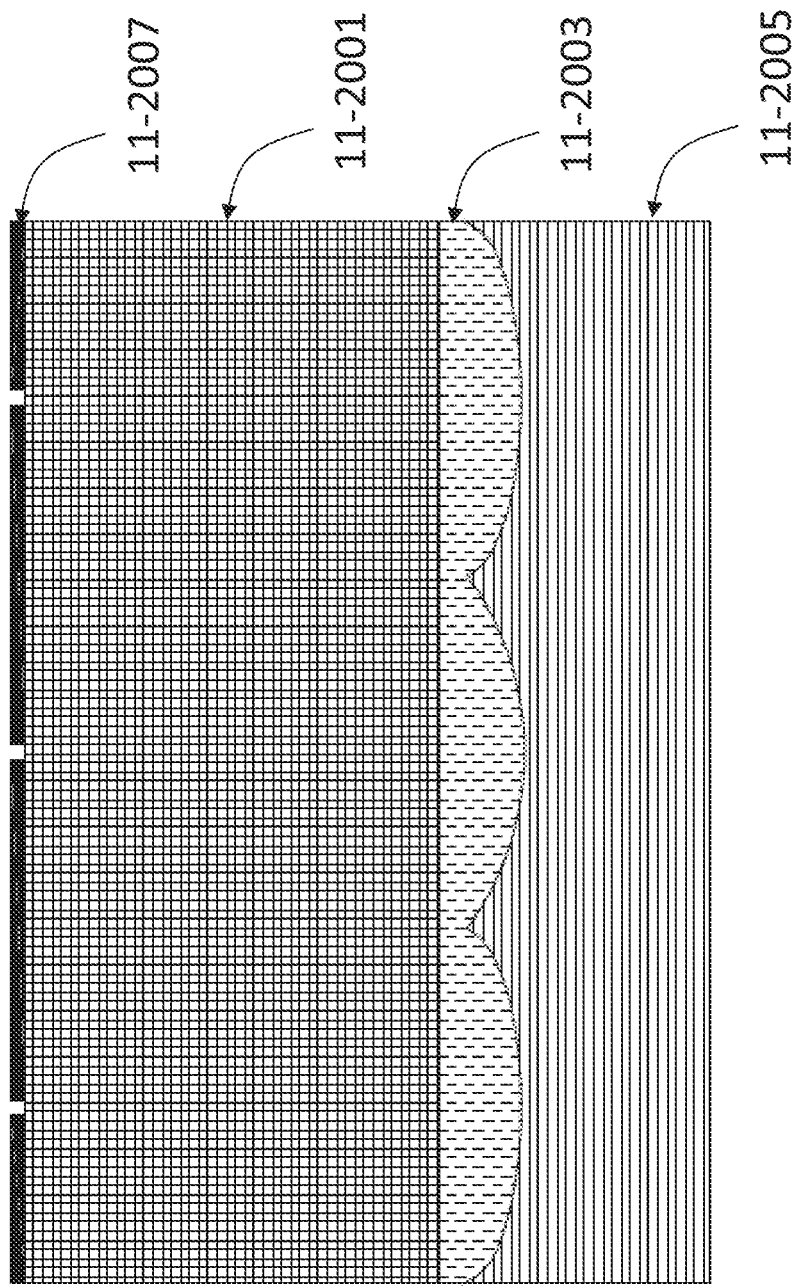
Figures 10, 11:
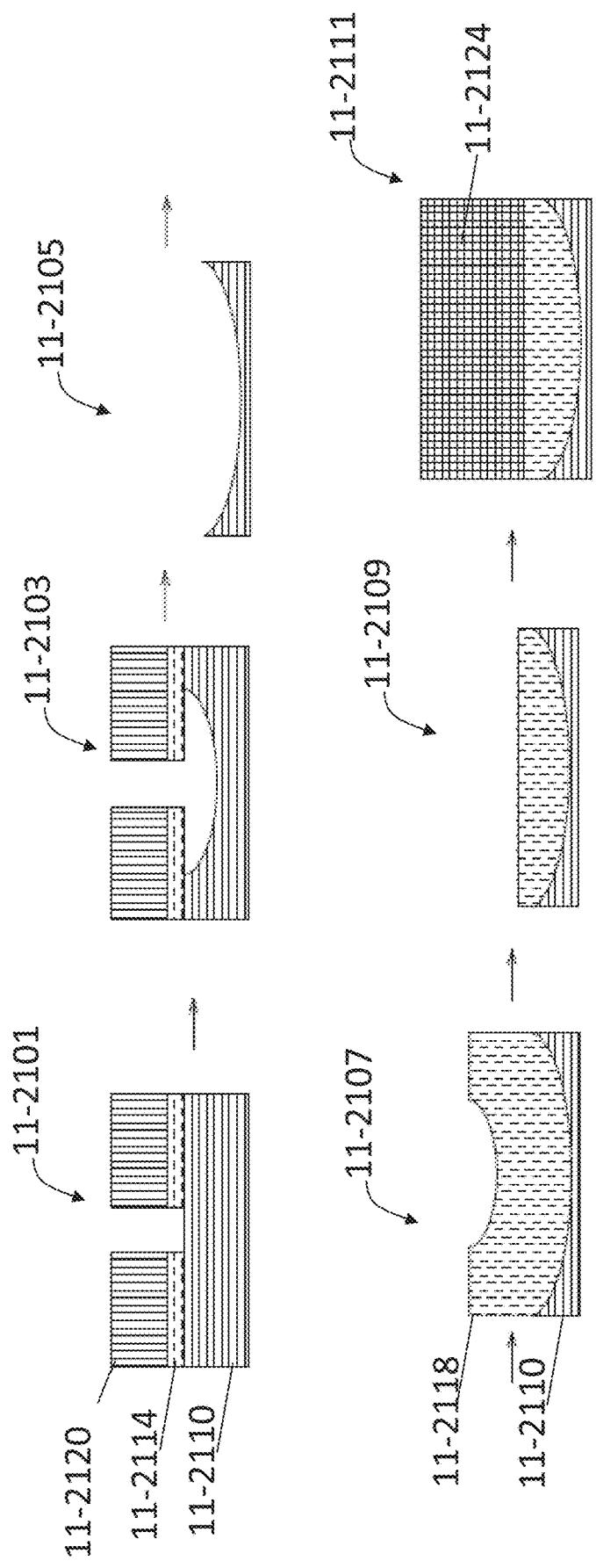
Figure 11:
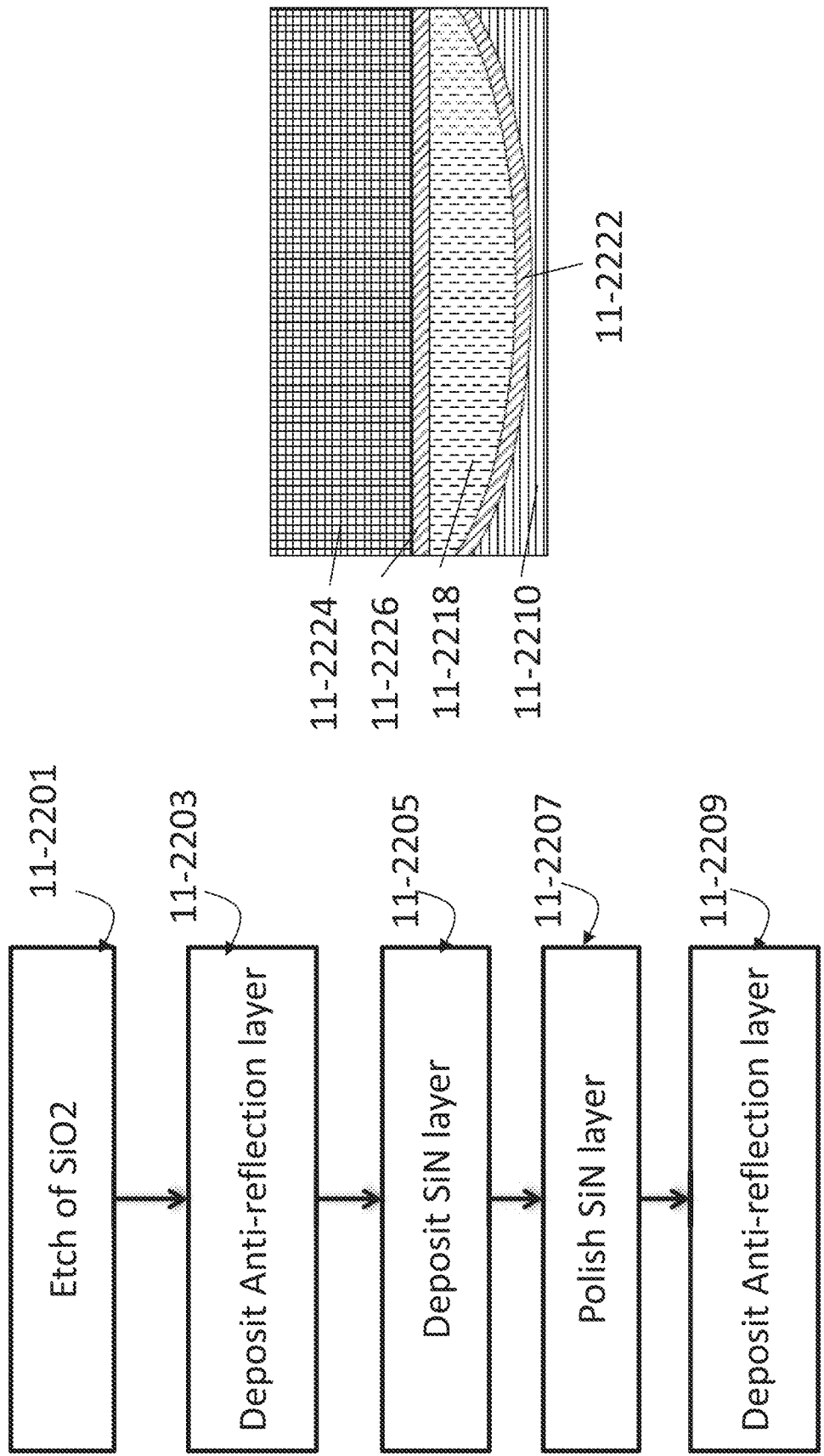
Figures 11, 12:
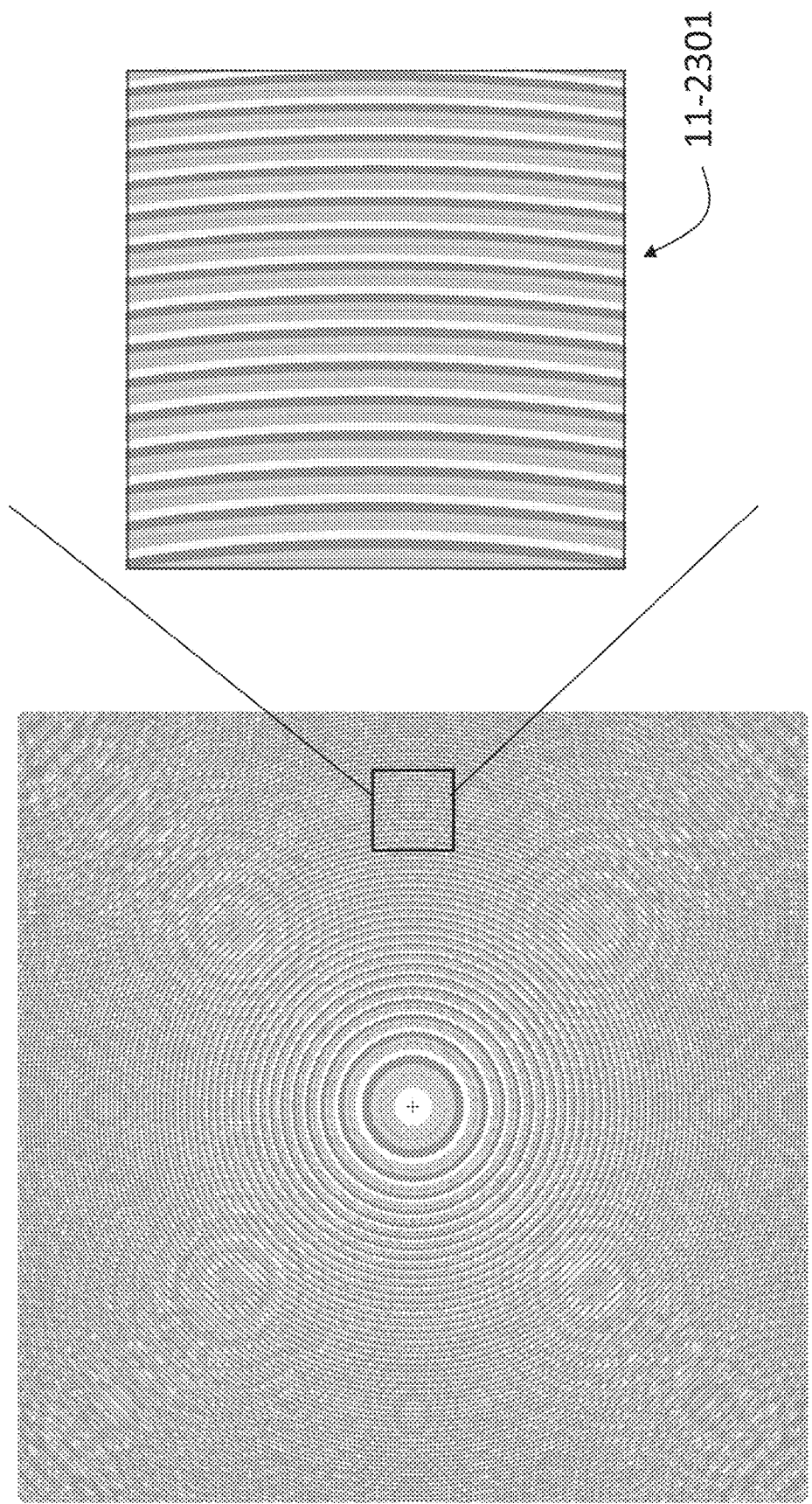
Figures 11, 12, 13:
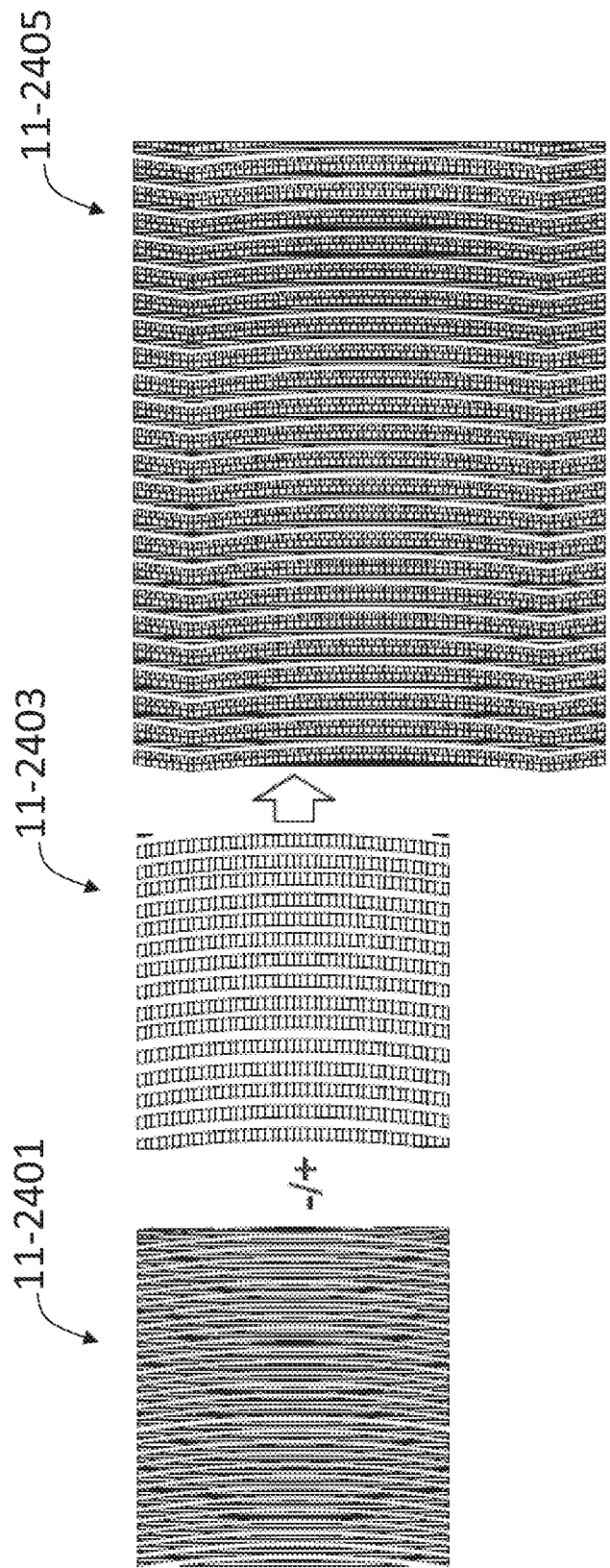
Figures 11, 12, 13, 14:
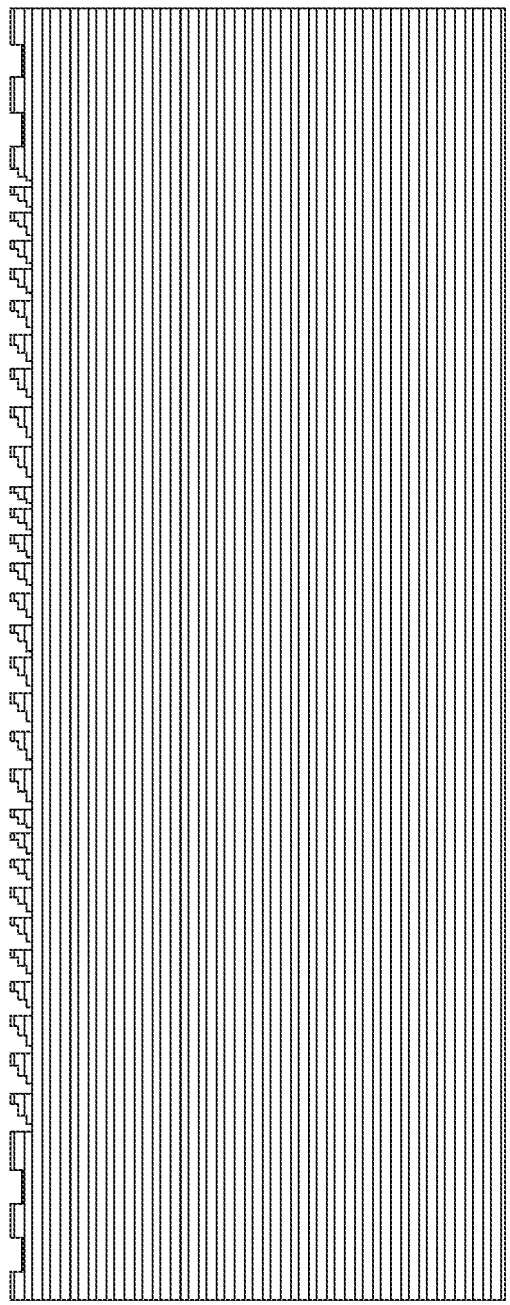
Figures 11, 12, 13, 14, 15:
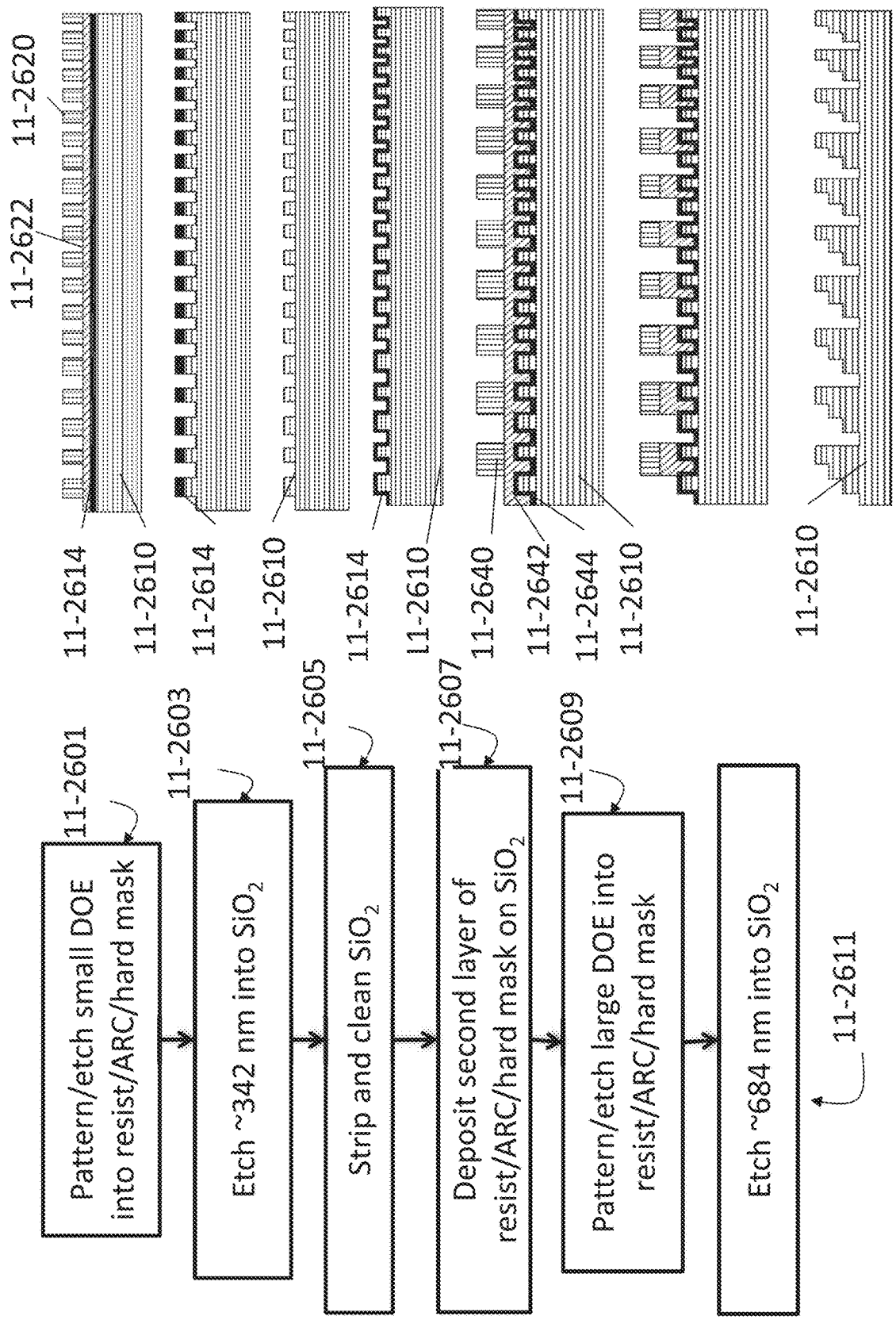
Figures 11, 12, 13, 14, 15, 16:
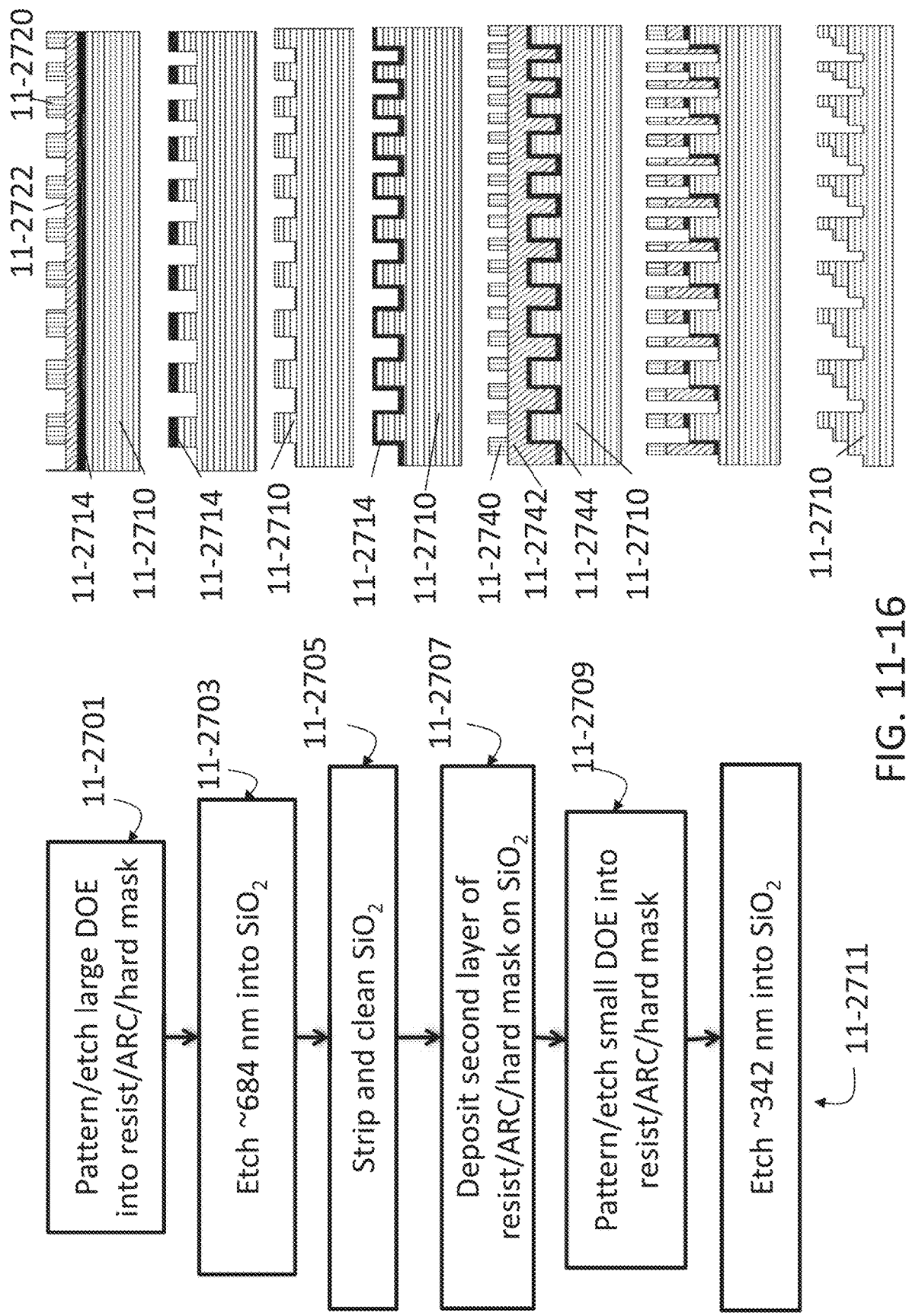
Figures 11, 12, 13, 14, 15, 16, 17:
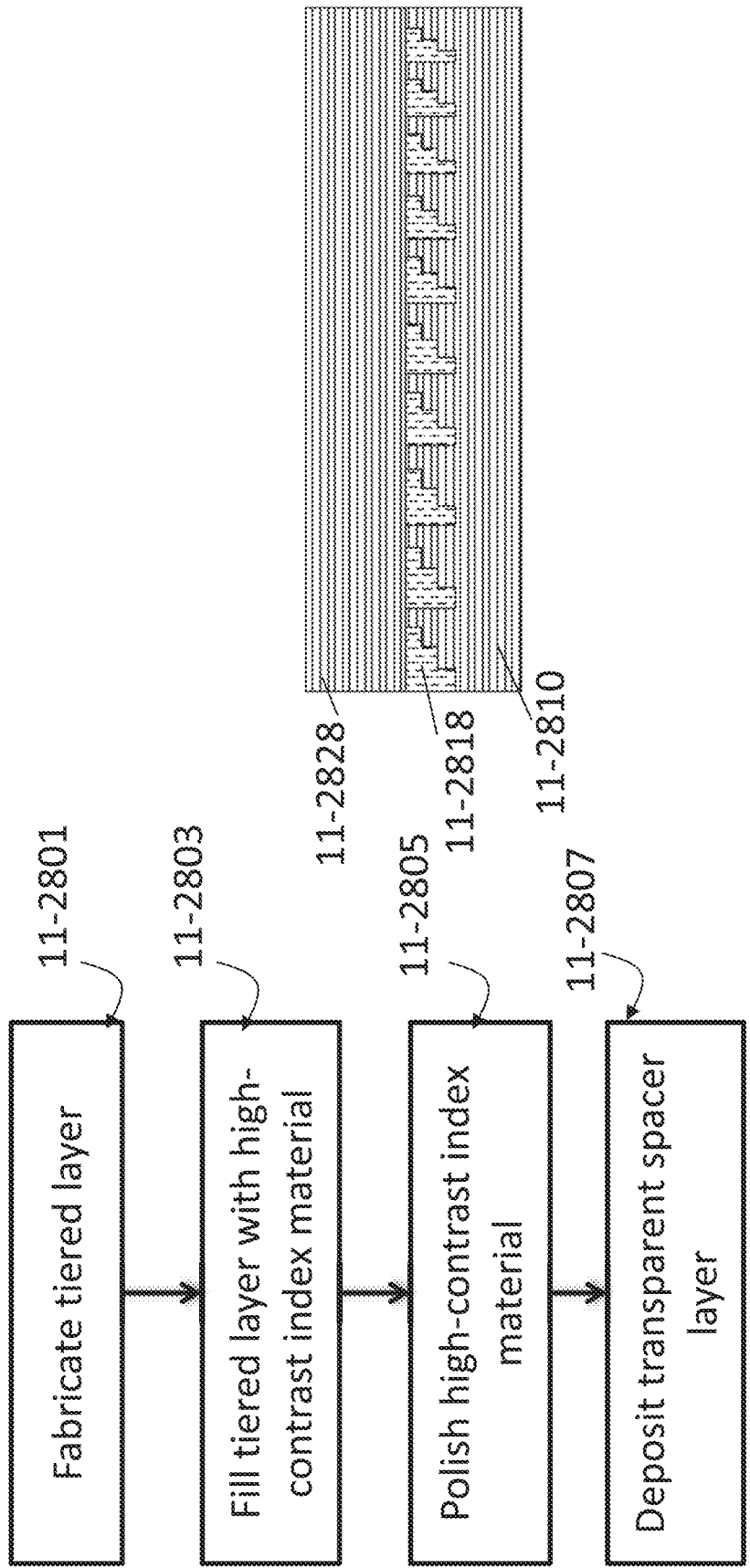
Figures 11, 12, 13, 14, 15, 16, 17, 18:
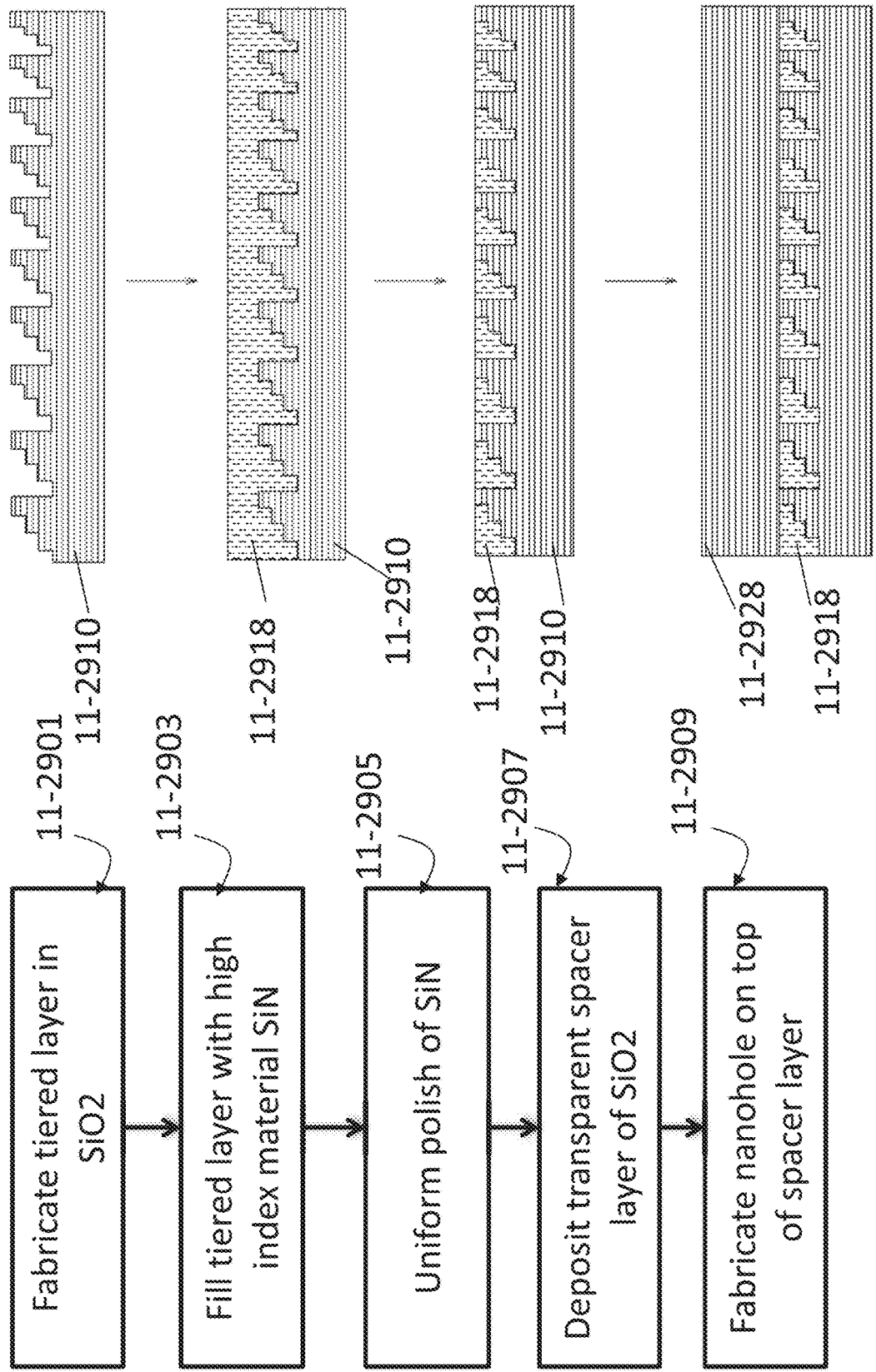
Figures 11, 12, 13, 14, 15, 16, 17, 18, 19:
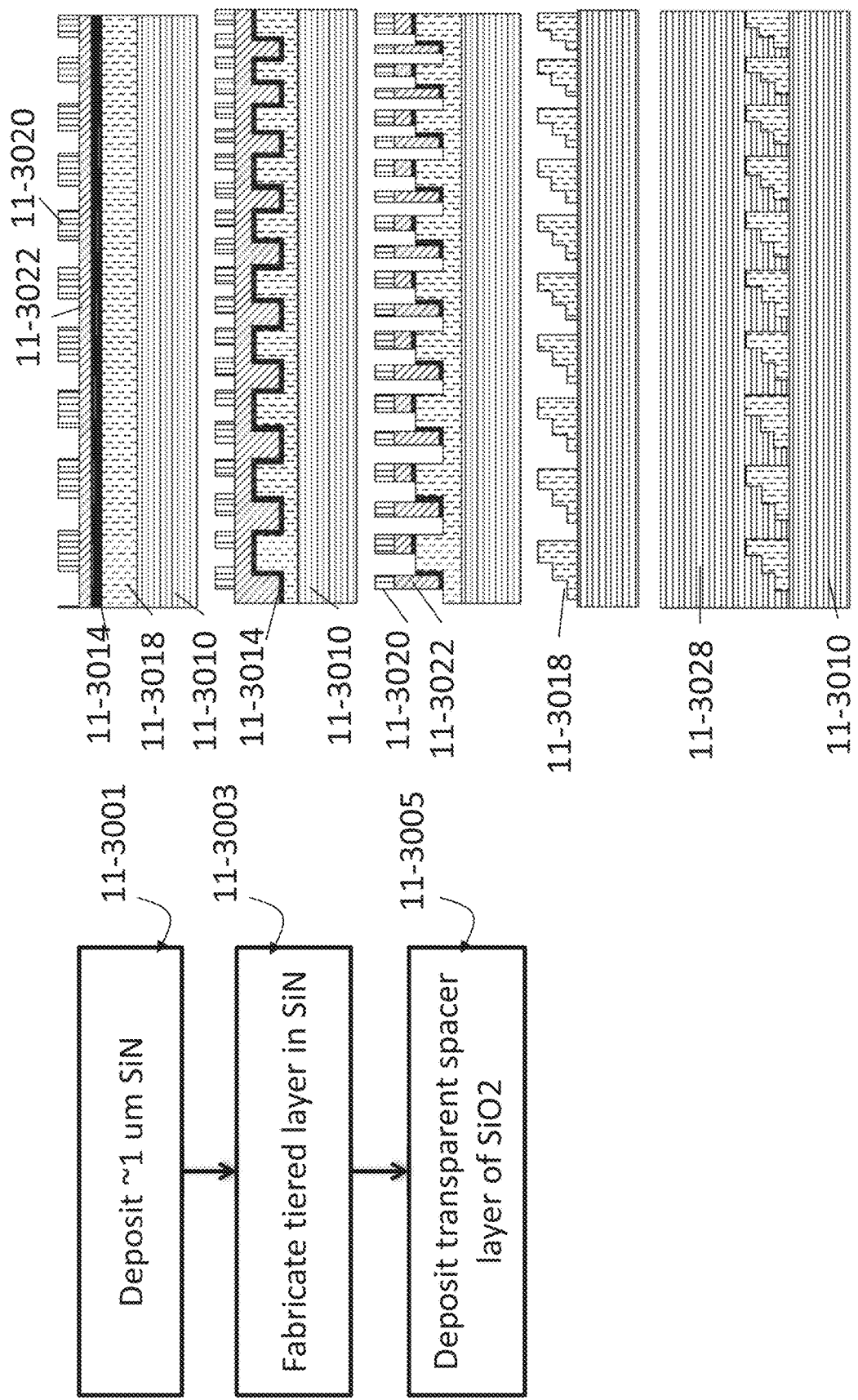

FIG. 7-4G and FIG. 7-4H illustrate first and second read signal levels associated with two emitters having temporally-distinct emission characteristics, according to some embodiments.

FIG. 7-5 illustrates a schematic diagram of a pixel with time resolution capability, according to some embodiments.

FIG. 7-6 illustrates a schematic diagram of a pixel with time resolution capability, according to some embodiments.

Figures 3, 4, 5, 6, 7, 8:
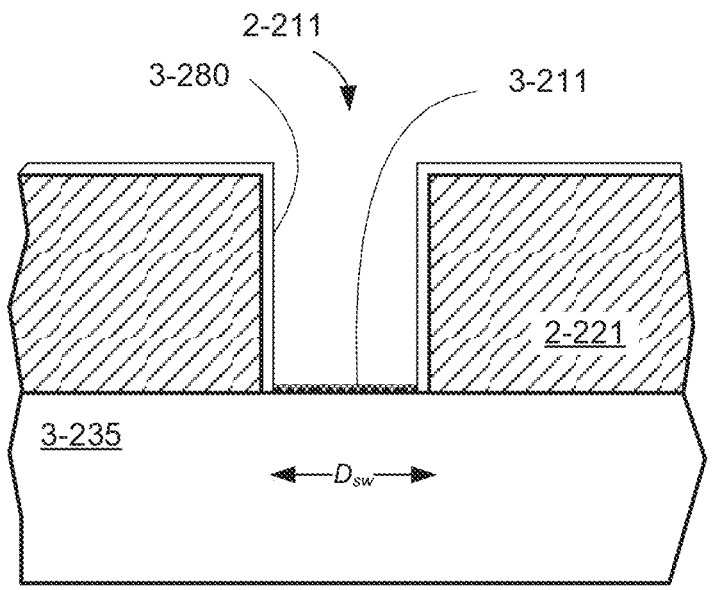

FIG. 8-1A and FIG. 8-1B depict spectral excitation bands of excitation sources, according to some embodiments.

FIG. 8-2A is a schematic of a coherent light source, according to some embodiments.

FIG. 8-2B illustrates temporal intensity profiles of an excitation source, according to some embodiments.

FIG. 8-3 illustrates relaxation oscillations and a light signal from of an excitation source, according to some embodiments.

FIG. 8-4 illustrates the use of a tailored electrical pulse to reduce the power of a tail in an output optical pulse, according to some embodiments.

FIG. 8-5 and FIG. 8-6 illustrates the optical output power of an excitation source as a function of time, according to some embodiments.

FIG. 8-7 illustrates a higher current at higher frequencies resulting from using a greater number of wire bonds, according to some embodiments.

Figures 4, 5, 6, 7, 8, 8A:
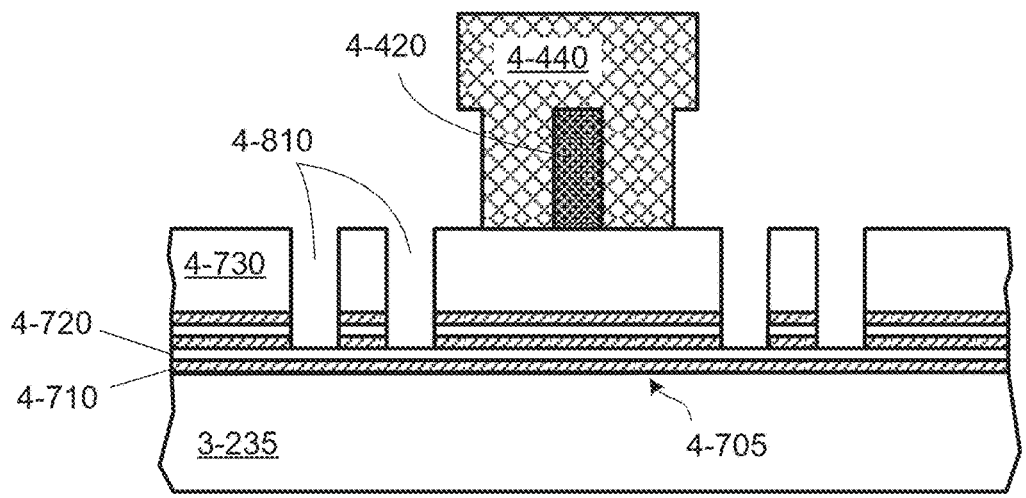

FIG. 8-8A is a schematic of a transmission line pulsar, according to some embodiments.

Figures 4, 5, 6, 7, 8, 8B:
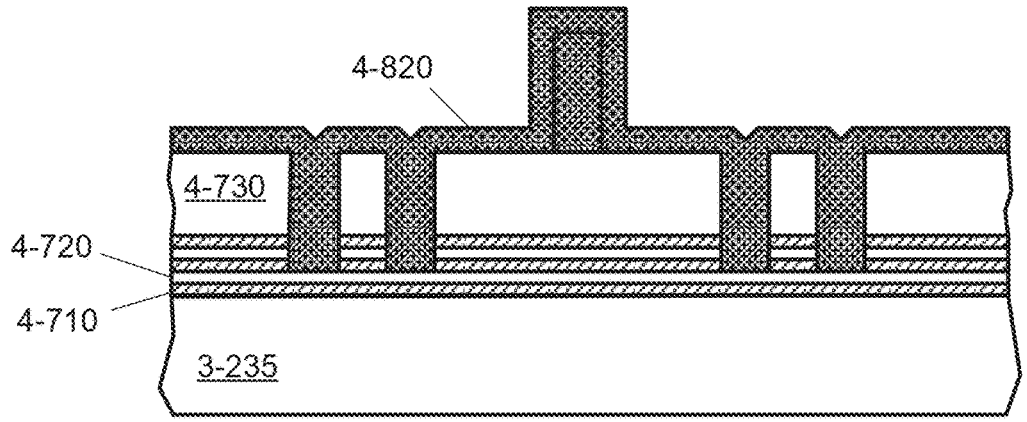
Figures 4, 5, 6, 7, 8, 8C:
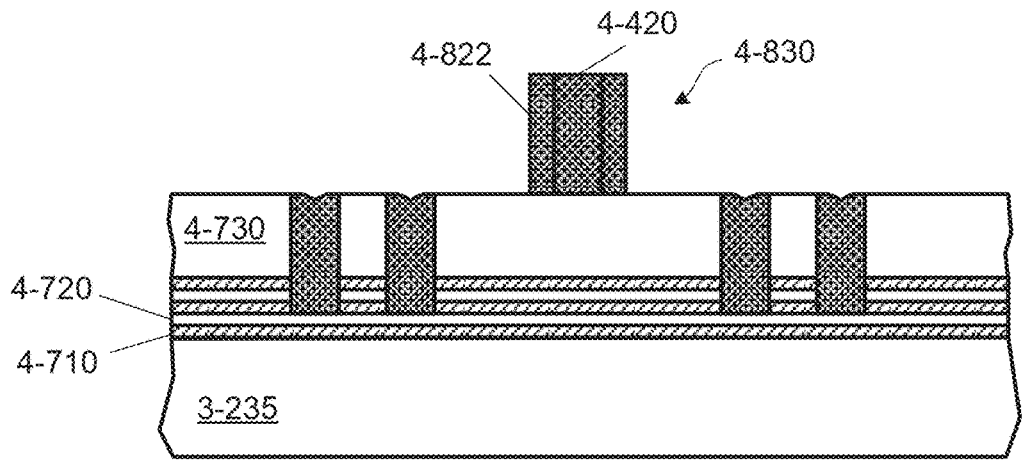
Figures 4, 5, 6, 7, 8, 8D:
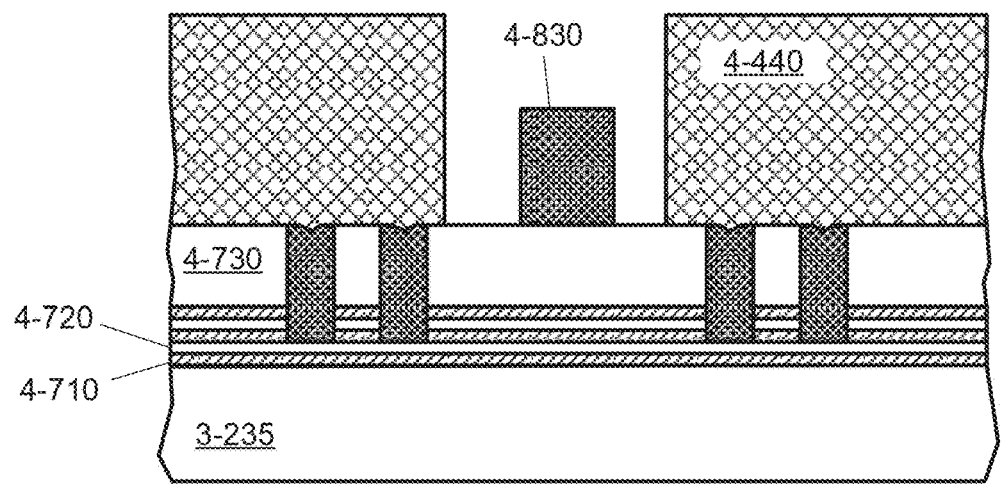
Figures 4, 5, 6, 7, 8, 8E:
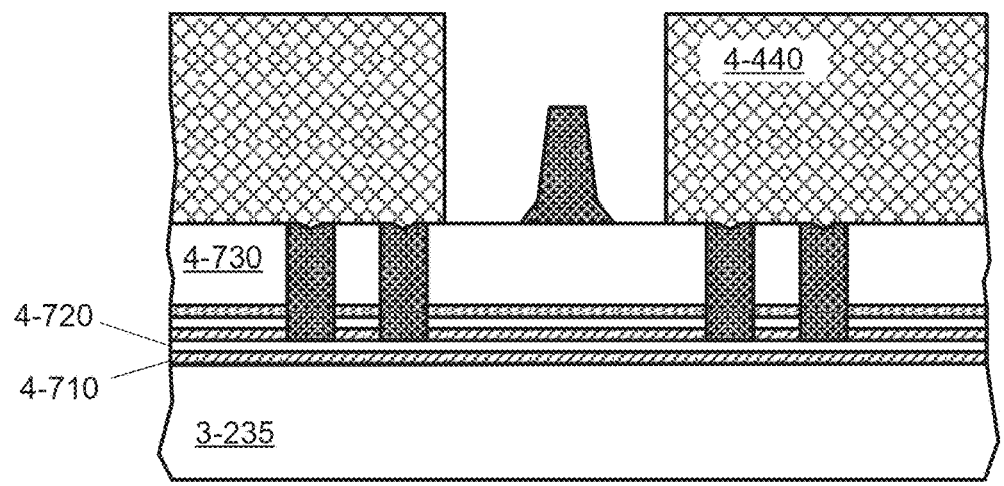
Figures 4, 5, 6, 7, 8, 8F:
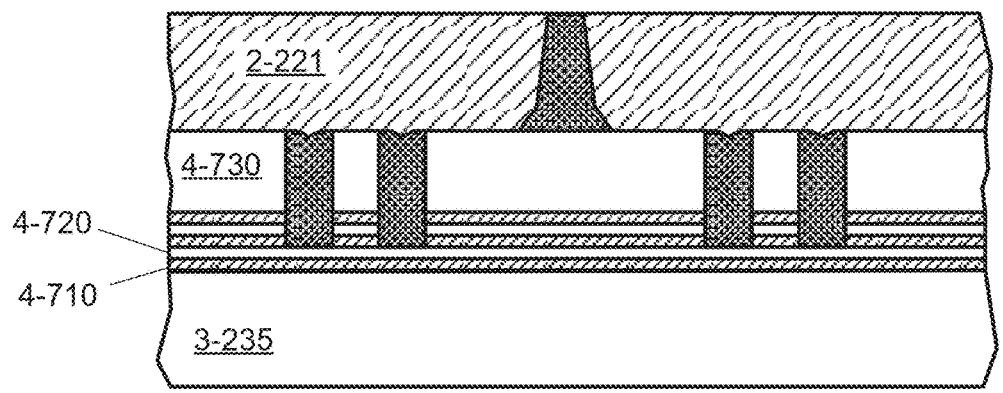
Figures 4, 5, 6, 7, 8, 8G:
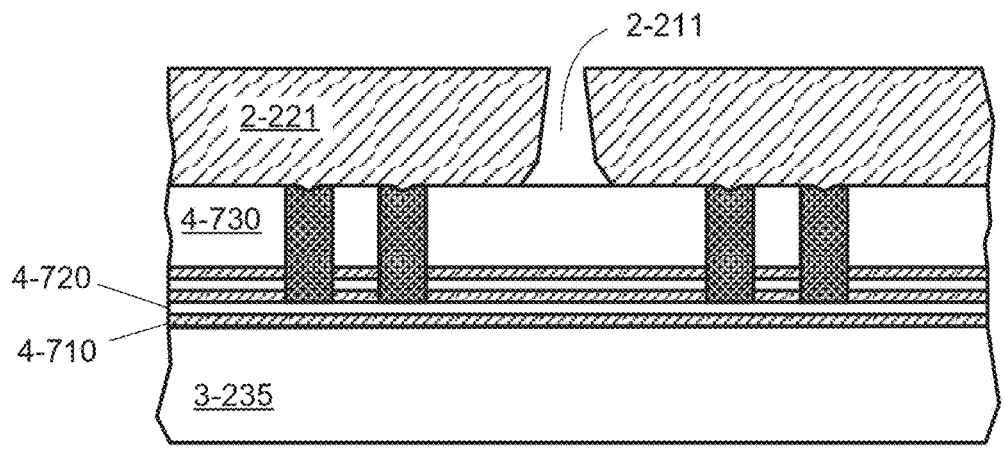
Figures 4, 5, 6, 7, 8, 9, 9A:
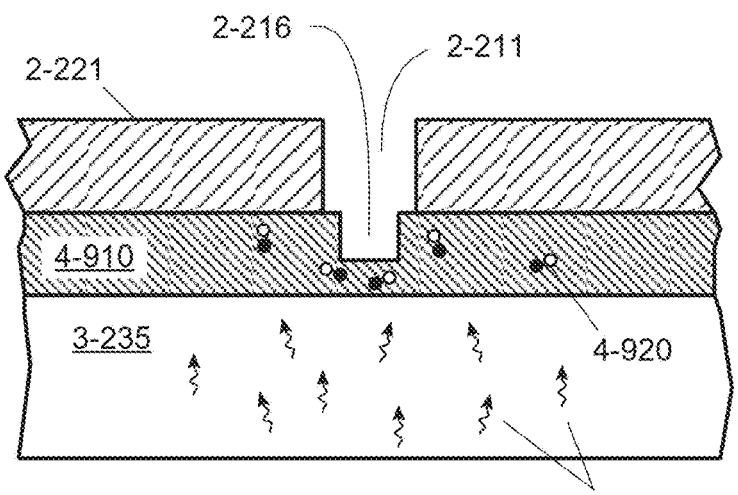
Figures 4, 5, 6, 7, 8, 9, 9B:
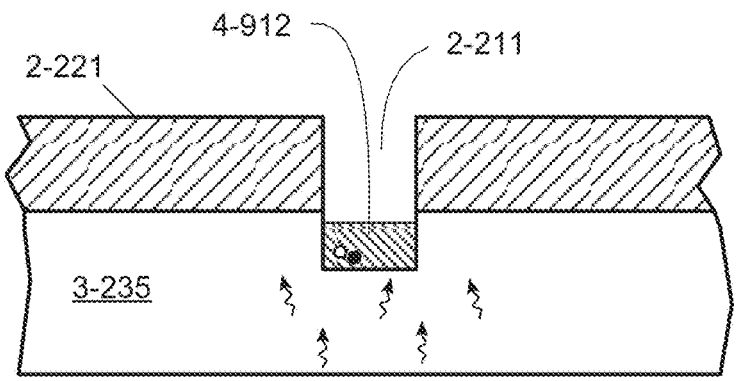
Figures 4, 5, 6, 7, 8, 9, 9C:
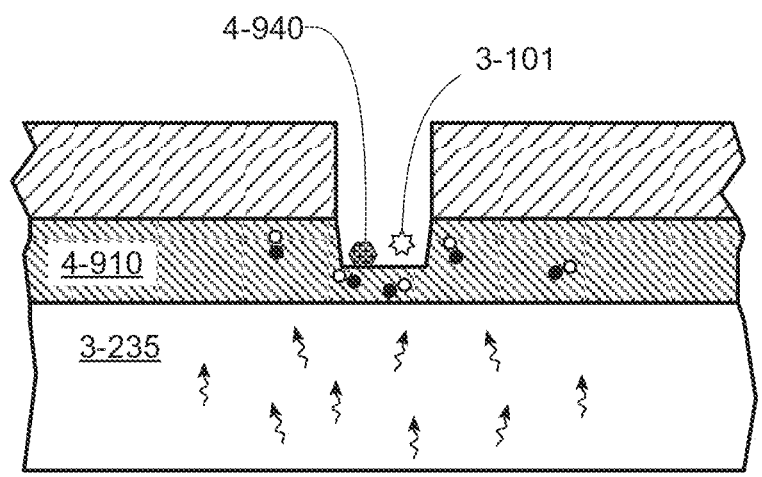
Figures 4, 5, 6, 7, 8, 9, 9D:
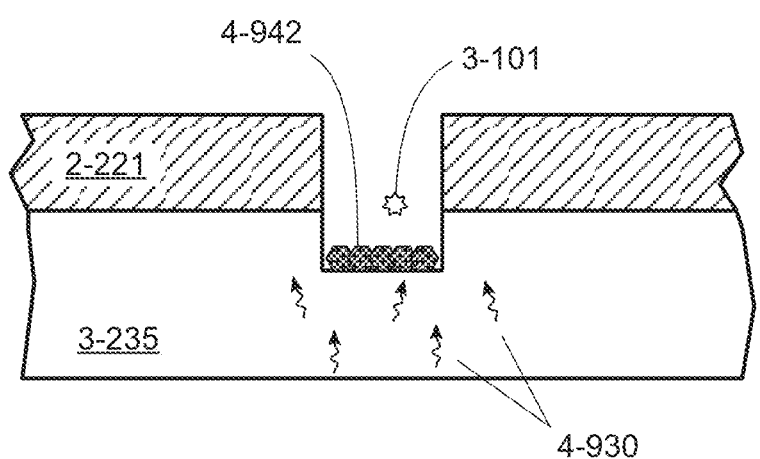
Figures 4, 5, 6, 7, 8, 9, 9E:
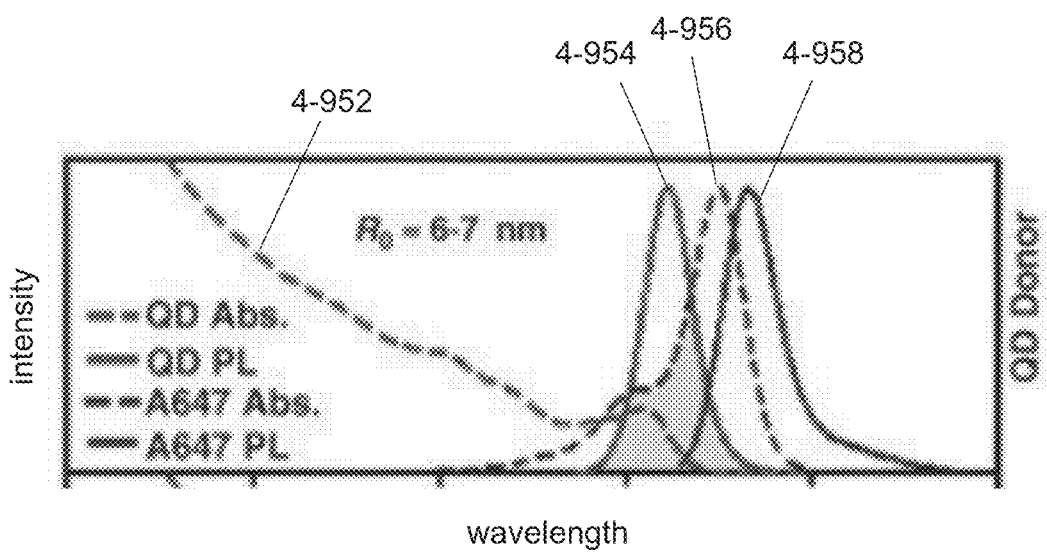
Figures 4, 5, 6, 7, 8, 9, 9F:
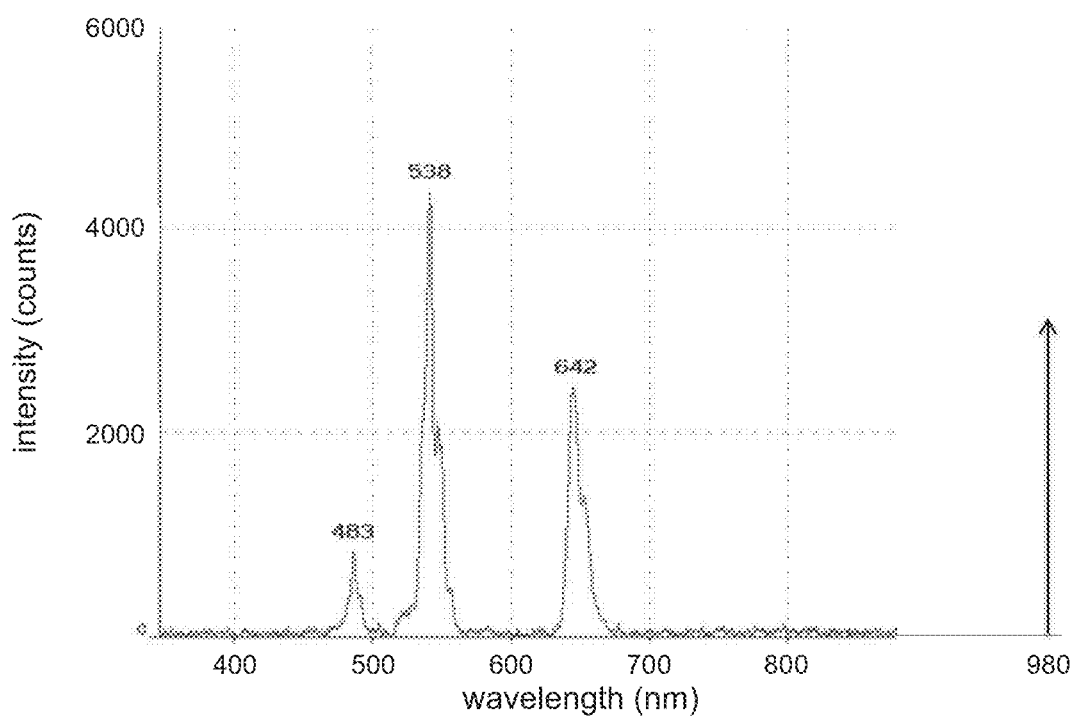
Figures 3B, 5:
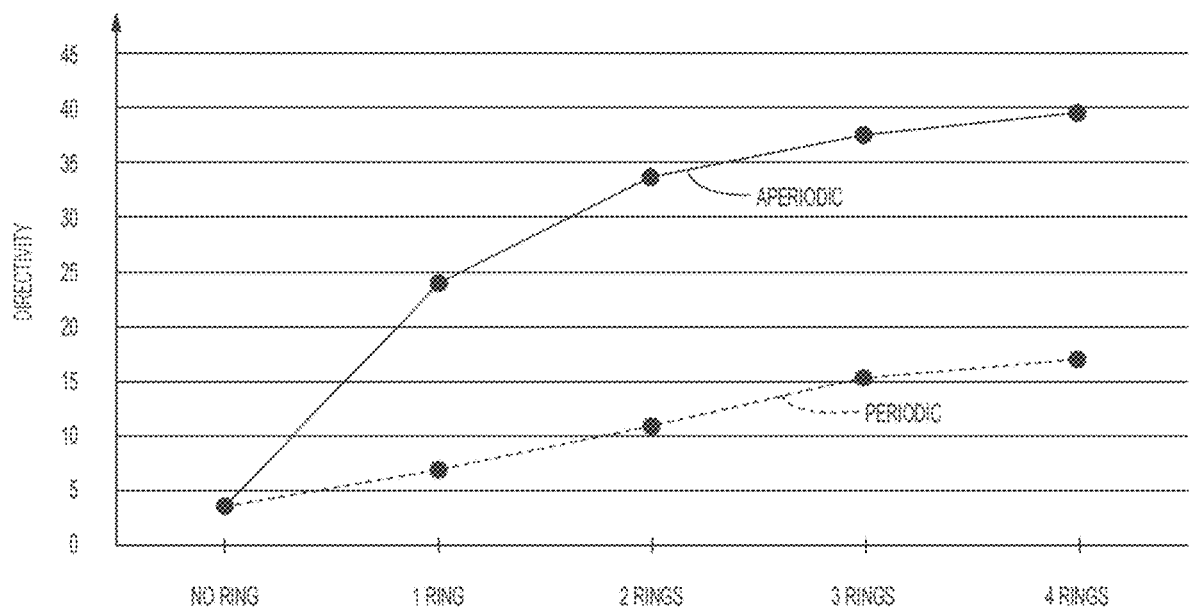
Figures 4A, 5:
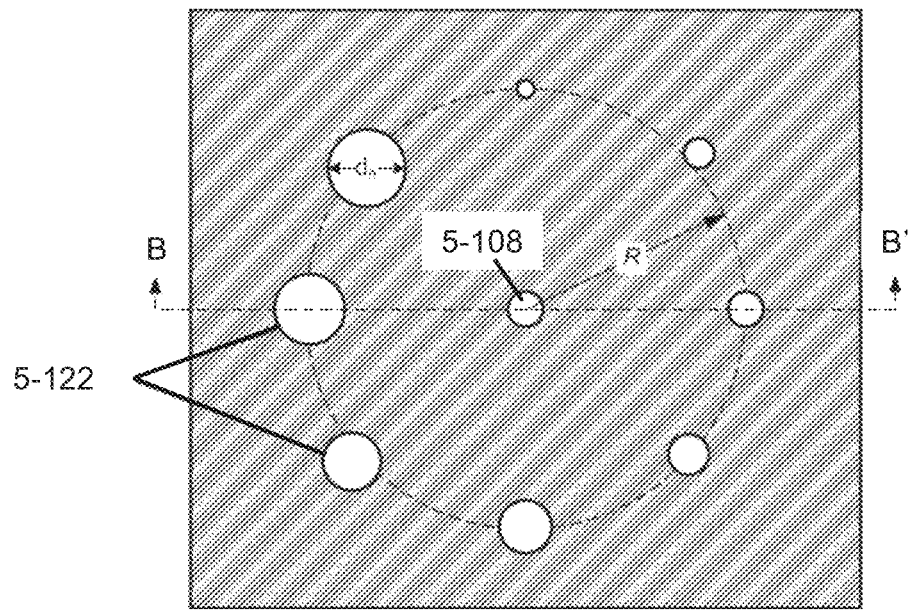
Figures 4B, 5:
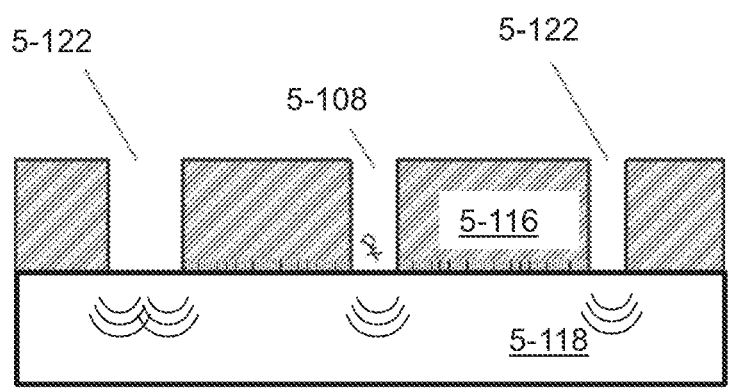
Figures 5, 5A:
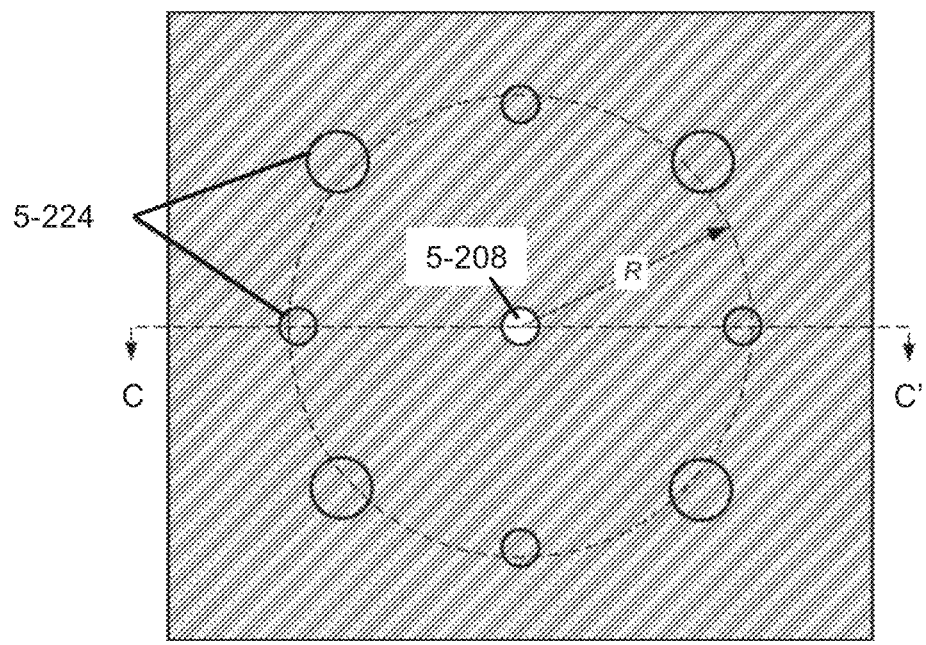
Figures 5, 5B:
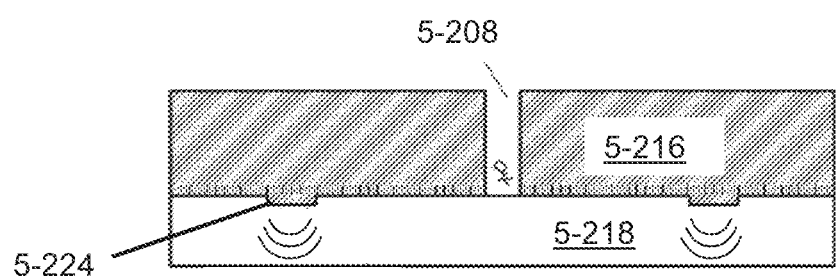
Figures 5, 5C:
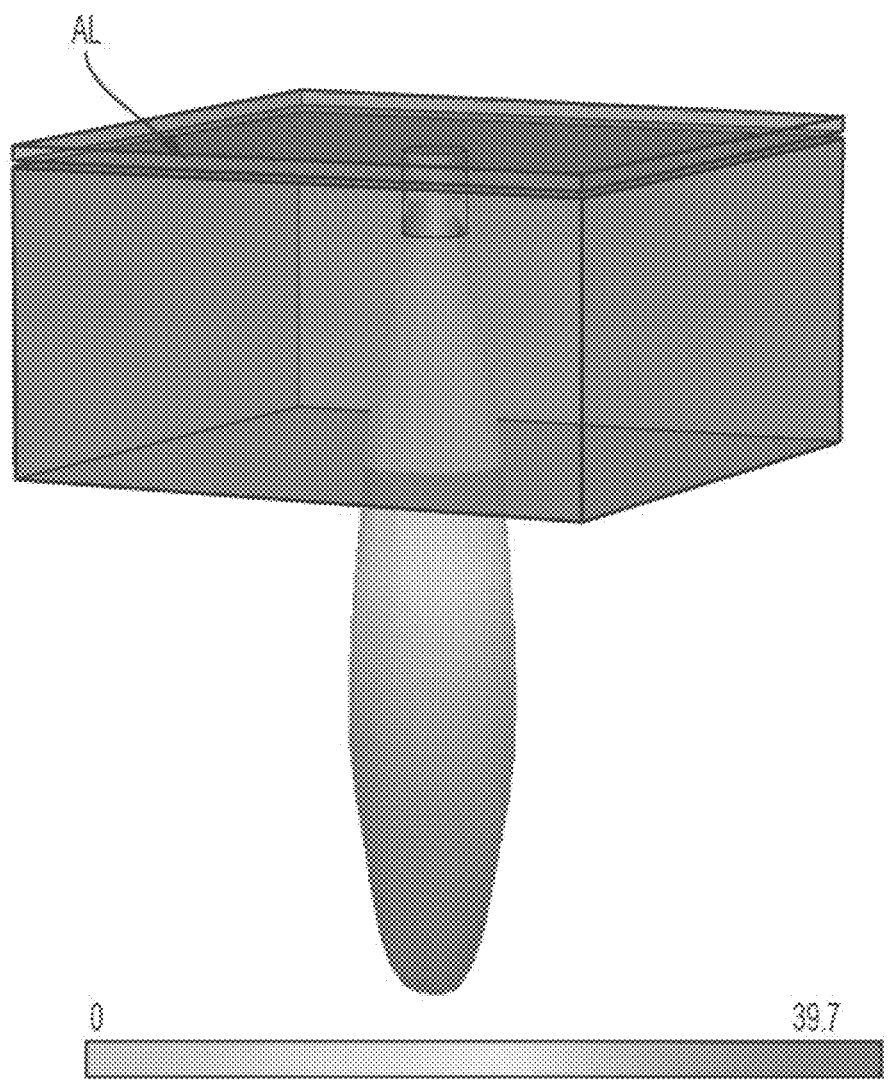
Figures 5, 6, 6A:
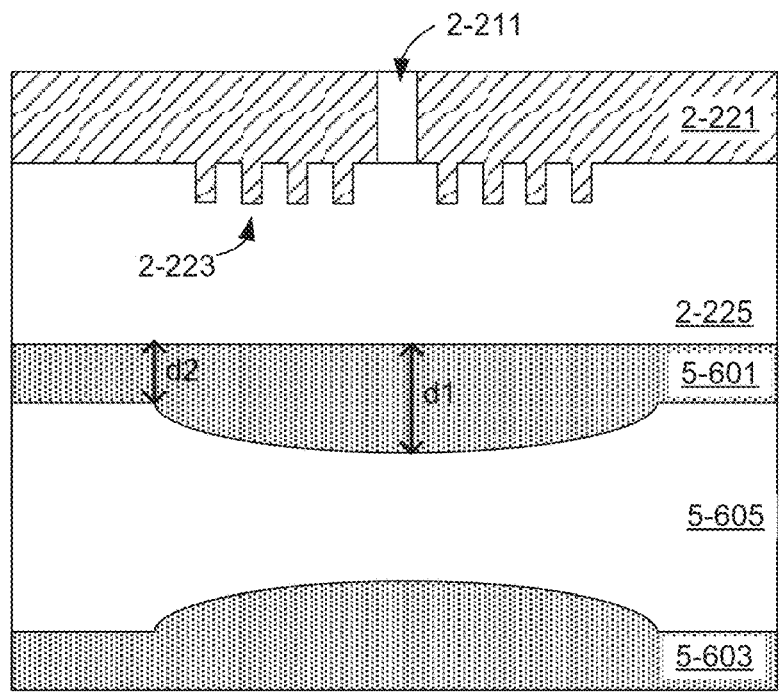
Figures 5, 6, 6B:
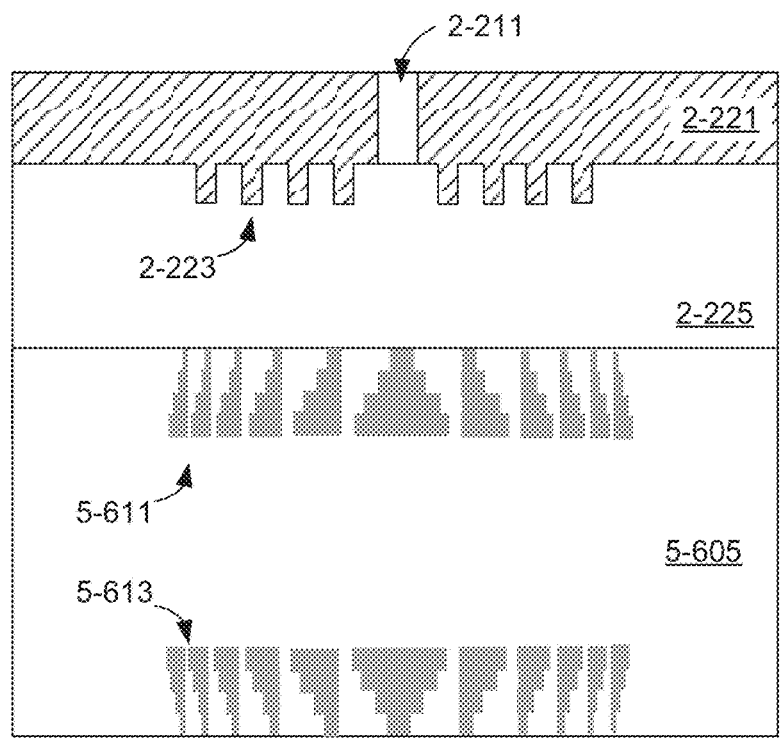
Figures 1, 6:
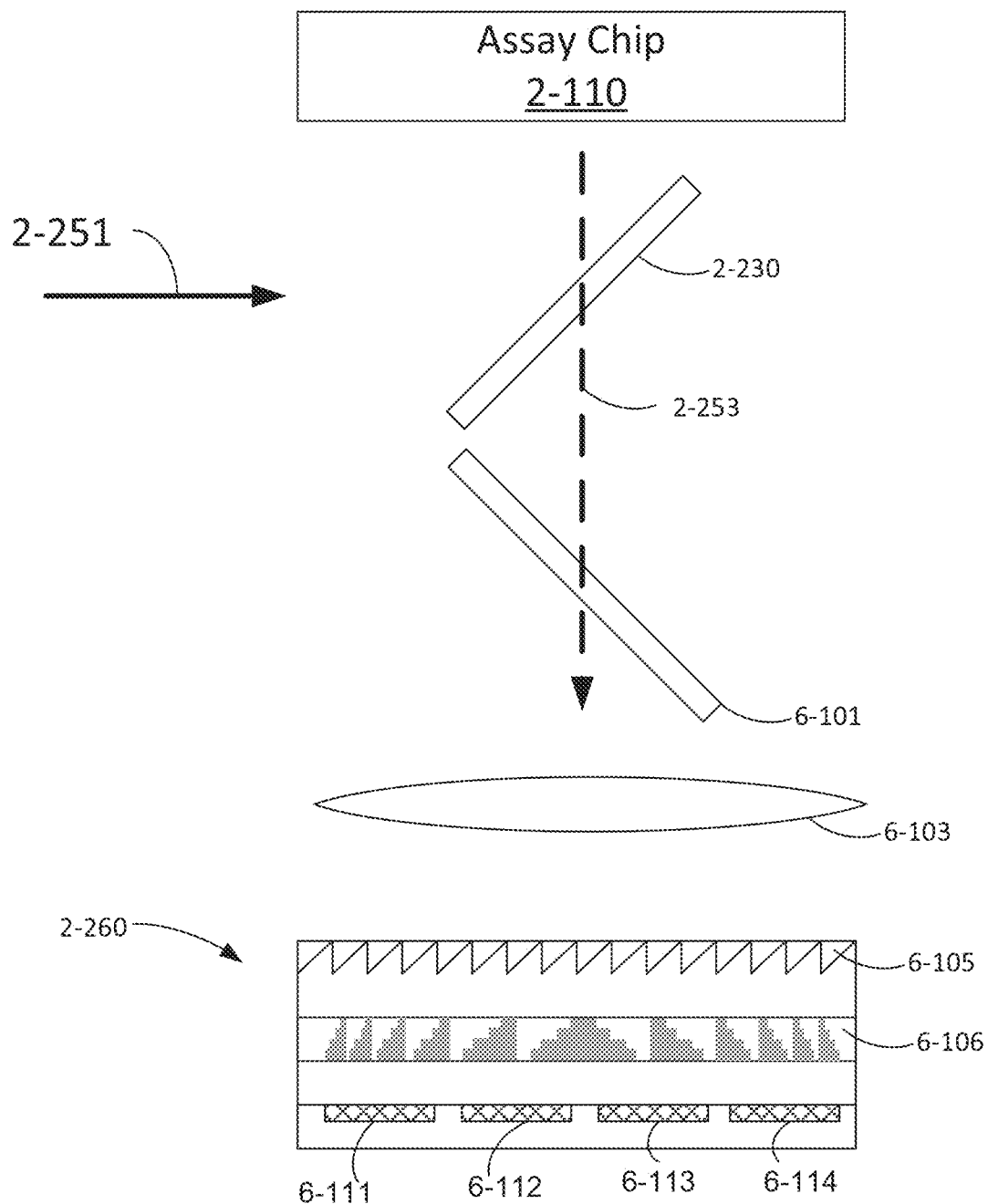
Figures 2A, 6:
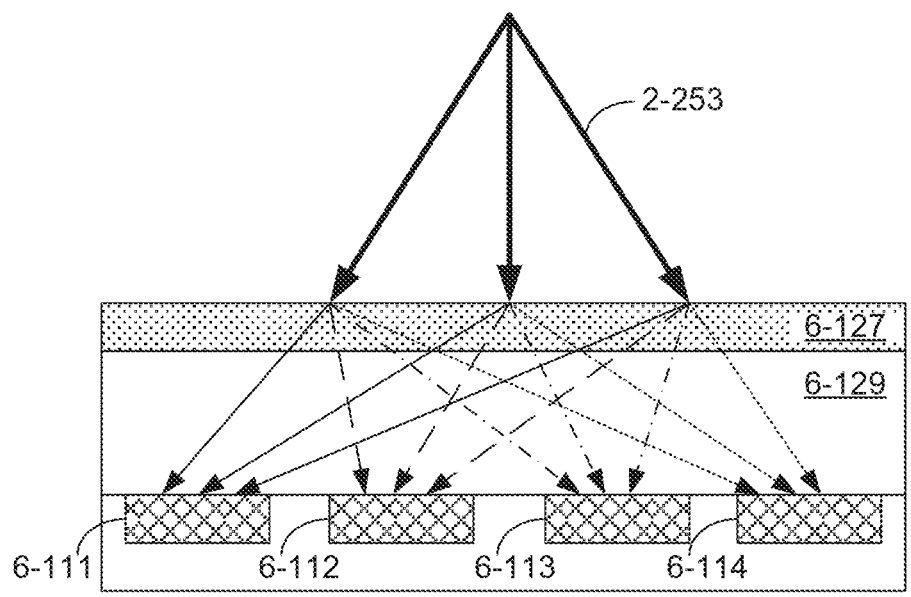
Figures 2B, 6:
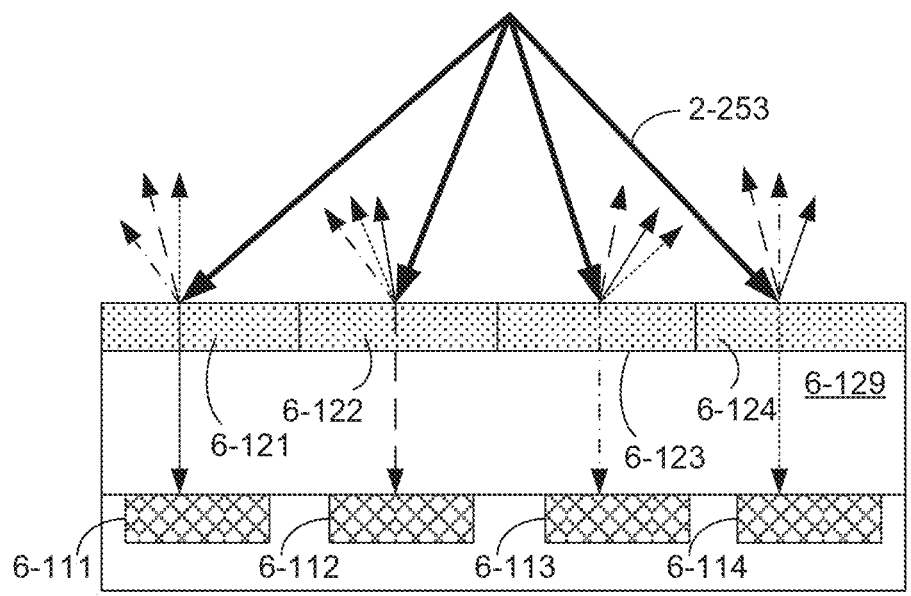
Figures 3A, 6:
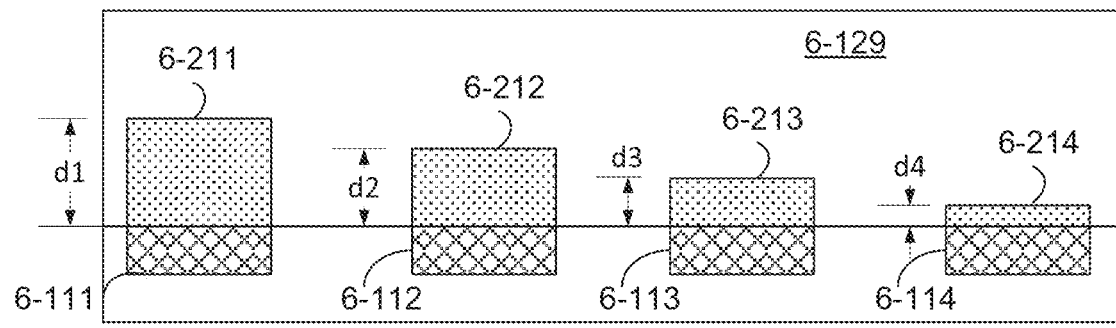
Figures 3B, 6:
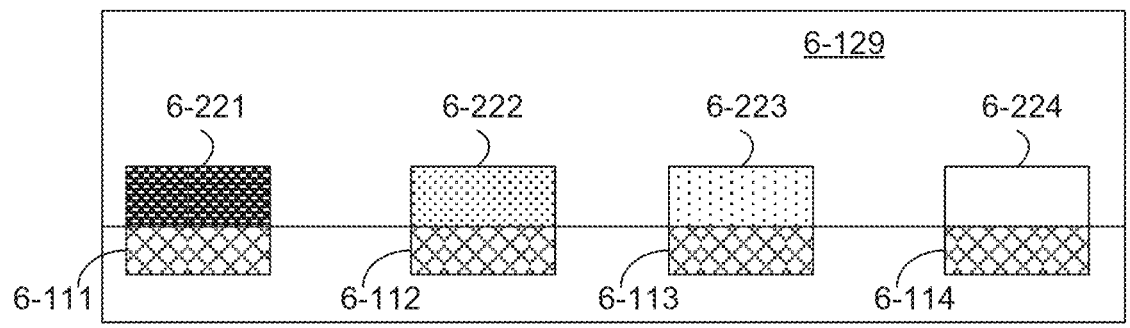
Figures 4A, 6:
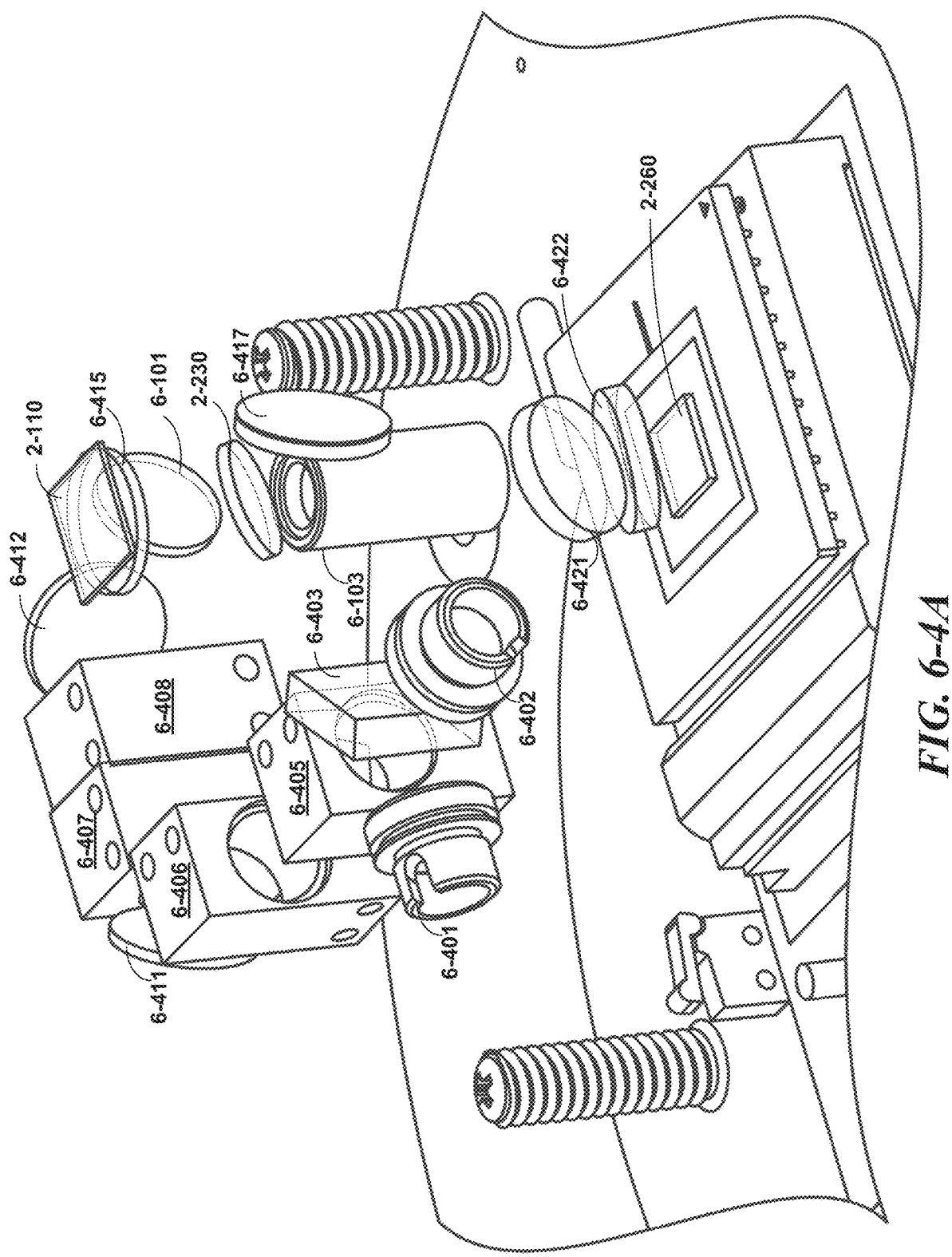
Figures 4B, 6:
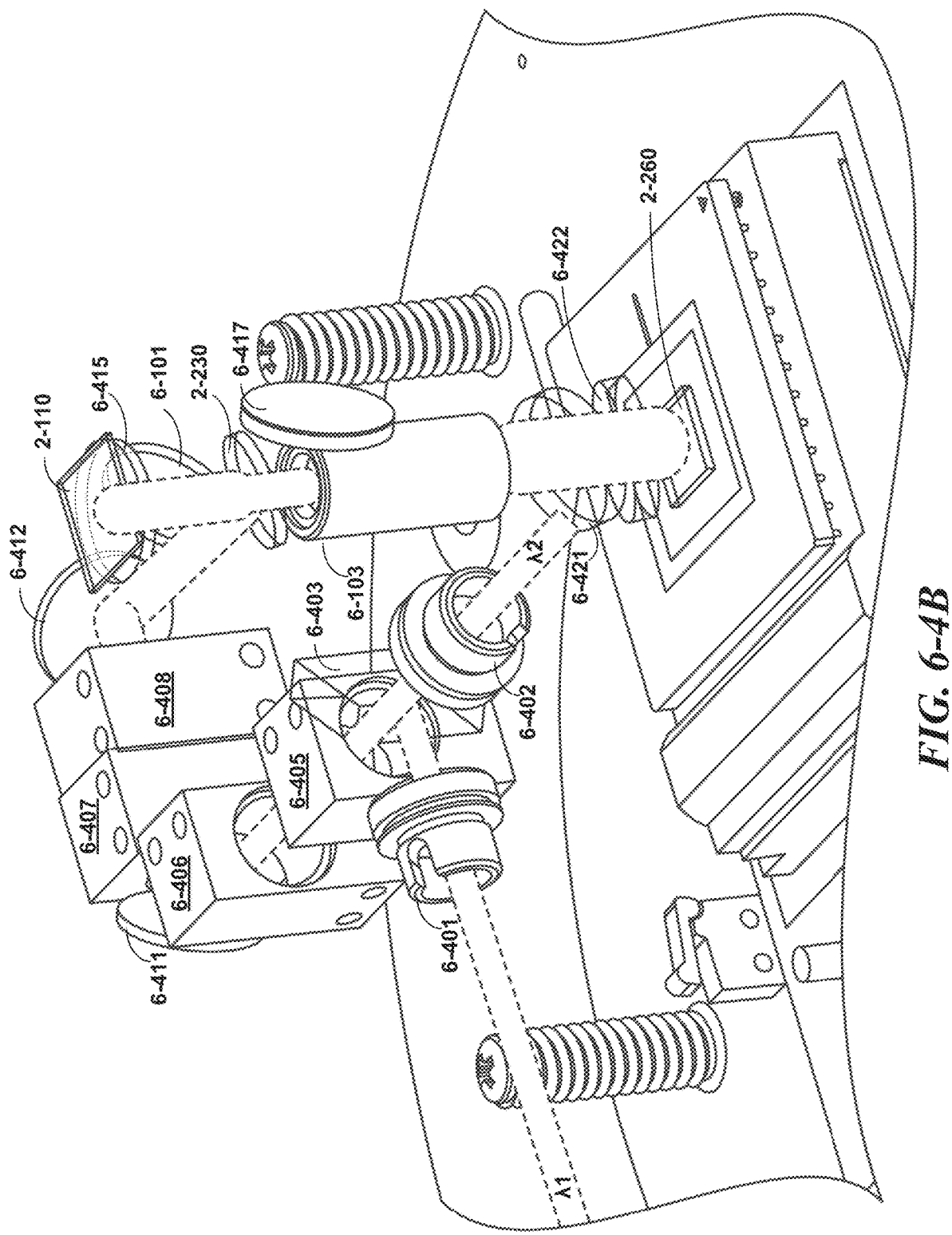
Figures 5, 6:
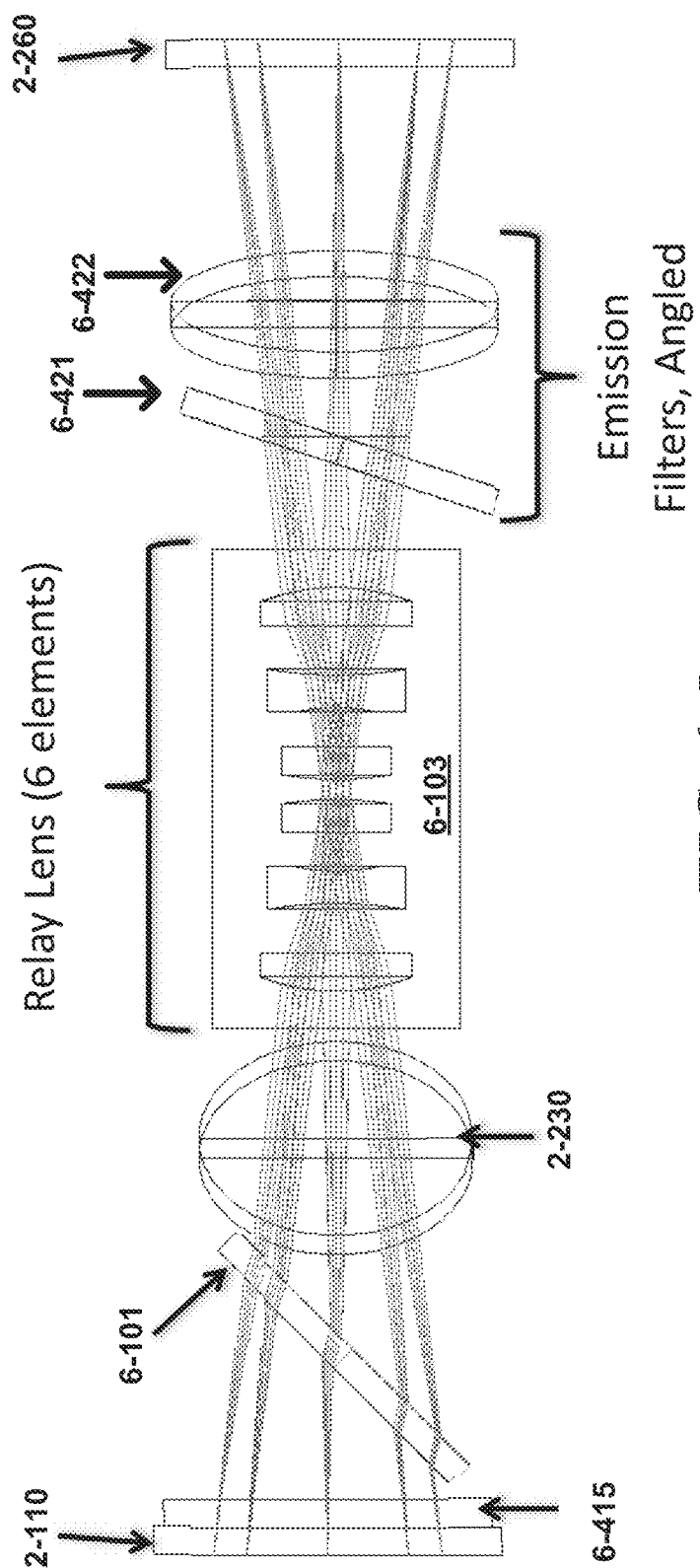

FIG. 8-8B illustrates temporal profiles of light pulses obtained from a transmission line, according to some embodiments.

Figures 3, 4, 5, 6, 7, 8, 9, 9A:
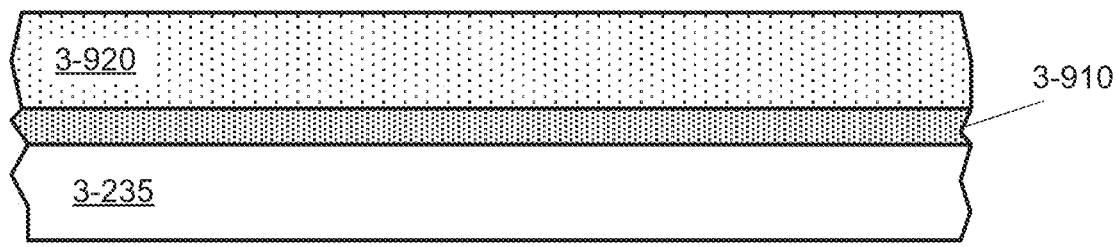
Figures 3, 4, 5, 6, 7, 8, 9, 9B:
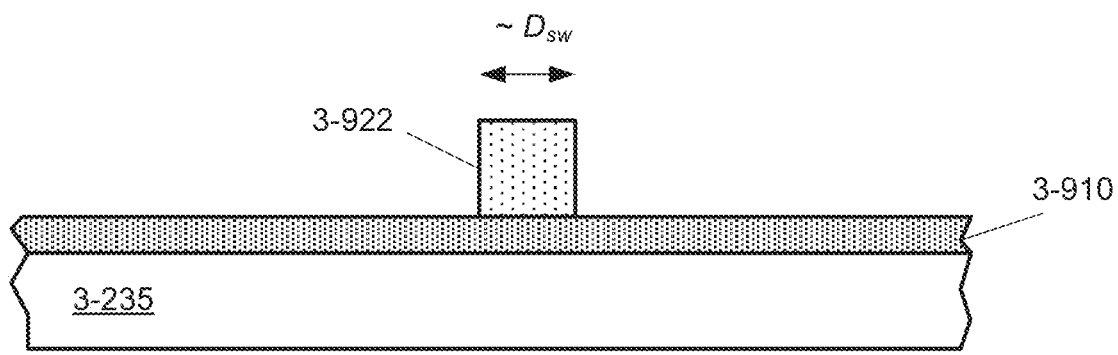
Figures 3, 4, 5, 6, 7, 8, 9, 9C:
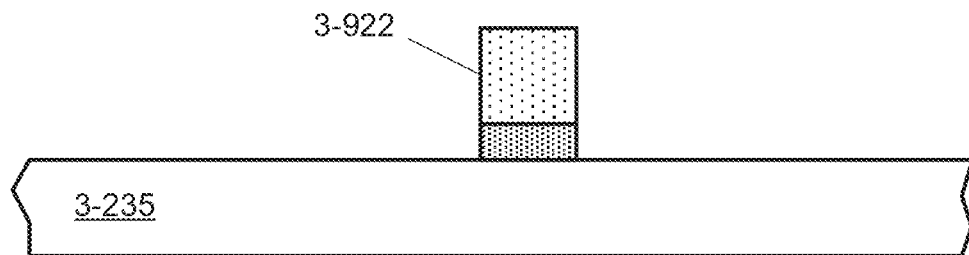
Figures 3, 4, 5, 6, 7, 8, 9, 9D:
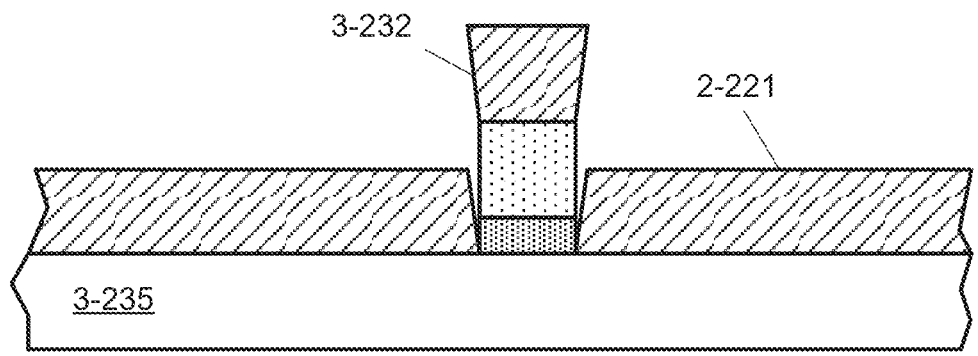
Figures 3, 4, 5, 6, 7, 8, 9, 9E:
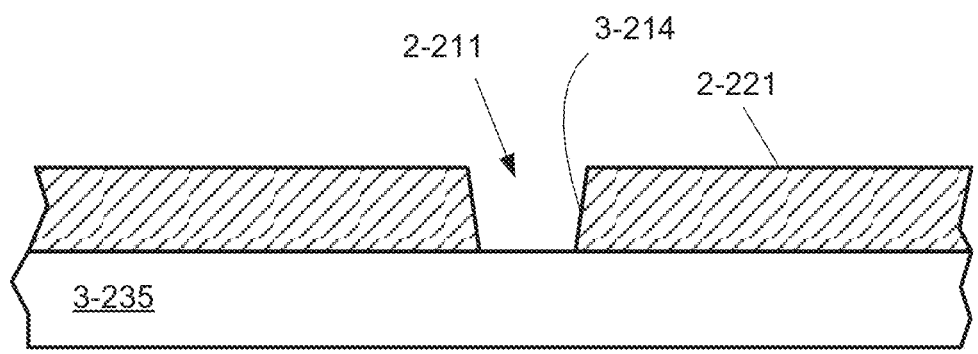
Figures 3, 4, 5, 6, 7, 8, 9, 9F:
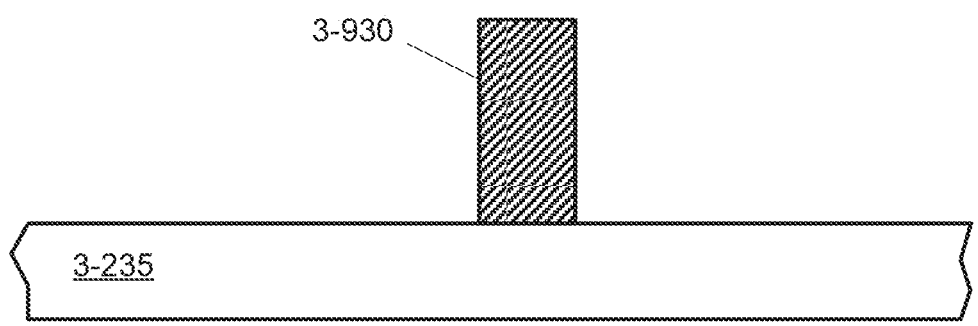
Figures 3, 4, 5, 6, 7, 8, 9, 10, 10A:
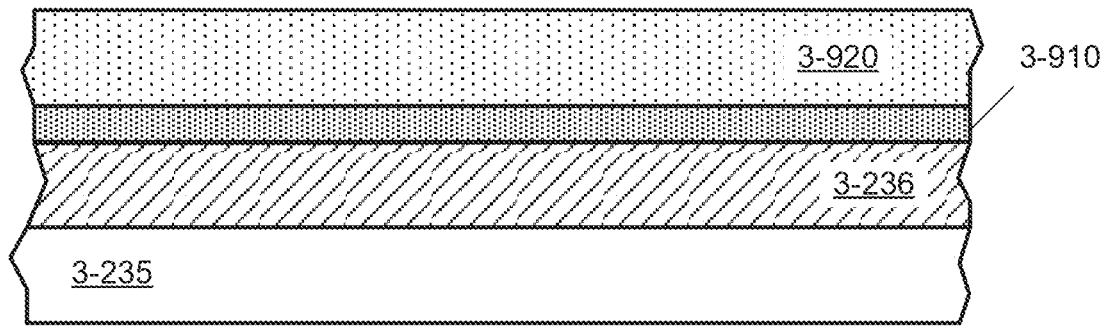
Figures 3, 4, 5, 6, 7, 8, 9, 10, 10B:
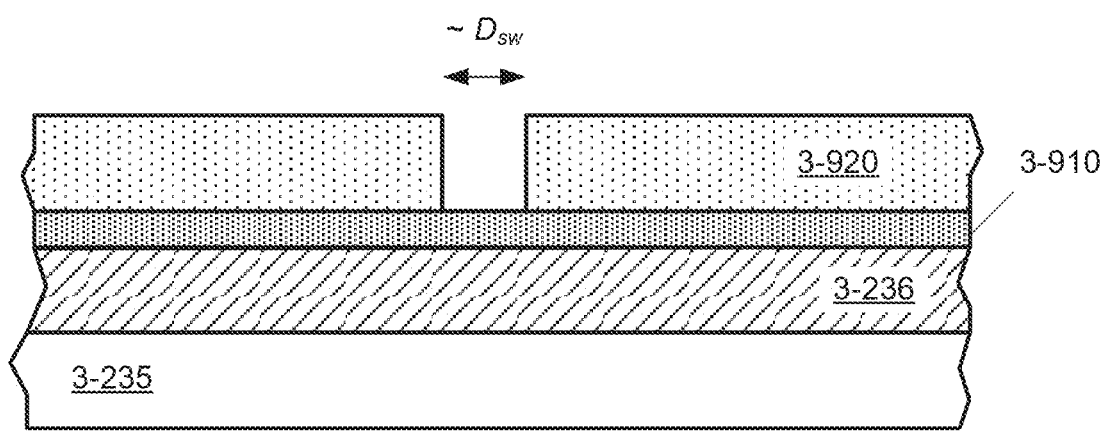
Figures 3, 4, 5, 6, 7, 8, 9, 10, 10C:
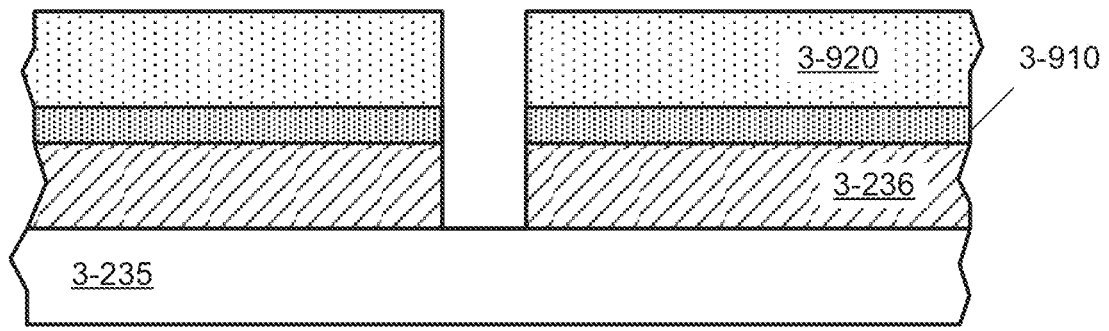
Figures 3, 4, 5, 6, 7, 8, 9, 10, 10D:
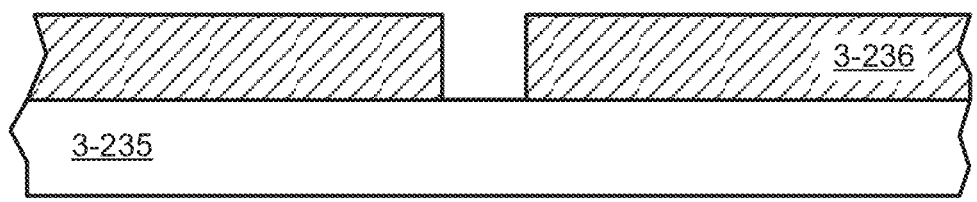

FIG. 8-9 and FIG. 8-10 are schematics of example circuits for generating pulsed excitation light, according to some embodiments.

FIG. 8-11A illustrates an example circuit having one RF amplifier that may be used to produce a tailored electrical signal as an output pulse, according to some embodiments.

FIG. 8-11B illustrates an electrical pulse profile obtained from the circuit of FIG. 8-11A.

FIG. 8-12A illustrates an example circuit having one RF amplifier that may be used to produce a tailored electrical signal as an output pulse, according to some embodiments.

FIG. 8-12B illustrates an electrical pulse profile obtained from the circuit of FIG. 8-12A.

FIG. 8-13A illustrates a schematic for combining four different sources, according to some embodiments.

FIG. 8-13B illustrates the current, power efficiency, and voltage for four sources as a function of impedance, according to some embodiments.

FIG. 9-1 depicts a method of operation of a compact apparatus that may be used for rapid, mobile analysis of biological and chemical specimens, according to some embodiments.

FIG. 9-2 depicts a calibration procedure, according to some embodiments.

FIG. 9-3 depicts a data-analysis procedure, according to some embodiments.

FIG. 10-1 is a schematic of single molecule nucleic acid sequencing, according to some embodiments.

FIG. 10-2 schematically illustrates a sequencing process in a single sample well over time.

FIG. 10-3 illustrates a process for preparing a sample well surface, according to some embodiments.

FIG. 10-4 illustrates example lifetime measurements, according to some embodiments.

FIG. 10-5 depicts a Fresnel lens integrated with a sensor, according to some embodiments.

FIG. 10-6 illustrates the luminescent lifetimes of four markers, according to some embodiments.

FIG. 10-7 illustrates 16 time bins used by a sensor to distinguish the markers from FIG. 10-6.

FIG. 10-8 illustrates the luminescent lifetimes of four markers, according to some embodiments.

FIG. 10-9 illustrates 13 time bins used by a sensor to distinguish the markers from FIG. 10-6.

FIG. 10-10 illustrates a lifetime and spectral measurement scheme, according to some embodiments.

Figures 3, 4, 5, 6, 7, 8, 9, 10, 11:
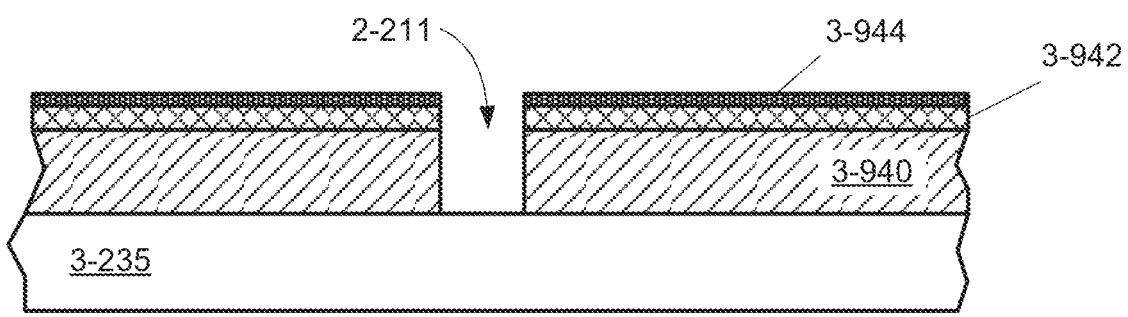

FIG. 10-11 illustrates the separation between four markers based on lifetime and emission wavelength, according to some embodiments.

Figures 3, 4, 5, 6, 7, 8, 9, 10, 11, 12:
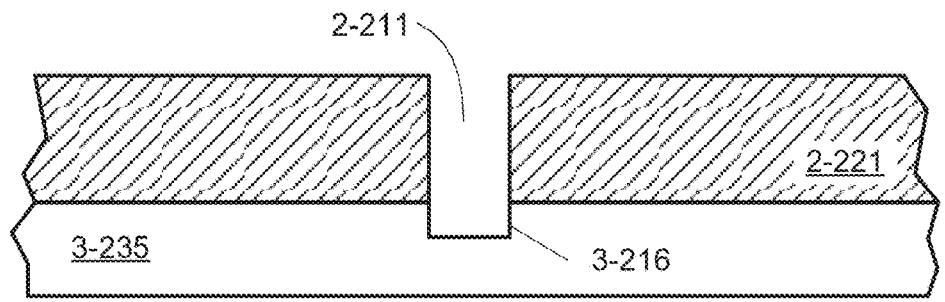

FIG. 10-12 illustrates the emission spectra of three markers, according to some embodiments.

FIG. 10-13 illustrates the fluorescence lifetimes of four markers, according to some embodiments.

FIG. 10-14 illustrates signal profiles of the three markers from FIG. 10-12 using a four-segment sensor, according to some embodiments.

FIG. 10-15 illustrates the fluorescence lifetimes of four markers, according to some embodiments.

FIG. 10-16 illustrates signal profiles of ATRho14 using a four-segment sensor, according to some embodiments.

FIG. 10-17 illustrates a lifetime and absorption energy measurement scheme, according to some embodiments.

FIG. 10-18 illustrates the absorption spectra of four markers, according to some embodiments.

FIG. 10-19 illustrates the lifetime measurements of two markers, according to some embodiments.

FIG. 10-20 illustrates 8 time bins used by a sensor to distinguish the markers from FIG. 10-19.

FIG. 10-21 illustrates the signal profiles of four markers, according to some embodiments.

FIG. 10-22 illustrates the emission spectrum of four markers, according to some embodiments.

FIG. 10-23 depicts a computing environment, according to some embodiments.

FIG. 11-1 illustrates a method of fabricating a sample well, according to some embodiments.

FIG. 11-2 illustrates a method of fabricating a sample well using a lift-off method, according to some embodiments.

FIG. 11-3 illustrates a method of forming a sample well, according to some embodiments.

FIG. 11-4 illustrates a method of forming a concentric grating, according to some embodiments.

FIG. 11-5 illustrates a method of forming a concentric grating, according to some embodiments.

FIG. 11-6 illustrates a method of positioning the nanoaperture, according to some embodiments.

FIG. 11-7 illustrates a method of lens array fabrication, according to some embodiments.

FIG. 11-8 illustrates a refractive lens array, according to some embodiments.

FIG. 11-9 illustrates a refractive lens array, according to some embodiments.

FIG. 11-10 illustrates a method of forming a lens, according to some embodiments.

FIG. 11-11 illustrates a method of forming a lens, according to some embodiments.

FIG. 11-12 illustrates a diffractive optical element, according to some embodiments.

Figures 3, 4, 5, 6, 7, 8, 9, 10, 11, 12, 13, 13A:
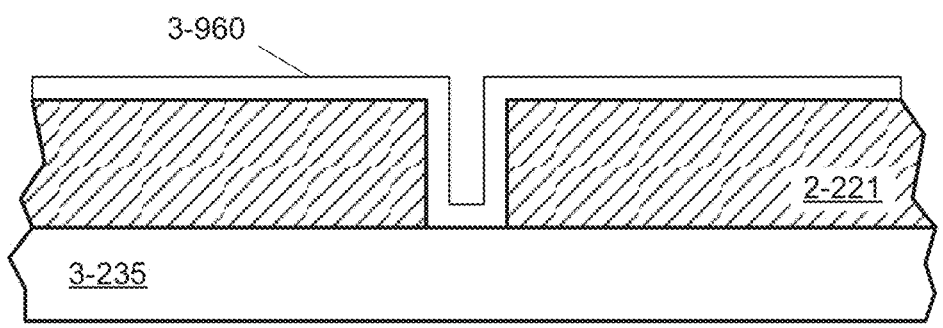
Figures 3, 4, 5, 6, 7, 8, 9, 10, 11, 12, 13, 13B:
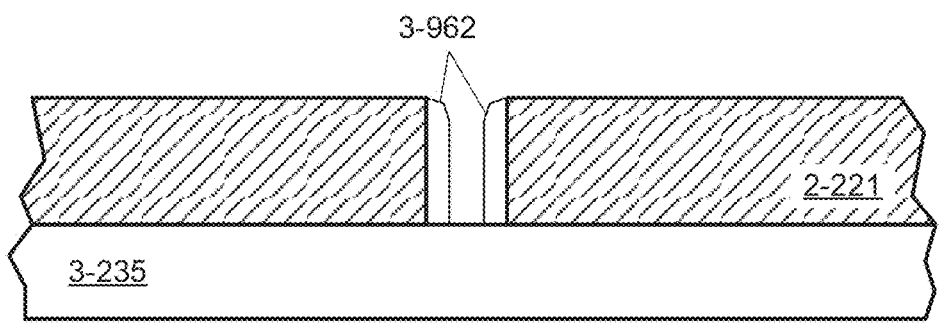
Figures 3, 4, 5, 6, 7, 8, 9, 10, 11, 12, 13, 13C:
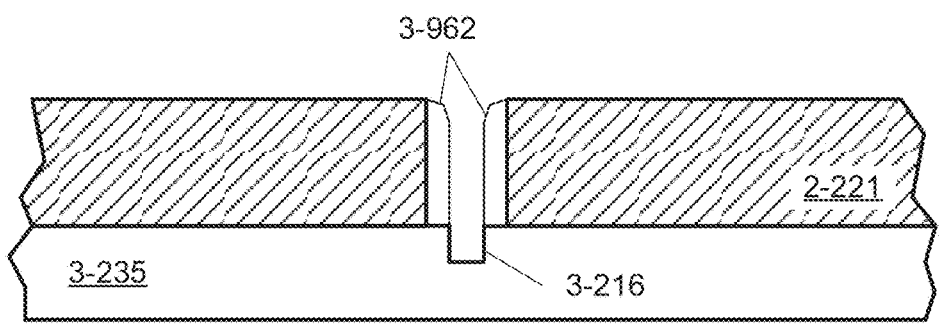
Figures 3, 4, 5, 6, 7, 8, 9, 10, 11, 12, 13, 14, 14A:
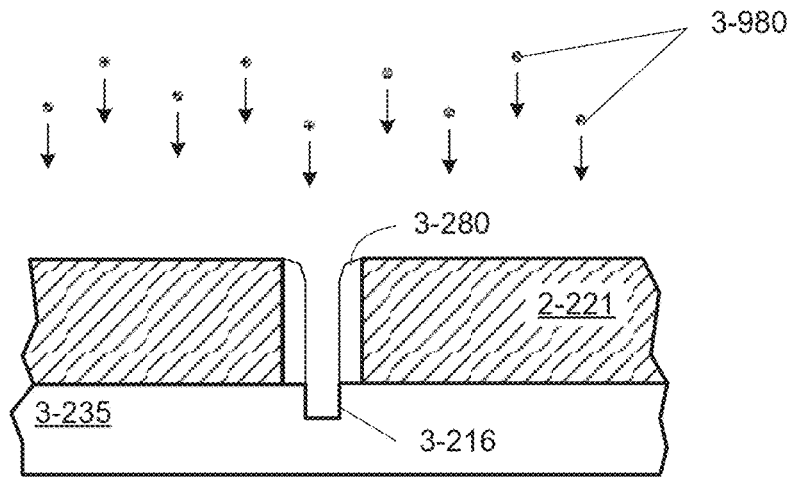
Figures 3, 4, 5, 6, 7, 8, 9, 10, 11, 12, 13, 14, 14B:
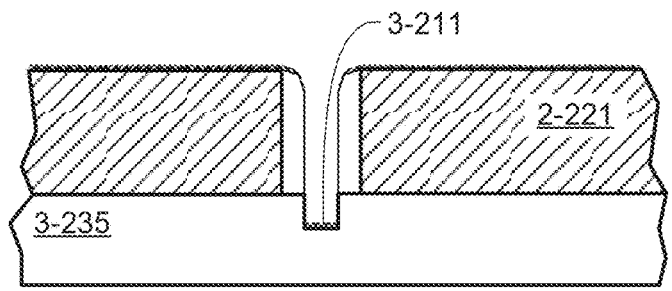
Figures 3, 4, 5, 6, 7, 8, 9, 10, 11, 12, 13, 14, 14C:
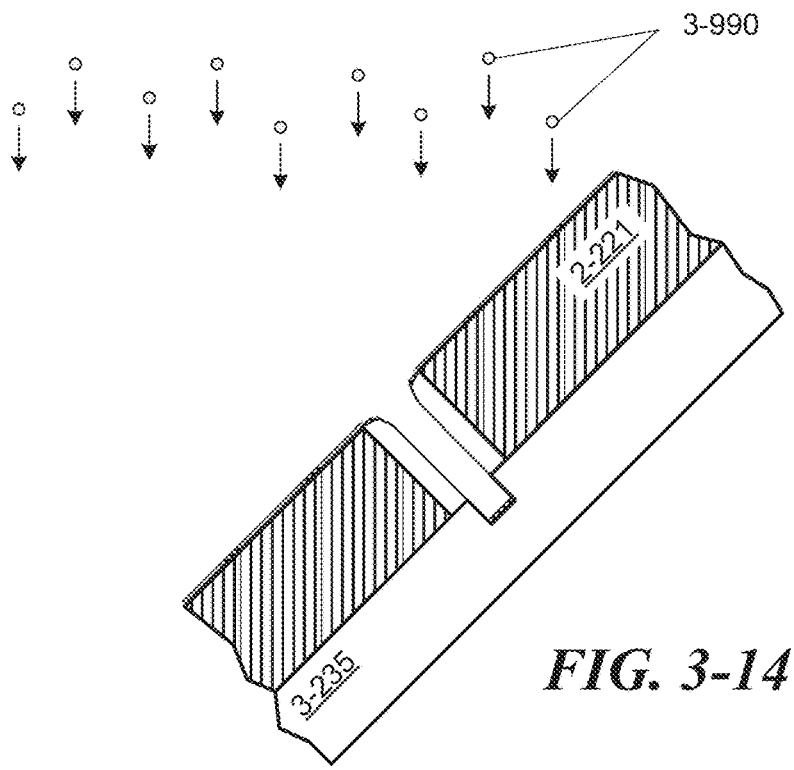
Figures 3, 4, 5, 6, 7, 8, 9, 10, 11, 12, 13, 14, 14D:
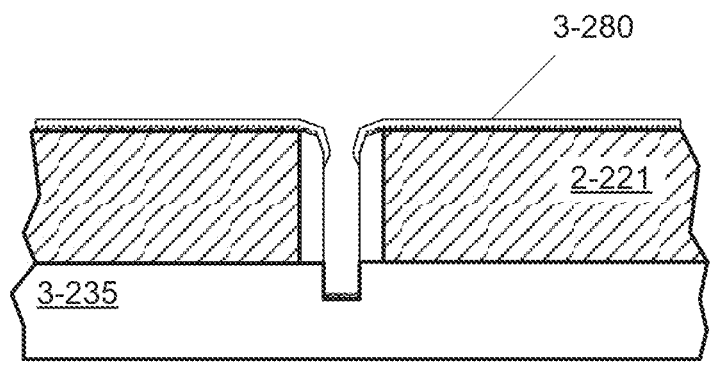
Figures 3, 4, 5, 6, 7, 8, 9, 10, 11, 12, 13, 14, 15:
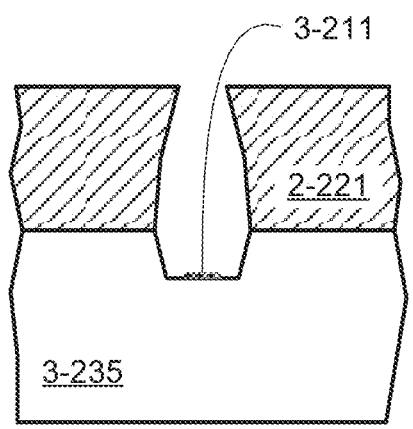

FIG. 11-13 illustrates two unit cell layers used to form a diffractive optical element, according to some embodiments.

FIG. 11-14 illustrates a diffractive lens pattern according to some embodiments.

FIG. 11-15 and FIG. 11-16 illustrate a method of fabricating a diffractive optical element, according to some embodiments.

FIG. 11-17 and FIG. 11-18 and FIG. 11-19 illustrate a method of fabricating an embedded Fresnel lens, according to some embodiments.

The features and advantages of embodiments of the present application will become more apparent from the detailed description set forth below when taken in conjunction with the drawings.

DETAILED DESCRIPTION

The inventors have recognized and appreciated that conventional apparatuses for performing bioassays are large, expensive and require advanced laboratory techniques to perform. Many types of bioassays depend on the detection of single molecules in a specimen. Conventionally single molecule detection may require large, bulky laser systems used to generate high intensity light needed for excitation of molecules. In addition, bulky optical components may be used to direct the laser light to the specimen and additional optical components may be used to direct luminescent light from the specimen to a sensor. These conventional optical components may require precise alignment and stabilization. The conventional laboratory equipment and training required to use this conventional equipment may result in complex, expensive bioassays.

The inventors have recognized and appreciated that there is a need for a device that can simply and inexpensively analyze biological and/or chemical specimens to determine the identity of its constituent parts. An application of such a device may be for sequencing a biomolecule, such as a nucleic acid molecule or a polypeptide (e.g., protein) having a plurality of amino acids. A compact, high-speed apparatus for performing detection and quantitation of single molecules or particles could reduce the cost of performing complex quantitative measurements of biological and/or chemical samples and rapidly advance the rate of biochemical technological discoveries. Moreover, a cost-effective device that is readily transportable could transform not only the way bioassays are performed in the developed world, but provide people in developing regions, for the first time, ready access to essential diagnostic tests that could dramatically improve their health and well-being. For example, in some embodiments, an apparatus for performing bioassays is used to perform diagnostic tests of biological samples, such as blood, urine and/or saliva. The apparatus may be used by individuals in their home, by a doctor in remote clinics of developing countries or any other location, such as rural doctors' offices. Such diagnostic tests can include the detection of biomolecules in a biological sample of a subject, such as a nucleic acid molecule or protein. In some examples, diagnostic tests include sequencing a nucleic acid molecule in a biological sample of a subject, such as sequencing of cell free deoxyribonucleic acid molecules or expression products in a biological sample of the subject.

The inventors have also recognized and appreciated that, when a sample is tagged with a plurality of different types of luminescent markers, any suitable characteristic of luminescent markers may be used to identify the type of marker that is present in a particular pixel of the integrated device. For example, characteristics of the luminescence emitted by the markers and/or characteristics of the excitation absorption may be used to identify the markers. In some embodiments, the emission energy of the luminescence (which is directly related to the wavelength of the light) may be used to distinguish a first type of marker from a second type of marker. Additionally, or alternatively, luminescence lifetime measurements may also be used to identify the type of marker present at a particular pixel. In some embodiments, luminescence lifetime measurements may be made with a pulsed excitation source using a sensor capable of distinguishing a time when a photon is detected with sufficient resolution to obtain lifetime information. Additionally, or alternatively, the energy of the excitation light absorbed by the different types of markers may be used to identify the type of marker present at a particular pixel. For example, a first marker may absorb light of a first wavelength, but not equally absorb light of a second wavelength, while a second marker may absorb light of the second wavelength, but not equally absorb light of the first wavelength. In this way, when more than one excitation light source, each with a different excitation energy, may be used to illuminate the sample in an interleaved manner, the absorption energy of the markers can be used to identify which type of marker is present in a sample. Different markers may also have different luminescent intensities. Accordingly, the detected intensity of the luminescence may also be used to identify the type of marker present at a particular pixel.

One non-limiting example of an application of a device contemplated by the inventors is a device capable of performing sequencing of a biomolecule, such as a nucleic acid or a polypeptide (e.g. protein) having a plurality of amino acids. Diagnostic tests that may be performed using such a device include sequencing a nucleic acid molecule in a biological sample of a subject, such as sequencing of cell free deoxyribonucleic acid molecules or expression products in a biological sample of the subject.

The present application provides devices, systems and methods for detecting biomolecules or subunits thereof, such as nucleic acid molecules. Such detection can include sequencing. A biomolecule may be extracted from a biological sample obtained from a subject. The biological sample may be extracted from a bodily fluid or tissue of the subject, such as breath, saliva, urine or blood (e.g., whole blood or plasma). The subject may be suspected of having a health condition, such as a disease (e.g., cancer). In some examples, one or more nucleic acid molecules are extracted from the bodily fluid or tissue of the subject. The one or more nucleic acids may be extracted from one or more cells obtained from the subject, such as part of a tissue of the subject, or obtained from a cell-free bodily fluid of the subject, such as whole blood.

Sequencing can include the determination of individual subunits of a template biomolecule (e.g., nucleic acid molecule) by synthesizing another biomolecule that is complementary or analogous to the template, such as by synthesizing a nucleic acid molecule that is complementary to a template nucleic acid molecule and identifying the incorporation of nucleotides with time (i.e., sequencing by synthesis). As an alternative, sequencing can include the direct identification of individual subunits of the biomolecule.

During sequencing, signals indicative of individual subunits of a biomolecule may be collected in memory and processed in real time or at a later point in time to determine a sequence of the biomolecule. Such processing can include a comparison of the signals to reference signals that enable the identification of the individual subunits, which in some cases yields reads. Reads may be sequences of sufficient length (e.g., at least about 30 base pairs (bp)) that can be used to identify a larger sequence or region, e.g., that can be aligned to a location on a chromosome or genomic region or gene.

Individual subunits of biomolecules may be identified using markers. In some examples, luminescent markers are used to identified individual subunits of biomolecules. Some embodiments use luminescent markers (also referred to herein as "markers"), which may be exogenous or endogenous markers. Exogenous markers may be external luminescent markers used as a reporter and/or tag for luminescent labeling. Examples of exogenous markers may include, but are not limited to, fluorescent molecules, fluorophores, fluorescent dyes, fluorescent stains, organic dyes, fluorescent proteins, species that participate in fluorescence resonance energy transfer (FRET), enzymes, and/or quantum dots. Other exogenous markers are known in the art. Such exogenous markers may be conjugated to a probe or functional group (e.g., molecule, ion, and/or ligand) that specifically binds to a particular target or component. Attaching an exogenous tag or reporter to a probe allows identification of the target through detection of the presence of the exogenous tag or reporter. Examples of probes may include proteins, nucleic acid (e.g., DNA, RNA) molecules, lipids and antibody probes. The combination of an exogenous marker and a functional group may form any suitable probes, tags, and/or labels used for detection, including molecular probes, labeled probes, hybridization probes, antibody probes, protein probes (e.g., biotin-binding probes), enzyme labels, fluorescent probes, fluorescent tags, and/or enzyme reporters.

Although the present disclosure makes reference to luminescent markers, other types of markers may be used with devices, systems and methods provided herein. Such markers may be mass tags, electrostatic tags, or electrochemical labels.

While exogenous markers may be added to a sample, endogenous markers may be already part of the sample. Endogenous markers may include any luminescent marker present that may luminesce or "autofluoresce" in the presence of excitation energy. Autofluorescence of endogenous fluorophores may provide for label-free and noninvasive labeling without requiring the introduction of exogenous fluorophores. Examples of such endogenous fluorophores may include hemoglobin, oxyhemoglobin, lipids, collagen and elastin crosslinks, reduced nicotinamide adenine dinucleotide (NADH), oxidized flavins (FAD and FMN), lipofuscin, keratin, and/or prophyrins, by way of example and not limitation.

While some embodiments may be directed to diagnostic testing by detecting single molecules in a specimen, the inventors have also recognized that the single molecule detection capabilities of the present disclosure may be used to perform polypeptide (e.g., protein) sequencing or nucleic acid (e.g., DNA, RNA) sequencing of one or more nucleic acid segments of, for example, genes. Nucleic acid sequencing technologies may vary in the methods used to determine the nucleic acid sequence as well as in the rate, read length, and incidence of errors in the sequencing process. For example, some nucleic acid sequencing methods are based on sequencing by synthesis, in which the identity of a nucleotide is determined as the nucleotide is incorporated into a newly synthesized strand of nucleic acid that is complementary to the target nucleic acid.

Having recognized the need for simple, less complex apparatuses for performing single molecule detection and/or nucleic acid sequencing, the inventors have conceived of techniques for detecting single molecules using sets of luminescent tags to label different molecules using sets of tags, such as optical (e.g., luminescent) tags, to label different molecules. Such single molecules may be nucleotides or amino acids having tags. Tags may be detected while bound to single molecules, upon release from the single molecules, or while bound to and upon release from the single molecules. In some examples, tags are luminescent tags. Each luminescent tag in a selected set is associated with a respective molecule. For example, a set of four tags may be used to "label" the nucleobases present in DNA—each tag of the set being associated with a different nucleobase, e.g., a first tag being associated with adenine (A), a second tag being associated with cytosine (C), a third tag being associated with guanine (G), and a fourth tag being associated with thymine (T). Moreover, each of the luminescent tags in the set of tags has different properties that may be used to distinguish a first tag of the set from the other tags in the set. In this way, each tag is uniquely identifiable using one or more of these distinguishing characteristics. By way of example and not limitation, the characteristics of the tags that may be used to distinguish one tag from another may include the emission energy and/or wavelength of the light that is emitted by the tag in response to excitation energy and/or the wavelength of the excitation light that is absorbed by a particular tag to place the tag in an excited state.

Luminescent markers vary in the wavelength of light they emit, the temporal characteristics of the light they emit (e.g., their emission decay time periods), and their response to excitation energy. Accordingly, luminescent markers may be identified or discriminated from other luminescent markers based on detecting these properties. Such identification or discrimination techniques may be used alone or in any suitable combination.

In some embodiments, an integrated photodetector as described in the present application can measure or discriminate luminance lifetimes, such as fluorescence lifetimes. Lifetime measurements are based on exciting one or more markers (e.g., fluorescent molecules), and measuring the time variation in the emitted luminescence. The probability of a marker to emit a photon after the marker reaches an excited state decreases exponentially over time. The rate at which the probability decreases may be characteristic of a marker, and may be different for different markers. Detecting the temporal characteristics of light emitted by markers may allow identifying markers and/or discriminating markers with respect to one another.

After reaching an excited state, a marker may emit a photon with a certain probability at a given time. The probability of a photon being emitted from an excited marker may decrease over time after excitation of the marker. The decrease in the probability of a photon being emitted over time may be represented by an exponential decay function $p(t)=e^{(-t/\tau)}$, where $p(t)$ is the probability of photon emission at a time, t, and $\tau$ is a temporal parameter of the marker. The temporal parameter $\tau$ indicates a time after excitation when the probability of the marker emitting a photon is a certain value. The temporal parameter, $\tau$, is a property of a marker that may be distinct from its absorption and emission spectral properties. Such a temporal parameter, $\tau$, is referred to as the luminance lifetime, the fluorescence lifetime or simply the "lifetime" of a marker.

FIG. 1-1 plots the probability of a photon being emitted as a function of time for two markers with different lifetimes. The marker represented by probability curve B has a probability of emission that decays more quickly than the probability of emission for the marker represented by probability curve A. The marker represented by probability curve B has a shorter temporal parameter, $\tau$, or lifetime than the marker represented by probability curve A. Markers may have lifetimes ranging from 0.1-20 ns, in some embodiments. However, the techniques described herein are not limited as to the lifetimes of the marker(s) used.

The lifetime of a marker may be used to distinguish among more than one marker, and/or may be used to identify marker(s). In some embodiments, lifetime measurements may be performed in which a plurality of markers having different lifetimes is excited by an excitation source. As an example, four markers having lifetimes of 0.5, 1, 2, and 3 nanoseconds, respectively, may be excited by a light source that emits light having a selected wavelength (e.g., 635 nm, by way of example). The markers may be identified or differentiated from each other based on measuring the lifetime of the light emitted by the markers.

Lifetime measurements may use relative intensity measurements by comparing how intensity changes over time, as opposed to absolute intensity values. As a result, lifetime measurements may avoid some of the difficulties of absolute intensity measurements. Absolute intensity measurements may depend on the concentration of markers present and calibration steps may be needed for varying marker concentrations. By contrast, lifetime measurements may be insensitive to the concentration of markers.

Embodiments may use any suitable combination of tag characteristics to distinguish a first tag in a set of tags from the other tags in the same set. For example, some embodiments may use only the timing information of the emission light from the tags to identify the tags. In such embodiments, each tag in a selected set of tags has a different emission lifetime from the other tags in the set and the luminescent tags are all excited by light from a single excitation source. FIG. 1-2A illustrates the emission timing from four luminescent tags according to an embodiment where the four tags exhibit different average emission lifetimes ($\tau$). The probability that a tag is measured to have a lifetime of a particular value is referred to herein as the tag's "emission timing." A first emission timing 1-101 from a first luminescent tag has a peak probability of having a lifetime of at $\tau 1$, a second emission timing 1-102 from a second luminescent tag has a peak probability of having a lifetime of at $\tau 2$, a third emission timing 1-103 from a third luminescent tag has a peak probability of having a lifetime of at $\tau 3$, and a fourth emission timing 1-104 from a fourth luminescent tag has a peak probability of having a lifetime of at $\tau 4$. In this embodiment, the lifetime probability peaks of the four luminescent tags may have any suitable values that satisfy the relation $\tau 1 < \tau 2 < \tau 3 < \tau 4$. The four timing emission graphs may or may not overlap due to slight variations in the lifetime of a particular luminescent tag, as illustrated in FIG. 1-2A. In this embodiment, the excitation wavelength at which each of the four tags maximally absorbs light from the excitation source is substantially equal, but that need not be the case. Using the above tag set, four different molecules may be labeled with a respective tag from the tag set, the tags may be excited using a single excitation source, and the tags can be distinguished from one another by detecting the emission lifetime of the tags using an optical system and sensors. While FIG. 1-2A illustrates four different tags, it should be appreciated that any suitable number of tags may be used.

Other embodiments may use any suitable combination of tag characteristics to determine the identity of the tag within a set of tags. Examples of the tag characteristics that may be used include, but are not limited to excitation wavelength, emission wavelength, and emission lifetime. The combination of tag characteristics form a phase space and each tag may be represented as a point within this phase space. Tags within a set of tags should be selected such that the "distance" between each tag within the set is sufficiently large that the detection mechanism can distinguish each tag from the other tags in the set. For example, in some embodiments a set of tags may be selected where a subset of the tags have the same emission wavelength, but have different emission lifetimes and/or different excitation wavelengths. In other embodiments, a set of tags may be selected where a subset of the tags have the same emission lifetime, but have different emission wavelengths and/or different excitation wavelengths. In other embodiments, a set of tags may be selected where a subset of the tags have the same excitation wavelength, but have different emission wavelengths and/or different emission lifetimes.

By way of example and not limitation, FIG. 1-2B illustrates the emission spectra from four luminescent tags according to an embodiment where two of the tags have a first peak emission wavelength and the other two tags have a second peak emission wavelength. A first emission spectrum 1-105 from a first luminescent tag has a peak emission wavelength at $\lambda 1$, a second emission spectrum 1-106 from a second luminescent tag also has a peak emission wavelength at $\lambda 1$, a third emission spectrum 1-107 from a third luminescent tag has a peak emission wavelength at $\lambda 2$, and a fourth emission spectrum 1-108 from a fourth luminescent tag also has a peak emission wavelength at $\lambda 2$. In this embodiment, the emission peaks of the four luminescent tags may have any suitable values that satisfy the relation $\lambda 1 < \lambda 2$. In embodiments such as this where the peak emission wavelength is the same for more than one luminescent tag, a separate characteristic of the tags that have the same emission wavelength must be different. For example, the two tags that emit at $\lambda 1$ may have different emission lifetimes. FIG. 1-3A illustrates this situation schematically in a phase space spanned by the emission wavelength and the emission lifetime. A first tag has an emission wavelength $\lambda 1$ and a emission lifetime $\tau 1$, a second tag has an emission wavelength $\lambda 1$ and a emission lifetime $\tau 4$, a third tag has an emission wavelength $\lambda 2$ and a emission lifetime $\tau 1$, and a fourth tag has an emission wavelength $\lambda 2$ and a emission lifetime $\tau 4$. In this way, all four tags in the tag set shown in FIG. 1-3A are distinguishable from one another. Using such a tag set allows distinguishing between four tags even when the absorption wavelengths for the four dyes are identical. This is possible using a sensor that can detect the time of emission of the photoluminescence as well as the emission wavelength.

By way of example and not limitation, FIG. 1-2C illustrates the absorption spectra from four luminescent tags according to another embodiment. In this embodiment, two of the tags have a first peak absorption wavelength and the other two tags have a second peak absorption wavelength. A first absorption spectrum 1-109 for the first luminescent tag has a peak absorption wavelength at $\lambda 3$, a second absorption spectrum 1-110 for the second luminescent tag has a peak absorption wavelength at $\lambda 4$, a third absorption spectrum 1-111 for the third luminescent tag has a peak absorption wavelength at $\lambda 3$, and a fourth absorption spectrum 1-112 for the fourth luminescent tag has a peak absorption wavelength at $\lambda 4$. Note that the tags that share an absorption peak wavelength in FIG. 1-2C are distinguishable via another tag characteristic, such as emission lifetime. FIG. 1-3B illustrates this situation schematically in a phase space spanned by the absorption wavelength and the emission lifetime. A first tag has an absorption wavelength $\lambda 3$ and an emission lifetime $\tau 1$, a second tag has an absorption wavelength $\lambda 3$ and an emission lifetime $\tau 4$, a third tag has an absorption wavelength $\lambda 4$ and a emission lifetime $\tau 1$, and a fourth tag has an absorption wavelength $\lambda 4$ and a emission lifetime $\tau 4$. In this way, all four tags in the tag set shown in FIG. 1-3A are distinguishable from one another.

Using such a tag set allows distinguishing between four tags even when the emission wavelengths for the four dyes are indistinguishable. This is possible using two excitation sources that emit at different wavelengths or a single excitation source capable of emitting at multiple wavelengths in connection with a sensor that can detect the time of emission of the photoluminescence. If the wavelength of the excitation light is known for each detected emission event, then it can be determined which tag was present. The excitation source(s) may alternate between a first excitation wavelength and a second excitation wavelength, which is referred to as interleaving. Alternatively, two or more pulses of the first excitation wavelength may be used followed by two or more pulses of the second excitation wavelength.

The number of excitation sources or excitation wavelengths used to distinguish the tags is not limited to two, and in some embodiments more than two excitation wavelengths or energies may be used to distinguish the tags. In such embodiments, tags may be distinguished by the intensity or number of photons emitted in response to multiple excitation wavelengths. A tag may be distinguishable from among multiple tags by detecting the amount of photons emitted in response to exposing the tag to a certain excitation wavelength. In some embodiments, a tag may be distinguished by identifying the excitation energy from among multiple excitation energies where the tag emitted the highest number of photons. In other embodiments, the amount of emitted photons from a tag in response to different excitation energies may be used to identify the tag. A first tag that has a higher probability of emitting photons in response to a first excitation energy than a second excitation energy may be distinguished from a second tag that has a higher probability of emitting photons in response to the second excitation energy than the first excitation energy. In this manner, tags having distinguishable probabilities of emitting certain amounts of photons in response to different excitation energies may be identified by measuring the emitted photons while exposing an unknown tag to the different excitation energies. In such embodiments, a tag may be exposed to multiple excitation energies and identification of the tag may be achieved by determining whether the tag emitted any light and/or an amount of photons emitted. Any suitable number of excitation energy sources may be used. In some embodiments, four different excitation energies may be used to distinguish among different tags (e.g., four different tags). In some embodiments, three different excitation energies may be used to distinguish among different tags. Other characteristics of a tag may be used to distinguish the presence of a tag in combination with the amount of photons emitted in response to different excitation energies, including emission lifetime and emission spectra.

In other embodiments more than two characteristics of the tags in a tag set may be used to distinguish which tag is present. FIG. 1-4 illustrates an illustrative phase space spanned by the absorption wavelength, the emission wavelength and the emission lifetime of the tags. In FIG. 1-4, eight different tags are distributed in phase space. Four of the eight tags have the same emission wavelength, a different four tags have the same absorption wavelength and a different four tags have the same emission lifetime. However, each of the tags is distinguishable from every other tag when all three characteristics of the tags are considered. Embodiments are not limited to any number of tags. This concept can be extended to include any number of tags that may be distinguished from one another using at least these three tag characteristics.

While not illustrated in the figures, other embodiments may determine the identity of a luminescent tag based on the absorption frequency alone. Such embodiments are possible if the excitation light can be tuned to specific wavelengths that match the absorption spectrum of the tags in a tag set. In such embodiments, the optical system and sensor used to direct and detect the light emitted from each tag does not need to be capable of detecting the wavelength of the emitted light. This may be advantageous in some embodiments because it reduces the complexity of the optical system and sensors because detecting the emission wavelength is not required in such embodiments.

As discussed above, the inventors have recognized and appreciated the need for being able to distinguish different luminescent tags from one another using various characteristics of the tags. The type of characteristics used to determine the identity of a tag impacts the physical device used to perform this analysis. The present application discloses several embodiments of an apparatus, device, instrument and methods for performing these different experiments.

Briefly, the inventors have recognized and appreciated that a pixelated sensor device with a relatively large number of pixels (e.g., hundreds, thousands, millions or more) that allows for the detection of a plurality of individual molecules or particles in parallel. Such single molecules may be nucleotides or amino acids having tags. Tags may be detected while bound to single molecules, upon release from the single molecules, or while bound to and upon release from the single molecules. In some examples, tags are luminescent tags. The molecules may be, by way of example and not limitation, proteins and/or nucleic acids (e.g., DNA, RNA). Moreover, a high-speed device that can acquire data at more than one hundred frames per second allows for the detection and analysis of dynamic processes or changes that occur over time within the sample being analyzed.

The inventors have recognized and appreciated that a low-cost, single-use disposable assay chip may be used in connection with an instrument that includes an excitation light source, optics, and a light sensor to measure an optical signal (e.g., luminescent light) emitted from biological samples. Using a low-cost assay chip reduces the cost of performing a given bioassay. A biological sample is placed onto the assay chip and, upon completion of a single bioassay, may be discarded. In some embodiments, more than one type of sample may be analyzed simultaneously, in parallel, by placing multiple samples on different portions of the assay chip at the same time. The assay chip interfaces with the more expensive, multi-use instrument, which may be used repeatedly with many different disposable assay chips. A low-cost assay chip that interfaces with a compact, portable instrument may be used anywhere in the world, without the constraint of high-cost biological laboratories requiring laboratory expertise to analyze samples. Thus, automated bioanalytics may be brought to regions of the world that previously could not perform quantitative analysis of biological samples. For example, blood tests for infants may be performed by placing a blood sample on a disposable assay chip, placing the disposable assay chip into the small, portable instrument for analysis, and processing the results by a computer that connects to the instrument for immediate review by a user. The data may also be transmitted over a data network to a remote location to be analyzed, and/or archived for subsequent clinical analyses. Alternatively, the instrument may include one or more processors for analyzing the data obtained from the sensors of the instrument.

Various embodiments are described in more detail below.

I. Overview of the Apparatus According to Some Embodiments

A schematic overview of the apparatus 2-100 is illustrated in FIG. 2-1. The system comprises both an assay chip 2-110 and an instrument 2-120 comprising an excitation source 2-121 and at least one sensor 2-122. The assay chip 2-110 interfaces with the instrument 2-120 using any suitable assay chip interface. For example, the assay chip interface of the instrument 2-120 may include a socket (not illustrated) for receiving the assay chip 2-110 and holding it in precise optical alignment with the excitation source 2-110 and the at least one sensor 2-122. The external excitation source 2-121 in the instrument 2-120 is configured to provide excitation energy to the assay chip 2-110 for the purpose of exciting a sample in the sample well 2-111 of the assay chip 2-110. In some embodiments, the assay chip 2-110 has multiple pixels, the sample well 2-111 of each pixel configured to receive a sample used in an analysis independent from the other pixels. Each pixel of the assay chip 2-110 comprises a sample well 2-211 for receiving, retaining and analyzing a sample from the specimen being analyzed. Such pixels may be referred to as "passive source pixels" since the pixels receive excitation energy from an excitation source separate from the pixel. In some embodiments, there is a pixel in the instrument 2-120 corresponding to each pixel present on the assay chip 2-110. Each pixel of the instrument 2-120 comprises at least one sensor for detecting emission energy emitted by the sample in response to the sample being illuminated with excitation energy from the excitation source 2-121. In some embodiments, each sensor may include multiple sub-sensors, each sub-sensor configured to detect a different wavelength of emission energy from the sample. While more than one sub-sensor may detect emission energy of a certain wavelength, each sub-sensor may detect a different wavelength band of emission energy.

In some embodiments, optical elements for guiding and coupling excitation energy from the excitation source 2-121 to the sample well 2-111 are located both on the assay chip 2-110 and the instrument 2-120, as represented by arrow 2-101 in FIG. 2-1. Such source-to-well elements may include mirrors, lenses, dielectric coatings and beam combiners located on the instrument 2-120 to couple excitation energy to the assay chip 2-110 and lenses, plasmonic elements and dielectric coatings on the assay chip 1-110 to direct the excitation energy received from the instrument 2-120 to the sample well 2-111. Additionally, in some embodiments, optical elements for guiding emission energy from the sample well 2-111 to the sensor 2-122 are located on the assay chip 2-110 and the instrument 2-120, as represented by arrow 2-102 in FIG. 2-1. Such well-to-sample elements may include may include lenses, plasmonic elements and dielectric coatings located on the assay chip 2-110 to direct emission energy from the assay chip 2-110 to the instrument 2-120 and lenses, mirrors, dielectric coatings, filters and diffractive optics on the instrument 1-120 to direct the emission energy received from the assay chip 2-110 to the sensor 2-111. In some embodiments, a single component may play a role both in coupling excitation energy to a sample well and delivering emission energy from the sample well to the sensor.

In some embodiments, the assay chip 2-110 comprises a plurality of pixels, each pixel associated with its own individual sample well 2-111 and its own associated sensor 2-122 on the instrument 2-120. The plurality of pixels may be arranged in an array and may have any suitable number of pixels. For example, the assay chip may include approximately 1,000 pixels, 10,000 pixels, approximately 100,000 pixels, approximately 1,000,000 pixels, approximately 10,000,000 pixels, or approximately 100,000,000 pixels.

In some embodiments, the instrument 2-120 includes a sensor chip comprising a plurality of sensors 2-122 arranged as a plurality of pixels. Each pixel of the sensor chip corresponds to a pixel in the assay chip 2-110. The plurality of pixels may be arranged in an array and may have any suitable number of pixels. In some embodiments, the sensor chip has the same number of pixels as the assay chip 2-110. For example, the sensor chip may include approximately 10,000 pixels, approximately 100,000 pixels, approximately 1,000,000 pixels, approximately 10,000,000 pixels, or approximately 100,000,000 pixels.

The instrument 2-120 interfaces with the assay chip 2-110 through an assay chip interface (not shown). The assay chip interface may include components to position and/or align the assay chip 2-110 to the instrument 2-120 to improve coupling of the excitation energy from the excitation source 2-121 to the assay chip 2-110. In some embodiments, excitation source 2-121 includes multiple excitation sources that are combined to deliver excitation energy to the assay chip 2-110. The multiple excitation sources may be configured to produce multiple excitation energies, corresponding to light of different wavelengths.

The instrument 2-120 includes a user interface 2-125 for controlling the operation of the instrument. The user interface 2-125 is configured to allow a user to input information into the instrument, such as commands and/or settings used to control the functioning of the instrument. In some embodiments, the user interface 2-125 may include buttons, switches, dials, and a microphone for voice commands. Additionally, the user interface 2-125 may allow a user to receive feedback on the performance of the instrument and/or assay chip, such as proper alignment and/or information obtained by readout signals from the sensors on the sensor chip. In some embodiments, the user interface 2-125 may provide feedback using a speaker to provide audible feedback, and indicator lights and/or a display screen for providing visual feedback. In some embodiments, the instrument 2-120 includes a computer interface 2-124 used to connect with a computing device 2-130. Any suitable computer interface 2-124 and computing device 2-130 may be used. For example, the computer interface 2-124 may be a USB interface or a firewire interface. The computing device 2-130 may be any general purpose computer, such as a laptop, desktop, or tablet computer, or a mobile device such as a cellular telephone. The computer interface 2-124 facilitates communication of information between the instrument 2-120 and the computing device 2-130. Input information for controlling and/or configuring the instrument 2-120 may be provided through the computing device 2-130 connected to the computer interface 2-124 of the instrument. Additionally, output information may be received by the computing device 2-130 through the computer interface 2-124. Such output information may include feedback about performance of the instrument 2-120 and information from the readout signals of the sensor 2-122. The instrument 2-120 may also include a processing device 2-123 for analyzing data received from the sensor 2-122. In some embodiments, the processing device 2-123 may be a general purpose processor (e.g., a central processing unit (CPU), a field programmable gate array (FPGA) or a custom integrated circuit, such as an application specific integrated circuit (ASIC). In some embodiments, the processing of data from the sensor 1-122 may be performed by both the processing device 2-123 and the external computing device 2-130. In other embodiments, the computing device 2-130 may be omitted and processing of data from the sensor 2-122 may be performed solely by processing device 2-123.

When the excitation source 2-121 illuminates the assay chip 2-110 with excitation energy, samples within one or more pixels of the assay chip 2-110 may be excited. In some embodiments, a specimen is labeled with multiple markers and the multiple markers, each associated with a different sample within the specimen, are identifiable by the emission energy. The path from the sample well 2-111 to the sensor 2-122 may include one or more components that aid in identifying the multiple markers based on emission energy. Components may focus emission energy towards the sensor 2-122 and may additionally or alternatively spatially separate emission energies that have different characteristic energies, and therefore different wavelengths. In some embodiments, the assay chip 2-110 may include components that direct emission energy towards the sensor 2-122 and the instrument 2-120 may include components for spatially separating emission energy of different wavelengths. For example, optical filters or diffractive optics may be used to couple the wavelength of the emission energy to a spatial degree of freedom. The sensor or sensor region may contain multiple sub-sensors configured to detect a spatial distribution of the emission energy that depends on the radiation pattern. Luminescent tags that emit different emission energies and/or spectral ranges may form different radiation patterns. The sensor or sensor region may detect information about the spatial distribution of the emission energy that can be used to identify a marker among the multiple markers.

The emission energy from the sample in the sample well 2-110 may be detected by the sensor 2-122 and converted to at least one electrical signal. The electrical signals may be transmitted along conducting lines in the circuitry of the instrument 2-120 and processed and/or analyzed by the processing device 2-123 and/or computing device 2-130.

FIG. 2-2 is a top view of the assay chip 2-110 and the top view of the sensor chip 2-260 and illustrates the correspondence between the pixels of the two chips. The assay chip 2-110 comprises a plurality of pixels, each pixel including a sample well 2-111 formed in layer 2-221. Layer 2-221 may comprise a conductive material including a metal, a highly degeneratively-doped semiconductor, and graphene. In some embodiments, layer 2-221 may comprise a plurality of layers formed from one or more different types of materials (e.g., metal, semiconductor, dielectric, insulator). The sensor chip 2-260 also comprises a plurality of pixels, each pixel including a sensor 2-121 formed in or on a substrate 2-247. The arrows in FIG. 2-2 illustrate the correspondence between two of the pixels of the assay chip 2-110 and two of the pixels of the sensor chip 2-260. While not illustrated for the sake of clarity, each pixel of the assay chip 2-110 is associated with a pixel of the sensor chip 2-260.

Pixels of the assay chip 2-110 and the sensor chip 2-260 may have any suitable size, shape, and arrangement. In some embodiments, pixels of the assay chip 2-100 and the sensor chip 2-260 may be arranged in a rectangular or square configuration, as shown in FIG. 2-2.

An overview of some components associated with a single pixel of the assay chip 2-110 and a single pixel of the sensor chip 2-260 is illustrated in FIG. 2-3. The apparatus 2-100 comprises both the assay chip 2-110 and the instrument 2-120. In some embodiments, the assay chip 2-110 is a disposable chip designed for the analysis of a single specimen. The assay chip 2-110 includes one or more metal layers 2-221, one or more dielectric layers 2-225 and focusing elements 2-227. In some embodiments, metal layer 2-221 includes a stack of layers, some of which may include absorbing layers. The instrument 2-120 includes one or more excitation sources 2-250, at least one polychroic mirror 2-230, and the sensor chip 2-260, which may include filtering elements 2-241, spectral sorting elements 2-243, focusing elements 2-245 and at least one sensor 2-122 in or on the substrate 2-247. While FIG. 2-3 illustrates only a single pixel of the assay chip 2-110 and only a single pixel of the sensor chip 2-260, some components of the instrument 2-120, such as the excitation source 2-250, the polychroic mirror 2-230 and filtering elements 2-241, may be common to a plurality of the pixels. For example, in some embodiments, a single excitation source 2-250 and polychroic mirror 2-230 may direct the excitation energy to every pixel of the assay chip 2-110.

The sample well 2-211 within the metal layer 2-221 forms a sample volume for a sample from the specimen to enter. In some embodiments, the specimen may include bodily fluid, such as blood, urine or saliva. The openings at the end of the sample well 2-211 may be referred to as a nanoaperture. The nanoaperture may have a width that is smaller than the wavelength of the excitation energy 2-251 emitted by excitation source 2-250. A portion of the specimen, referred to as a sample, may enter the sample volume defined by the sample well 2-211. The sample may be any particle, molecule, protein, genetic material or any other sample present in the specimen.

Excitation source 2-250 emits excitation energy 2-251, which is directed towards the sample well 2-211 to illuminate the sample. In some embodiments, excitation source 2-251 may be a single light source that provides excitation energy for all the pixels of assay chip 2-110. The polychroic mirror 2-230 reflects light from the excitation source 2-250 and directs the excitation energy 2-251 towards one or more sample wells 2-211 of the assay chip 2-110. Thus, in some embodiments, there may be only a single polychroic mirror 2-230 that directs the excitation energy towards all the sample wells, rather than each pixel being associated with its own polychroic mirror. Similarly, there may be a one-to-many relationship between other optical elements used to direct the excitation energy towards sample wells 2-211.

A concentric circular grating 2-223 may be formed adjacent to the bottom nanoaperture of the sample well 2-211. The concentric circular gratings 2-223 may protrude from a bottom surface of the metal layer 2-221. The sample well 2-211 may be located at or near the center of the circular grating 2-223. Both the sub-wavelength scale of the nanoaperture of the sample well 2-211 and the concentric circular gratings 2-223 create a field enhancement effect that increases the intensity of the excitation energy in the sample well 2-211, resulting in increased coupling of the excitation energy to a sample present in the sample well 2-211. At least some of the time, the sample absorbs a photon from the excitation energy and emits a photon (referred to as "emission energy" 2-253) with an energy less than that of the excitation energy 2-251. The emission energy 2-253 may be emitted in a downward direction. The circular gratings 2-223 act as plasmonic elements which may be used to decrease the spread of the emission energy 2-253 and direct the emission energy 2-253 towards an associated sensor.

The emission energy 2-253 travels through the dielectric layer 2-225, which may be a spacer layer used to allow the emission energy 2-253 to propagate some distance. The dielectric layer 2-225 may also provide structural strength to the assay chip 2-110. The emission energy 2-253 then travels through one or more focusing elements 2-227 used to further direct the emission energy 2-253 to the sensor 2-122 in the associated pixel of the sensor chip 2-2260 within the instrument 2-120.

The polychroic mirror 2-230 may transmit the emission energy 2-253 and/or reflect a portion of any excitation energy 2-251 reflected from the assay chip 2-110. The portion of the excitation light that is not reflected by the assay chip 2-110 is either transmitted through the assay chip or absorbed by the assay chip. To further reduce the amount of excitation energy 2-251 reflected by the assay chip 2-110 and not reflected by the polychroic mirror 2-230, filtering elements 2-241 may be disposed in the optical path towards the sensor chip 2-260. The filtering components 2-241 may act to reduce excitation energy 2-251 detected by sensor 2-122. The filtering elements 2-241 may include, by way of example and not limitation, a broadband filter, a notch filter or an edge filter, which transmit emission energy 2-253 but absorb and/or reflect excitation energy 2-251.

In some embodiments, to facilitate using spectral properties of the emission energy 2-253 to determine the identity of the marker in the sample well 2-211, spectral sorting elements 2-243 may be included on the sensor chip 2-260 to couple the spectral degree of freedom of the emission energy 2-253 to the direction the emission energy 2-253 is traveling. For example, a diffractive optical element may be used to direct emission energy 2-253 of a first wavelength in a first direction and emission energy 2-253 of a second wavelength in a second direction. One or more focusing elements 2-245 may be used to direct the spectrally sorted light onto the sensor 2-122. The sensor 2-122 may include one or more sub-sensors (not shown), each of which is associated with a different wavelength of the emission energy 2-253 based on the redirection of light of different wavelengths by the spectral sorting element 2-243. In this manner, the one or more focusing elements 2-245 may form different distribution patterns for emission energy having different characteristic wavelengths, which may allow for identification of markers based on characteristic wavelength of emission energy.

In embodiments where lifetime of the emission energy 2-253 is used to determine the identity of the marker in sample well 2-211, sensor 2-122 may be capable of detecting when a photon of emission energy is absorbed by sensor 2-122. The sensor 2-122 may, for example, be a CMOS device capable of sorting detected photons into a plurality of time bins. The lifetime may be determined by detecting a plurality of emission energy photons resulting from a plurality of excitation pulses.

The above description of FIG. 2-3 is an overview of some, but not necessarily all, of the components of the apparatus according to some embodiments. In some embodiments, one or more elements of FIG. 2-3 may be absent or in a different location. The components of the assay chip 2-210 and instrument 2-220 are described in more detail below.

The assay chip 2-110 and the instrument 2-120 may be mechanically aligned, detachably coupled and separable from one another. The instrument 2-120 may include an instrument housing, inside which a mounting board is disposed. FIG. 2-4 illustrates at least some of the components that may be included on the mounting board 2-405 of the instrument 2-120. The mounting board 2-405, which may include a printed circuit board, may have the sensor chip 2-260 (not visible in FIG. 2-4), a heat sink 2-407 and an optical housing 2-401 mounted thereto. The various optical components of the instrument 2-120 may be disposed within the optical housing 2-401. In some embodiments, instrument housing and mounting board may have any suitable size and shape. For example, the mounting board may be substantially circular with a diameter of approximately 7-8". The assay chip 2-110 couples to the optical housing 2-401 to ensure alignment with the optical components within the optical housing 2-401.

A chip holder frame 3-102 may be aligned with an opening of the optical housing 2-401. The assay chip 2-110 may be housed in chip holder frame 2-401. In some embodiments, assay chip 2-110 may be situated on the underside of chip holder frame 3-102 such that positioning of the chip holder frame 3-102 relative to instrument 2-120 locates assay chip 2-110 on a side of chip holder frame 3-102 proximate to instrument 2-120. The chip holder frame 3-102 may comprise any suitable material. In some embodiments, chip holder frame 3-102 may include a ferromagnetic metal (e.g., steel) such that chip holder frame 3-102 may align with an opening of optical housing 2-401 by one or more magnetic components positioned on a surface of the optical housing 2-401 that act to hold chip holder frame 3-102 in place.

In some embodiments, the assay chip 2-110 may be detachably coupled to the instrument 2-120. One or more magnetic components 2-403a, 2-403b, and 2-403c of any suitable shape and size, such as magnetic cylinders as shown in FIG. 2-4, may be placed around an opening of the optical housing 3-401 through which excitation energy exits the optical housing 2-401. Additionally, the magnetic components 2-403a, 2-403b, and 2-2-403c may be calibrated such that the chip holder frame 3-102 is held in alignment with the opening. The chip holder frame 3-102 may be positioned with a micron-level accuracy using the magnetic components 2-403a, 2-403b, and 2-2-403c. In some embodiments, magnetic components 2-403a, 2-403b, and 2-2-403c are used to create chip holder frame alignment. However, embodiments are not so limited and any suitable number of magnetic, spring-loaded, pneumatic or other such components may be used to hold the chip in place in an aligned configuration. For example, the chip holder frame 3-102 may be held in place with a non-magnetic element, such as a spring, air pressure, or suction from a vacuum. Optionally, the chip holder frame 3-102 may be constructed using any stiff material suitable for positioning the chip in alignment with the optical block.

According to some aspects of the present application, when the assay chip 2-110 is connected to the instrument 2-120, the distance between the sample wells of the assay chip 2-110 and the sensors of the sensor chip 2-260 in instrument 2-120 may be within a desired distance to achieve a sufficient level of performance for the system. In some embodiments, the optical distance between the sample wells and the sensors may be less than 30 cm, less than 10 cm, less than 5 cm, or less than 1 cm.

II. Assay Chip

In some embodiments, the assay chip 2-110 does not include any active electronic components. Both the excitation source 2-250 and the sensor 2-122 for each pixel are located off-chip in the instrument 2-120.

In some embodiments, the assay chip 2-110 may be housed in a chip holder frame 3-102 as illustrated in FIG. 3-1A. The chip holder frame 3-102 may be disposable and may be disposed of along with the assay chip 2-110 after a single use. The assay chip 2-110 may be situated on the underside of the chip holder frame 3-102, as illustrated in FIG. 3-1B. The chip holder frame 3-102 may comprise any suitable ferromagnetic metal, such as steel, such that the magnetic components 2-403a, 2-403b, and 2-403c fixed to the optical housing 2-401 hold the chip holder frame 3-102, and thus the assay chip 2-110, in place. In some embodiments, the chip holder frame 3-102 may be attached to the top surface of the optical housing 2-401 as illustrated in FIG. 2-4.

In other embodiments, illustrated in FIG. 3-1C, the assay chip 2-110 may be attached to a top surface of the chip holder frame 3-102. A plastic cap 3-103 surrounds the assay chip 2-110 such that the pixel array of the assay chip 2-110 is exposed via an opening in the plastic cap 3-103. A user of the assay chip 2-110 may place a specimen into the opening of the plastic cap 3-103. By being in contact with the top surface of the assay chip 2-110, the samples within the specimen may be introduced to one or more of the plurality of pixels of the assay chip 2-110 for analysis. In some embodiments, no fluidic channels or device for delivering portions of the sample to the pixels via forced fluid flow are necessary.

In some embodiments, the assay chip may include layers of components stacked vertically. These components may include optical, electrical, chemical, biochemical, and structural elements. In some embodiments, each layer of the assay chip is the same for each pixel. What follows is a description of a single pixel, but every pixel in the array of pixels on an assay chip may have exactly same layout according to some embodiments.

A. Sample Well Layer

As illustrated in FIG. 2-3, and in more detail at FIG. 3-2, some embodiments include a sample well 2-211 formed at one or more pixels of the assay chip 2-110. A sample well may comprise a small volume or region formed within metal layer 2-221 and arranged such that samples may diffuse into and out of the sample well from a specimen deposited on the surface of the assay chip 2-110. In various embodiments, a sample well 2-211 may be arranged to receive excitation energy from an excitation source 2-250. Samples that diffuse into the sample well may be retained, temporarily or permanently, within an excitation region 3-215 of the sample well by an adherent 3-211. In the excitation region, a sample may be excited by excitation energy (e.g., excitation light 3-245), and subsequently emit energy that may be observed and evaluated to characterize the sample.

In further detail of operation, at least one sample 3-101 to be analyzed may be introduced into a sample well 2-211, e.g., from a specimen (not shown) containing a fluid suspension of samples. Excitation energy 3-245 from an excitation source 2-250 in the instrument 2-120 may excite the sample or at least one tag (also referred to as a biological marker, reporter, or probe) attached to the sample or otherwise associated with the sample while it is within an excitation region 3-215 within the sample well. According to some embodiments, a tag may be a luminescent molecule (e.g., a luminescent tag or probe) or quantum dot. In some implementations, there may be more than one tag that is used to analyze a sample (e.g., distinct tags that are used for single-molecule genetic sequencing as described in "Real-Time DNA Sequencing from Single Polymerase Molecules," by J. Eid, et al., Science 323, p. 133 (2009), which is incorporated by reference). During and/or after excitation, the sample or tag may emit emission energy. When multiple tags are used, they may emit at different characteristic energies (and therefore have different wavelengths) and/or emit with different temporal characteristics. In some embodiments, emission energy may include any number of wavelengths, for example, two, three, four, five, six, seven, or eight different wavelengths. The emissions from the sample well 2-211 may radiate to a sensor 2-122 on the instrument 2-120 where they are detected and converted into electrical signals that can be used to characterize the sample.

According to some embodiments, a sample well 2-211 may be a partially enclosed structure, as depicted in FIG. 3-2. In some implementations, a sample well 2-211 comprises a sub-micron-sized hole or opening (characterized by at least one transverse dimension $D_{sw}$) formed in at least one layer of material 2-221. The transverse dimension of the sample well may be between approximately 20 nanometers and approximately 1 micron, according to some embodiments, though larger and smaller sizes may be used in some implementations. A volume of the sample well 2-211 may be between about $10^{-21}$ liters and about $10^{-15}$ liters, in some implementations. A sample well may be formed as a waveguide that may, or may not, support a propagating mode. In some embodiments, a sample well may be formed as a zero-mode waveguide (ZMW) having a cylindrical shape (or similar shape) with a diameter (or largest transverse dimension) $D_{sw}$. A ZMW may be formed in a single metal layer as a nano-scale hole that does not support a propagating optical mode through the hole.

Because the sample well 2-211 has a small volume, detection of single-sample events (e.g., single-molecule events) at each pixel may be possible even though samples may be concentrated in an examined specimen at concentrations that are similar to those found in natural environments. For example, micromolar concentrations of the sample may be present in a specimen that is placed in contact with the assay chip, but at the pixel level only about. Sample wells of the assay 2-110 are sized such that, statistically, they most likely contain no sample or one sample, so that single molecule analysis may be performed. For example, in some embodiments 30-40% of the sample wells contain a single sample. However, sample wells may contain more than one sample. Because single-molecule or single-sample events may be analyzed at each pixel, the assay chip makes it possible to detect rare events that may otherwise go unnoticed in ensemble averaged measurements.

A transverse dimension $D_{sw}$ of a sample well may be between about 500 nanometers (nm) and about one micron in some embodiments, between about 250 nm and about 500 nm in some embodiments, between about 100 nm and about 250 nm in some embodiments, and yet between about 20 nm and about 100 nm in some embodiments. The transverse dimension of a sample well may be approximately 100 nm, approximately 130 nm, or approximately 190 nm. According to some implementations, a transverse dimension of a sample well is between approximately 80 nm and approximately 180 nm, or between approximately one-quarter and one-eighth of the excitation wavelength or emission wavelength. According to other implementations, a transverse dimension of a sample well is between approximately 120 nm and approximately 170 nm. In some embodiments, the depth or height of the sample well 2-211 may be between about 50 nm and about 500 nm. In some implementations, the depth or height of the sample well 2-211 may be between about 80 nm and about 200 nm. The layer of material 2-221 that forms the sample well 2-211 may have a thickness or height or approximately 50 nm, approximately 100 nm, approximately 150 nm, approximately 200 nm, or approximately 250 nm.

A sample well 2-211 having a sub-wavelength, transverse dimension can improve operation of a pixel 2-100 of an assay chip 2-110 in at least two ways. For example, excitation energy 3-245 incident on the sample well from a side opposite the specimen may couple into the excitation region 3-215 with exponentially decreasing power, and not propagate through the sample well to the specimen. As a result, excitation energy is increased in the excitation region where it excites a sample of interest, and is reduced in the specimen where it could excite other samples that would contribute to background noise. Also, emission from a sample retained at a base of the well is preferably directed toward the sensor on the instrument 2-120, since emission cannot propagate up through the sample well. Both of these effects can improve signal-to-noise ratio at the pixel. The inventors have recognized several aspects of the sample well that can be improved to further boost signal-to-noise levels at the pixel. These aspects relate to well shape and structure, and placement relative to adjacent optical and plasmonic structures (described below) that aid in coupling excitation energy to the sample well and emitted energy from the sample well.

According to some embodiments, a sample well 2-211 may be formed as a sub-cutoff nano-aperture (SCN), which does not support a propagating mode. For example, the sample well 2-211 may comprise a cylindrically-shaped hole or bore in a conductive layer 2-221. The cross-section of a sample well need not be round, and may be elliptical, square, rectangular, or polygonal in some embodiments. Excitation energy 3-245 (e.g., visible or near infrared radiation) may enter the sample well through an entrance aperture 3-212 that may be defined by walls 3-214 of the sample well 2-211 at a first end of the well, as depicted in FIG. 3-2. When formed as an SCN, the excitation energy 3-245 may decay exponentially along the SCN. In some implementations, the waveguide may comprise an SCN for emitted energy from the sample, but may not be an SCN for excitation energy. For example, the aperture and waveguide formed by the sample well may be large enough to support a propagating mode for the excitation energy, since it may have a shorter wavelength than the emitted energy. The emission, at a longer wavelength, may be beyond a cut-off wavelength for a propagating mode in the waveguide. According to some embodiments, the sample well 2-211 may comprise an SCN for the excitation energy 3-245, such that the greatest intensity of excitation energy is localized to an excitation region 3-215 of the sample well at an entrance to the sample well 2-211 (e.g., localized near the interface between layer 3-235 and layer 2-221 as depicted in FIG. 3-2). Such localization of the excitation energy can increase the emission energy density from the sample, and further confine the excitation energy near the entrance aperture 3-212, thereby limiting the observed emission to a single sample (e.g., a single molecule).

An example of excitation localization near an entrance of a sample well that comprises an SCN is depicted in FIG. 3-3. A numerical simulation was carried out to determine intensity of excitation energy within and near a sample well 2-211 formed as an SCN. The results show that the intensity of the excitation energy is about 70% of the incident energy at an entrance aperture of the sample well and drops to about 20% of the incident intensity within about 100 nm in the sample well. For this simulation, the characteristic wavelength of the excitation energy was 633 nm and the diameter of the sample well 2-211 was 140 nm. The sample well 2-211 was formed in a layer of gold metal. Each horizontal division in the graph is 50 nm. As shown by the graph, more than one-half of the excitation energy received in the sample well is localized to about 50 nm within the entrance aperture 3-212 of the sample well 2-211.

To improve the intensity of excitation energy that is localized at the sample well 2-211, other sample well structures were developed and studied by the inventors. FIG. 3-4 depicts an embodiment of a sample well that includes a cavity or divot 3-216 at an excitation end of the sample well 2-211. As can be seen in the simulation results of FIG. 3-3, a region of higher excitation intensity exists just before the entrance aperture 2-212 of the sample well. Adding a divot 3-216 to the sample well 2-211 allows a sample to move into a region of higher excitation intensity, according to some embodiments. In some implementations, the shape and structure of the divot alters the local excitation field (e.g., because of a difference in refractive index between the layer 3-235 and fluid of the specimen in the sample well), and can further increase the intensity of the excitation energy in the divot.

The divot may have any suitable shape. The divot may have a transverse shape that is substantially equivalent to a transverse shape of the sample well, e.g., round, elliptical, square, rectangular, polygonal, etc. In some embodiments, the sidewalls of the divot may be substantially straight and vertical, like the walls of the sample well. In some implementations, the sidewalls of the divot may be sloped and/or curved, as depicted in the drawing. The transverse dimension of the divot may be approximately the same size as the transverse dimension of the sample well in some embodiments, may be smaller than the transverse dimension of the sample well in some embodiments, or may be larger than the transverse dimension of the sample well in some embodiments. The divot 3-216 may extend between approximately 10 nm and approximately 200 nm beyond the metallic layer 2-221 of the sample well. In some implementations, the divot may extend between approximately 50 nm and approximately 150 nm beyond the metallic layer 2-221 of the sample well. By forming the divot, the excitation region 3-215 may extend outside the metallic layer 2-221 of the sample well, as depicted in FIG. 3-4.

FIG. 3-5 depicts improvement of excitation energy at the excitation region for a sample well containing a divot (shown in the left simulation image). For comparison, the excitation field is also simulated for a sample well without a divot, shown on the right. The field magnitude has been converted from a color rendering in these plots, and the dark region at the base of the divot represents higher intensity than the light region within the sample well. The dark regions above the sample well represents the lowest intensity. As can be seen, the divot allows a sample 3-101 to move to a region of higher excitation intensity, and the divot also increases the localization of region of highest intensity at an excitation end of the sample well. Note that the region of high intensity is more distributed for the sample well without the divot. In some embodiments, the divot 3-216 provides an increase in excitation energy at the excitation region by a factor of two or more. In some implementations, an increase of more than a factor of two can be obtained depending on the shape and depth of the divot. In these simulations, the sample well comprises a layer of Al that is 100 nm thick, with a divot that is 50 nm deep, with excitation energy at 635 nm wavelength.

FIG. 3-6 depicts another embodiment of a sample well 2-211 in which the sample well, including the divot 3-216, are formed over a protrusion 3-615 at a surface of a substrate. A resulting structure for the sample well may increase the excitation energy at the sample by more than a factor of two compared to a sample well shown in FIG. 3-2, and may direct emission from the sample well toward the sensor in the instrument 2-120. According to some embodiments, a protrusion 3-615 is patterned in a first layer 3-610 of material. The protrusion may be formed as a circular pedestal or a ridge with rectangular cross-section in some implementations, and a second layer 3-620 of material may be deposited over the first layer and the protrusion. At the protrusion, the second layer may form a shape above the protrusion that approximates a cylindrical portion 3-625, as depicted. In some embodiments, a conductive layer 3-230 (e.g., a reflective metal) may be deposited over the second layer 3-620 and patterned to form a sample well 3-210 in the conductive layer above the protrusion. A divot 3-216 may then be etched into the second layer. The divot may extend between about 50 nm and about 150 nm below the conductive layer 3-230. According to some embodiments, the first layer 3-610 and second layer 3-620 may be optically transparent, and may or may not be formed of a same material. In some implementations, the first layer 3-610 may be formed from an oxide (e.g., $SiO_2$) or a nitride (e.g., $Si_3N_4$), and the second layer 3-620 may be formed from an oxide or a nitride.

According to some embodiments, the conductive layer 3-230 above the protrusion 3-625 is shaped approximately as a spherical reflector 3-630. The shape of the spherical portion may be controlled by selection of the protrusion height h, diameter or transverse dimension w of the protrusion, and a thickness t of the second layer 3-620. The location of the excitation region and position of the sample can be adjusted with respect to an optical focal point of the cylindrical reflector by selection of the divot depth d. It may be appreciated that the spherical reflector 3-630 can concentrate excitation energy at the excitation region 3-215, and can also collect energy emitted from a sample and reflect and concentrate the radiation toward the sensor 3-260.

As noted above, a sample well may be formed in any suitable shape, and is not limited to only cylindrical shapes. In some implementations, a sample well may be conic, tetrahedron, pentahedron, etc. FIG. 3-7A through FIG. 3-7F illustrates some example sample well shapes and structures that may be used in some embodiments. A sample well 2-211 may be formed to have a first aperture 3-212 that is larger than a second aperture 3-218 for the excitation energy, according to some embodiments. The sidewalls of the sample well may be tapered or curved. Forming a sample well in this manner can admit more excitation energy to the excitation region, yet still appreciably attenuate excitation energy that travels toward the specimen. Additionally, emission radiated by a sample may preferentially radiate toward the end of the sample well with the larger aperture, because of favorable energy transfer in that direction.

In some embodiments, a divot 3-216 may have a smaller transverse dimension than the base of the sample well, as depicted in FIG. 3-7B. A smaller divot may be formed by coating sidewalls of the sample well with a sacrificial layer before etching the divot, and subsequently removing the sacrificial layer. A smaller divot may be formed to retain a sample in a region that is more equidistant from the conductive walls of the sample well. Retaining a sample equidistant from the walls of the sample well may reduce undesirable effects of the sample well walls on the radiating sample, e.g., quenching of emission and/or altering of radiation lifetimes.

FIGS. 3-7C and 3-7D depict another embodiment of a sample well. According to this embodiment, a sample well 2-211 may comprise excitation-energy-enhancing structures 3-711 and an adherent 3-211 formed adjacent the excitation-energy-enhancing structures. The energy-enhancing structures 3-711 may comprise surface plasmon or nano-antenna structures formed in conductive materials on an optically transparent layer 3-235, according to some embodiments. FIG. 3-7C depicts an elevation view of the sample well 2-211 and nearby structure, and FIG. 3-7D depicts a plan view. The excitation-energy-enhancing structures 3-711 may be shaped and arranged to enhance excitation energy in a small localized region. For example, the structures may include pointed conductors having acute angles at the sample well that increase the intensity of the excitation energy within an excitation region 3-215. In the depicted example, the excitation-energy-enhancing structures 3-711 are in the form of a bow-tie. Samples 3-101 diffusing into the region may be retained, temporarily or permanently, by the adherent 3-211 and excited by excitation energy that may be delivered from an excitation source 2-250 located in the instrument 2-120. According to some embodiments, the excitation energy may drive surface-plasmon currents in the energy-enhancing structures 3-711. The resulting surface-plasmon currents may produce high electric fields at the sharp points of the structures 3-711, and these high fields may excite a sample retained in the excitation region 3-215. In some embodiments, a sample well 2-211 depicted in FIG. 3-7C may include a divot 3-216.

Another embodiment of a sample well is depicted in FIG. 3-7E, and shows an excitation-energy-enhancing structure 3-720 formed along interior walls of the sample well 2-211. The excitation-energy-enhancing structure 3-720 may comprise a metal or conductor, and may be formed using an angled (or shadow), directional deposition where the substrate on which the sample well is formed is rotated during the deposition. During the deposition, the base of the sample well 2-211 is obscured by the upper walls of the well, so that the deposited material does not accumulate at the base. The resulting structure 3-720 may form an acute angle 3-722 at the bottom of the structure, and this acute angle of the conductor can enhance excitation energy within the sample well.

In an embodiment as depicted in FIG. 3-7E, the material 3-232 in which the sample well is formed need not be a conductor, and may be any suitable material such as a dielectric material. According to some implementations, the sample well 2-211 and excitation-energy-enhancing structure 3-720 may be formed at a blind hole etched into a dielectric layer 3-235, and a separate layer 3-232 need not be deposited.

In some implementations, a shadow evaporation may be subsequently performed on the structure shown in FIG. 3-7E to deposit a metallic or conductive energy-enhancing structure, e.g., a trapezoidal structure or pointed cone at the base of the sample well, as depicted by the dashed line. The energy-enhancing structure may enhance the excitation energy within the well via surface plasmons. After the shadow evaporation, a planarizing process (e.g., a chemical-mechanical polishing step or a plasma etching process) may be performed to remove or etch back the deposited material at the top of the sample well, while leaving the energy-enhancing structure within the well.

In some embodiments, a sample well 2-211 may be formed from more than a single metal layer. FIG. 3-7F illustrates a sample well formed in a multi-layer structure, where different materials may be used for the different layers. According to some embodiments, a sample well 2-211 may be formed in a first layer 3-232 (which may be a semiconducting or conducting material), a second layer 3-234 (which may be an insulator or dielectric), and a third layer 2-221 (which may be a conductor or semiconductor). In some embodiments, a degeneratively-doped semiconductor or graphene may be used for a layer of the sample well. In some implementations, a sample well may be formed in two layers, and in other implementations a sample well may be formed in four or more layers. In some embodiments, multi-layer materials used for forming a sample well may be selected to increase surface-plasmon generation at a base of the sample well or suppress surface-plasmon radiation at a top of the well. In some embodiments, multi-layer materials used for forming a sample well may be selected to suppress excitation energy from propagating beyond the sample well and multi-layer structure into the bulk specimen.

In some embodiments, multi-layer materials used for forming a sample well may be selected to increase or suppress interfacial excitons which may be generated by excitation energy incident on the sample well. For example, multi-excitons, such as biexcitons and triexitons, may be generated at an interface between two different semiconductor layers adjacent a sample well. The sample well may be formed in both the metal layer and the first semiconductor layer such that the interface between the first semiconductor layer and a second semiconductor layer is at an excitation region 3-215 of the sample well. Interfacial excitons may have longer lifetimes than excitons within the volume of a single semiconductor layer, increasing the likelihood that the excitons will excite a sample or tag via FRET or DET. In some embodiments, at least one quantum dot at which multi-excitons may be excited may be attached to a bottom of the sample well (e.g., by a linking molecule). Excitons excited at a quantum dot may also have longer lifetimes than excitons within the volume of a single semiconductor layer. Interfacial excitons or excitons generated at a quantum dot may increase the rate of FRET or DET, according to some embodiments.

Various materials may be used to form sample wells described in the foregoing embodiments. According to some embodiments, a sample well 2-211 may be formed from at least one layer of material 2-221, which may comprise any one of or a combination of a conductive material, a semiconductor, and an insulator. In some embodiments, the sample well 2-211 comprises a highly conductive metallic layer, e.g., gold, silver, aluminum, copper. In some embodiments, the layer 2-221 may comprise a multi-layer stack that includes any one of or a combination of gold, silver, aluminum, copper, titanium, titanium nitride, and chromium. In some implementations, other metals may be used additionally or alternatively. According to some embodiments, a sample well may comprise an alloy such as AlCu or AlSi.

In some embodiments, the multiple layers of different metals or alloys may be used to form a sample well. In some implementations, the material in which the sample well 2-211 is formed may comprise alternating layers of metals and non-metals, e.g., alternating layers of metal and one or more dielectrics. In some embodiments, the non-metal may include a polymer, such as polyvinyl phosphonic acid or a polyethylene glycol (PEG)-thiol.

A layer 2-221 in which a sample well is formed may be deposited on or adjacent to at least one optically transparent layer 3-235, according to some embodiments, so that excitation energy (e.g., in the form of visible or near-infrared radiation) and emission energy (e.g., in the form of visible or near-infrared radiation) may travel to and from the sample well 2-211 without significant attenuation. For example, excitation energy from an excitation source 2-250 may pass through the at least one optically transparent layer 3-235 to the excitation region 3-215, and emission from the sample may pass through the same layer or layers to the sensor 2-250.

In some embodiments, at least one surface of the sample well 2-211 may be coated with one or more layers 3-211, 3-280 of material that affect the action of a sample within the sample well, as depicted in FIG. 3-8. For example, a thin dielectric layer 3-280 (e.g., alumina, titanium nitride, or silica) may be deposited as a passivating coating on sidewalls of the sample well. Such a coating may be implemented to reduce sample adhesion of a sample outside the excitation region 3-215, or to reduce interaction between a sample and the material 2-221 in which the sample well 2-211 is formed. The thickness of a passivating coating within the sample well may be between about 5 nm and about 50 nm, according to some embodiments.

In some implementations, a material for a coating layer 3-280 may be selected based upon an affinity of a chemical agent for the material, so that the layer 3-280 may be treated with a chemical or biological substance to further inhibit adhesion of a sample species to the layer. For example, a coating layer 3-280 may comprise alumina, which may be passivated with a polyphosphonate passivation layer, according to some embodiments. Additional or alternative coatings and passivating agents may be used in some embodiments.

According to some embodiments, at least a bottom surface of the sample well 2-211 and/or divot 3-216 may be treated with a chemical or biological adherent 3-211 (e.g., biotin) to promote retention of a sample. The sample may be retained permanently or temporarily, e.g., for at least a period of time between about 0.5 milliseconds and about 50 milliseconds. In another embodiment, the adherent may promote temporary retention of a sample 3-101 for longer periods. Any suitable adherent may be used in various embodiments, and is not limited to biotin.

According to some embodiments, the layer of material 3-235 adjacent the sample well may be selected based upon an affinity of an adherent for the material of that layer. In some embodiments, passivation of the sample well's side walls may inhibit coating of an adherent on the sidewalls, so that the adherent 3-211 preferentially deposits at the base of the sample well. In some embodiments, an adherent coating may extend up a portion of the sample well's sidewalls. In some implementations, an adherent may be deposited by an anisotropic physical deposition process (e.g., evaporation, sputtering), such that the adherent accumulates at the base of a sample well or divot and does not appreciably form on sidewalls of the sample well.

Various fabrication techniques may be employed to fabricate sample wells 2-211 for an assay chip. A few example processes are described below, but the invention is not limited to only these examples.

The sample well 2-211 may be formed by any suitable micro- or nano-fabrication process, which may include, but is not limited to, processing steps associated with photolithography, deep-ultraviolet photolithography, immersion photolithography, near-field optical contact photolithography, EUV lithography, x-ray lithography, nanoimprint lithography, interferometric lithography, step-and-flash lithography, direct-write electron beam lithography, ion beam lithography, ion beam milling, lift-off processing, reactive-ion etching, selective epitaxy, molecular self-assembly, organic synthesis, etc. According to some embodiments, a sample well 2-211 may be formed using photolithography and lift-off processing. Example fabrication steps associated with lift-off processing of a sample well are depicted in FIG. 3-9A through FIG. 3-9E. Although fabrication of only a single sample well or structure at a pixel is typically depicted in the drawings, it will be understood that a large number of sample wells or structures may be fabricated on a substrate (e.g., at each pixel) in parallel.

According to some embodiments, a layer 3-235 (e.g., an oxide layer) on a substrate may be covered with an anti-reflection coating (ARC) layer 3-910 and photoresist 3-920, as depicted in FIG. 3-9A. The photoresist 3-920 may be exposed and patterned using photolithography and development of the resist. The photoresist 3-920 may be developed to remove exposed portions or unexposed portions (depending on the resist type), leaving a pillar 3-922 that has a diameter approximately equal to a desired diameter for the sample well, as depicted in FIG. 3-9B. The height of the pillar 3-922 may be greater than a desired depth of the sample well.

The pattern of the pillar 3-922 may be transferred to the ARC layer 3-910 via anisotropic, reactive ion etching (RIE), for example as shown in FIG. 3-9C. The region may then be coated with at least one material 2-221, e.g., a conductor or metal, that is desired to form the sample well. A portion of the deposited material, or materials, forms a cap 3-232 over the pillar 3-922, as depicted in FIG. 3-9D. The photoresist 3-920 and ARC layer 3-910 may then be stripped from the substrate, using a selective removal process (e.g., using a chemical bath with or without agitation which dissolves at least the resist and releases or "lifts off" the cap). If the ARC layer 3-910 remains, it may be stripped from the substrate using a selective etch, leaving the sample well 3-210 as shown in FIG. 3-9E. According to some embodiments, the sidewalls 3-214 of the sample well may be sloped due to the nature of the deposition of the at least one material 2-221.

As used herein, a "selective etch" means an etching process in which an etchant selectively etches one material that is desired to be removed or etched at a higher rate (e.g., at least twice the rate) than the etchant etches other materials which are not intended to be removed.

Because the resist and ARC layer are typically polymer based, they are considered soft materials which may not be suitable for forming sample wells having high aspect ratios (e.g., aspect ratios greater than about 2:1 with respect to height-to-width). For sample wells having higher aspect ratios, a hard material may be included in the lift-off process. For example, before depositing the ARC layer and photoresist, a layer of a hard (e.g., an inorganic material) may be deposited. In some embodiments, a layer of titanium or silicon nitride may be deposited. The layer of hard material should exhibit preferential etching over the material, or materials, 2-221 in which the sample well is formed. After the photoresist is patterned, a pattern of the pillar may be transferred into the ARC layer and the underlying hard material 3-930 yielding a structure as depicted in FIG. 3-9F. The photoresist and ARC layer may be then stripped, the material(s) 2-221 deposited, and a lift-off step performed to form the sample well.

According to some embodiments, a lift-off process may be used to form a sample well comprising energy-enhancing structures 3-711, as depicted in FIG. 3-7C and FIG. 3-7D.

An alternative process for forming a sample well is depicted in FIGS. 3-10A through 3-10D. In this process, the sample well may be directly etched into at least one material 3-236. For example, at least one material 3-236 in which a sample well is to be formed may be deposited on a substrate 3-325. The layer may be covered by an ARC layer 3-910 and a photoresist 3-920, as illustrated in FIG. 3-10A. The photoresist may be patterned to form a hole having a diameter approximately equal to a desired diameter of the sample well, as depicted in FIG. 3-10B. The pattern of the hole may be transferred to the ARC layer and through the layer 3-230 using an anisotropic, reactive ion etch, as shown in FIG. 3-10C for example. The resist and ARC layer may be stripped, yielding a sample well as depicted in FIG. 3-10D. According to some embodiments, the sidewalls of a sample well formed by etching into the layer of material 3-230 may be more vertical than sidewalls resulting from a lift-off process.

In some embodiments, the photoresist and ARC layer may be used to pattern a hard mask (e.g., a silicon nitride or oxide layer, not shown) over the material 3-236. The patterned hole may then be transferred to the hard mask, which is then used to transfer the pattern into the layer of material 2-221. A hard mask may allow greater etching depths into the layer of material 2-221, so as to form sample wells of higher aspect ratio.

It will be appreciated that lift-off processes and direct etching fabrication techniques described above may be used to form a sample well when multiple layers of different materials are used to form a stack of material in which the sample well is formed. An example stack is shown in FIG. 3-11. According to some embodiments, a stack of material may be used to form a sample well to improve coupling of excitation energy to the excitation region of a sample well, or to reduce transmission or re-radiation of excitation energy into the bulk specimen. For example, an absorbing layer 3-942 may be deposited over a first layer 3-940. The first layer may comprise a metal or metal alloy, and the absorbing layer may comprise a material that inhibits surface plasmons, e.g., amorphous silicon, TaN, TiN, or Cr. In some implementations, a surface layer 3-944 may also be deposited to passivate the surface surrounding the sample well (e.g., inhibit adhesion of molecules).

Formation of a sample well including a divot 3-216 may be done in any suitable manner. In some embodiments, a divot may be formed by etching further into an adjacent layer 3-235, and/or any intervening layer or layers, adjacent the sample well. For example, after forming a sample well in a layer of material 2-221, that layer 2-221 may be used as an etch mask for patterning a divot, as depicted in FIG. 3-12. For example, the substrate may be subjected to a selective, anisotropic reactive ion etch so that a divot 3-216 may be etched into adjacent layer 3-235. For example, in an embodiment where the material 2-221 is metallic and the adjacent layer 3-235 silicon oxide, a reactive-ion plasma etch having a feed gas comprising CHF3 or CF4 may be used to preferentially remove exposed silicon oxide below the sample well and form the divot 3-216. As used herein, "silicon oxide" generally refers to SiOx and may include silicon dioxide, for example.

In some embodiments, conditions within the plasma (e.g., bias to the substrate and pressure) during an etch may be controlled to determine the etch profile of the divot 3-216. For example, at low pressure (e.g., less than about 100 mTorr) and high DC bias (e.g., greater than about 20V), the etching may be highly anisotropic and form substantially straight and vertical sidewalls of the divot, as depicted in the drawing. At higher pressures and lower bias, the etching may be more isotropic yielding tapered and/or curved sidewalls of the divot. In some implementations, a wet etch may be used to form the divot, which may be substantially isotropic and form an approximately spherical divot that may extend laterally under the material 2-221, up to or beyond the sidewalls of the sample well.

FIG. 3-13A through FIG. 3-13C depict process steps that may be used to form a divot 3-216 having a smaller transverse dimension than the sample well 2-211 (for example, a divot like that depicted in FIG. 3-7B). In some implementations, after forming a sample well, a conformal sacrificial layer 3-960 may be deposited over a region including the sample well. According to some embodiments, the sacrificial layer 3-960 may be deposited by a vapor deposition process, e.g., chemical vapor deposition (CVD), plasma-enhanced CVD, or atomic layer deposition (ALD). The sacrificial layer may then be etched back using a first anisotropic etch that is selective to the sacrificial layer 3-960, removes the layer from horizontal surfaces, leaves side wall coatings 3-962 on walls of the sample well, as depicted in FIG. 3-13B. The etch back may be selective and stop on the material 2-221 and adjacent layer 3-235 in some embodiments, or may be a non-selective, timed etch in some embodiments.

A second anisotropic etch that is selective to the adjacent layer 3-235 may be executed to etch a divot 3-216 into the adjacent layer as depicted in FIG. 3-13C. The sacrificial side wall coatings 3-962 may then optionally be removed by a selective wet or dry etch. The removal of the sidewall coatings open up the sample well to have a larger transverse dimension than the divot 3-216.

According to some embodiments, the sacrificial layer 3-960 may comprise the same material as the adjacent layer 3-235. In such embodiments, the second etch may remove at least some of the side wall coating 3-962 as the divot is etched into the adjacent layer 3-235. This etch back of the side wall coating can form tapered sidewalls of the divot in some embodiments.

In some implementations, the sacrificial layer 3-960 may be formed from, or include a layer of, a material that is used to passivate the sidewalls of the sample well (e.g., reduce adhesion of samples at the sidewalls of the sample well). At least some of the layer 3-960 may then be left on the walls of the sample well after formation of the divot.

According to some embodiments, the formation of the sidewall coatings 3-962 occurs after the formation of the divot. In such an embodiment the layer 3-960 coats the sidewalls of the divot. Such a process may be used to passivate the sidewalls of the divot and localize the sample at the center of the divot.

Process steps associated with depositing an adherent 3-211 at a base of a sample well 2-211, and a passivation layer 3-280 are depicted in FIGS. 3-14A through 3-14D. According to some embodiments, a sample well may include a first passivation layer 3-280 on walls of the sample well. The first passivation layer may be formed, for example, as described above in connection with FIG. 3-13B or FIG. 3-8. In some embodiments, a first passivation layer 3-280 may be formed by any suitable deposition process and etch back. In some embodiments, a first passivation layer may be formed by oxidizing the material 3-230 in which the sample well is formed. For example, the sample well may be formed of aluminum, which may be oxidized to create a coating of alumina on sidewalls of the sample well.

An adherent 3-980 or an adherent precursor (e.g., a material which preferentially binds an adherent) may be deposited on the substrate using an anisotropic physical deposition process, e.g., an evaporative deposition, as depicted in FIG. 3-14A. The adherent or adherent precursor 3-980 may form an adherent layer 3-211 at the base of the sample well, as depicted in FIG. 3-14B, and may coat an upper surface of the material 2-221 in which the sample well is formed. A subsequent angled, directional deposition depicted in FIG. 3-14C (sometimes referred to as a shadow deposition or shadow evaporation process) may be used to deposit a second passivation layer 2-280 over an upper surface of the material 2-221 without covering the adherent layer 3-211. During the shadow deposition process, the substrate may be rotated around an axis normal to the substrate while the passivation layer precursors 3-990 are deposited, so that the second passivation layer 3-280 deposits more uniformly around an upper rim of the sample well. A resulting structure is depicted in FIG. 3-14D, according to some embodiments. As an alternative to depositing the second passivation layer, a planarizing etch (e.g., a CMP step) may be used to remove adherent from an upper surface of the material 3-230.

According to some implementations, an adherent layer 3-211 may be deposited centrally at the base of a tapered sample well, as depicted in FIG. 3-15. For example, an adherent, or adherent precursor, may be directionally deposited, as depicted in FIG. 3-14A, in a tapered sample well, formed as described above. Walls of the sample well may be passivated by an oxidation process before or after deposition of the adherent layer 3-211. Adherent or precursor remaining on a surface of the material 2-221 may be passivated as described in connection with FIG. 3-14D. In some embodiments, an adherent on an upper surface of the material 2-221 may be removed by a chemical-mechanical polishing step. By forming an adherent layer, or an adherent layer precursor, centrally at the base of a sample well, deleterious effects on emission from a sample (e.g., suppression or quenching of sample radiation from sample walls, unfavorable radiation distribution from a sample because it is not located centrally with respect to energy coupling structures formed around a sample well, adverse effects on luminescent lifetime for a sample) may be reduced.

In some embodiments, lift-off patterning, etching, and deposition processes used to form the sample well and divot may be compatible with CMOS processes that are used to form integrated CMOS circuits on a sensor chip. Accordingly, sensor may be fabricated using conventional CMOS facilities and fabrication techniques, though custom or specialized fabrication facilities may be used in some implementations.

Variations of the process steps described above may be used to form alternative embodiments of sample wells. For example, a tapered sample well such as depicted in FIG. 3-7A or FIG. 3-7B may be formed using an angled deposition process depicted in FIG. 3-14C. For the sample well of FIG. 3-7B, the angle of deposition may be changed during the deposition process. For such embodiments, a sample well having substantially straight and vertical sidewalls may first be formed, and then additional material 2-221 deposited by an angled deposition to taper the sidewalls of the sample well.

B. Coupling Excitation Energy to the Sample Well

As illustrated in FIG. 2-1 and FIG. 2-3, excitation energy 2-251 from the excitation source 2-250 is guided to the sample well 2-211 using components of the instrument 2-120 and components of the assay chip 2-110. This section describes the components of the assay chip 2-110 that may aid in the coupling of excitation energy 2-251 to the sample well 2-211.

Coupling of energy from an excitation source to a sample well may be improved or affected by forming excitation-coupling structures within and/or adjacent a sample well. Excitation-coupling structures may comprise micro- or nano-scale structures fabricated around a sample well in some embodiments, or may comprise structures or particles formed at a sample well in some embodiments. Excitation-coupling structures may affect radiative excitation of a sample in some implementations, and may affect non-radiative excitation of a sample in some implementations. In various embodiments, radiative excitation-coupling structures may increase an intensity of excitation energy within an excitation region of a sample well. Non-radiative excitation-coupling structures may improve and/or alter non-radiative energy-transfer pathways from an excitation source (which may be radiative or non-radiative) to a sample.

C. Radiative Excitation-Coupling Structures

There are a number of different types of radiative, excitation-coupling structures that may be used to affect coupling of excitation energy from an excitation source to an excitation region within a sample well. Some radiative coupling structures may be formed of a conductor (e.g., include a metal layer), and support surface plasmon oscillations that locally affect the excitation energy (e.g., locally alter an electromagnetic field) near and/or within the sample well. In some cases, surface-plasmon structures may enhance the excitation energy within an excitation region of the sample well by a factor of two or more. Some radiative coupling structures may alter the phase and/or amplitude of an excitation field to enhance excitation energy within a sample well. Various embodiments of radiative excitation-coupling structures are described in this section.

FIG. 4-1A depicts just one example of a surface-plasmon structure 4-120 that may be used to enhance coupling of excitation energy into a sample well. The drawing depicts a plan view of a region around a surface-plasmon structure 4-120, and represents results of a numerical simulation of electric field intensity around the structure. The drawing depicts a surface-plasmon structure comprising three triangular features having sharp apexes that are located in close proximity to a sample well (not shown). According to some embodiments, a surface-plasmon structure may comprise a metal or conductor (e.g., a patterned thin film of any one or combination of the following metals or metal alloys: Al, Au, Ag, Ti, TiN). A thickness of the film may be between approximately 10 nm and approximately 100 nm in some embodiments, though other thicknesses may be used in other embodiments. A surface-plasmon structure, in some embodiments, may include sharp features 4-110 located in close proximity to a sample well (e.g., within about 100 nm).

FIG. 4-1B depicts a cross-section, elevation view of the surface-plasmon structure of FIG. 4-1A, taken at the dashed line. The simulation shows a localized, high-intensity region 4-505 of the excitation energy adjacent an apex of a triangle of the surface-plasmon structure. For this simulation, the surface-plasmon structure 4-120 was located on a dielectric layer 4-135 (silicon dioxide). The surface-plasmon structure taps energy from an evanescent field of the waveguide, and enhances the intensity at the sample well.

In some embodiments, enhancement of excitation energy by a surface-plasmon structure may be localized to an extent that a deep sample well 2-211 is not needed. For example, if a high-intensity region 4-505 is formed having a diameter of approximately 100 nm with a peak intensity value greater than about 80% of the intensity outside the region, then a deep sample well may not be needed. Only samples within the high-intensity region 4-505 would contribute appreciable emission for purposes of detection.

When an incident electromagnetic field interacts with a surface-plasmon structure, surface-wave currents are generated in the structure. The shape of the structure can affect the intensity and distribution of these surface-plasmons. These localized currents can interact with and significantly alter and intensify the incident electromagnetic field in the immediate vicinity of the surface-plasmon structure, e.g., as depicted by the high-intensity region 4-505 in FIG. 4-1B. In some embodiments, an emitter (e.g., a fluorescing tag) that emits energy near a surface-plasmon structure can have its emission altered by the structure, so as to alter a far-field radiation pattern from the emitter.

Another embodiment of a surface-plasmon structure 4-122 is depicted in the plan view of FIG. 4-1C. The illustrated bow-tie structure comprises two triangular metallic structures located adjacent a sample well 2-211. The structures may be patterned below a sample well, for example, and/or adjacent an excitation region of the sample well. There may be a gap 4-127 between the sample well and sharp features 4-125 of the surface-plasmon structure, in some implementations. The gap 4-127 may be between approximately 10 nm and approximately 200 nm, according to some embodiments. In some implementations, the gap 4-127 may be between approximately 10 nm and approximately 100 nm. The sharp features 4-125 may comprise a point or sharp bend in an edge of the surface-plasmon structure, as depicted in the drawing. The sharp features may have any suitable shape. In some embodiments a bend radius of a sharp feature 4-125 may be less than approximately five wavelengths associated with the incident excitation energy. In some embodiments a bend radius of a sharp feature 4-125 may be less than approximately two wavelengths associated with the incident excitation energy. In some embodiments a bend radius of a sharp feature 4-125 may be less than approximately five wavelengths associated with a surface-plasmon wave that is excited by the incident excitation energy. In some embodiments a bend radius of a sharp feature 4-125 may be less than approximately two wavelengths associated with a surface-plasmon wave that is excited by the incident excitation energy.

According to some embodiments, surface-plasmon structures 4-122 may be patterned within a sample well 2-211 as illustrated in the elevation view of FIG. 4-1D. In some embodiments, a surface-plasmon structure within a sample well may comprise one or more fingers (e.g., metallic fingers) patterned onto sidewalls of the sample well, as depicted in the drawing. FIG. 4-1E depicts a plan view of the sample well 2-211 showing the surface-plasmon structures 4-122 formed on sidewalls within the sample well. In some embodiments, the lower ends of these surface-plasmon structures 4-122 form sharp features or bends where the electromagnetic field will be enhanced. The surface-plasmon structures 4-122 may, or may not, extend to a base of the sample well.

In some embodiments, the surface-plasmon structures 4-122 may be arranged to affect the polarization of the excitation energy and/or emitted energy from the sample well. For example, a pattern as depicted in FIG. 4-1E may be used to affect a preferred orientation of linear or elliptical excitation polarization and/or a preferred orientation of linear or elliptical polarization from an emitter within the sample well.

Surface-plasmon structures may be patterned in shapes other than those depicted in FIG. 4-1A through FIG. 4-1E. For example, surface-plasmon structures may be patterned as regular or periodic structures, as depicted in FIG. 4-2A, according to some embodiments. For example, a surface-plasmon structure may be patterned is an array of protruding features 4-210 on a lower surface of a material 2-221 in which the sample well 2-211 is formed. Periodic surface-plasmon structures may be formed in a regular array, for example, a grating, a grid, a lattice, a circular grating, a spiral grating, an elliptical grating, or any other suitable structure. There may be a substantially uniform spacing s between the protrusions 4-210 of a surface-plasmon structure. In some implementations, the spacing s may have any value between approximately 40 nm and approximately 250 nm. According to some embodiments, the protrusions may have a height h between approximately 20 nm and approximately 100 nm. In some implementations, the spacing s may be non-uniform or may be chirped (having a decreasing value at larger radial distances). In some embodiments, the protrusions 4-210 of a surface-plasmon structure may be patterned as a Fresnel zone plate. According to some embodiments, a surface-plasmon structure of 4-210 may be formed adjacent to a transparent layer and/or dielectric layer 3-235. In some embodiments, the spacing between the protrusions 4-210 may be periodic, while in other embodiments the protrusions 4-210 may be aperiodic.

In some implementations, a surface-plasmon structure 4-212 may be spaced from a material 2-221 in which the sample well is formed as depicted in FIG. 4-2B. For example, there may be an intervening dielectric layer 4-247 between the surface-plasmon structure 4-212 and the material 4-230. According to some embodiments, a surface plasmons structure 4-212 may be located adjacent a divot 3-216 of a sample well, as depicted in FIG. 4-2B. For example, a surface-plasmon structure 4-212 may be located adjacent sidewalls of a divot 3-216, as depicted in FIG. 4-2B.

FIG. 4-2C illustrates a surface-plasmon structure 4-214 that is formed as a concentric, circular grating. The structure 4-214 may comprise concentric conducting rings 4-215, according to some embodiments. The rings may be separated by a regular spacing s and have a height h, as described in connection with FIG. 4-2A. According to some embodiments, a sample well 4-210 with an optional divot may be located at a center of the rings. The circular grating may be patterned adjacent a base of the sample well.

A periodicity of a surface-plasmon structure may be selected to form a resonant structure according to some embodiments. For example a spacing s of a surface-plasmon structure may be selected to be approximately one-half wavelength of a surface-plasmon wave that is generated in the structure by the excitation energy. When formed as a resonant structure, a surface-plasmon structure may accumulate and resonate excitation energy along the direction of the periodic surface-plasmon structure. Such a resonant behavior can intensify electromagnetic energy within a sample well, or adjacent a sample well, as depicted in FIG. 4-2D. While the spacing of the surface plasmon structure may be periodic in some embodiments, in other embodiments the spacing may be aperiodic. Using aperiodic spacing allows the field enhancement to be specifically designed for the wavelengths of excitation energy and wavelengths of emission energy involved. FIG. 4-2D represents numerically simulated electromagnetic field results at the base of the sample well and around a periodic surface-plasmon structure. The surface-plasmon structure 4-216 is located adjacent the material 2-221 in which the sample well is formed, and is adjacent a base of a sample well 2-211. The surface-plasmon structure may be in the form of a grating or circular grating that repeats at regular or irregular spacing intervals in regions away from the sample well and outside the simulated region. For example, there may be between three and fifty repeated grating protrusions of the surface-plasmon structure 4-216. A region of high intensity 4-240 can be seen at the base of the sample well 2-211. The intensity within this region has been enhanced by more than a factor of 2 over the surrounding region just below the surface-plasmon structure.

FIG. 4-2E depicts, in elevation view, an alternative embodiment of a resonant surface-plasmon structure 4-218. According to some embodiments, a surface-plasmon structure may be formed as periodic or aperiodic grating or grid patterns, and may be patterned in multiple layers 4-247. A sample well 2-211 may be patterned through the multiple layers 4-247 and within the resonant surface-plasmon structure 4-218, according to some embodiments. In some implementations, a resonant surface-plasmon structure may comprise discrete conductive elements 4-222 is depicted in the plan view of FIG. 4-2F. In some implementations, a resonant surface-plasmon structure may comprise a continuous lattice pattern 4-250, as depicted in FIG. 4-2G. A dielectric filler 4-252 may be located in voids of the conductive material 4-250, and a sample well 2-211 may be located with a void.

There are a variety of different surface-plasmon structures that may be used to enhance coupling into a sample well or to affect emission from a sample within the sample well. FIG. 4-2H depicts, in plan view, yet an alternative embodiment of the surface-plasmon structure. A cross-section view of the structure is depicted in FIG. 4-2I taken through line 4-2I of FIG. 4-2H. According to some implementations, a surface-plasmon structure may comprise an array of discs 4-260 distributed around a sample well 2-211. In some embodiments, each disc 4-260 may be approximately a distance R from the sample well 2-211. However, as illustrated, the distance from each disc 4-260 to the sample well 2-211 may vary. Also, the size of each disc 4-260 may be different. In some implementations, instead of using conductive discs 4-260, a surface-plasmon structure may comprise a conductive layer through which a distributed pattern of holes are formed. Such a structure may be referred to as a "nano-antenna."

A variety of different processes may be used to pattern surface-plasmon structures adjacent a sample well. FIG. 4-3A through FIG. 4-5E depict structures associated with process steps that may be used to form surface-plasmon structures adjacent to a sample well, according to some embodiments. Referring now to FIG. 4-3A, a process for forming a surface-plasmon structure may comprise forming a resist layer 4-310 on an anti-reflective coating (ARC) 4-320 on a masking layer 4-330. The layers may be disposed on a transparent dielectric layer 3-235, according to some implementations. The resist layer 4-310 may comprise a photoresist or an electron- or ion-beam resist that may be lithographically patterned. The masking layer 4-330 may comprise a hard mask formed of an inorganic material (e.g., silicon or silica nitride, or any other suitable material), according to some embodiments.

In some implementations, a photolithographic process may be used to pattern the resist 4-310 as depicted in FIG. 4-3B. The selected pattern may comprise a layout of protrusions or holes that will be used to form a desired surface-plasmon structure. After development of the resist 4-310, regions of the ARC will be exposed, and the pattern may be etched into the ARC layer 4-320 and then into the masking layer 4-330. The resist and ARC may be stripped from the substrate, and a resulting structure may appear as shown in FIG. 4-3C. The masking layer 4-330 may then be used as an etch mask, so that the pattern may be transferred into the underlying dielectric layer 3-235 via a selective anisotropic etch, as depicted in FIG. 4-3D.

A conductive material 2-221, or a layer of materials comprising a conductor, may then be deposited over the region, as illustrated in FIG. 4-3E. Any suitable conductive material may be used for forming a surface plasmon structure, whether or not it is deposited as a separate layer from the material 2-221. For example, in some cases, a first conductive material may be deposited as a base layer of material 2-221 in which a surface-plasmon structure is formed. Examples of materials that may be used for forming a surface-plasmon structure include, but are not limited to, Au, Al, Ti, TiN, Ag, Cu, and alloys or combination layers thereof.

The material 2-221, or layer of materials, may be deposited by any suitable deposition process, including but not limited to a physical deposition process or a chemical vapor deposition process. In some embodiments, the material 2-221 may have a thickness between approximately 80 nm and approximately 300 nm. In some implementations, the material 2-221 may be planarized (e.g., using a CMP process), though planarization is not necessary. A sample well may be formed in the material 2-221 using any suitable process described herein in connection with fabricating a sample well.

The inventors have recognized that forming a surface-plasmon structure according to the steps shown in FIG. 4-3A through FIG. 4-3E may require accurate alignment of the sample well to the surface-plasmon structure. For example, a surface-plasmon structure comprising a concentric grating, as depicted in FIG. 4-2C, may require accurate alignment of the sample well 2-211 to the center of the surface-plasmon structure 4-214. To avoid fabrication difficulties associated with such accurate alignment, self-alignment processes depicted in FIG. 4-4A through FIG. 4-5E may be used.

Referring now to FIG. 4-4A, a process for forming a surface-plasmon structure and sample well that is self-aligned to the surface-plasmon structure may comprise forming a masking layer 4-410 on a transparent dielectric layer 3-235. The masking layer may comprise a hard mask formed of an inorganic material, such as silicon or silica nitride, according to some embodiments. A thickness of the masking layer 4-410 may be approximately equal to a desired height of a sample well 2-212. For example, the thickness of the masking layer may be between approximately 50 nm and approximately 200 nm, according to some embodiments, though other thicknesses may be used in other embodiments.

The masking layer 4-410 may be patterned to create voids 4-430 having the desired pattern of a surface-plasmon structure that will be patterned in the dielectric layer 3-235. The patterning of the masking layer 4-410 may be done with any suitable lithography process (e.g., photolithography, electron-beam lithography, ion-beam lithography, EUV lithography, x-ray lithography). The resulting structure may appear as shown in FIG. 4-4B. The structure may include a central pillar 4-420, which will be used subsequently to form the self-aligned sample well.

A resist 4-440 (e.g., a photoresist) may then be patterned over the patterned masking layer 4-410, as depicted in FIG. 4-4C. Alignment for patterning the resist 4-440 (e.g., mask to substrate alignment) need not be highly accurate, and only requires the resist 4-440 to cover a central pillar 4-420 and not cover voids 4-430 that will be used to form the surface-plasmon structure.

A selective anisotropic etch may then be used to etch the dielectric layer 3-235 and transfer the pattern of the surface-plasmon structure into the dielectric, as depicted in FIG. 4-4D according to some embodiments. A selective isotropic etch may then be used to remove the exposed portions of the masking layer 4-410. The isotropic etch may be a wet etch, for example, though an isotropic dry etch may be used in some embodiments. Because the resist 4-440 covers the central pillar 4-420, the central pillar will not be etched and remain on the substrate, as depicted in FIG. 4-4E. The resist 4-440 may then be stripped from the substrate exposing the pillar 4-420, as depicted in FIG. 4-4F.

According to some embodiments, a metal conductive material 2-221, or a stack of materials including a conductive material, may then be deposited over the region as illustrated in FIG. 4-4G. The central pillar 4-420 and a cap of deposited material over the pillar may then be removed by a selective wet etch of the pillar, lifting off the cap. The removal of the central pillar leaves a sample well that is self-aligned to the underlying surface-plasmon structure 4-450.

An alternative process may be used to form a sample well that is self-aligned to a surface-plasmon structure, and is depicted in FIG. 4-5A through FIG. 4-5E. According to some embodiments, one or more conductive layers 4-510, 4-520 may be patterned on a transparent dielectric layer 3-235 using any suitable lithography process, as depicted in FIG. 4-5A. In some implementations, a first layer 4-510 may comprise aluminum, and a second layer 4-520 may comprise titanium nitride, though other material combinations may be used in various embodiments. A total thickness of the one or more layers may be approximately equivalent to a desired height of the sample well, according to some embodiments. The patterning may form a sample well 2-211, and voids 4-525 adjacent the sample well in the one or more metal layers. The voids may be arranged in the pattern of a desired surface-plasmon structure.

In some implementations, the dielectric layer 3-235 may be etched to transfer the pattern of the surface-plasmon structure and sample well 2-211 into the dielectric layer to form dielectric voids 4-530, as depicted in FIG. 4-5B. The etch depth of the dielectric voids 4-530 may be between approximately 20 nm and approximately 150 nm, according to some embodiments. A resist 4-440 may be patterned to cover the sample well, as depicted in FIG. 4-5C. Alignment for patterning the resist need not be highly accurate, and only need cover the sample well without covering adjacent etched regions of the dielectric layer 3-235 that will be used to form the surface-plasmon structure.

As illustrated in FIG. 4-5D, a conductive material 4-512, or layers of materials including a conductor, may be deposited over the region using any suitable deposition process. The material 4-512 may fill the etched regions of the dielectric layer, and may extend above the one or more layers 4-510, 4-520. The resist 4-440 and the material covering the resist may then be removed according to a lift-off process. The resulting structure, shown in FIG. 4-5E, leaves a sample well that is self-aligned to the surrounding surface-plasmon structure. The sample well includes a divot 3-216.

In some embodiments the process depicted in FIG. 4-5A through FIG. 4-5E may be used to form a sample well that does not have a divot 3-216. For example, the resist 4-440 may be patterned over the sample well 2-211 before the dielectric layer 3-235 is etched. The dielectric layer 3-235 may then be etched, which will transfer the pattern of the surface-plasmon structure to the dielectric layer but not form a divot. The process may then proceed as illustrated in FIG. 4-5D and FIG. 4-5E to create a self-aligned sample well having no divot.

Other structures, in addition to or as an alternative to surface-plasmon structures, may be patterned in the vicinity of the sample well 2-211 to increase the excitation energy within the sample well. For example some structures may alter the phase and/or the amplitude of the incident excitation field so as to increase the intensity of the excitation energy within the sample well. FIG. 4-6A depicts a thin lossy film 4-610 that may be used to alter the phase and amplitude of incident excitation energy and increase the intensity of electromagnetic radiation within the sample well.

According to some embodiments, a thin lossy film 4-610 may create constructive interference of the excitation energy, resulting in field enhancement within an excitation region of the sample well. FIG. 4-6B depicts a numerical simulation of excitation energy incident upon a sample well where a thin lossy film 4-610 has been formed immediately adjacent the sample well. For the simulation, the sample well has a diameter of approximately 80 nm and is formed in a metallic layer of gold approximately 200 nm thick. The sample well comprises an SCN, and suppresses propagation of excitation energy through the sample well. The thin lossy film 4-610 is approximately 10 nm thick, is formed from germanium, and covers an underlying transparent dielectric comprising silicon dioxide. The thin lossy film extends across an entrance aperture of the sample well. The simulation shows that the intensity of the excitation energy is a highest value at the entrance aperture of the sample well. The intensity of the excitation energy in this bright region 4-620 is more than twice the value of the intensity to the left and right of the sample well.

A thin lossy film may be made from any suitable material. For example, a thin lossy film may be made from a material where the index of refraction n is approximately the same order of magnitude as the extinction coefficient k for the material. In some embodiments, a thin lossy film may be made from a material where the index of refraction n is within about two orders of magnitude difference from the value of the extinction coefficient k of the material. Non-limiting examples of such materials at visible wavelengths are germanium and silicon.

A thin lossy film may be any suitable thickness, which may depend upon a characteristic wavelength, or wavelengths, associated with the excitation source, or sources. In some embodiments, a thin lossy film may be between approximately 1 nm and approximately 45 nm thick. In other embodiments, a thin lossy film may be between approximately 15 nm and approximately 45 nm thick. In still other embodiments, a thin lossy film may be between approximately 1 nm and approximately 20 nm thick.

Effects of a thin lossy film on reflectance from the material 2-221 in which a sample well is formed, excitation energy loss within the thin lossy film, and excitation energy loss within the material 2-221 are shown in the graph of FIG. 4-6C. One curve plotted in the graph represents a reflectance curve 4-634, and shows how reflectance from the material 2-221 and the thin lossy film 4-610 vary as the thickness of the thin lossy film changes from 0 nm to 100 nm. The reflectance reaches a minimum value at about 25 nm, according to the simulated embodiment. The reflectance minimum will occur at different thicknesses depending on a characteristic wavelength of the excitation energy and materials used for the thin lossy film and material 2-221. In some implementations a thickness of thin lossy film is selected such that the reflectance is approximately at its minimal value. Curve 4-632 represents the loss in the film as a function of the thin film thickness, and curve 4-636 represents the loss in the metal as a function of the thin film thickness.

In some embodiments, a thin lossy film 4-610 may be spaced from a sample well 2-211 and material 2-221, as depicted in FIG. 4-6D. For example, a thin dielectric layer 4-620 (e.g., a silicon oxide SiOx) may be formed over a thin lossy film, and a sample well 2-211 may be formed adjacent the dielectric layer 4-620. A thickness of the dielectric layer 4-620 may be between approximately 10 nm and approximately 150 nm according to some embodiments, though other thicknesses may be used in some embodiments.

Although depicted as a single layer, a thin lossy film may comprise multiple layers of two or more materials. In some implementations, a multilayer stack comprising alternating layers of a thin lossy film 4-610 and a dielectric layer 4-620 may be formed adjacent a sample well 2-211, as depicted in FIG. 4-6E. A thickness of a thin lossy film 4-610 in a stack of layers may be between approximately 5 nm and approximately 100 nm, and a thickness of a dielectric layer 4-620 within the stack may be between approximately 5 nm and approximately 100 nm, according to some embodiments. In some implementations, the multilayer stack may comprise a layer of silicon dioxide (4.2 nm thick), a layer of silicon (14.35 nm thick), and a layer of germanium (6.46 nm thick), though other thicknesses may be used in other embodiments. In some implementations, the multilayer stack may comprise a layer of silicon dioxide (approximately 4.2 nm thick), a layer of silicon (approximately 14.4 nm thick), and a layer of germanium (approximately 6.5 nm thick), though other thicknesses may be used in other embodiments.

A thin lossy film may be fabricated from any suitable material that exhibits at least some loss to the incident radiation. In some embodiments, a thin lossy film may comprise a semiconductor material, for example silicon and germanium, though other materials may be used. In some implementations, a thin lossy film may comprise inorganic material or a metal. In some embodiments, a thin lossy film may comprise an alloy or compound semiconductor. For example, a thin lossy film may comprise an alloy including Si (57.4% by weight), Ge (25.8% by weight), and SiO2 (16.8% by weight), though other ratios and compositions may be used in other embodiments.

According to some embodiments, a thin lossy film may be formed on the substrate using any suitable blanket deposition process, for example, a physical deposition process, a chemical vapor deposition process, a spin on process, or a combination thereof. In some embodiments, a thin lossy film may be treated after deposition, e.g., baked, annealed and/or subjected to ion implantation.

Other phase/amplitude altering structures may be used additionally or alternatively to enhance excitation energy within the sample well. According to some implementations and as shown in FIG. 4-7A, a reflective stack 4-705 may be spaced from a sample well 2-211. In some embodiments, a reflective stack may comprise a dielectric stack of materials having alternating indices of refraction. For example a first dielectric layer 4-710 may have a first index of refraction, and a second dielectric layer 4-720 may have a second index of refraction different than the first index of refraction. The reflective stack 4-705 may exhibit a high reflectivity for excitation energy in some embodiments, and exhibit a low reflectivity for radiative emission from an emitter within the sample well. For example, a reflective stack 4-705 may exhibit a reflectivity greater than approximately 80% for excitation energy and a reflectivity lower than approximately 40% for emission from a sample, though other reflectivity values may be used in some embodiments. A dielectric layer 4-730 that transmits the excitation energy may be located between the reflective stack and the sample well.

According to some implementations, a reflective stack 4-705 depicted in FIG. 4-7A may form a resonator with the material 2-221 in which the sample well 2-211 is formed. For example, the reflective stack may be spaced from the material 2-221 by a distance that is approximately equal to one-half the wavelength of the excitation energy within the dielectric material 4-730, or an integral multiple thereof. By forming a resonator, excitation energy may pass through the reflective stack, resonate, and build up in the space between the material 2-221 and the reflective stack 4-705. This can increase excitation intensity within the sample well 2-211. For example, the intensity may increase within the resonant structure by more than a factor of 2 in some embodiments, and more than a factor of 5 in some embodiments, and yet more than a factor of 10 in some embodiments.

Additional structures may be added in the vicinity of the sample well, as depicted in FIG. 4-7B and FIG. 4-7C. According to some embodiments, a dielectric plug 4-740 having a first index of refraction that is higher than a second index of refraction of the dielectric layer 4-730 may be formed adjacent the sample well 2-211, as depicted in FIG. 4-7B. The plug may be in the shape of a cylinder having a diameter approximately equal to that of the sample well, though other shapes and sizes may be used. Because of its higher refractive index, the dielectric plug 4-740 may condense and guide excitation energy toward the sample well.

A dielectric structure, such as the plug 4-740, may be used with or without a reflective stack 4-705, according to some embodiments. Such a dielectric structure may be referred to as a dielectric resonant antenna. The dielectric resonant antenna may have any suitable shape, for example, cylindrical, rectangular, square, polygon old, trapezoidal, or pyramid.

FIG. 4-7C and FIG. 4-7D depict a photonic bandgap (PBG) structure that may be formed in the vicinity of a sample well 2-211, according to some embodiments. A photonic bandgap structure may comprise a regular array or lattice of optical contrast structures 4-750. The optical contrast structures may comprise dielectric material having a refractive index that is different from a refractive index of the surrounding dielectric material, according to some embodiments. In some implementations, the optical contrast structures 4-750 may have a loss value that is different from the surrounding medium. In some implementations, a sample well 2-211 may be located at a defect in the lattice as depicted in FIG. 4-7D. According to various embodiments, the defect in the photonic lattice may confine photons within the region of the defect can enhance the intensity of the excitation energy at the sample well. The confinement due to the photonic bandgap structure may be substantially in two dimensions transverse to a surface of the substrate. When combined with the reflective stack 4-705, confinement may be in three dimensions at the sample well. In some embodiments, a photonic bandgap structure may be used without a reflective stack.

Various methods have been contemplated for fabricating the excitation-coupling structures depicted in FIG. 4-6A through FIG. 4-7D. Structures that require thin planar films (e.g., dielectric films of alternating refractive index) may be formed by planar deposition processes, according to some embodiments. Planar deposition processes may comprise physical deposition (for example, electron beam evaporation or sputtering) or chemical vapor deposition processes. Structures that require discrete embedded dielectrics formed in three-dimensional shapes, such as a dielectric resonant antenna 4-740 shown in FIG. 4-7B or the optical contrast structures 4-750 shown in FIG. 4-7C, may be formed using lithographic patterning and etching processes to etch the pattern into the substrate, and using subsequent deposition of a dielectric layer, and a planarization of the substrate, for example. Also contemplated are self-alignment processing techniques for forming dielectric resonant antennas as well as photonic bandgap structures in the vicinity of the sample well 2-211.

FIG. 4-8A through FIG. 4-8G depict structures associated with process steps for just one self-alignment process that may be used to form a photonic bandgap structure and a self-aligned sample well as illustrated in FIG. 4-7C. According to some embodiments, a reflective stack 4-705 may be first formed on a substrate above a dielectric layer 3-235, as illustrated in FIG. 4-8A. A second dielectric layer 4-730 may then be deposited over the reflective stack. The thickness of the dielectric layer 4-730 may be approximately equal to about one-half a wavelength of the excitation energy in the material, or an integral multiple thereof. Process steps described in connection with FIG. 4-4A through FIG. 4-4E may then be carried out to form a pillar 4-420 above the dielectric layer 4-730 and a pattern of etched features 4-810 for the photonic bandgap structure. The etched features may extend into the dielectric layer 4-730 and optionally into the reflective stack 4-705. The resulting structure may appear as shown in FIG. 4-8A.

A resist 4-440 covering the pillar 4-420 may be stripped from the substrate and a conformal deposition performed to fill the etched features with a filling material 4-820, as depicted in FIG. 4-8B. The filling material 4-820 may be the same material that is used to form the pillar 4-420, according to some embodiments. For example the filling material 4-820 and the pillar 4-420 may be formed of silicon nitride and the dielectric layer 4-730 may comprise an oxide, e.g., SiO$_2$.

An anisotropic etch may then be carried out to etch back the filling material 4-820. The filling material may be etched back to expose a surface of the dielectric layer 4-730, according to some embodiments, resulting in a structure as depicted in FIG. 4-8C. The etch may leave a pillar 4-830 comprising the original pillar 4-420 and sidewalls 4-822 that remain from the filling material 4-820.

A resist 4-440 may then be patterned over the substrate as depicted in FIG. 4-8D. For example, the resist may be coated onto the substrate, a hole patterned in the resist, and the resist developed to open up a region in the resist around the pillar 4-830. Alignment of the hole to the pillar need not be highly accurate, and only need expose the pillar 4-830 without exposing the underlying photonic bandgap structures embedded in the dielectric layer 4-730.

After the pillar 4-830 is exposed, and isotropic etch may be used to reduce the transverse dimension of the pillar. According to some embodiments, the resulting pillar shape may appear as depicted in FIG. 4-8E. The resist 4-440 may then be stripped from the substrate and a material 2-221, or layers of materials, may be deposited over the region. In some embodiments, the material 2-221 may be etched back using a CMP process to planarize the region as depicted in FIG. 4-8F. Subsequently, a selective dry or wet etch may be used to remove the remaining pillar structure leaving a sample well 2-211, as illustrated in FIG. 4-8G. As indicated by the drawings, the sample well 2-211 is self-aligned to the photonic bandgap structure patterned in the dielectric layer 4-730.

As an alternative process, the filling material 4-820 may comprise a different material than the material used to form the pillar 4-420. In this process, the steps associated with FIG. 4-8D and FIG. 4-8E may be omitted. After deposition of material 2-221 and planarization, as depicted in FIG. 4-8F, a selective etch may be performed to remove the pillar 4-420. This may leave sidewalls of the filling material 4-820 lining the sample well 2-211.

D. Non-Radiative Excitation-Coupling Structures

The present disclosure provides structures for non-radiative coupling of excitation energy to a sample within the sample well. Just one embodiment of a non-radiative coupling structure is depicted in FIG. 4-9A. According to some embodiments, a non-radiative coupling structure may comprise a semiconductor layer 4-910 formed immediately adjacent a sample well 2-211. The semiconductor layer 4-910 may be an organic semiconductor in some embodiments, or an inorganic semiconductor in some embodiments. In some implementations, a divot 3-216 may, or may not, be formed in the semiconductor layer. The semiconductor layer 4-910 may have a thickness between approximately 5 nm and approximately 100 nm according to some embodiments, though other thicknesses may be used in some embodiments. According to some implementations, excitation energy or photons 4-930 from an excitation source may impinge upon the semiconductor layer 4-910 and produce excitons 4-920. The excitons may diffuse to a surface of the sample well where they may non-radiatively recombine and transfer energy to a sample adjacent the walls of the sample well.

FIG. 4-9B depicts another embodiment in which a semiconductor layer 4-912 may be used to non-radiatively transfer energy from excitation energy to a sample. In some embodiments, a semiconductor layer 4-912 may be formed at the bottom of a sample well or in a divot of the sample well 2-211, as depicted in the drawing. The semiconductor layer 4-912 may be formed in a sample well by using a directional deposition process as described herein in connection with process steps for depositing an adherent at the base of the sample well, according to some embodiments. The semiconductor layer 4-912 may have a thickness between approximately 5 nm and approximately 100 nm according to some embodiments, though other thicknesses may be used in other embodiments. Incident radiation may generate excitons within the semiconductor layer, which may then diffuse to the a bottom surface of the sample well 2-211. The excitons may then non-radiatively transfer energy to a sample within the sample well.

The present disclosure also provides multiple non-radiative pathways for transferring excitation energy to a sample. According to some embodiments, and as depicted in FIG. 4-9C, an energy-transfer particle 4-940 may be deposited within a sample well. The energy-transfer particle may comprise a quantum dot in some embodiments, or may comprise a molecule in some embodiments. In some implementations, the energy-transfer particle 4-940 may be functionalized to a surface of the sample well through a linking molecule. A thin semiconductor layer 4-910 may be formed adjacent the sample well, or within the sample well, and excitons may be generated within the semiconductor layer from the excitation energy incident upon the semiconductor layer, as depicted in the drawing. The excitons may diffuse to the surface of the sample well, and non-radiatively transfer energy to the energy-transfer particle 4-940. The energy-transfer particle 4-940 may then non-radiatively transfer energy to a sample 3-101 within the sample well.

According to some implementations, there may be more than one energy-transfer particle 4-940 within a sample well. For example, a layer of energy-transfer particles 4-942 may be deposited within a sample well, such as the sample well depicted in FIG. 4-9C.

In some implementations, energy-transfer particles 4-942, or a single energy-transfer particle 4-940, may be deposited at a base of a sample well, as depicted in FIG. 4-9D. The energy-transfer particle, or particles, may radiatively or non-radiatively transfer excitation energy to a sample 3-101 within the well. For example, an energy-transfer particle may absorb incident energy to form an excited state of the energy-transfer particle, and then radiatively or non-radiatively transfer energy to the sample 3-101.

In some implementations, an energy-transfer particle may absorb incident excitation energy, and then re-emit radiative energy at a wavelength that is different than the wavelength of the absorbed excitation energy. The re-emitted energy may then be used to excite a sample within the sample well. FIG. 4-9E represents spectral graphs associated with a down-converting energy-transfer particle. According to some embodiments, a down-converting energy-transfer particle comprises a quantum dot that may absorb short wavelength radiation (higher energy), and emit one or more longer wavelength radiations (lower energy). An example absorption curve 4-952 is depicted in the graph as a dashed line for a quantum dot having a radius between 6 to 7 nm. The quantum dot may emit a first band of radiation illustrated by the curve 4-954, a second band of radiation illustrated by the curve 4-956, and a third band of radiation illustrated by the curve 4-958.

In some implementations an energy-transfer particle may up convert energy from an excitation source. FIG. 4-9F depicts spectra associated with up conversion from an energy-transfer particle. According to some embodiments, a quantum dot may be excited with radiation at approximately 980 nm, and then re-emit into one of three spectral bands as illustrated in the graph. A first band may be centered at approximately 483 nm, a second band may be centered at approximately 538 nm, and a third band may be centered at approximately 642 nm. The re-emitted photons from the quantum dot are more energetic than the photons of the radiation used to excite the quantum dot. Accordingly, energy from the excitation source is up-converted. One or more of the emitted spectral bands may be used to excite one or more one or more samples within the sample well.

E. Directing Emission Energy Towards the Sensor

The assay chip 2-110 may include one or more components per pixel to improve collection of emission energy by the sensors on the instrument. Such components may be designed to spatially direct emission energy towards the sensors and increase the directionality of the emission energy from the sample well 2-211. Both surface optics and far-field optics may be used to direct the emission energy towards the sensor.

1. Surface Optics

Components within a pixel of the assay chip 2-110 located near the sample well of the pixel may be configured to couple with the emission energy emitted by a sample. Such components may be formed at the interface between two layers of the assay chip. For example, some emission energy coupling elements may be formed at the interface between a sample well layer and the layer adjacent to the sample well layer opposite to where the sample wells are formed. In some instances, the layer underneath the sample well layer is a dielectric layer and the emission energy coupling elements may support surface plasmons. In other embodiments, the sample well layer may be a conductive material adjacent to an optically-transparent material. Surface-energy coupling elements may be surface optical structures that are excited by and interact with radiative emission from the sample well.

A characteristic dimension of a surface optical structure such as a grating period, feature size, or distance from the sample well may be selected to maximally couple a parallel component of an emission energy momentum vector into a surface wave momentum vector for a surface plasmon. For example, the parallel component of the emission energy momentum vector may be matched to the surface wave momentum vector for a surface plasmon supported by the structure, according to some embodiments. In some embodiments, a distance d from the sample well to an edge or characteristic feature of a surface optical structure may be selected so as to direct emission energy from the sample well in a selected direction, such as normal to the surface or inclined at an angle θ from normal to the surface. For example, the distance, d, may be an integral number of surface-plasmon wavelengths for directing emission normal to the surface. In some embodiments, distance, d, may be selected to be a fractional surface-plasmon wavelength, or wavelength modulo thereof.

According to some embodiments, the surface optical structures may direct radiative emission energy from a sample well in a direction normal to the sample well layer. The coupled energy may be directed in the normal direction in a narrowed, directional radiation pattern.

An example of a surface optical structure is a concentric grating. A concentric grating structure that may be formed in a pixel of the assay chip to direct emission energy towards one or more sensors of the pixel. The concentric grating structure may be formed around a sample well. An example of a concentric circular grating surface 5-102 as a surface plasmon structure is depicted in FIG. 5-1. The circular grating may comprise any suitable number of rings and the number of rings (six) shown in FIG. 10-1 is a non-limiting example. The circular grating may comprise protruding rings from a surface of a conductive layer. For example, the circular grating may be formed at the interface of the sample well layer and a dielectric layer formed underneath the sample well layer. The sample well layer may be a conductive material and the concentric grating may be formed by patterning the grating structure at the interface between the conductive material and the dielectric. The rings of the circular grating may be on a regular periodic spacing, or may have irregular or aperiodic spacings between the rings. The sample well may be located at or near the center of the circular grating. In some embodiments, the sample well may be located off-center to the circular grating and may be positioned a certain distance from the center of the grating. In some embodiments, a grating-type surface energy-coupling component may comprise a spiral grating. An example of a spiral grating 5-202 is depicted in FIG. 5-2. The spiral grating 5-202 may comprise a spiral aperture in a conductive film. Any suitable dimensions of the spiral grating may be used to form the spiral grating.

A concentric grating may have any suitable number of rings and be of any suitable size By way of example and not limitation, a concentric grating may have six rings with radii having approximately 234 nm, approximately 606 nm, approximately 1005 nm, approximately 1397 nm, approximately 1791 nm, and approximately 2186 nm. In other embodiments, the concentric ring may have two, three, four or eight rings.

FIG. 5-3A illustrates a radiation pattern 5-302 for emission energy from the sample well 2-211. The concentric grating structure 2-223 causes the emission energy to have greater directionality compared to the radiation pattern formed in the absence of the grating structure 2-223. In some embodiments, the emission energy is directed downward, normal to the metal layer 2-221. The radiation pattern may focus the emission energy such that the majority of the light is focused in substantially the same direction toward the sensor. In some embodiments, the radiation pattern may focus the luminescence such that the majority of the luminescence forms a narrow column-like shape centered below the target volume and directed downward towards the sensors. In some embodiments, a concentric grating may provide a directivity of more than 10 for 1 ring, more than 15 for 2 rings, more than 18 for 3 rings, more than 20 for four rings, or more than 15 for 1 ring, as shown by the plot in FIG. 5-3B

Another example of a surface optic or surface plasmon structure is a nano-antenna structure. A nano-antenna structure may be designed to spatially direct emission energy from the sample well. In some embodiments, the location of the sample well with respect to the nano-antenna structure is selected so as to direct the emission energy from the sample well in a particular direction towards one or more sensors. Nano-antennas may comprise nano-scale dipole antenna structures that are designed to produce a directional radiation pattern when excited by emission energy. The nano-antennas may be distributed around a sample well. The directional radiation pattern may result from a summation of the antennas' electromagnetic fields. In some embodiments, the directional radiation pattern may result from a summation of the antennas' electromagnetic fields with the field emitted directly from the sample. In some implementations, the field emitted directly from the sample may be mediated by a surface plasmon between the sample well and nano-antenna structure.

The dimensions of the individual nano-antennas that form the nano-antenna structure may be selected for the combined ability of the overall nano-antenna structure to produce specific distribution patterns. For example, the diameters of the individual nano-antennas may vary within a nano-antenna structure. However, in some instances, the diameters may be the same within a set of nano-antennas. In other implementations, a few selected diameters may be used throughout the overall nano-antenna structure. Some nano-antennas may be distributed on a circle of radius R and some may be shifted in a radial direction from the circle. Some nano-antennas may be equally spaced around a circle of radius R (e.g., centered on equivalent polar-angle increments), and some may be shifted from equal spacing around the circle. In some embodiments, the nano-antennas may be arranged in a spiral configuration around a sample well. Additionally or alternatively, other configurations of nano-antennas are possible, such as a matrix array around the sample well, a cross distribution, and star distributions. Individual nano-antennas may be shapes other than a circle, such as square, rectangular, cross, triangle, bow-tie, annular ring, pentagon, hexagon, polygons, etc. In some embodiments, the circumference of an aperture or disc may be approximately an integer multiple of a fractional wavelength, e.g., $(N/2)\lambda$.

A nano-antenna array may direct emission energy from a sample into concentrated radiation lobes. When a sample emits energy, it may excite surface plasmons that propagate from the sample well to the nano-antennas distributed around the sample well. The surface plasmons may then excite radiation modes or dipole emitters at the nano-antennas that emit radiation perpendicular to the surface of the sample well layer. The phase of an excited mode or dipole at a nano-antenna will depend upon the distance of the nano-antenna from the sample well. Selecting the distance between the sample well and an individual nano-antenna controls the phase of radiation emitted from the nano-antenna. The spatial radiation mode excited at a nano-antenna will depend upon the geometry and/or size of the nano-antenna. Selecting the size and/or geometry of an individual nano-antenna controls the spatial radiation mode emitted from the nano-antenna. Contributions from all nano-antennas in the array and, in some instances the sample well, may determine an overall radiation lobe or lobes that form the radiation pattern. As may be appreciated, phase and spatial radiation mode emitted from an individual nano-antenna may depend upon wavelength, so that the overall radiation lobe or lobes that form the radiation pattern will also be dependent upon wavelength. Numerical simulations of the electromagnetic fields may be employed to determine overall radiation lobe patterns for emission energies of different characteristic wavelengths.

The nano-antenna may comprise an array of holes or apertures in a conductive film. For example, the nano-antenna structure may be formed at the interface between a conductive sample well layer and an underlying dielectric layer. The holes may comprise sets of holes distributed in concentric circles surrounding a central point. In some embodiments, a sample well is located at the central point of the array, while in other embodiments the sample well may be off-center. Each circularly-distributed set of holes may comprise a collection of different diameters arranged smallest to largest around the circular distribution. The hole diameters may be different between the sets (e.g., a smallest hole in one set may be larger than a smallest hole in another set), and the location of the smallest hole may be oriented at a different polar angle for each set of circles. In some embodiments, there may be one to seven sets of the circularly-distributed holes in a nano-antenna. In other embodiments, there may be more than seven sets. In some embodiments, the holes may not be circular, but may be any suitable shape. For example, the holes may be ellipses, triangles, rectangles, etc. In other embodiments, the distribution of holes may not be circular, but may create a spiral shape.

FIGS. 5-4A and 5-4B illustrate an exemplary nano-antenna structure comprised of holes or apertures in a conductive layer. FIG. 5-4A shows a top planar view of the surface of an assay chip with a sample well 5-108 surrounded by holes 5-122. The nano-antenna holes are distributed with their centers approximately around a circle of radius R. In this non-limiting example, the hole diameters vary by incrementally increasing around the circumference of the circle of holes. FIG. 5-4B shows a schematic of a cross-sectional view of the assay chip shown in FIG. 5-4A along line B-B'. The sample well layer 5-116 that includes sample well 5-108 and apertures 5-122 that are part of the nano-antenna structure. Layer 5-118 of the assay chip lies underneath sample well layer 5-116. Layer 5-118 may be a dielectric material and/or an optically transparent material.

In some embodiments, the nano-antenna structure may comprise a plurality of disks. The disks of the nano-antenna structure may be formed as conductive disks protruding from a surface of a conductive material. The conductive material may be adjacent an optically-transparent material. In some embodiments, the nano-antennas may be distributed around a sample well. In some instances, the nano-antennas may be distributed approximately around a sample well at a circle of radius R. A nano-antenna array may comprise multiple sets of nano-antennas distributed approximately on additional circles of different radii around a sample well.

FIGS. 5-5A and 5-5B illustrate an exemplary embodiment of a nano-antenna structure comprising disks protruding from a conductive layer. FIG. 5-5A shows a top planar view schematic of the surface of an assay chip with a sample well 5-208 surrounded by disks 5-224. The nano-antenna disks are distributed approximately around a circle of radius R. In this non-limiting example, two diameters are used for the disks and the disks alternate between these two diameters around the circumference of the circle of nano-antenna. FIG. 5-5B shows a schematic of a cross-sectional view of the assay chip shown in FIG. 5-5A along line C-C'. The sample well layer 5-216 that includes sample well 5-208 and disks 5-224 that are part of the nano-antenna structure. The disks 5-224 protrude from the sample well layer 5-216 by a certain distance. In some embodiments, the distance the disks extend from the sample well layer may vary within a nano-antenna structure. Layer 5-218 of the assay chip lies underneath sample well layer 5-216. Layer 5-18 may be a dielectric material and/or an optically transparent material. The sample well layer 5-216 and the protruding disks may be a conductive material.

In some embodiments a nano-antenna structure may be centered proximate to a sample well. The nano-antenna may take any suitable shape. By way of example and not limitation, the nano-antenna may be a symmetrical shape such as a cylinder, disk or cube. The nano-antenna may be made of any suitable dielectric material, for example, silicon nitride. Alternatively, titanium oxide may be used. The nano-antenna dimensions may be depend on the dielectric material used and may be tailored to perform the desired enhancement. In some embodiments, the nano-antenna may have a width of approximately 800 nm and a depth of approximately 1050 nm. The nano-antenna may the radiation pattern of emission energy from a sample well such that the majority of the light is focused in substantially the same direction, such as in a narrow column-like shape centered below the target volume and the corresponding nano-antenna and directed downward towards the sensors, as illustrated in FIG. 5-5C. In some embodiments, a directivity of 39.7 is predicted.

In addition to focusing the luminescence toward the sensor, the nano-antenna may enhance the excitation energy into the sample well. Excitation energy from below the nano-antenna and directed toward the target volume enters the nano-antenna and is largely concentrated at the target volume. In some embodiments, an enhancement of 57.4 is predicted at the sample well for a nano-antenna of a width of 400 nm and a height of 1050 µm 2. Far Field Optics In some embodiments, the layer directly under the surface optics may be a spacer layer 2-225 of any suitable thickness and be made of any suitable dielectric material. The spacer layer may be, for example, 10 µm in thickness and may be made of silicon dioxide. Alternatively, this spacer layer may be 48 µm or 50 µm. The under the spacer layer may be one or more lens layers with additional spacer layers. For example, FIG. 5-6A illustrates an upper lens layer 5-601 which may include at least one refractive lens. In some embodiments, the upper lens layer may be located 5 µm below the sample well layer 2-221. There may be one or more lenses associated with each sample well. In some embodiments, a lens array may be used, such as a refractive lens array. In some embodiments, each lens of the upper lens layer 5-601 is centered below sample well 2-211 and may have a radius, for example, smaller than 10.5 µm. The upper lens layer may be made of any suitable dielectric material such as, by way of example and not limitation, silicon nitride.

In some embodiments, the dimensions of the upper lens layer are as follows: d1 may be approximately 12 µm; d2 may be approximately 2 µm; distance between d1 on neighboring lenses may be approximately 20.966 µm; and the radius of curvature of the lens may be approximately 20.35 µm. Alternatively, d1 may be approximately 8 µm and d2 may be approximately 6 µm.

The layer directly under the upper lens layer may be a structural and/or optical layer 5-605 made of any suitable dielectric. This structural and/or optical layer 5-605 may be made of silicon dioxide in the form of fused silica. The layer directly under the structural layer may be a lower lens layer 5-603 which may include at least one additional lens. In some embodiments, each lens in the lower lens layer 5-603 may also be centered below the sample well. The lower lens layer 5-603 may be made of any suitable dielectric material such as, by way of example and not limitation, silicon nitride. The distance from the top of the upper lens layer to the bottom of the lower lens layer may be 100-500 µm. The layer directly under the lower lens layer may include an anti-reflection layer that passes both excitation energy and the emission energy and reduces the amount of light reflected. The layer directly under the anti-reflection layer may include structural components to allow the chip to align with and mount onto the instrument. The layer directly under the chip-mounting layer may include a protective cover to protect the system from damage and contamination, including dust.

While FIG. 5-6A illustrates two lens layers using refractive lenses, any suitable lens may be used. For example, Fresnel lenses, microlenses, refractive lens pairs and/or flat lenses may be used. FIG. 5-6B illustrates an embodiment using Fresnel lenses in both an upper lens layer 5-611 and a lower lens layer 5-613, separated by a structural and/or optical layer 5-605.

In some embodiments, any of the interfaces between the layers described above in the chip may include an anti-reflection coating or anti-reflection layer. Both the upper lens layer and the second lens layer may be arranged below the sample well to focus the luminescence emitted from the array of sample wells into a relay lens of the instrument. The distance from the bottom of the sample well layer to a focal point of the luminescence from the target volumes may be approximately 30.3 mm, for example. This focal point may occur within the relay lens, for example, at a longitudinal center point of the relay lens.

III. Instrument Components

A. Microscopy Layer of the Instrument

In some embodiments, the instrument may include a microscopy layer which may include sub-layers as illustrated in FIG. 6-1. In particular, the microscopy layer may include a sub-layer that includes a polychroic mirror 2-230 tilted at an angle θ to direct the excitation energy toward the assay chip. This polychroic mirror may be substantially dielectric, and reflects the excitation energy while substantially transmitting the emission energy from the sample in one or more of the sample wells on the assay chip. Optionally, an astigmatism compensation element 6-101 that includes an additional dielectric layer may be provided underneath the polychroic mirror and tilted at the same angle θ, but about an axis that is orthogonal to that of the polychroic mirror's tilt, to provide compensation for astigmatism introduced by the polychroic mirror. In FIG. 6-1, the astigmatism compensation element 6-101 is illustrated as tilted in the same plane as the top filter, but it should be appreciated that the illustration represents a tilting with respect to the top filter and it is not meant to limit the orientation of the astigmatism compensation element 6-101 in any way. This astigmatism compensation element 6-101 may also provide additional filtering. For example, the astigmatism compensation element 6-101 may be another polychroic mirror that further filters the excitation energy while transmitting the emission energy. A lens 6-103 may be provided underneath the astigmatism compensation element 6-101 to further help process the emission energy from the sample wells. The lens 6-103 may be, for example, 25.4 µm in diameter, but any suitable diameter may be used. In some embodiments, the lens is a relay lens comprising a plurality of lens elements. For example, the relay lens may include six separate lens elements. In some embodiments, the relay lens may be, approximately 17.5 mm in length. Additional filtering elements may be used before or after lens 6-103 to further reject the excitation energy to prevent it from reaching the sensors.

B. Sensor Chip

Emission energy emitted from a sample in the sample well may be transmitted to the sensor of a pixel in a variety of ways, some examples of which are described in detail below. Some embodiments may use optical and/or plasmonic components to increase the likelihood that light of a particular wavelength is directed to an area or portion of the sensor that is dedicated to detecting light of that particular wavelength. The sensor may include multiple sub-sensors for simultaneously detecting emission energy of different wavelengths.

FIG. 6-2A is a schematic diagram of a single pixel of the sensor chip according to some embodiments where at least one sorting element 6-127 is used to direct emission energy of a particular wavelength to a respective sub-sensor 6-111, 6-112, 6-113, and 6-114. The emission energy 2-253 travels from a sample well through the assay chip and the optical system of the instrument until it reaches a sorting element 6-127 of the sensor chip. The sorting element 6-127 couples the wavelength of the emission energy 2-253 to a spatial degree of freedom, thereby separating the emission energy into its constituent wavelength components, referred to as sorted emission energy. FIG. 6-2A illustrates schematically the emission energy 2-253 being split into four sorted emission energy paths through a dielectric material 6-129, each of the four paths associated with a sub-sensor 6-111 through 6-114 of the pixel. In this way, each sub-sensor is associated with a different portion of the spectrum, forming a spectrometer for each pixel of the sensor chip.

Any suitable sorting element 6-127 may be used to separate the different wavelengths of the emission energy. Embodiments may use optical or plasmonic elements. Examples of optical sorting elements include, but are not limited to, holographic gratings, phase mask gratings, amplitude mask gratings, and offset Fresnel lenses. Examples of plasmonic sorting elements include, but are not limited to phased nano-antenna arrays, and plasmonic quasi-crystals.

FIG. 6-2B is a schematic diagram of a single pixel of the sensor chip according to some embodiments where filtering elements 6-121, 6-122, 6-123 and 6-124 are used to direct emission energy of a particular wavelength to a respective sub-sensor and prevent emission energy of other wavelengths from reaching the other sub-sensors. The emission energy 2-253 travels from a sample well through the assay chip and the optical system of the instrument until it reaches one of the filtering elements 6-121 through 6-124. The filtering elements 6-121 through 6-124, each associated with a particular sub-sensor 6-111 through 6-114, are each configured to transmit emission energy of a respective wavelength and reject emission energy of other wavelengths by absorbing the emission energy (not illustrated in FIG. 6-1B) and/or reflecting the emission energy. After passing through a respective filtering element, the filtered emission energy travels through a dielectric material 6-129 and impinges on a corresponding sub-sensor 6-111 through 6-114 of the pixel. In this way, each sub-sensor is associated with a different portion of the spectrum, forming a spectrometer for each pixel of the sensor chip.

Any suitable filtering elements may be used to separate the different wavelengths of the emission energy. Embodiments may use optical or plasmonic filtering elements. Examples of optical sorting elements include, but are not limited to, reflective multilayer dielectric filters or absorptive filters. Examples of plasmonic sorting elements include, but are not limited to frequency selective surfaces designed to transmit energy at a particular wavelength and photonic band-gap crystals.

Alternatively, or in addition to the above mentioned sorting elements and filtering elements, additional filtering elements may be place adjacent to each sub-sensor 6-111 through 6-114. The additional filtering elements may include a thin lossy film configured to create constructive interference for emission energy of a particular wavelength. The thin lossy film may be a single or multi-layer film. The thin lossy film may be made from any suitable material. For example, the thin lossy film may be made from a material where the index of refraction n is approximately the same order of magnitude as the extinction coefficient k. In other embodiments, the thin lossy film may be made from a material where the index of refraction n is within about two orders of magnitude difference from the value of the extinction coefficient k of the material. Non-limiting examples of such materials at visible wavelengths are germanium and silicon.

The thin lossy film may be any suitable thickness. In some embodiments, the thin lossy film may be 1-45 nm thick. In other embodiments, the thin lossy film may be 15-45 nm thick. In still other embodiments, the thin lossy film may be 1-20 nm thick. FIG. 6-3A illustrates an embodiment where the thin lossy films 6-211 through 6-214 each have a different thickness determined at least in part by the wavelength that is associated with each sub-sensor 6-11 through 6-114. The thickness of the film determines, at least in part, a distinct wavelength that will selectively pass through the thin lossy film to the sub-sensor. As illustrated in FIG. 6-211, thin lossy film 6-211 has a thickness d1, thin lossy film 6-212 has a thickness d2, thin lossy film 6-213 has a thickness d3, and thin lossy film 6-214 has a thickness d4. The thickness of each subsequent thin lossy film is less than the previous thin lossy film such that d1>d2>d3>d4.

Additionally, or alternatively, the thin lossy films may be formed of a different material with a different properties such that emission energy of different wavelengths constructively interfere at each respective sub-sensor. For example, the index of refraction n and/or the extinction coefficient k may be selected to optimize transmission of emission energy of a particular wavelength. FIG. 6-3B illustrates thin lossy films 6-221, 6-222, 6-223 and 6-224 with the same thickness but each thin lossy film is formed from a different material. In some embodiments, both the material of the thin lossy films and the thickness of the thin lossy films may be selected such that emission energy of a desired wavelength constructively interferes and is transmitted through the film.

FIG. 6-1 illustrates an embodiment where a combination of diffractive elements and lenses are used to sort the emission energy by wavelength. A first layer 6-105 of the sensor chip may include a blazed phase grating. The blazed grating may be blazed, for example, at an angle ϕ substantially equal to 40 degrees and the line spacing of the blazed grating (Λ) may be substantially equal to 1.25 μm. One of skill in the art would appreciate that different blaze angles and periodicities may be used to achieve separation of light of different wavelengths of emission energy. Moreover, any suitable diffractive optical element may be used to separate the different wavelengths of the emission energy. For example, a phase mask, an amplitude mask, a blazed grating or an offset Fresnel lens may be used.

A second layer 6-106 of the sensor chip 2-260 may include one or more Fresnel lenses disposed beneath the first layer 6-105 to further sort and direct the emission energy to the sensors 6-107. Moreover, any suitable lens element may be used to further separate the different wavelengths of the emission energy. For example, a refractive lens may be used instead of a Fresnel lens.

The Fresnel lens of the third lens layer and the blazed phase grating may be collectively referred to as diffractive optical elements (DOE). In some embodiments, the DOEs of have a thickness in the range of approximately 400 to 600 μm where width is in the range of approximately 10 microns to 30 microns. An air spacer layer may be positioned directly under the DOEs and may have a thickness of approximately 150 μm, in some embodiments. Alternatively, the spacer layer may have the same optical thickness as the DOE focal length and/or be made of silicon dioxide.

The various components of FIG. 6-1 may be spaced apart at any suitable distances. For example, the surface of the sensors may be located at a distance of 5 μm beneath the Fresnel lens layer 6-106; the distance from the center of the lens 6-103 of the microscopy layer to the Fresnel lens layer 6-106 may be 50.6 mm; the blazed phase grating 6-105 may be located at a distance of approximately 100 μm above the surface of the sensors. Alternatively, the distance from the bottom of the assay chip to the top of the grating 6-105 may be approximately 53 mm. The width of the sensor layer may be approximately 10 mm. The Fresnel lens may be spaced apart from each other within the layer by a distance of approximately 10 microns, approximately 20 microns, and approximately 30 microns.

In some embodiments, an offset Fresnel lens may be used in which the Fresnel lens has a center that may be offset from the center of the lens, such as lens 6-103 shown in FIG. 6-1. The center of the offset Fresnel lens, may be offset by approximately 50 microns, approximately 60 microns, approximately 70 microns, or approximately 80 microns, but other distances are possible. In some embodiments, the offset Fresnel lens may have a second offset which is the offset from the center of the offset Fresnel lens to the center of the sensor, which may be, for example, on the order of 10 um or 100 um, but other distances are possible. The offset Fresnel lens may be created in any suitable way. For example, two sections, each with a different pitch of grating may be overlaid to create a single offset Fresnel with improved efficiency over a binary offset Fresnel lens structure. In some embodiments, a "small" section with pitch 220 nm and a "big" section with pitch 440 nm may be overlaid to create the offset Fresnel lens shown. The offset Fresnel lens array may be positioned on top of the sensor array, may have a lateral offset from the offset Fresnel lens element center to the sensor center, and may be designed to operate with a focal length in the range of approximately 80 microns to approximately 150 microns and designed for a wavelength of 625 nm.

The layer directly under the imaging optics and the air spacer layer may be a sensor layer. The sensor layer may include a plurality of sensors, including CMOS photosensitive sensors. The sensor layer may have any suitable thickness, including in the range of approximately 6 microns to approximately 8 microns. Alternatively, the sensor layer thickness may be within the range of 2 um to 15 um. The sensors may be separated into a plurality of segments or pixels and may have a width of approximately 21 μm. The distance from the top of the sensor layer to a focal point of the emission energy may be approximately 30.3 mm.

The various layers of the assay chip and instrument need not be in the order described above. In some embodiments, the focusing and/or sorting elements and the imaging optics of the instrument may be in reverse order. For example, the blazed phase grating 6-105 may be placed after the Fresnel lens layer 6-106. Alternatively, the focusing and/or sorting elements and the imaging optics may be incorporated into a single diffractive optical element (DOE). In addition, various components of the assay chip and instrument may be intermingled such that, for example, imaging optics may occur both above and below the focusing and/or sorting elements.

Any of the interfaces between the layers, including the interface between air and a layer of the system, described above in the system may include an anti-reflection coating.

C. Optical Block of the Instrument

In some embodiments, the optical block of the instrument 1-120 may include some or all of the optical components described above. The optical block may provide the optical components as arranged in FIGS. 6-4A. FIG. 6-4A illustrates light having λ1 and λ2 passing through the optical components shown in FIG. 6-4A. In addition to the components described above, the optical block may include a first fiber connector 6-401 where a first optical fiber carrying a first wavelength of excitation energy, λ1, may connect and a second fiber connector 6-402 where a second optical fiber carrying a second wavelength of excitation energy, λ2, may connect. By way of example and not limitation, the first excitation wavelength of the excitation energy may be 630-640 nm. The optical fiber connectors may be any suitable conventional connector, such as an FC or an LC connector. If two different wavelengths are input, the wavelengths may be combined with a wavelength combiner 6-403, such as a dichroic or polychroic mirror. The second excitation wavelength may be 515-535 nm. The input excitation energy may be any suitable polarization, such as linear polarization. In some embodiments, the fiber carrying the excitation energy may be a polarization-maintaining fiber. Optionally, excitation filters and polarizers, such as optical fiber-to-free-space couplers, may be used after the optical fiber input to further filter or modify characteristics of the excitation energy.

The optical block may include one or more metal housings to hold lenses and other optical components for optical processing such as beam shaping. FIG. 6-4A illustrates four metal housings 6-405 through 6-408, each holding a lens and/or other optical components. There may be any number of lenses used to collimate and focus the excitation energy. One or more mirrors 6-411 and 6-412 are situated between some of the metal housings for guiding the excitation energy towards the assay chip 2-110. In FIG. 6-4A, the first mirror 6-411 directs the excitation energy from the second housing 6-406 to the third housing 6-407 and the second mirror 6-412 reflects the excitation energy from the fourth housing 6-408 to a polychroic dielectric mirror 2-230. The polychroic dielectric mirror 2-230 directs the excitation energy towards an astigmatism compensation filter 6-601.

In some embodiments, circularly polarized light may be directed into the sample well to cause the luminescent markers to emit luminescence with similar strength. A quarter-wave plate may be used to transfer the linearly polarized light to circularly polarized light before it reaches the assay chip. The polychroic dielectric mirror 2-230 directs the excitation energy to the quarter wave plate 6-415. As illustrated in FIG. 6-4A, the quarter-wave plate 6-415 may be disposed between the astigmatism compensation filter 6-101 and the assay chip 2-110. The circularly polarized excitation energy is then directed towards the plurality of pixels on the assay chip. Excitation energy that is not directed towards the pixels may be absorbed by a beam dump component 6-417. Excitation energy that reaches the sample inside one or more sample wells will cause the sample to emit emission energy, which is directed toward the sensor 2-260. The emission energy may pass through optical components such as polarization optics, the astigmatism compensating element 6-101, the polychroic mirror 2-230 and a relay lens 6-103. The polychroic mirror acts as a filer, which may be, by way of example, a notch filter, a spike filter or a cut-off filter. The relay lens 6-103 may image the emission energy toward the sensor. A portion of the emission energy may then pass through one or more emission filters 6-421 and 6-422, situated above the sensor 2-260, which may further filter the emission energy. In some embodiments, the emission filters may be tilted at an angle relative to the incident emission energy propagation direction in order to tune the transmission characteristics of the filters and/or reduce interference caused by back reflections. If the top filter 6-421 is tilted at an angle θ, the bottom filter 6-422 may be tilted at the same angle θ, but about an axis that is orthogonal to that of the top filter's tilt, to ensure no astigmatism is introduced into the emission radiation beam path.

FIG. 6-5 illustrates an example of a ray trace that represents an optical path through the apparatus from the assay chip 2-110 to the sensor chip 2-260. Each starting point in assay chip 2-110 represents a pixel that emits emission energy and is imaged by the system to a corresponding pixel on sensor chip 2-260. The path may exists along a distance of approximately 55.4 mm but any suitable distance may be used. In the example illustrated, rays emitted from the sample well array are filtered and focused toward the sensor using the optical elements described above. FIG. 6-5 illustrates one possible relay lens 6-103 that comprises six individual lenses. It should be recognized that any number of lens and/or other optical elements may be used as a relay lens.

IV. Sensors

The present disclosure provides various embodiments of sensors, sensor operation, and signal processing methods. According to some embodiments, a sensor 2-122 at a pixel of the sensor chip 2-260 may comprise any suitable sensor capable of receiving emission energy from one or more tags in the sample well, and producing one or more electrical signals representative of the received emission energy. In some embodiments, a sensor may comprise at least one a photodetector (e.g., a p-n junction formed in a semiconductor substrate). FIG. 7-1A and FIG. 7-1B depicts one embodiment of a sensor that may be fabricated within a pixel 2-100 of a sensor chip.

According to some embodiments, a sensor 2-122 may be formed at each pixel 2-100 of a sensor chip. The sensor may be associated with a sample well 2-211 of the assay chip. There may be one or more transparent layers 7-110 above the sensor, so that emission from the sample well may travel to the sensor without significant attenuation. The sensor 2-122 may be formed in a semiconductor substrate 7-120 at a base of the pixel, according to some embodiments, and be located on a same side of the sample well as the assay chip (not shown).

The sensor may comprise one or more semiconductor junction photodetector segments. Each semiconductor junction may comprise a well of a first conductivity type. For example, each semiconductor junction may comprise an n-type well formed in a p-type substrate, as depicted in the drawing. According to some embodiments, a sensor 2-122 may be arranged as a bulls-eye detector 7-162, as depicted in the plan view of FIG. 7-1B. A first photodetector 7-124 may be located at a center of the sensor, and a second annular photodetector 7-122 may surround the center photodetector. Electrical contacts to the wells may be made through conductive traces 7-134 formed at a first or subsequent metallization level and through conductive vias 7-132. There may be a region of highly doped semiconductor material 7-126 at contact regions of the vias. In some embodiments, a field oxide 7-115 may be formed at surfaces between the photodetectors and may cover a portion of each photodetector. In some implementations, there may be additional semiconductor devices 7-125 (e.g., transistors, amplifiers, etc.) formed within the pixel adjacent to the sensor 2-122. There may be additional metallization levels 7-138, 7-136 within the pixel.

In some implementations, a metallization level 7-136 may extend across a majority of the pixel and have an opening centered above the photodetector 7-124, so that emission from the sample well can reach the sensor. In some cases, a metallization level 7-136 may serve as a reference potential or a ground plane, and additionally serve as an optical block to prevent at least some background radiation (e.g., radiation from an excitation source or from the ambient environment) from reaching the sensor 2-260.

As depicted in FIG. 7-1A and FIG. 7-1B, a sensor 2-122 may be subdivided into a plurality of photodetector segments 7-122, 7-124 that are spatially and electrically separated from each other. In some embodiments, segments of a sensor 2-122 may comprise regions of oppositely-doped semiconductor material. For example, a first charge accumulation well 7-124 for a first sensor segment may be formed by doping a first region of a substrate to have a first conductivity type (e.g., n-type) within the first well. The substrate may be p-type. A second charge accumulation well 7-122 for a second sensor segment may be formed by doping a second region of the substrate to have the first conductivity type within the second well. The first and second wells may be separated by a p-type region of the substrate.

The plurality of segments of the sensor 2-122 may be arranged in any suitable way other than a bulls-eye layout, and there may be more than two segments in a sensor. For example, in some embodiments, a plurality of photodetector segments 7-142 may be laterally separated from one another to form a stripe sensor 7-164, as depicted in FIG. 7-1C. In some embodiments, a quad (or quadrant) sensor 7-166 may be formed by arranging the segments 7-144 in a quad pattern, as depicted in FIG. 7-1D. In some implementations, arc segments 7-146 may be formed in combination with a bulls-eye pattern, as depicted in FIG. 7-1E, to form an arc-segmented sensor 7-168. Another sensor configuration may comprise pie-piece sections, which may include individual sensors arranged in separate section of a circle. In some cases, sensor segments may be arranged symmetrically around a sample well 2-211 or asymmetrically around a sample well. The arrangement of sensor segments is not limited to only the foregoing arrangements, and any suitable distribution of sensor segments may be used.

The inventors have found that a quadrant sensor 7-166, pie-sector sensor, or similar sector sensor can scale to smaller pixel sizes more favorably than other sensor configurations. Quadrant and sector detectors may consume less pixel area for a number of wavelengths detected and active sensor area.

Sensors may be arranged in various geometric configurations. In some examples, sensors are arranged in a square configurations or hexagonal configuration.

Sensors may be sized and positioned in any suitable way to capture the emitted emission energy from a sample well. For example, the sensor may be centered underneath the sample well and have planar dimensions of 5 um×5 um. Alternatively, each sub-sensor may have dimensions of 1.6 um×10 um with a pitch of 4.6 um (i.e. 3 um gap in between each sub-sensor).

Sensors of the present disclosure may be independently (or individually) addressable. An individually addressable is capable of detecting a signal and providing an output independent of other sensors. An individually addressable sensor may be individually readable.

In some embodiments, a stacked sensor 7-169 may be formed by fabricating a plurality of separated sensor segments 7-148 in a vertical stack, as depicted in FIG. 7-1F. For example, the segments may be located one above the other, and there may, or may not, be insulating layers between the stacked segments. Each vertical layer may be configured to absorb emission energy of a particular energy, and pass emission at different energies. For example, a first detector may absorb and detect shorter-wavelength radiation (e.g., blue-wavelength radiation below about 500 nm from a sample). The first detector may pass green- and red-wavelength emissions from a sample. A second detector may absorb and detect green-wavelength radiation (e.g., between about 500 nm and about 600 nm) and pass red emissions. A third detector may absorb and detect the red emissions. Reflective films 7-149 may be incorporated in the stack, in some embodiments, to reflect light of a selected wavelength band back through a segment. For example, a film may reflect green-wavelength radiation that has not been absorbed by the second segment back through the second segment to increase its detection efficiency.

In some embodiments with vertically-stacked sensor segments, emission-coupling components may not be included at the sample well to produce distinct spatial distribution patterns of sample emission that are dependent on emission wavelength. Discernment of spectrally different emissions may be achieved with a vertically-stacked sensor 7-169 by analyzing the ratio of signals from its stacked segment, according to some embodiments.

In some embodiments, segments of a sensor 2-122 are formed from silicon, though any suitable semiconductor (e.g., Ge, GaAs, SiGe, InP, etc.) may be used. In some embodiments, a sensor segment may comprise an organic photoconductive film. In other embodiments, quantum dot photodetectors may be used for sensor segments. Quantum dot photodetectors may respond to different emission energies based on the size of the quantum dot. In some embodiments, a plurality of quantum dots of varying sizes may be used to discriminate between different emission energies or wavelengths received from the sample well. For example, a first segment may be formed from quantum dots having a first size, and a second segment may be formed from quantum dots having a second size. In various embodiments, sensors 2-122 may be formed using conventional CMOS processes.

As described above, emission-coupling components may be fabricated adjacent the sample well in some embodiments. The sorting elements 2-243 can alter emission from a sample within the sample well 2-211 to produce distinct spatial distribution patterns of sample emission that are dependent on emission wavelength. FIG. 7-2A depicts an example of a first spatial distribution pattern 7-250 that may be produced from a first sample at a first wavelength. The first spatial distribution pattern 7-250 may have a prominent central lobe directed toward a central segment of a bulls-eye sensor 7-162, for example, as shown in FIG. 7-2B. Such a pattern 7-250 may be produced by any suitable diffractive element when the sample emits at a wavelength of about 663 nm. A projected pattern 7-252 incident on the sensor may appear as illustrated in FIG. 7-2B.

FIG. 7-2C depicts a spatial distribution pattern 7-260 that may be produced from a second sample emitting at a second wavelength from the same sample well, according to some embodiments. The second spatial distribution pattern 7-260 may comprise two lobes of radiation and differ from the first spatial distribution pattern 7-250. A projected pattern 7-262 of the second spatial distribution pattern 7-260 may appear as depicted in FIG. 7-2D, according to some embodiments. The second spatial distribution pattern 7-260 may be produced by any suitable diffractive element when the sample emits at a wavelength of about 687 nm.

The segments of a sensor 2-122 may be arranged to detect particular emission energies, according to some embodiments. For example, emission-coupling structures adjacent the sample well and segments of a sensor may be designed in combination to increase signal differentiation between particular emission energies. The emission energies may correspond to selected tags that will be used with the sensor chip. As an example, a bulls-eye sensor 7-162 could have its segments sized and/or located to better match the projected patterns 7-260, 7-262 from a sample, so that regions of higher intensity fall more centrally within active segments of the sensor. Alternatively or additionally, diffractive elements may be designed to alter the projected patterns 7-260, 7-262 so that intense regions fall more centrally within segments of the sensor.

Although a sensor 2-122 may comprise two segments, it is possible in some embodiments to discern more than two spectrally-distinct emission bands from a sample. For example, each emission band may produce a distinct projected pattern on the sensor segments and yield a distinct combination of signals from the sensor segments. The combination of signals may be analyzed to discern and identify the emission band. FIG. 7-2E through FIG. 7-2H represent results from numerical simulations of signals from a two-segment sensor 2-122 exposed to four distinct emission patterns. As can be seen, each combination of signals from the two sensor segments is distinct, and can be used to discriminate between emitters at the four wavelengths. For the simulation, because the outer detector segment of the bulls-eye sensor 7-162 had a larger area, more signal was integrated for that detector. Additionally, light that impinged on an area between the detectors generated carriers that may drift towards either detector segment and contribute to signals from both segments.

In some embodiments, there may be N photodetector segments per pixel, where N may be any integer value. In some embodiments, N may be greater than or equal to 1 and less than or equal to 10. In other embodiments, N may be greater than or equal to 2 and less than or equal to 5. The number M of discernible sample emissions (e.g., distinct emission wavelengths from different luminescent tags) that may be detected by the N detectors may be equal to or greater than N. The discernment of M sample emissions may be achieved by evaluating the ratio of signals from each sensor segment, according to some embodiments. In some implementations, the ratio, sum and/or amplitudes of the received signals may be measured and analyzed to determine a characteristic wavelength of emission from the sample well.

In some embodiments, more than one emitter may emit at different characteristic wavelengths in a given time window within a sample well 2-211. A sensor 2-122 may simultaneously detect signals from multiple emissions at different wavelengths and provide the summed signal for data processing. In some implementations, multi-wavelength emission may be distinguishable as another set of signal values from the sensor segments (e.g., signal values different from those shown in FIG. 7-2E through FIG. 7-2H). The signal values may be analyzed to discern that multi-wavelength emission has occurred and to identify a particular combination of emitters associated with the emissions.

The inventors have also contemplated and analyzed a bulls-eye sensor having four concentric segments. Signals from the segments are plotted in FIG. 7-2I and FIG. 7-2J for the same emission conditions associated with FIG. 7-2G and FIG. 7-2H, respectively. The four-segment bulls-eye sensor also shows discernable signals that may be analyzed to identify a particular emitter within the sample well.

When wavelength filtering is used at each sensor segment, or the spectral separation is high, each segment of a sensor may detect substantially only a selected emission band. For example, a first wavelength may be detected by a first segment, a second wavelength may be detected by a second segment, and a third wavelength may be detected by a third segment.

Referring again to FIG. 7-1A, there may be additional electronic circuitry 7-125 within a pixel 2-100 that may be used to collect and readout signals from each segment of a sensor 2-122. FIG. 7-3A and FIG. 7-3D depict circuitry that may be used in combination with a multi-segment sensor, according to some embodiments. As an example, signal collection circuitry 7-310 may comprise three transistors for each sensor segment. An arrangement of the three transistors is depicted in FIG. 7-3B, according to some implementations. A signal level at a charge accumulation node 7-311 associated with each segment may be reset by a reset transistor RST, and a signal level for the segment (determined by the amount of charge at the charge accumulation node) may be read out with a read transistor RD.

The pixel circuitry may further include amplification and correlated double-sampling circuitry 7-320, according to some embodiments. The amplification and double-sampling circuitry may comprise transistors configured to amplify signals from the sensor segments as well as transistors configured to reset the voltage level at the charge-accumulation node and to read a background, or "reset", signal at the node when no emission energy is present on the sensor (e.g., prior to application of excitation energy at the sample well) and to read a subsequent emission signal, for example.

According to some embodiments, correlated double sampling is employed to reduce background noise by subtracting a background or reset signal level from the detected emission signal level. The collected emission signal and background signal associated with each segment of the sensor may be read out onto column lines 7-330. In some embodiments, an emission signal level and background signal are time-multiplexed onto a common column line. There may be a separate column line for each sensor segment. Signals from the column lines may be buffered and/or amplified with amplification circuitry 7-340 (which may be located outside of an active pixel array), and provided for further processing and analysis. In some embodiments the subtraction of the double-sampled signals is calculated off-chip, e.g., by a system processor. In other embodiments, the subtraction may be performed on chip or in circuitry of the instrument.

Some embodiments of correlated double sampling may operate by selecting a row to sample, wherein the sensors associated with the row have integrated signal charges over a sampling period and contain signal levels. The signal levels may be simultaneously read out onto the columns lines. After sampling the integrated signal levels, all the pixels in the selected row may be reset and immediately sampled. This reset level may be correlated to the next integrated signal that starts accumulating after the reset is released, and finishes integrating a frame time later when the same row is selected again. In some embodiments, the reset values of the frame may be stored off-chip so that when the signals have finished integrating and have been sampled, the stored correlated reset values can be subtracted.

In some embodiments, a sensor 2-122 with more than two segments may require additional circuitry. FIG. 7-3C depicts signal-collection 7-312, amplification 7-320, and double-sampling circuitry associated with a quad sensor. According to some embodiments, signals from two or more segments may be time-multiplexed onto a common signal channel at the pixel, as depicted in the drawing. The time-multiplexed signals may include sampled background signals for each segment for noise cancellation. Additionally, the signals from two or more segments may be time-multiplexed onto a common column line.

According to some embodiments, temporal signal-acquisition techniques may be used to reduce background signal levels from an excitation source or sources, and/or discern different emissions from different emitters associated with a sample. FIG. 7-4A depicts fluorescent emission and decay from two different emitters that may be used to tag a sample, according to some embodiments. The two emissions have appreciably different time-decay characteristics. A first time-decay curve 7-410 from a first emitter may correspond to a common fluorescent molecule such as rhodamine. A second time-decay curve 7-420 may be characteristic of a second emitter, such as a quantum dot or a phosphorescent emitter. Both emitters exhibit an emission-decay tail that extends for some time after initial excitation of the emitter. In some embodiments, signal-collection techniques applied during the emission-decay tail may be timed to reduce a background signal from an excitation source, in some embodiments, and to distinguish between the emitters, in some embodiments.

According to some implementations, time-delayed sampling may be employed during the emission-decay tail to reduce a background signal due to radiation from an excitation source. FIG. 7-4B and FIG. 7-4C illustrate time-delay sampling, according to some embodiments. FIG. 7-4B depicts the temporal evolution of an excitation pulse 7-440 of excitation energy from an excitation source, and a subsequent emission pulse 7-450 that may follow from a sample that is excited within the sample well. The excitation pulse 7-440 may result from driving the excitation source with a drive signal 7-442 for a brief period of time, as depicted in FIG. 7-4C. For example, the drive signal may begin at a first time $t_1$ and end at a second time $t_2$. The duration of the drive signal $(t_2-t_1)$ may be between about 1 picosecond and about 50 nanoseconds, according to some embodiments, though shorter durations may be used in some implementations.

At a time $t_3$ following termination of the drive signal for the excitation source, a sensor 2-260 (or sensor segment) at the pixel may be gated to accumulate charge at a charge accumulation node 7-311 during a second time interval 7-452 extending from a time $t_3$ to a time $t_4$. The second time interval may be between about 1 nanosecond and about 50 microseconds, according to some embodiments, though other durations may be used in some implementations. As can be seen in reference to FIG. 7-4B, a charge accumulation node will collect more signal charges due to the emitting sample then due to the excitation source. Accordingly, an improved signal-to-noise ratio may be obtained.

Referring again to FIG. 7-4A, because of the different temporal emission characteristics of the emitters, corresponding signals at a sensor may peak at different times. In some implementations, signal-acquisition techniques applied during the emission-decay tail may be used to discern different emitters. In some embodiments, temporal detection techniques may be used in combination with spatial and spectral techniques (as described above in connection with FIG. 7-2, for example) to discern different emitters.

FIG. 7-4D through FIG. 7-4H illustrate how double-sampling at a sensor, or sensor segment, can be used to distinguish between two emitters having different temporal emission characteristics. FIG. 7-4D depicts emission curves 7-470, 7-475 associated with a first emitter and second emitter, respectively. As an example, the first emitter may be a common fluorophore such as rhodamine, and the second emitter may be a quantum dot or phosphorescent emitter.

FIG. 7-4E represents dynamic voltage levels at a charge accumulation node 7-311 that may occur in response to the two different emission characteristics of FIG. 7-4D. In the example, a first voltage curve 7-472 corresponding to the fluorescent emitter may change more rapidly, because of the shorter emission span, and reach its maximum (or minimum, depending on the polarity of the node) at a first time $t_1$. The second voltage curve 7-477 may change more slowly due to the longer emission characteristics of the second emitter, and reach its maximum (or minimum) at a second time $t_2$.

In some embodiments, sampling of the charge-accumulation node may be done at two times $t_3$, $t_4$ after the sample excitation, as depicted in FIG. 7-4F. For example, a first read signal 7-481 may be applied to read out a first voltage value from the charge-accumulation node at a first time $t_3$. Subsequently, a second read signal 7-482 may be applied to read out a second voltage value from the charge-accumulation node at a second time $t_4$ without resetting the charge-accumulation node between the first read and second read. An analysis of the two sampled signal values may then be used to identify which of the two emitters provided the detected signal levels.

FIG. 7-4G depicts an example of two signals from the first read and second read that may be obtained for the first emitter having an emission curve 7-470 as depicted in FIG. 7-4D. FIG. 7-4H depicts an example of two signals from the first read and second read that may be obtained for the second emitter having an emission curve 7-475 as depicted in FIG. 7-4D. For example the sampling sequence shown in FIG. 7-4F for the first emitter will sample the curve 7-472 and obtain approximately the same values at the two read times. In the case of the second emitter, the sampling sequence depicted in FIG. 7-4F samples two different values of the curve 7-477 at the two read times. The resulting pairs of signals from the two read times distinguish between the two emitters, and can be analyzed to identify each emitter. According to some embodiments, double sampling for background subtraction may also be executed to subtract a background signal from the first and second read signals.

In operation, sensors 2-260 of a sensor chip may be subjected to a wavelength calibration procedure prior to data collection from a specimen to be analyzed. The wavelength calibration procedure may include subjecting the sensors to different known energies having characteristic wavelengths that may, or may not, correspond to fluorophore wavelengths that may be used with a sensor chip. The different energies may be applied in a sequence so calibration signals can be recorded from the sensors for each energy. The calibration signals may then be stored as reference signals, that may be used to process real data acquisition and to determine what emission wavelength or wavelengths are detected by the sensors.

Any suitable sensor capable of acquiring time bin information may be used for measurements to detect lifetimes of luminescent markers. The sensors are aligned such that each sample well has at least one sensor region to detect luminescence from the sample well. In some embodiments, the integrated device may include Geiger mode avalanche photodiode arrays and/or single photon avalanche diode arrays (SPADs). The sensor may include IR-enhanced CMOS sensors which may include Si—Ge materials and/or modified layers such as "black silicon". These materials may enable the sensor to detect luminescent markers that emit in the infrared, and/or are otherwise poorly detected by non-IR-enhanced CMOS sensors.

Described herein is an integrated photodetector that can accurately measure, or "time-bin," the timing of arrival of incident photons, and which may be used in a variety of applications, such as sequencing of nucleic acids (e.g., DNA sequencing), for example. In some embodiments, the integrated photodetector can measure the arrival of photons with nanosecond or picosecond resolution, which can facilitate time-domain analysis of the arrival of incident photons.

Some embodiments relate to an integrated circuit having a photodetector that produces charge carriers in response to incident photons and which is capable of discriminating the timing at which the charge carriers are generated by the arrival of incident photons with respect to a reference time (e.g., a trigger event). In some embodiments, a charge carrier segregation structure segregates charge carriers generated at different times and directs the charge carriers into one or more charge carrier storage regions (termed "bins") that aggregate charge carriers produced within different time periods. Each bin stores charge carriers produced within a selected time interval. Reading out the charge stored in each bin can provide information about the number of photons that arrived within each time interval. Such an integrated circuit can be used in any of a variety of applications, such as those described herein.

An example of an integrated circuit having a photodetection region and a charge carrier segregation structure will be described. In some embodiments, the integrated circuit may include an array of pixels, and each pixel may include one or more photodetection regions and one or more charge carrier segregation structures, as discussed below.

FIG. 7-5 shows a diagram of a pixel 100, according to some embodiments. Pixel 100 includes a photon absorption/carrier generation region 102 (also referred to as a photodetection region), a carrier travel/capture region 106, a carrier storage region 108 having one or more charge carrier storage regions, also referred to herein as "charge carrier storage bins" or simply "bins," and readout circuitry 110 for reading out signals from the charge carrier storage bins.

The photon absorption/carrier generation region 102 may be a region of semiconductor material (e.g., silicon) that can convert incident photons into photogenerated charge carriers. The photon absorption/carrier generation region 102 may be exposed to light, and may receive incident photons. When a photon is absorbed by the photon absorption/carrier generation region 102 it may generate photogenerated charge carriers, such as an electron/hole pair. Photogenerated charge carriers are also referred to herein simply as "charge carriers."

An electric field may be established in the photon absorption/carrier generation region 102. In some embodiments, the electric field may be "static," as distinguished from the changing electric field in the carrier travel/capture region 106. The electric field in the photon absorption/carrier generation region 102 may include a lateral component, a vertical component, or both a lateral and a vertical component. The lateral component of the electric field may be in the downward direction of FIG. 7-5, as indicated by the arrows, which induces a force on photogenerated charge carriers that drives them toward the carrier travel/capture region 106. The electric field may be formed in a variety of ways.

In some embodiments, one or more electrodes may be formed over the photon absorption/carrier generation region 102. The electrodes(s) may have voltages applied thereto to establish an electric field in the photon absorption/carrier generation region 102. Such electrode(s) may be termed "photogate(s)." In some embodiments, photon absorption/ carrier generation region 102 may be a region of silicon that is fully depleted of charge carriers.

In some embodiments, the electric field in the photon absorption/carrier generation region 102 may be established by a junction, such as a PN junction. The semiconductor material of the photon absorption/carrier generation region 102 may be doped to form the PN junction with an orientation and/or shape that produces an electric field that induces a force on photogenerated charge carriers that drives them toward the carrier travel/capture region 106. In some embodiments, the P terminal of the PN junction diode may connected to a terminal that sets its voltage. Such a diode may be referred to as a "pinned" photodiode. A pinned photodiode may promote carrier recombination at the surface, due to the terminal that sets its voltage and attracts carriers, which can reduce dark current. Photogenerated charge carriers that are desired to be captured may pass underneath the recombination area at the surface. In some embodiments, the lateral electric field may be established using a graded doping concentration in the semiconductor material.

As illustrated in FIG. 7-5, a photon may be captured and a charge carrier 101A (e.g., an electron) may be produced at time t1. In some embodiments, an electrical potential gradient may be established along the photon absorption/carrier generation region 102 and the carrier travel/capture region 106 that causes the charge carrier 101A to travel in the downward direction of FIG. 7-5 (as illustrated by the arrows shown in FIG. 7-5). In response to the potential gradient, the charge carrier 101A may move from its position at time t1 to a second position at time t2, a third position at time t3, a fourth position at time t4, and a fifth position at time t5. The charge carrier 101A thus moves into the carrier travel/capture region 106 in response to the potential gradient.

The carrier travel/capture region 106 may be a semiconductor region. In some embodiments, the carrier travel/capture region 106 may be a semiconductor region of the same material as photon absorption/carrier generation region 102 (e.g., silicon) with the exception that carrier travel/capture region 106 may be shielded from incident light (e.g., by an overlying opaque material, such as a metal layer).

In some embodiments, and as discussed further below, a potential gradient may be established in the photon absorption/carrier generation region 102 and the carrier travel/capture region 106 by electrodes positioned above these regions. However, the techniques described herein are not limited as to particular positions of electrodes used for producing an electric potential gradient. Nor are the techniques described herein limited to establishing an electric potential gradient using electrodes. In some embodiments, an electric potential gradient may be established using a spatially graded doping profile. Any suitable technique may be used for establishing an electric potential gradient that causes charge carriers to travel along the photon absorption/carrier generation region 102 and carrier travel/capture region 106.

A charge carrier segregation structure may be formed in the pixel to enable segregating charge carriers produced at different times. In some embodiments, at least a portion of the charge carrier segregation structure may be formed over the carrier travel/capture region 106. As will be described below, the charge carrier segregation structure may include one or more electrodes formed over the carrier travel/capture region 106, the voltage of which may be controlled by control circuitry to change the electric potential in the carrier travel/capture region 106.

The electric potential in the carrier travel/capture region 106 may be changed to enable capturing a charge carrier. The potential gradient may be changed by changing the voltage on one or more electrodes overlying the carrier travel/capture region 106 to produce a potential barrier that can confine a carrier within a predetermined spatial region. For example, the voltage on an electrode overlying the dashed line in the carrier travel/capture region 106 of FIG. 7-5 may be changed at time t5 to raise a potential barrier along the dashed line in the carrier travel/capture region 106 of FIG. 7-5, thereby capturing charge carrier 101A. As shown in FIG. 7-5, the carrier captured at time t5 may be transferred to a bin "bin0" of carrier storage region 108. The transfer of the carrier to the charge carrier storage bin may be performed by changing the potential in the carrier travel/capture region 106 and/or carrier storage region 108 (e.g., by changing the voltage of electrode(s) overlying these regions) to cause the carrier to travel into the charge carrier storage bin.

Changing the potential at a certain point in time within a predetermined spatial region of the carrier travel/capture region 106 may enable trapping a carrier that was generated by photon absorption that occurred within a specific time interval. By trapping photogenerated charge carriers at different times and/or locations, the times at which the charge carriers were generated by photon absorption may be discriminated. In this sense, a charge carrier may be "time binned" by trapping the charge carrier at a certain point in time and/or space after the occurrence of a trigger event. The time binning of a charge carrier within a particular bin provides information about the time at which the photogenerated charge carrier was generated by absorption of an incident photon, and thus likewise "time bins," with respect to the trigger event, the arrival of the incident photon that produced the photogenerated charge carrier.

FIG. 7-6 illustrates capturing a charge carrier at a different point in time and space. As shown in FIG. 7-6, the voltage on an electrode overlying the dashed line in the carrier travel/capture region 106 may be changed at time t9 to raise a potential barrier along the dashed line in the carrier travel/capture region 106 of FIG. 7-6, thereby capturing carrier 101B. As shown in FIG. 7-6, the carrier captured at time t9 may be transferred to a bin "bin1" of carrier storage region 108. Since charge carrier 101B is trapped at time t9, it represents a photon absorption event that occurred at a different time (i.e., time t6) than the photon absorption event (i.e., at t1) for carrier 101A, which is captured at time t5.

Performing multiple measurements and aggregating charge carriers in the charge carrier storage bins of carrier storage region 108 based on the times at which the charge carriers are captured can provide information about the times at which photons are captured in the photon absorption/carrier generation area 102. Such information can be useful in a variety of applications, as discussed above.

In some embodiments, the duration of time each time bin captures after an excitation pulse may vary. For example, shorter time bins may be used to detect luminescence shortly after the excitation pulse, while longer time bins may be used at times further from an excitation pulse. By varying the time bin intervals, the signal to noise ratio for measurements of the electrical signal associated with each time bin may be improved for a given sensor. Since the probability of a photon emission event is higher shortly after an excitation pulse, a time bin within this time may have a shorter time interval to account for the potential of more photons to detect. While at longer times, the probability of photon emission may be less and a time bin detecting within this time may be longer to account for a potential fewer number of photons. In some embodiments, a time bin with a significantly longer time duration may be used to distinguish among multiple lifetimes. For example, the majority of time bins may capture a time interval in the range of approximately 0.1-0.5 ns, while a time bin may capture a time interval in the range of approximately 2-5 ns. The number of time bins and/or the time interval of each bin may depend on the sensor used to detect the photons emitted from the sample object. Determining the time interval for each bin may include identifying the time intervals needed for the number of time bins provided by the sensor to distinguish among luminescent markers used for analysis of a sample. The distribution of the recorded histogram may be compared to known histograms of markers under similar conditions and time bins to identify the type of marker in the sample well. Different embodiments of the present application may measure lifetimes of markers but vary in the excitation energies used to excite a marker, the number of sensor regions in each pixel, and/or the wavelength detected by the sensors.

V. Excitation Sources

The excitation source 2-250 may be any suitable source that is arranged to deliver excitation energy to at least one sample well 2-111 of the assay chip. Pixels on the assay chip may be passive source pixels. The term "passive source pixel" is used to refer to a pixel wherein the excitation energy is delivered to the pixel from a region outside the pixel or pixel array of the assay chip, e.g., the excitation may be in the instrument.

According to some embodiments, an excitation source may excite a sample via a radiative process. For example, an excitation source may provide visible radiation (e.g., radiation having a wavelength between about 350 nm and about 750 nm), near-infrared radiation (e.g., radiation having a wavelength between about 0.75 micron and about 1.4 microns), and/or short wavelength infrared radiation (e.g., radiation having a wavelength between about 1.4 microns and about 3 microns) to at least one excitation region 3-215 of at least one sample well of the assay chip. In some embodiments, a radiative excitation source may provide energy to excite an intermediary (e.g., a molecule, a quantum dot, or a layer of material comprising selected molecules and/or quantum dots) that is immediately adjacent an excitation region of a sample well. The intermediary may transfer its energy to a sample via a non-radiative process (e.g., via FRET or DET).

In some embodiments, an excitation source may provide more than one source of excitation energy. For example, a radiative excitation source may deliver excitation energies having two or more distinct spectral characteristics. As an example, a multi-color LED may emit energies centered at two or more wavelengths, and these energies may be delivered to an excitation region of a sample well.

In overview and according to some embodiments, an instrument may include at least one excitation source 2-250 to provide excitation energy to at least one excitation region of at least one sample well of the assay chip or to at least one intermediary that converts or couples the excitation energy to at least one sample within one or more excitation regions. As depicted in FIG. 2-3, radiation excitation energy 2-251 from an excitation source 2-250 may impinge on a region around a sample well 2-211, for example. In some embodiments, there may be excitation coupling structures 2-223 that aid in concentrating the incident excitation energy within an excitation region 2-215 of the sample well.

An excitation source may be characterized by one or more distinct spectral bands each having a characteristic wavelength. For instructional purposes only, an example of spectral emission from an excitation source is depicted in spectral graph of FIG. 8-1A. The excitation energy may be substantially contained within a spectral excitation band 8-110. A peak wavelength 8-120 of the spectral excitation band may be used to characterize the excitation energy. The excitation energy may also be characterized by a spectral distribution, e.g., a full-width-half-maximum (FWHM) value as shown in the drawing. An excitation source producing energy as depicted in FIG. 8-1A, may be characterized as delivering energy at a wavelength of approximately 540 nm radiation and having a FWHM bandwidth of approximately 55 nm.

FIG. 8-1B depicts spectral characteristics of an excitation source (or excitation sources) that can provide two excitation energy bands to one or more sample wells. According to some embodiments, a first excitation band 8-112 is at approximately 532 nm, and a second excitation band 8-114 is at approximately 638 nm, as illustrated in the drawing. In some embodiments, a first excitation band may be at approximately 638 nm, and a second excitation band may be at approximately 650 nm. In some embodiments, a first excitation band may be at approximately 680 nm, and a second excitation band may be at approximately 690 nm. According to some embodiments, the peaks of the excitation bands may be within ±5 nm of these values.

In some cases, a radiative excitation source may produce a broad excitation band as depicted in FIG. 8-1A. A broad excitation band 8-110 may have a bandwidth greater than approximately 20 nm, according to some embodiments. A broad excitation band may be produced by a light emitting diode (LED), for example. In some implementations, a radiative excitation source may produce a narrow excitation band, as depicted in FIG. 8-1B. A narrow excitation band may be produced by a laser diode, for example, or may be produced by spectrally filtering an output from an LED.

In some embodiments, the excitation source may be a light source. Any suitable light source may be used. Some embodiments may use incoherent sources and other embodiments may use coherent light sources. By way of example and not limitation, incoherent light sources according to some embodiments may include different types of light emitting diodes (LEDs) such as organic LEDs (OLEDs), quantum dots (QLEDs), nanowire LEDs, and (in)organic semiconductor LEDs. By way of example and not limitation, coherent light sources according to some embodiments may include different types of lasers such as organic lasers, quantum dot lasers, vertical cavity surface emitting lasers (VCSELs), edge emitting lasers, and distributed-feedback (DFB) laser diodes. Additionally or alternatively, slab-coupled optical waveguide laser (SCOWLs) or other asymmetric single-mode waveguide structures may be used. Additionally or alternatively, a solid state laser such as Nd:YAG or Nd:Glass, pumped by laser diodes or flashlamps, may be used. Additionally or alternatively, a laser-diode-pumped fiber laser may be used. In some embodiments, the output of a laser excitation source may be doubled in frequency to half the wavelength, in a nonlinear crystal, or a Periodically Poled Lithium Niobate (PPLN) or other similar periodically poled nonlinear crystal. This frequency doubling process may allow use of efficient lasers to generate wavelengths more suitable for excitation. There may be more than one type of excitation source for an array of pixels. In some embodiments, different types of excitation sources may be combined. The excitation source may be fabricated according to conventional technologies that are used to fabricate a selected type of excitation source.

The characteristic wavelength of a source of excitation energy may be selected based upon a choice of luminescent markers that are used in the assay analysis. In some implementations, the characteristic wavelength of a source of excitation energy is selected for direct excitation (e.g., single photon excitation) of a chosen fluorophore. In some implementations, the characteristic wavelength of a source of excitation energy is selected for indirect excitation (e.g., multi-photon excitation or harmonic conversion to a wavelength that will provide direct excitation). In some embodiments, excitation energy may be generated by a light source that is configured to generate excitation energy at a particular wavelength for application to a sample well. In some embodiments, a characteristic wavelength of the excitation source may be less than a characteristic wavelength of corresponding emission from the sample. In some implementations, a characteristic wavelength of the excitation source may be greater than a characteristic wavelength of emission from the sample, and excitation of the sample may occur through multi-photon absorption.

The excitation source may include a battery or any other power supply, which may be located somewhere other than the integrated bioanalysis device. For example, the excitation source may be located in an instrument and the power may be coupled to the integrated bioanalysis device via conducting wires and connectors.

According to some embodiments, one or more excitation sources may be located external to the integrated device, and may be arranged to deliver pulses of light to an integrated device having sample wells. The pulses of light may be coupled to a plurality of sample wells and used to excite one or more markers within the wells, for example. The one or more excitation sources may deliver pulses of light at one or more characteristic wavelengths, according to some implementations. In some cases, an excitation source may be packaged as an exchangeable module that mounts in or couples to a base instrument, into which the integrated device may be loaded. Energy from an excitation source may be delivered radiatively or non-radiatively to at least one sample well or to at least one sample in at least one sample well. In some implementations, an excitation source having a controllable intensity may be arranged to deliver excitation energy to a plurality of pixels of an integrated device. The pixels may be arranged in a linear array (e.g., row or column), or in a 2D array (e.g., a sub-area of the array of pixels or the full array of pixels).

Any suitable light source may be used for an excitation source. Some embodiments may use incoherent light sources and other embodiments may use coherent light sources. By way of non-limiting examples, incoherent light sources according to some embodiments may include different types of light emitting diodes (LEDs) such as organic LEDs (OLEDs), quantum dots (QLEDs), nanowire LEDs, and (in)organic semiconductor LEDs. By way of non-limiting examples, coherent light sources according to some embodiments may include different types of lasers such as semiconductor lasers (e.g., vertical cavity surface emitting lasers (VCSELs), edge emitting lasers, and distributed-feedback (DFB) laser diodes). Additionally or alternatively, slab-coupled optical waveguide laser (SCOWLs) or other asymmetric single-mode waveguide structures may be used. In some implementations, coherent light sources may comprise organic lasers, quantum dot lasers, and solid state lasers (e.g., a Nd:YAG or ND:Glass laser, pumped by laser diodes or flashlamps). In some embodiments, a laser-diode-pumped fiber laser may be used. A coherent light source may be passively mode locked to produce ultrashort pulses. There may be more than one type of excitation source for an array of pixels on an integrated device. In some embodiments, different types of excitation sources may be combined. An excitation source may be fabricated according to conventional technologies that are used to fabricate a selected type of excitation source.

By way of introduction and without limiting the invention, an example arrangement of a coherent light source is depicted in FIG. 8-2A. The drawing illustrates an analytical instrument 8-200 that may include an ultrashort-pulsed laser excitation source 8-210 as the excitation source. The ultrashort pulsed laser 8-210 may comprise a gain medium 8-205 (which may be a solid-state material is some embodiments), a pump source for exciting the gain medium (not shown), and at least two cavity mirrors 8-202, 8-204 that define ends of an optical laser cavity. In some embodiments, there may be one or more additional optical elements in the laser cavity for purposes of beam shaping, wavelength selection, and/or pulse forming. When operating, the pulsed-laser excitation source 8-210 may produce an ultrashort optical pulse 8-220 that circulates back-and-forth in the laser cavity between the cavity's end mirrors 8-202, 8-204 and through the gain medium 8-205. One of the cavity mirrors 8-204 may partially transmit a portion of the circulating pulse, so that a train of optical pulses 8-222 is emitted from the pulsed laser 8-210. The emitted pulses may sweep out a beam (indicated by the dashed lines) that is characterized by a beam waist w.

Measured temporal intensity profiles 8-224 of the emitted pulses 8-222 may appear as depicted in FIG. 8-2B. In some embodiments, the peak intensity values of the emitted pulses may be approximately equal, and the profiles 8-224 may have a Gaussian temporal profile, though other profiles such as a sech profile may be possible. In some cases, the pulses may not have symmetric temporal profiles and may have other temporal shapes. In some embodiments, gain and/or loss dynamics may yield pulses having asymmetric profiles. The duration of each pulse may be characterized by a full-width-half-maximum (FWHM) value, as indicated in FIG. 8-2B. Ultrashort optical pulses may have FWHM values less than 100 picoseconds.

The pulses emitting from a laser excitation source may be separated by regular intervals T. In some embodiments, T may be determined by active gain and/or loss modulation rates in the laser. For mode-locked lasers, T may be determined by a round-trip travel time between the cavity end mirrors 8-202, 8-204. According to some embodiments, the pulse separation time T may be between about 1 ns and about 100 ns. In some cases, the pulse separation time T may be between about 0.1 ns and about 1 ns. In some implementations, the pulse separation time T may be between about 100 ns and about 2 μs.

In some embodiments, an optical system 8-240 may operate on a beam of pulses 8-222 from a laser excitation source 8-210. For example, the optical system may include one or more lenses to reshape the beam and/or change the divergence of the beam. Reshaping of the beam may include increasing or decreasing the value of the beam waist and/or changing a cross-sectional shape of the beam (e.g., elliptical to circular, circular to elliptical, etc.). Changing the divergence of the beam may comprise converging or diverging the beam flux. In some implementations, the optical system 8-240 may include an attenuator or amplifier to change the amount of beam energy. In some cases, the optical system may include wavelength filtering elements. In some implementations, the optical system may include pulse shaping elements, e.g., a pulse stretcher and/or pulse compressor. In some embodiments, the optical system may include one or more nonlinear optical elements, such as a saturable absorber for reducing a pulse length. According to some embodiments, the optical system 8-240 may include one or more elements that alter the polarization of pulses from a laser excitation source 8-210.

In some implementations, an optical system 8-240 may include a nonlinear crystal for converting the output wavelength from an excitation source 8-210 to a shorter wavelength via frequency doubling or to a longer wavelength via parametric amplification. For example, an output of the laser may be frequency-doubled in a nonlinear crystal (e.g., in periodically-poled lithium niobate (PPLN)) or other non-poled nonlinear crystal. Such a frequency-doubling process may allow more efficient lasers to generate wavelengths more suitable for excitation of selected fluorophores.

The phrase "characteristic wavelength" or "wavelength" may refer to a central or predominant wavelength within a limited bandwidth of radiation produced by an excitation source. In some cases, it may refer to a peak wavelength within a bandwidth of radiation produced by an excitation source. A characteristic wavelength of an excitation source may be selected based upon a choice of luminescent markers or probes that are used in a bioanalysis device, for example. In some implementations, the characteristic wavelength of a source of excitation energy is selected for direct excitation (e.g., single photon excitation) of a chosen fluorophore. In some implementations, the characteristic wavelength of an excitation source is selected for indirect excitation (e.g., multi-photon excitation or harmonic conversion to a wavelength that will provide direct excitation). In some embodiments, excitation radiation may be generated by a light source that is configured to generate excitation energy at a particular wavelength for application to a sample well. In some embodiments, a characteristic wavelength of the excitation source may be less than a characteristic wavelength of corresponding emission from the sample. For example, an excitation source may emit radiation having a characteristic wavelength between 500 nm and 700 nm (e.g., 515 nm, 532 nm, 563 nm, 594 nm, 612 nm, 632 nm, 647 nm). In some embodiments, an excitation source may provide excitation energy centered at two different wavelengths, such as 532 nm and 593 nm for example.

In some embodiments, a pulsed excitation source may be used to excite a luminescent marker in order to measure an emission lifetime of the luminescent marker. This can be useful for distinguishing luminescent markers based on emission lifetime rather than emission color or wavelength. As an example, a pulsed excitation source may periodically excite a luminescent marker in order to generate and detect subsequent photon emission events that are used to determine a lifetime for the marker. Lifetime measurements of luminescent markers may be possible when the excitation pulse from an excitation source transitions from a peak pulse power or intensity to a lower (e.g., nearly extinguished) power or intensity over a duration of time that is less than the lifetime of the luminescent marker. It may be beneficial if the excitation pulse terminates quickly, so that it does not re-excite the luminescent marker during a post-excitation phase when a lifetime of the luminescent marker is being evaluated. By way of example and not limitation, the pulse power may drop to approximately 20 dB, approximately 40 dB, approximately 80 dB, or approximately 120 dB less than the peak power after 250 picoseconds. In some implementations, the pulse power may drop to approximately 20 dB, approximately 40 dB, approximately 80 dB, or approximately 120 dB less than the peak power after 100 picoseconds.

An additional advantage of using ultrashort excitation pulses to excite luminescent markers is to reduce photobleaching of the markers. Applying continuous excitation energy to a marker may bleach and/or damage a luminescent marker over time. Even though a peak pulse power of the excitation source may be considerably higher than a level that would rapidly damage a marker at continuous exposure, the use of ultrashort pulses may increase the amount of time and number of useful measurements before the marker becomes damaged by the excitation energy.

When using a pulsed excitation source to discern lifetimes of luminescent markers, the time between pulses of excitation energy may be as long as or longer than a longest lifetime of the markers in order to observe and evaluate emission events after each excitation pulse. For example, the time interval T (see FIG. 8-2B) between excitation pulses may be longer than any emission lifetime of the examined fluorophores. In this case, a subsequent pulse may not arrive before an excited fluorophore from a previous pulse has had a reasonable amount of time to fluoresce. In some embodiments, the interval T needs to be long enough to determine a time between an excitation pulse that excites a fluorophore and a subsequent photon emitted by the fluorophore after termination of excitation pulse and before the next excitation pulse.

Although the interval between excitation pulses T should be long enough to observe decay properties of the fluorophores, it is also desirable that T is short enough to allow many measurements to be made in a short period of time. By way of example and not limitation, emission lifetimes of fluorophores used in some applications may be in the range of about 100 picoseconds to about 10 nanoseconds. Accordingly, excitation pulses used to detect and/or discern such lifetimes may have durations (FWHM) ranging from about 25 picoseconds to about 2 nanoseconds, and may be provided at pulse repetition rates ranging from about 20 MHz to about 1 GHz.

In further detail, any suitable techniques for modulating the excitation energy to create a pulsed excitation source for lifetime measurements may be used. Direct modulation of an excitation source, such as a laser, may involve modulating the electrical drive signal of the excitation source so the emitted power is in the form of pulses. The input power for a light source, including the optical pumping power, and excited-state carrier injection and/or carrier removal from a portion of the gain region, may be modulated to affect the gain of the gain medium, allowing the formation of pulses of excitation energy through dynamic gain shaping. Additionally, the quality (Q) factor of the optical resonator may be modulated by various means to form pulses using Q-switching techniques. Such Q-switching techniques may be active and/or passive. The longitudinal modes of a resonant cavity of a laser may be phase-locked to produce a series of pulses of emitted light through mode-locking. Such mode-locking techniques may be active and/or passive. A laser cavity may include a separate absorbing section to allow for modulation of the carrier density and control of the absorption loss of that section, thus providing additional mechanisms for shaping the excitation pulse. In some embodiments, an optical modulator may be used to modulate a beam of continuous wave (CW) light to be in the form of a pulse of excitation energy. In other embodiments, a signal sent to an acoustic optic modulator (AOM) coupled to an excitation source may be used to change the deflection, intensity, frequency, phase, and/or polarization of the outputted light to produce a pulsed excitation energy. AOMs may also be used for continuous wave beam scanning, Q-switching, and/or mode-locking. Although the above techniques are described for creating a pulsed excitation source, any suitable way to produce a pulsed excitation source may be used for measuring lifetimes of luminescent markers.

In some embodiments, techniques for forming a pulsed excitation source suitable for lifetime measurements may include modulation of an input electrical signal that drives photon emission. Some excitation sources (e.g., diode lasers and LEDs) convert an electrical signal, such as an input current, into a light signal. The characteristics of the light signal may depend on characteristics of the electrical signal. In producing a pulsed light signal, the electrical signal may vary over time in order to produce a variable light signal. Modulating the electrical signal to have a specific waveform may produce an optical signal with a specific waveform. The electrical signal may have a sinusoidal waveform with a certain frequency and the resulting pulses of light may occur within time intervals related to the frequency. For example, an electrical signal with a 500 MHz frequency may produce a light signal with pulses every 2 nanoseconds. Combined beams produced by distinct pulsed excitation sources, whether similar or different from each other, may have a relative path difference below 1 mm.

In some excitation sources, such as laser diodes, the electrical signal changes the carrier density and photons are produced through the recombination of electron and hole pairs. The carrier density is related to the light signal such that when the carrier density is above a threshold, a substantial number of coherent photons are generated via stimulated emission. Current supplied to a laser diode may inject electrons or carriers into the device, and thereby increase the carrier density. When the carrier density is above a threshold, photons may be generated at a faster rate than the current supplying the carriers, and thus the carrier density may decrease below the threshold and photon generation reduces. With the photon generation reduced, the carrier density begins to increase again, due to continued current injection and the absorption of photons, and eventually increases above the threshold again. This cycle leads to oscillations of the carrier density around the threshold value for photon generation, resulting in an oscillating light signal. These dynamics, known as relaxation oscillations, can lead to artifacts in the light signal due to oscillations of the carrier density. When current is initially supplied to a laser, there may be oscillations before the light signal reaches a stable power due to oscillations in the carrier density. When forming a pulsed excitation source, oscillations of the carrier density may introduce artifacts for a pulsed light signal. For example, the plot in FIG. 8-3 illustrates how the carrier density may have relaxation oscillations and a corresponding light signal with oscillating power through modulation by gain switching. Artifacts from such relaxation oscillations may broaden a pulsed light signal and/or produce a tail in the light signal, limiting the lifetimes that can be detected by such a pulsed light source since the excitation signal may overlap with emitted photons by a luminescent marker.

In some embodiments, techniques for shortening the time duration of an excitation pulse may be used to reduce the excitation energy required to detect luminescent markers and thereby reduce or delay bleaching and other damage to the luminescent markers. Techniques for shortening the time duration of the excitation pulse may be used to reduce the power and/or intensity of the excitation energy after a maximum value or peak of the excitation pulse, allowing the detection of shorter lifetimes. Such techniques may electrically drive the excitation source in order to reduce the excitation power after the peak power. This may suppress a tail of the pulse as shown in plot 8-401 of FIG. 8-4. An electrical driving signal may be tailored to drive the intensity of the pulse of excitation energy to zero as quickly as possible after the peak pulse. An example of a tailored electrical driving signal combined with gain switching is shown in plot 8-402 of FIG. 8-4. Such a technique may involve reversing the sign of an electrical driving signal after the peak power is produced. Such a tailored electrical driving signal may produce an optical output shown in plot 8-403 of FIG. 8-4. The electrical signal may be tailored to quickly reduce the carrier density after the first relaxation oscillation or first oscillation of the optical signal. By reducing the carrier density after the first oscillation, a light pulse of just the first oscillation may be generated. The electrical signal may be configured to generate a short pulse that turns the light signal off quickly by reducing the number of photons emitted after a peak in the signal, such as shown by the plot in FIG. 8-5 showing the optical output of such an electrical signal. A picosecond laser diode system may be designed to emit light pulses, according to some embodiments. FIG. 8-6 illustrates a plot of an exemplary light pulse with a peak of 985 mW, a width of 84.3 picoseconds, and a signal reduced by approximately 24.3 dB approximately 250 picoseconds after the peak. In some embodiments, saturable absorbers, including semiconductor saturable absorbers (SESAMs) may be used to suppress the optical tail. In such embodiments, using the saturable absorbers may suppress the optical tail by 3-5 dB or, in some instances, greater than 5 dB. Reducing the effects of a tail in the excitation pulse may reduce and/or eliminate any requirements on additional filtering of the excitation energy, increase the range of lifetimes that can be measured, and/or enable faster pulse rates. Increasing the excitation pulse rate may enable more experiments to be conducted in a given time, which may decrease the time needed to acquire enough statistics to identify a lifetime for a marker labeling a sample object.

Additionally, two or more of these techniques may be used together to generate pulsed excitation energy. For example, pulsed excitation energy emitted from a directly modulated source may be further modified using optical modulation techniques. Techniques for modulating the excitation pulse and tailoring the electrical pulse driving signal may be combined in any suitable way to optimize a pulsed excitation energy for performing lifetime measurements. A tailored electrical drive signal may be applied to a pulsed excitation energy from a directly modulated source.

In some embodiments, a laser diode having a certain number of wire bonds may be used as a pulsed excitation source. Laser diodes with more wire bonds may reduce the inductance of the excitation source. Laser diodes having a lower inductance (represented by inductor 8-701 of FIG. 8-7) may enable the current into the laser to operate at a higher frequency. As shown in FIG. 8-7, when driven by an 18V pulse in a 50 ohm transmission line, an Oclaro laser source 8-700 with a 3 ohm series resistance (represented by resistor 8-702) and 36 wire bonds has a higher current at higher frequencies than the laser sources with fewer wire bonds. Selecting a packaging method to minimize inductance may improve the power supplied to the excitation source at higher frequencies, enabling shorter excitation pulses, faster reductions of optical power after the peak, and/or increased pulse repetition rate for detecting luminescent markers.

In some embodiments, a transmission line in combination with an excitation source may be used for generating light pulses. The transmission line may match the impedance of a laser diode in order to improve performance and/or quality of light pulses. In some embodiments, the transmission line impedance may be 50 ohms. In some instances, the terminating resistance may be similar to the resistance of the line in order to avoid reflections. Alternatively or additionally, the terminating impedance may be similar to the impedance of the line in order to avoid reflections. The terminating impedance may less than the impedance of the line in order to reflect a negative pulse. In other embodiments, the terminating impedance may have a capacitive or inductive component in order to control the shape of the negative reflection pulse. In other embodiments, the transmission line may allow for a higher frequency of pulses. FIG. 8-8A illustrates an example prototype of a transmission line pulsar, and FIG. 8-8B illustrates exemplary temporal profiles of light pulses obtained with such a transmission line. Using a transmission line may produce electrical pulses having a frequency within a range of 40 MHz to 500 MHz. A transmission line may be used in combination with a tailored electrical signal described above in order to produce a pulsed light source with light pulses having a certain time duration and a specific time interval.

Techniques for tailoring the electrical signal to improve the production of light pulses may include connecting the excitation source to a circuit with a negative bias capability. In some embodiments, a negative bias may be provided on an excitation source after a light pulse emits to reduce emission of a tail in the light pulse. FIG. 8-9 illustrates an exemplary circuit 8-900 containing a current source 8-901, diode laser 8-902, resistor 8-903, capacitor 8-904, and switch 8-905 that may be implemented to reduce the presence of a tail in a light pulse. Such a circuit 8-900 may create a constant current that bypasses the diode laser 8-902 when the switch 8-905 is closed, or in a conducting state. When the switch 8-905 is open, the switch 8-905 may have a high resistance and current may flow through the diode laser 8-902. Light pulses may be generated by opening and closing the switch 8-905 to provide intermittent current to the diode 8-902 laser. In some instances, the resistor 8-903 may be sufficiently high and the capacitor 8-904 sufficiently small such that there is a voltage across the capacitor 8-904 when the switch 8-905 is open and the diode laser 8-902 emits light. When the switch 8-905 is closed, the voltage across the capacitor 8-904 will reverse bias the diode laser 8-902. Such a reverse bias may reduce or eliminate the presence of a tail in the light pulse. In such instances, the switch 8-905 may be configured to close after the peak of the light pulse in order to reduce the laser power shortly after the peak light pulse. The value of the resistor 8-903 in the circuit 8-900 may be selected such that the charge on the capacitor 8-904 will discharge before the switch is subsequently opened and/or a subsequent light pulse is generated by the laser diode 8-902.

Additional circuit components may be provided to tailor an electrical signal of a laser diode in order to produce light pulses. In some embodiments, multiple capacitors, resistors, and voltages may be connected as a network circuit to control the waveform of an electrical signal supplied to a laser diode. A controlled waveform may be created by switching a number of voltages, V1, V2, . . . , VN with corresponding signals S1, S2, . . . , SN when there are N capacitor sub-circuits. An exemplary network circuit of four capacitor sub-circuits is shown in FIG. 8-10 where a controlled electrical waveform may be created by switching voltages V1, V2, V3, and V4 with signals S1, S2, S3, and S4, respectively. In some embodiments, voltages V1, V2, V3, and V4 may be variable. In the example shown in FIG. 8-10, V4 is negative to the laser and may create a reverse bias depending on signal S4. Timing of the frequency of light pulses emitted by the laser, the duration of each light pulse, and features of each light pulse may be adjusted with the signal inputs S1, S2, S3, and S4. In some embodiments, additional resistance may be added to lower the peak current. In such instances, the resistance may be added after one or more of the switches S1, S2, S3, S4. Although FIG. 8-10 shows one configuration with four capacitors and four voltages, any suitable configuration and any suitable number of additional circuit components may be provided to produce a tailored electrical signal to the laser diode to generate light pulses for lifetime measurements.

In some embodiments, an electrical signal for generating light pulses may use a circuit having discrete components, including radio frequency (RF) and/or microwave components. Discrete components that may be included in such a circuit are DC blocks, adaptors, logic gates, terminators, phase shifters, delays, attenuators, combiners, and/or RF amplifiers. Such components may be used to create a positive electrical signal having a certain amplitude followed by a negative electrical signal with another amplitude. There may be a delay between the positive and negative electrical signals. FIG. 8-11A illustrates an exemplary circuit having one RF amplifier that may be used to produce a tailored electrical signal as an output pulse, such as the pulse profile shown in FIG. 8-11B, that may be supplied to an excitation source, such as a laser diode, to emit a light pulse. In other embodiments, a circuit may produce multiple electrical signals combined to form an electrical pulse signal configured to drive an excitation source. Such a circuit may produce a differential output which may be used to increase the power of the light pulse. By adjusting the discrete components of the circuit, the electrical output signal may be adjusted to produce a light pulse suitable for lifetime measurements. In an example shown in FIG. 8-12A, two RF amplifiers are used to produce an output pulse signal having a profile shown in FIG. 8-12B consisting of a positive electrical signal pulse and a corresponding negative electrical signal pulse where the positive and negative electrical signal pulses overlap and have a similar width.

In some embodiments, excitation sources may be combined to generate light pulses for lifetime measurements. Synchronized pulsed sources may be coupled to a circuit or load over a certain distance. In some embodiments, excitation sources may be coupled in parallel to a circuit. The excitation sources may be from the same source or from multiple sources. In some embodiments with multiple sources, the multiple sources may vary in type of excitation source. When combining sources, it may be important to consider the impedance of the circuit and the excitation sources in order to have sufficient power supplied to the excitation sources. Combination of sources may be achieved by using one or more of the above-described techniques for producing a pulsed excitation source. FIG. 8-13A illustrates a schematic for combining four different sources having one or more impedance values. FIG. 8-13B shows a plot of current, power efficiency, and voltage as a function of impedance. This exemplary embodiment shows 4 sources delivering power on 50 ohms transmission lines and that optimal power delivery occurs when the impedance of the load equals the ratio of the impedance of the individual lines to the number of sources.

An excitation source may include a battery or any other power supply arranged to provide power to the excitation source. For example, an excitation source may be located in a base instrument and its operating power may be received through an integrated bioanalysis device to which it is coupled (e.g., via conducting power leads). An excitation source may be controlled independently of or in collaboration with control of an integrated bioanalysis device. As just one example, control signals for an excitation source may be provided to the excitation source wirelessly or via a wired interconnection (e.g., a USB interconnect) with a personal computer and/or the integrated bioanalysis device.

In some implementations, an excitation source may be operated in a time-gated and/or synchronized manner with one or more sensors of an integrated device. For example, an excitation source may be turned on to excite a luminescent marker, and then turned off. The sensor may be turned off while the excitation source is turned on, and then may be turned on for a sampling interval after the excitation source is turned off. In some embodiments, the sensor may be turned on for a sampling interval while the excitation source is turned on.

In some embodiments, an Osram PL 50 mW laser is used, as an example, to provide an excitation light of 520 nm. Alternatively, an excitation light of 530 nm or 532 nm is used. Alternatively and/or additionally, Thorlabs LP637-SF70 70 mW laser is used, as an example, to provide an excitation light of 637 nm. Another example is an Oclaro HL63133 laser diode that provides excitation at 638 nm. These laser sources or other suitable lasers sources may be used alone or in combination. One or more laser sources are used and the excitation light from each source is combined at a beam combiner and then directed to the assay chip. Each light source may be coupled to an optical fiber, the total of which may then be bundled. The optical characteristics of the light exiting the fiber bundle may be controlled using an optical shaping element (OSE). Optionally, a multiplexer may be used where the laser light from multiple light sources is multiplexed by polarization, wavelength and/or spatial parameters and sent over a single optical fiber. A diffractive optical element (DOE) may be used to spectrally separate the different wavelengths so that they are directed toward one of the four sub-sensors.

A. Multiple Excitation Sources

Multiple excitation sources may provide light having different energies or wavelengths to the plurality of sample wells. Each of the multiple excitation sources may provide light having a different characteristic wavelength or energy. One or more markers may be identified based on whether light from an excitation source excites a marker such that the marker emits a photon. In this manner, markers may be identified based on their absorption spectra by measuring the response of a sample after illuminating the sample with light from the different excitation sources. For example, a sample having a marker may be illuminated with light from a first excitation source followed by light from a second excitation source. If the marker emits luminescence in response to being illuminated by light from the first excitation source, then the marker may have an absorption spectrum that overlaps with the characteristic wavelength of the first excitation source.

In some embodiments, it is possible to use a plurality of excitation sources for the excitation energy. This plurality of sources may be, for example, implemented as a diode laser bar comprising multiple diode laser emitters. In the manufacture of laser diodes, multiple emitters are commonly fabricated lithographically on a single substrate, and then diced into single-emitter pieces for individual packaging. But it is also possible to dice the substrate into pieces with a plurality of emitters. In some embodiments, the emitters are nearly identical, and may be spaced equally from each other to lithographic tolerances, typically of the order of 0.1 micrometer.

VI. Method of Use, Instrument Operation and User Interface

The instrument 2-120 may be controlled using software and/or hardware. For example, the instrument may be controlled using a processing device 1-123, such as an ASIC, an FPGA and/or a general purpose processor executing software.

FIG. 9-1 illustrates a flowchart of operation of the instrument 2-120 according to some embodiments. After a user has acquired a specimen to analyze, the user begins a new analysis at act 9-101. This may be done by providing an indication to the instrument 2-120 via the user interface 2-125 by, e.g., pressing a button. At act 9-103, the instrument 2-120 checks whether the assay chip 2-110 from a previously performed analysis is still inserted in the instrument 2-120. If it is determined that an old assay chip is present, then the power to excitation source may be turned off at act 9-105, the user is prompted at act 9-107 to eject the previous assay chip using an indicator of the user interface 2-125 and the instrument 2-120 waits for the old assay chip to be ejected at act 9-109.

When the previous assay chip is ejected by the user, or if the instrument 2-120 determined at act 9-103 that the previous assay chip was already removed, the user is prompted to insert a new assay chip 2-110 for the new analysis at act 9-111. The instrument 2-120 then waits for the new assay chip 2-110 to be inserted at act 9-113. When the user inserts the new assay chip, the user is prompted at act 9-115 by an indicator of the user interface 2-125 to place the specimen to be analyzed onto the exposed top surface of the assay chip 2-110 and also prompted to close the lid on the instrument 2-120. The instrument 2-120 then waits for the lid to be closed at act 9-117. When the lid is closed by the user, at act 9-119 the excitation source may be driven to produce excitation energy for exciting the sample portions of the specimen present in the sample wells of the assay chip 2-110. At act 9-121, the emission energy from the samples is detected by the sensor 2-122 and data from the sensor 2-122 is streamed to the processing device 2-123 for analysis. In some embodiments, the data may be streamed to external computing device 2-130. At act 2-123, the instrument 2-120 checks whether the data acquisition is complete. The data acquisition may be complete after a particular length of time, a particular number of excitation pulses from the excitation source or one a particular target has been identified. When the data acquisition is completed, the data analysis is finished at 9-125.

FIG. 9-2 illustrates an example self-calibration routine according to some embodiments. The calibration routine may be executed at any suitable time prior to the analysis of a specimen. For example, it may be done once by the manufacturer for each instrument prior to shipment to the end user. Alternatively, the end user may perform a calibration at any suitable time. As discussed above, the instrument 2-120 is capable of distinguishing between emission energy having different wavelengths emitted from different samples. The instrument 2-120 and/or computing device 2-130 may be calibrated with calibration associated with each particular color of light associated with, for example, a luminescent tag used to tag molecules of a specimen being analyzed. In this way, the precise output signal associated with a particular color may be determined.

To calibrate the device, a calibration specimen associated with a single luminescent tag is provided to the instrument 2-120 one at a time. The self-calibration begins at act 9-201 when a user places a specimen comprising luminescent tags that emit emission energy of a single wavelength on an assay chip 2-110 and inserts the assay chip 2-110 into the instrument 2-120. Using the user interface 2-125, the user instructs the instrument 2-120 to begin the self-calibration. In response, at act 9-203, the instrument 2-120 runs the calibration analysis by illuminating the assay chip 2-110 with excitation energy and measuring the single wavelength emission energy from the calibration specimen. The instrument 2-120 may then, at act 9-205, save the detection pattern measured on the array of sub-sensors of the sensor 2-122 for each pixel of the sensor array. The detection pattern for each luminescent tag may be considered a detection signature associated with the luminescent tag. In this way, the signatures may be used as a training data set used to analyze the data received from unknown samples analyzed in subsequent analysis runs.

The above calibration routine may then be executed for every calibration specimen associated with a single luminescent tag. In this way, each sensor 2-122 of the array of pixels is associated with calibration data that may be used to determine the luminescent tag present in a sample well during a subsequent analysis implemented at act 9-207 after the competition of the calibration routine.

FIG. 9-3 further illustrates how the calibration data may be acquired and used to analyze the data according to some embodiments. At act 9-301 calibration data is obtained from the sensors. This may be done using the aforementioned self-calibration routine. At act 9-303, a transformation matrix is generated based on the calibration data. The transformation matrix maps sensor data to the emission wavelength of a sample and is a m×n matrix, where m is the number of luminescent tags with different emission wavelengths and n is the number of sub-sensors used to detect the emission energy per pixel. Thus, each column of the transformation matrix represents the calibration values for the sensor. For example, if there are four sub-sensors per pixel and five different luminescent tags, then the transformation matrix is a 4×5 matrix (i.e., four rows and five columns) and each column is associated with a different luminescent tag, the values in the column corresponding to the measured values obtained from the sub-sensors during the self-calibration routine. In some embodiments, each pixel may have its own transformation matrix. In other embodiments, the calibration data from at least some of the pixels may be averaged and all the pixels may then use the same transformation matrix based on the averaged data.

At act 9-305, the analysis data associated with a bioassay is obtained from the sensors. This may be done in any of the ways described above. At act 9-307, the wavelength of the emission energy and/or the identity of the luminescent tag may be determined using the transformation matrix and the analysis data. This may be done in any suitable way. In some embodiments, the analysis data is multiplied by the pseudo-inverse of the transformation matrix, resulting in a m×1 vector. The luminescent tag associated with the vector component with the maximum value may then be identified as the luminescent tag present in the sample well. Embodiments are not limited to this technique. In some embodiments, to prevent possible pathologies that may arise when the inverse of a matrix with small values is taken, a constrained optimization routine, such as a least square method or a maximum likelihood technique, may be performed to determine the luminescent tag present in the sample well.

The foregoing method of using the calibration data to analyze data from the sensors may be implement by any suitable processor. For example, processing device 2-123 of the instrument 2-120 may perform the analysis, or computing device 2-130 may perform the analysis.

VII. Example Measurements with the Assay Chip and Instrument

Measurements for detecting, analyzing, and/or probing molecules in a sample may be obtained using any combination of the assay chip and instrument described in the present application. The excitation source may be a pulsed excitation source or, in some instances, a continuous wave source. A luminescent marker tagged to a specific sample may indicate the presence of the sample. Luminescent markers may be distinguished by excitation energy, emission energy, and/or the lifetime of emission energy emitted by a marker. Markers with similar luminescence emission wavelengths may be identified by determining the lifetime for each marker. Additionally, markers with similar lifetimes may be identified by the luminescence emission wavelength for each marker. By using markers, where markers are identified by a combination of the temporal and/or spectral properties of the emitted luminescence, a quantitative analysis and/or identification of markers and associated samples can be performed.

Lifetime measurements may be used to determine that a marker is present in a sample well. The lifetime of a luminescent marker may be identified by performing multiple experiments where the luminescent marker is excited into an excited state and then the time when a photon emits is measured. The excitation source is pulsed to produce a pulse of excitation energy and directed at the marker. The time between the excitation pulse and a subsequent photon emission event from a luminescent marker is measured. By repeating such experiments with a plurality of excitation pulses, the number of instances a photon emits within a particular time interval may be determined. Such results may populate a histogram representing the number of photon emission events that occur within a series of discrete time intervals or time bins. The number of time bins and/or the time interval of each bin may be adjusted to identify a particular set of lifetimes and/or markers.

What follows is a description of example measurements that may be made to identify luminescent markers in some embodiments. Specifically, examples of distinguishing luminescent markers using only a luminescent lifetime measurement, a joint spectral and luminescent lifetime measurement, and only a luminescent lifetime measurement, but using two different excitation energies are discussed. Embodiments are not limited to the examples detailed below. For example, some embodiments may identify the luminescent markers using only spectral measurements.

Any suitable luminescent markers may be used. In some embodiments, commercially available fluorophores may be used. By way of example and not limitation, the following fluorophores may be used: Atto Rho14 ("ATRho14"), Dylight 650 ("D650"), SetaTau 647 ("ST647"), CF 633

("C633"), CF 647 ("C647"), Alexa fluor 647 ("AF647"), BODIPY 630/650 ("B630"), CF 640R ("C640R") and/or Atto 647N ("AT647N").

Additionally and/or optionally, luminescent markers may be modified in any suitable way to increase the speed and accuracy of the sample analysis process. For example, a photostabilizer may be conjugated to a luminescent marker. Examples of photostabilizers include but are not limited to oxygen scavengers or triplet-state quenchers. Conjugating photostabilizers to the luminescent marker may increase the rate of photons emitted and may also reduce a "blinking" effect where the luminescent marker does not emit photons. In some embodiments, when a biological event occurs on the millisecond scale, an increased rate of photon emission may increase the probability of detection of the biological event. Increased rates of photon events may subsequently increase the signal-to-noise ratio of luminescence signal and increase the rate at which lifetime measurements are made, leading to a faster and more accurate sample analysis.

Furthermore, the environment in a sample well of an integrated device may be tuned to engineer the lifetime of the markers as needed. This can be achieved by recognizing that the lifetime of a marker is effected by the density of state of the marker, which can be tuned using the environment. For example, the farther a marker is from the bottom metal layer of the sample well, the longer the lifetime. Accordingly, to increase the lifetime of a marker, the depth of a bottom surface of a sample well, such as a divot, may extend a certain distance from a metal layer. Also, the materials used to form the sample well can affect the lifetime of the markers. While different markers typically have their lifetimes shifted in the same direction (e.g., either longer or shorter), the affect may scale differently for different markers. Accordingly, two markers that cannot be distinguished via lifetime measurements in free-space may be engineered to be distinguishable by fabricating the sample well environment to adjust the lifetimes of the various markers.

A. Single Molecule Detection and Sequencing

According to an aspect of the present application, a single molecule can be identified (e.g., distinguished from other possible molecules in a reaction sample) based on one or more properties of a series of photons that are emitted from the molecule when it is exposed to a plurality of separate light pulses. In some embodiments, the molecule is labelled with a luminescent marker. In some embodiments, the luminescent marker is a fluorophore. In some embodiments, the luminescent marker can be identified or distinguished based on a property of the luminescent marker. Properties of a luminescent label (e.g., a fluorophore) include, but are not limited to luminescent lifetimes, absorption spectra, emission spectra, luminescence quantum yield, and luminescent intensity, and combinations of two or more thereof.

A biological sample may be processed in preparation for detection (e.g., sequencing). Such processing can include isolation and/or purification of the biomolecule (e.g., nucleic acid molecule) from the biological sample, and generation of more copies of the biomolecule. In some examples, one or more nucleic acid molecules are isolated and purified form a bodily fluid or tissue of the subject, and amplified through nucleic acid amplification, such as polymerase chain reaction (PCR). Then, the one or more nucleic acids molecules or subunits thereof can be identified, such as through sequencing. However, in some embodiments nucleic acid samples can be evaluated (e.g., sequenced) as described in this application without requiring amplification.

Sequencing can include the determination of individual subunits of a template biomolecule (e.g., nucleic acid molecule) by synthesizing another biomolecule that is complementary or analogous to the template, such as by synthesizing a nucleic acid molecule that is complementary to a template nucleic acid molecule and identifying the incorporation of nucleotides with time (e.g., sequencing by synthesis). As an alternative, sequencing can include the direct identification of individual subunits of the biomolecule.

During sequencing, a polymerizing enzyme may couple (e.g., attach) to a priming location of a target nucleic acid molecule. The priming location can be a primer that is complementary to the target nucleic acid molecule. As an alternative the priming location is a gap or nick that is provided within a double stranded segment of the target nucleic acid molecule. A gap or nick can be from 0 to at least 1, 2, 3, 4, 5, 6, 7, 8, 9, 10, 20, 30, or 40 nucleotides in length. A nick can provide a break in one strand of a double stranded sequence, which can provide a priming location for a polymerizing enzyme, such as, for example, a strand displacing polymerase enzyme.

In some cases, a sequencing primer can be annealed to a target nucleic acid molecule that may or may not be immobilized to a solid support, such as a sample well. In some embodiments, a sequencing primer may be immobilized to a solid support and hybridization of the target nucleic acid molecule also immobilizes the target nucleic acid molecule to the solid support. Via the action of an enzyme (e.g., a polymerase) capable of adding or incorporating a nucleotide to the primer, nucleotides can be added to the primer in 5' to 3', template bound fashion. Such incorporation of nucleotides to a primer (e.g., via the action of a polymerase) can generally be referred to as a primer extension reaction. Each nucleotide can be associated with a detectable tag that can be detected and used to determine each nucleotide incorporated into the primer and, thus, a sequence of the newly synthesized nucleic acid molecule. Via sequence complementarity of the newly synthesized nucleic acid molecule, the sequence of the target nucleic acid molecule can also be determined. In some cases, annealing of a sequencing primer to a target nucleic acid molecule and incorporation of nucleotides to the sequencing primer can occur at similar reaction conditions (e.g., the same or similar reaction temperature) or at differing reaction conditions (e.g., different reaction temperatures). Moreover, some sequencing by synthesis methods can include the presence of a population of target nucleic acid molecules (e.g, copies of a target nucleic acid) and/or a step of amplification of the target nucleic acid to achieve a population of target nucleic acids.

Embodiments are capable of sequencing single nucleic acid molecules with high accuracy and long read length. In some embodiments, the target nucleic acid molecule used in single molecule sequencing is a single-stranded target nucleic acid (e.g. deoxyribonucleic acid (DNA), DNA derivatives, ribonucleic acid (RNA), RNA derivatives) template that is added or immobilized to a sample well containing at least one additional component of a sequencing reaction (e.g., a polymerase such as, a DNA polymerase, a sequencing primer) immobilized or attached to a solid support such as the bottom of the sample well. The target nucleic acid molecule or the polymerase can be attached to a sample wall, such as at the bottom of the sample well directly or through a linker. The sample well can also contain any other reagents needed for nucleic acid synthesis via a primer extension reaction, such as, for example suitable buffers, co-factors, enzymes (e.g., a polymerase) and deoxyribonucleoside polyphosphates, such as, e.g., deoxyribonucleoside triphosphates, including deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include luminescent tags, such as fluorophores. Each class of dNTPs (e.g. adenine-containing dNTPs (e.g., dATP), cytosine-containing dNTPs (e.g., dCTP), guanine-containing dNTPs (e.g., dGTP), uracil-containing dNTPs (e.g., dUTPs) and thymine-containing dNTPs (e.g., dTTP)) is conjugated to a distinct luminescent tag such that detection of light emitted from the tag indicates the identity of the dNTP that was incorporated into the newly synthesized nucleic acid. Emitted light from the luminescent tag can be detected and attributed to its appropriate luminescent tag (and, thus, associated dNTP) via any suitable device and/or method, including such devices and methods for detection described elsewhere herein. The luminescent tag may be conjugated to the dNTP at any position such that the presence of the luminescent tag does not inhibit the incorporation of the dNTP into the newly synthesized nucleic acid strand or the activity of the polymerase. In some embodiments, the luminescent tag is conjugated to the terminal phosphate (the gamma phosphate) of the dNTP.

The single-stranded target nucleic acid template can be contacted with a sequencing primer, dNTPs, polymerase and other reagents necessary for nucleic acid synthesis. In some embodiments, all appropriate dNTPs can be contacted with the single-stranded target nucleic acid template simultaneously (e.g., all dNTPs are simultaneously present) such that incorporation of dNTPs can occur continuously. In other embodiments, the dNTPs can be contacted with the single-stranded target nucleic acid template sequentially, where the single-stranded target nucleic acid template is contacted with each appropriate dNTP separately, with washing steps in between contact of the single-stranded target nucleic acid template with differing dNTPs. Such a cycle of contacting the single-stranded target nucleic acid template with each dNTP separately followed by washing can be repeated for each successive base position of the single-stranded target nucleic acid template to be identified.

The sequencing primer anneals to the single-stranded target nucleic acid template and the polymerase consecutively incorporates the dNTPs (or other deoxyribonucleoside polyphosphate) to the primer via the single-stranded target nucleic acid template. The unique luminescent tag associated with each incorporated dNTP can be excited with the appropriate excitation light during or after incorporation of the dNTP to the primer and its emission can be subsequently detected, using, any suitable device(s) and/or method(s), including devices and methods for detection described elsewhere herein. Detection of a particular emission of light can be attributed to a particular dNTP incorporated. The sequence obtained from the collection of detected luminescent tags can then be used to determine the sequence of the single-stranded target nucleic acid template via sequence complementarity.

While the present disclosure makes reference to dNTPs, devices, systems and methods provided herein may be used with various types of nucleotides, such as ribonucleotides and deoxyribonucleotides (e.g., deoxyribonucleoside polyphosphates with at least 4, 5, 6, 7, 8, 9, or 10 phosphate groups). Such ribonucleotides and deoxyribonucleotides can include various types of tags (or markers) and linkers.

Signals emitted upon the incorporation of nucleosides can be stored in memory and processed at a later point in time to determine the sequence of the target nucleic acid template. This may include comparing the signals to a reference signals to determine the identities of the incorporated nucleosides as a function of time. Alternative or in addition to, signal emitted upon the incorporation of nucleoside can be collected and processed in real time (i.e., upon nucleoside incorporation) to determine the sequence of the target nucleic acid template in real time.

Nucleic acid sequencing of a plurality of single-stranded target nucleic acid templates may be completed where multiple sample wells are available, as is the case in devices described elsewhere herein. Each sample well can be provided with a single-stranded target nucleic acid template and a sequencing reaction can be completed in each sample well. Each of the sample wells may be contacted with the appropriate reagents (e.g., dNTPs, sequencing primers, polymerase, co-factors, appropriate buffers, etc.) necessary for nucleic acid synthesis during a primer extension reaction and the sequencing reaction can proceed in each sample well. In some embodiments, the multiple sample wells are contacted with all appropriate dNTPs simultaneously. In other embodiments, the multiple sample wells are contacted with each appropriate dNTP separately and each washed in between contact with different dNTPs. Incorporated dNTPs can be detected in each sample well and a sequence determined for the single-stranded target nucleic acid in each sample well as is described above.

Embodiments directed toward single molecule RNA sequencing may use any reverse transcriptase that is capable of synthesizing complementary DNA (cDNA) from an RNA template. In such embodiments, a reverse transcriptase can function in a manner similar to polymerase in that cDNA can be synthesized from an RNA template via the incorporation of dNTPs to a reverse transcription primer annealed to an RNA template. The cDNA can then participate in a sequencing reaction and its sequence determined as described above. The determined sequence of the cDNA can then be used, via sequence complementarity, to determine the sequence of the original RNA template. Examples of reverse transcriptases include Moloney Murine Leukemia Virus reverse transcriptase (M-MLV), avian myeloblastosis virus (AMV) reverse transcriptase, human immunodeficiency virus reverse transcriptase (HIV-1) and telomerase reverse transcriptase.

Sequence reads can be used to reconstruct a longer region of a genome of a subject (e.g., by alignment). Reads can be used to reconstruct chromosomal regions, whole chromosomes, or the whole genome. Sequence reads or a larger sequence generated from such reads can be used to analyze a genome of a subject, such as to identify variants or polymorphisms. Examples of variants include, but are not limited to, single nucleotide polymorphisms (SNPs) including tandem SNPs, small-scale multi-base deletions or insertions, also referred to as indels or deletion insertion polymorphisms (DIPs), Multi-Nucleotide Polymorphisms (MNPs), Short Tandem Repeats (STRs), deletions, including microdeletions, insertions, including microinsertions, structural variations, including duplications, inversions, translocations, multiplications, complex multi-site variants, copy number variations (CNV). Genomic sequences can comprise combinations of variants. For example, genomic sequences can encompass the combination of one or more SNPs and one or more CNVs.

In some embodiments, the molecules are identified or distinguished based on luminescent lifetime. In some embodiments, the molecules are identified or distinguished based on luminescent intensity. In some embodiments, the molecules are identified or distinguished based on the wavelength of the delivered excitation energy necessary to observe an emitted photon. In some embodiments, the molecules are identified or distinguished based on the wavelength of an emitted photon. In some embodiments, the molecules are identified or distinguished based on both luminescent lifetime and the wavelength of the delivered excitation energy necessary to observe an emitted photon. In some embodiments, the molecules are identified or distinguished based on both a luminescent intensity and the wavelength of the delivered excitation energy necessary to observe an emitted photon. In some embodiments, the molecules are identified or distinguished based on luminescent lifetime, luminescent intensity, and the wavelength of the delivered excitation energy necessary to observe an emitted photon. In some embodiments, the molecules are identified or distinguished based on both luminescent lifetime and the wavelength of an emitted photon. In some embodiments, the molecules are identified or distinguished based on both a luminescent intensity and the wavelength of an emitted photon. In some embodiments, the molecules are identified or distinguished based on luminescent lifetime, luminescent intensity, and the wavelength of an emitted photon.

In certain embodiments, different types of molecules in a reaction mixture or experiment are labeled with different luminescent markers. In some embodiments, the different markers have different luminescent properties which can be distinguished. In some embodiments, the different markers are distinguished by having different luminescent lifetimes, different luminescent intensities, different wavelengths of emitted photons, or a combination thereof. The presence of a plurality of types of molecules with different luminescent markers may allow for different steps of a complex reaction to be monitored, or for different components of a complex reaction product to be identified. In some embodiments, the order in which the different types of molecules react or interact can be determined.

In certain embodiments, the luminescent properties of a plurality of types of molecules with different luminescent markers are used to identify the sequence of a biomolecule, such as a nucleic acid or protein. In some embodiments, the luminescent properties of a plurality of types of molecules with different luminescent markers are used to identify single molecules as they are incorporated during the synthesis of a biomolecule. In some embodiments, the luminescent properties of a plurality of types of nucleotides with different luminescent markers are used to identify single nucleotides as they are incorporated during a sequencing reaction. In some embodiments, methods, compositions, and devices described in the application can be used to identify a series of nucleotides that are incorporated into a template-dependent nucleic acid sequencing reaction product synthesized by a polymerase enzyme.

In certain embodiments, the template-dependent nucleic acid sequencing product is carried out by naturally occurring nucleic acid polymerases. In some embodiments, the polymerase is a mutant or modified variant of a naturally occurring polymerase. In some embodiments, the template-dependent nucleic acid sequence product will comprise one or more nucleotide segments complementary to the template nucleic acid strand. In one aspect, the application provides a method of determining the sequence of a template (or target) nucleic acid strand by determining the sequence of its complementary nucleic acid strand.

In another aspect, the application provides methods of sequencing target nucleic acids by sequencing a plurality of nucleic acid fragments, wherein the target nucleic acid comprises the fragments. In certain embodiments, the method comprises combining a plurality of fragment sequences to provide a sequence or partial sequence for the parent target nucleic acid. In some embodiments, the step of combining is performed by computer hardware and software. The methods described herein may allow for a set of related target nucleic acids, such as an entire chromosome or genome to be sequenced.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes the human genome. In some embodiments, the sequence of an entire genome is determined. However, in some embodiments, sequence information for a subset of a genome (e.g., one or a few chromosomes, or regions thereof) or for one or a few genes (or fragments thereof) are sufficient for diagnostic, prognostic, and/or therapeutic applications.

In some cases, a sequencing primer can be annealed to a target nucleic acid molecule that may or may not be immobilized to a solid support, such as a sample well (e.g., nanoaperture). In some embodiments, a sequencing primer may be immobilized to a solid support and hybridization of the target nucleic acid molecule also immobilizes the target nucleic acid molecule to the solid support. In some embodiments, a polymerase is immobilized to a solid support and soluble primer and target nucleic acid are contacted to the polymerase. However, in some embodiments a complex comprising a polymerase, a target nucleic acid and a primer is formed in solution and the complex is immobilized to a solid support (e.g., via immobilization of the polymerase, primer, and/or target nucleic acid).

Under appropriate conditions, a polymerase enzyme that is contacted to an annealed primer/target nucleic acid can add or incorporate one or more nucleotides onto the primer, and nucleotides can be added to the primer in a 5' to 3', template bound fashion. Such incorporation of nucleotides onto a primer (e.g., via the action of a polymerase) can generally be referred to as a primer extension reaction. Each nucleotide can be associated with a detectable tag that can be detected and identified (e.g., based on its luminescent lifetime, emission spectra, absorption spectra, and/or other characteristics) and used to determine each nucleotide incorporated into the primer and, thus, a sequence of the newly synthesized nucleic acid molecule. Via sequence complementarity of the newly synthesized nucleic acid molecule, the sequence of the target nucleic acid molecule can also be determined. In some embodiments, sequencing by synthesis methods can include the presence of a population of target nucleic acid molecules (e.g., copies of a target nucleic acid) and/or a step of amplification of the target nucleic acid to achieve a population of target nucleic acids. However, in some embodiments sequencing by synthesis is used to determine the sequence of a single molecule in each reaction that is being evaluated (and nucleic acid amplification is not required to prepare the target template for sequencing). In some embodiments, a plurality of single molecule sequencing reactions are performed in parallel (e.g., on a single integrated device or chip) according to aspects of the present application.

Embodiments are capable of sequencing single nucleic acid molecules with high accuracy and long read lengths, such as an accuracy of at least about 50%, 60%, 70%, 75%, 80%, 85%, 90%, 95%, 96%, 97%, 98%, 99%, 99.9%, 99.99%, 99.999%, or 99.9999%, and/or read lengths greater than or equal to about 10 base pairs (bp), 50 bp, 100 bp, 200 bp, 300 bp, 400 bp, 500 bp, 1000 bp, 10,000 bp, 20,000 bp, 30,000 bp, 40,000 bp, 50,000 bp, or 100,000 bp.

The target nucleic acid molecule or the polymerase can be attached to a sample wall, such as at the bottom of the sample well directly or through a linker. The sample well (e.g., nanoaperture) also can contain any other reagents needed for nucleic acid synthesis via a primer extension reaction, such as, for example suitable buffers, co-factors, enzymes (e.g., a polymerase) and deoxyribonucleoside polyphosphates, such as, e.g., deoxyribonucleoside triphosphates, including deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include luminescent tags, such as fluorophores. In some embodiments, each class of dNTPs (e.g. adenine-containing dNTPs (e.g., dATP), cytosine-containing dNTPs (e.g., dCTP), guanine-containing dNTPs (e.g., dGTP), uracil-containing dNTPs (e.g., dUTPs) and thymine-containing dNTPs (e.g., dTTP)) is conjugated to a distinct luminescent tag such that detection of light emitted from the tag indicates the identity of the dNTP that was incorporated into the newly synthesized nucleic acid. Emitted light from the luminescent tag can be detected and attributed to its appropriate luminescent tag (and, thus, associated dNTP) via any suitable device and/or method, including such devices and methods for detection described elsewhere herein. The luminescent tag may be conjugated to the dNTP at any position such that the presence of the luminescent tag does not inhibit the incorporation of the dNTP into the newly synthesized nucleic acid strand or the activity of the polymerase. In some embodiments, the luminescent tag is conjugated to the terminal phosphate (the gamma phosphate) of the dNTP.

In some embodiments, the sequencing primer anneals to the single-stranded target nucleic acid template and the polymerase consecutively incorporates the dNTPs (or other deoxyribonucleoside polyphosphate) to the primer via the single-stranded target nucleic acid template. The unique luminescent tag associated with each incorporated dNTP can be excited with the appropriate excitation light during or after incorporation of the dNTP to the primer and its emission can be subsequently detected, using, any suitable device(s) and/or method(s), including devices and methods for detection described elsewhere herein. Detection of a particular emission of light (e.g., having a particular emission lifetime, intensity, and/or combination thereof) can be attributed to a particular dNTP incorporated. The sequence obtained from the collection of detected luminescent tags can then be used to determine the sequence of the single-stranded target nucleic acid template via sequence complementarity.

While the present disclosure makes reference to dNTPs, devices, systems and methods provided herein may be used with various types of nucleotides, such as ribonucleotides and deoxyribonucleotides (e.g., deoxyribonucleoside polyphosphates with at least 4, 5, 6, 7, 8, 9, or 10 phosphate groups). Such ribonucleotides and deoxyribonucleotides can include various types of tags (or markers) and linkers.

As an example, FIG. 10-1 schematically illustrates the setup of a single molecule nucleic acid sequencing method. The example is not meant to limit the invention in any way. 610 is a sample well (e.g., nanoaperture) configured to contain a single complex comprising a nucleic acid polymerase 601, a target nucleic acid 602 to be sequenced, and a primer 604. In this example, a bottom region of sample well 610 is depicted as a target volume 620. In FIG. 10-1 the complex comprising polymerase 601 is confined in target volume 620. The complex may optionally be immobilized by attachment to a surface of the sample well. In this example the complex is immobilized by a linker 603 comprising one or more biomolecules (e.g., biotin) suitable for attaching the linker to the polymerase 601.

The volume of the sample well also contains a reaction mixture with suitable solvent, buffers, and other additives necessary for the polymerase complex to synthesize a nucleic acid strand. The reaction mixture also contains a plurality of types of luminescently labeled nucleotides. Each type of nucleotide is represented by the symbols *-A, @-T, $-G, #-C, wherein A, T, G, and C represent the nucleotide base, and the symbols *, @, $, and # represent a unique luminescent label attached to each nucleotide, through linker -. In FIG. 10-1, a #-C nucleotide is currently being incorporated into the complementary strand 602. The incorporated nucleotide is located within the target volume 620.

FIG. 10-1 also indicates with arrows the concept of an excitation energy being delivered to a vicinity of the target volume, and luminescence being emitted towards a detector. The arrows are schematic, and are not meant to indicate the particular orientation of excitation energy delivery or luminescence. Some luminescences may emit on a vector which is not directed to the detector (e.g., towards the sidewall of the sample well) and may not be detected.

FIG. 10-2 schematically illustrates a sequencing process in a single sample well over time. Stages A through D depict a sample well with a polymerase complex as in FIG. 10-1. Stage A depicts the initial state before any nucleotides have been added to the primer. Stage B depicts the incorporation event of a luminescently labeled nucleotide (#-C). Stage C, depicts the period between incorporation events. In this example, nucleotide C has been added to the primer, and the label and linker previously attached to the luminescently labeled nucleotide (#-C) has been cleaved. Stage D depicts a second incorporation event of a luminescently labeled nucleotide (*-A). The complementary strand after Stage D consists of the primer, a C nucleotide, and an A nucleotide.

Stage A and C, both depict the periods before or between incorporation events, which are indicated in this example to last for about 10 milliseconds. In stages A and C, because there is no nucleotide being incorporated, there is no luminescently labeled nucleotide in the target volume (not drawn in FIG. 10-2), though background luminescence or spurious luminescence from a luminescently labeled nucleotide which is not being incorporated may be detected. Stage B and D show incorporation events of different nucleotides (#-C, and *-A, respectively). In this example these events are also indicated to last for about 10 milliseconds.

The row labeled "Raw bin data" depicts the data generated during each Stage. Throughout the example experiment, a plurality of pulses of light is delivered to the vicinity of the target volume. For each pulse a detector is configured to record any emitted photon received by the detector, and assign the detected photon to a time bin based on the time duration since the last pulse of excitation energy. In this example there are 3 bins, and the "Raw bin data" records a value of 1 (shortest bars), 2 (medium bars), or 3 (longest bars), corresponding to the shortest, middle, and longest bins, respectively. Each bar indicates detection of an emitted photon.

Since there is no luminescently labeled nucleotide present in the target volume for Stage A or C, there are no photons detected. For each of Stage B and D a plurality of luminescences is detected during the incorporation event. Luminescent label # has a shorter luminescence lifetime than luminescent label *. The Stage B data is thus depicted as having recorded lower average bin values, than Stage D where the bin values are higher.

The row labeled "Processed data" depicts raw data which has been processed to indicate the number (counts) of emitted photons at times relative to each pulse. In this example the data is only processed to determine luminescent lifetime, but the data may also be evaluated for other luminescent properties, such as luminescent intensity or the wavelength of the absorbed or emitted photons. The exemplary processed data approximates an exponential decay curve characteristic for the luminescence lifetime of the luminescent marker in the target volume. Because luminescent label # has a shorter luminescence lifetime than luminescent label *, the processed data for Stage B has fewer counts at longer time durations, while the processed data for Stage D has relatively more counts at longer time durations.

The example experiment of FIG. 10-2 would identify the first two nucleotides added to the complementary strand as CA. For DNA, the sequence of the target strand immediately after the region annealed to the primer would thus be identified as GT. In this example the nucleotides C and A could be distinguished from amongst the plurality of C, G, T, and A, based on luminescent lifetime alone. In some embodiments, other properties, such as the luminescent intensity or the wavelength of the absorbed or emitted photons may be necessary to distinguish one or more particular nucleotides.

B. Luminescent Properties

As described herein, a luminescent molecule is a molecule that absorbs one or more photons and may subsequently emit one or more photons after one or more time durations. The luminescence of the molecule is described by several parameters, including but not limited to luminescent lifetime, absorption and/or emission spectra, luminescent quantum yield, and luminescent intensity.

The emitted photon from a luminescent emission event will emit at a wavelength within a spectral range of possible wavelengths. Typically the emitted photon has a longer wavelength (e.g., has less energy or is red-shifted) compared to the wavelength of the excitation photon. In certain embodiments, a molecule is identified my measuring the wavelength of an emitted photon. In certain embodiments, a molecule is identified by measuring the wavelength of a plurality of emitted photons. In certain embodiments, a molecule is identified by measuring the emission spectrum.

Luminescent lifetime refers to a time duration (e.g., emission decay time) associated with an excitation event and an emission event. In some embodiments, luminescent lifetime is expressed as the constant in an equation of exponential decay. In some embodiments, wherein there are one or more pulse events delivering excitation energy, the time duration is the time between the pulse and the subsequent emission event.

Luminescent quantum yield refers to the fraction of excitation events at a given wavelength or within a given spectral range that lead to an emission event, and is typically less than 1. In some embodiments, the luminescent quantum yield of a molecule described herein is between 0 and about 0.001, between about 0.001 and about 0.01, between about 0.01 and about 0.1, between about 0.1 and about 0.5, between about 0.5 and about 0.9, or between about 0.9 and 1. In some embodiments, a molecule is identified by determining or estimating the luminescent quantum yield.

As used herein for single molecules luminescent intensity refers to the number of emitted photons per unit time that are emitted by a molecule which is being excited by delivery of a pulsed excitation energy. In some embodiments, the luminescent intensity refers to the detected number of emitted photons per unit time that are emitted by a molecule which is being excited by delivery of a pulsed excitation energy, and are detected by a particular sensor or set of sensors.

In one aspect, the application provides a method of determining the luminescent lifetime of a single luminescent molecule comprising: providing the luminescent molecule in a target volume; delivering a plurality of pulses of an excitation energy to a vicinity of the target volume; and detecting a plurality of luminescences from the luminescent molecule. In some embodiments, the method further comprises recording a plurality of time durations between each pair of pulses and luminescences and evaluating the distribution of the plurality of time durations between each pair of pulses and luminescences.

C. Luminescently Labeled Nucleotides

In one aspect, methods and compositions described herein comprises one or more luminescently labeled nucleotide. In certain embodiments, one or more nucleotides comprise deoxyribose nucleosides. In some embodiments, all nucleotides comprises deoxyribose nucleosides. In certain embodiments, one or more nucleotides comprise ribose nucleosides. In some embodiments, all nucleotides comprise ribose nucleosides. In some embodiments, one or more nucleotides comprise a modified ribose sugar or ribose analog (e.g., a locked nucleic acid). In some embodiments, one or more nucleotides comprise naturally occurring bases (e.g., cytosine, guanine, adenine, thymine, uracil). In some embodiments, one or more nucleotides comprise derivatives or analogs of cytosine, guanine, adenine, thymine, or uracil.

In certain embodiments, a method comprises the step of exposing a polymerase complex to a plurality of luminescently labeled nucleotides. In certain embodiments, a composition or device comprises a reaction mixture comprising a plurality of luminescently labeled nucleotides. In some embodiments, the plurality of nucleotides comprises four types of nucleotides. In some embodiments, the four types of nucleotides each comprise one of cytosine, guanine, adenine, and thymine. In some embodiments, the four types of nucleotides each comprise one of cytosine, guanine, adenine, and uracil.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. In some examples, a nucleic acid is deoxyribonucleic acid (DNA) or ribonucleic acid (RNA), or derivatives thereof. A nucleic acid may be single-stranded or double stranded. A nucleic acid may be circular.

The term "nucleotide," as used herein, generally refers to a nucleic acid subunit, which can include A, C, G, T or U, or variants or analogs thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant or analogs thereof) or a pyrimidine (i.e., C, T or U, or variant or analogs thereof). A subunit can enable individual nucleic acid bases or groups of bases (e.g., AA, TA, AT, GC, CG, CT, TC, GT, TG, AC, CA, or uracil-counterparts thereof) to be resolved.

A nucleotide generally includes a nucleoside and at least 1, 2, 3, 4, 5, 6, 7, 8, 9, 10, or more phosphate (PO3) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate, which can be selected from deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include detectable tags, such as luminescent tags or markers (e.g., fluorophores).

A nucleoside polyphosphate can have 'n' phosphate groups, where 'n' is a number that is greater than or equal to 2, 3, 4, 5, 6, 7, 8, 9, or 10. Examples of nucleoside polyphosphates include nucleoside diphosphate and nucleoside triphosphate. A nucleotide can be a terminal phosphate labeled nucleoside, such as a terminal phosphate labeled nucleoside polyphosphate. Such label can be a luminescent (e.g., fluorescent or chemiluminescent) label, a fluorogenic label, a colored label, a chromogenic label, a mass tag, an electrostatic label, or an electrochemical label. A label (or marker) can be coupled to a terminal phosphate through a linker. The linker can include, for example, at least one or a plurality of hydroxyl groups, sulfhydryl groups, amino groups or haloalkyl groups, which may be suitable for forming, for example, a phosphate ester, a thioester, a phosphoramidate or an alkyl phosphonate linkage at the terminal phosphate of a natural or modified nucleotide. A linker can be cleavable so as to separate a label from the terminal phosphate, such as with the aid of a polymerization enzyme. Examples of nucleotides and linkers are provided in U.S. Pat. No. 7,041,812, which is entirely incorporated herein by reference.

D. Labels

In certain embodiments, the incorporated molecule is a luminescent molecule, e.g., without attachment of a distinct luminescent marker. Typical nucleotide and amino acids are not luminescent, or do not luminesce within suitable ranges of excitation and emission energies. In certain embodiments, the incorporated molecule comprises a luminescent marker. In certain embodiments, the incorporated molecule is a luminescently labeled nucleotide. In certain embodiments, the incorporated molecule is a luminescently labeled amino acid or luminescently labeled tRNA. In some embodiments, a luminescently labeled nucleotide comprises a nucleotide and a luminescent marker. In some embodiments, a luminescently labeled nucleotide comprises a nucleotide, a luminescent marker, and a linker. In some embodiments, the luminescent marker is a fluorophore.

For nucleotide sequencing, certain combinations of luminescently labeled nucleotides may be preferred. In some embodiments, at least one of the luminescently labeled nucleotides comprises a cyanine dye, or analog thereof. In some embodiments, at least one luminescently labeled nucleotides comprises a rhodamine dye, or analog thereof. In some embodiments, at least one of the luminescently labeled nucleotides comprises a cyanine dye, or analog thereof, and at least one luminescently labeled nucleotides comprises a rhodamine dye, or analog thereof.

In certain embodiments, the luminescent marker is a dye selected from Table FL-1. The dyes listed in Table FL-1 are non-limiting, and the luminescent markers of the application may include dyes not listed in Table FL-1. In certain embodiments, the luminescent markers of one or more luminescently labeled nucleotides is selected from Table FL-1. In certain embodiments, the luminescent markers of four or more luminescently labeled nucleotides is selected from Table FL-1.

TABLE FL-1

Exemplary fluorophores.
Fluorophores

5/6-Carboxyrhodamine 6G
5-Carboxyrhodamine 6G
6-Carboxyrhodamine 6G
6-TAMRA
Abberior Star 4405XP
Abberior Star 4705XP
Abberior Star 488
Abberior Star 512
Abberior Star 5205XP
Abberior Star 580
Abberior Star 600
Abberior Star 635
Abberior Star 635P
Abberior Star RED
Alexa Fluor 350
Alexa Fluor 405
Alexa Fluor 430
Alexa Fluor 480
Alexa Fluor 488
Alexa Fluor 514
Alexa Fluor 532
Alexa Fluor 546
Alexa Fluor 555
Alexa Fluor 568
Alexa Fluor 594
Alexa Fluor 610-X
Alexa Fluor 633
Alexa Fluor 647
Alexa Fluor 660
Alexa Fluor 680
Alexa Fluor 700
Alexa Fluor 750
Alexa Fluor 790
AMCA
ATTO 390
ATTO 425
ATTO 465
ATTO 488
ATTO 495
ATTO 514
ATTO 520
ATTO 532
ATTO 542
ATTO 550
ATTO 565
ATTO 590
ATTO 610
ATTO 620
ATTO 633
ATTO 647
ATTO 647N
ATTO 655
ATTO 665
ATTO 680
ATTO 700
ATTO 725
ATTO 740
ATTO Oxa12
ATTO Rho101
ATTO Rho11
ATTO Rho12
ATTO Rho13
ATTO Rho14
ATTO Rho3B
ATTO Rho6G
ATTO Thio12
BD Horizon V450
BODIPY 493/501
BODIPY 530/550

TABLE FL-1-continued

Exemplary fluorophores.
Fluorophores

| Fluorophores |
|---|
| BODIPY 558/568 |
| BODIPY 564/570 |
| BODIPY 576/589 |
| BODIPY 581/591 |
| BODIPY 630/650 |
| BODIPY 650/665 |
| BODIPY FL |
| BODIPY FL-X |
| BODIPY R6G |
| BODIPYTMR |
| BODIPY TR |
| C5.5 |
| C7 |
| CAL Fluor Gold 540 |
| CAL Fluor Green 510 |
| CAL Fluor Orange 560 |
| CAL Fluor Red 590 |
| CAL Fluor Red 610 |
| CAL Fluor Red 615 |
| CAL Fluor Red 635 |
| Cascade Blue |
| CF350 |
| CF405M |
| CF405S |
| CF488A |
| CF514 |
| CF532 |
| CF543 |
| CF546 |
| CF555 |
| CF568 |
| CF594 |
| CF620R |
| CF633 |
| CF633-V1 |
| CF640R |
| CF640R-V1 |
| CF640R-V2 |
| CF660C |
| CF660R |
| CF680 |
| CF68OR |
| CF680R-V1 |
| CF750 |
| CF770 |
| CF790 |
| Chromeo 642 |
| Chromis 425N |
| Chromis 500N |
| Chromis 515N |
| Chromis 530N |
| Chromis 550A |
| Chromis 550C |
| Chromis 550Z |
| Chromis 560N |
| Chromis 570N |
| Chromis 577N |
| Chromis 600N |
| Chromis 630N |
| Chromis 645A |
| Chromis 645C |
| Chromis 645Z |
| Chromis 678A |
| Chromis 678C |
| Chromis 678Z |
| Chromis 770A |
| Chromis 770C |
| Chromis 800A |
| Chromis 800C |
| Chromis 830A |
| Chromis 830C |
| Cy3 |
| Cy3.5 |
| Cy3B |
| Cy5 |
| DyLight 350 |
| DyLight 405 |

TABLE FL-1-continued

Exemplary fluorophores.
Fluorophores

| Fluorophores |
|---|
| DyLight 415-Co1 |
| DyLight 425Q |
| DyLight 485-LS |
| DyLight 488 |
| DyLight 504Q |
| DyLight 510-LS |
| DyLight 515-LS |
| DyLight 521-LS |
| DyLight 530-R2 |
| DyLight 543Q |
| DyLight 550 |
| DyLight 554-R0 |
| DyLight 554-R1 |
| DyLight 590-R2 |
| DyLight 594 |
| DyLight 610-B1 |
| DyLight 615-B2 |
| DyLight 633 |
| DyLight 633-B1 |
| DyLight 633-B2 |
| DyLight 650 |
| DyLight 655-B1 |
| DyLight 655-B2 |
| DyLight 655-B3 |
| DyLight 655-B4 |
| DyLight 662Q |
| DyLight 675-B1 |
| DyLight 675-B2 |
| DyLight 675-B3 |
| DyLight 675-B4 |
| DyLight 679-C5 |
| DyLight 680 |
| DyLight 683Q |
| DyLight 690-B1 |
| DyLight 690-B2 |
| DyLight 696Q |
| DyLight 700-B1 |
| DyLight 730-B1 |
| DyLight 730-B2 |
| DyLight 730-B3 |
| DyLight 730-B4 |
| DyLight 747 |
| DyLight 747-B1 |
| DyLight 747-B2 |
| DyLight 747-B3 |
| DyLight 747-B4 |
| DyLight 755 |
| DyLight 766Q |
| DyLight 775-B2 |
| DyLight 775-B3 |
| DyLight 775-B4 |
| DyLight 780-B1 |
| DyLight 780-B2 |
| DyLight 780-B3 |
| DyLight 800 |
| DyLight 830-B2 |
| Dyomics-350 |
| Dyomics-350XL |
| Dyomics-360XL |
| Dyomics-370XL |
| Dyomics-375XL |
| Dyomics-380XL |
| Dyomics-390XL |
| Dyomics-405 |
| Dyomics-415 |
| Dyomics-430 |
| Dyomics-431 |
| Dyomics-478 |
| Dyomics-480XL |
| Dyomics-481XL |
| Dyomics-485XL |
| Dyomics-490 |
| Dyomics-495 |
| Dyomics-505 |
| Dyomics-510XL |
| Dyomics-511XL |
| Dyomics-520XL |

TABLE FL-1-continued

Exemplary fluorophores.
Fluorophores

| Fluorophores |
|---|
| Dyomics-521XL |
| Dyomics-530 |
| Dyomics-547 |
| Dyomics-547P1 |
| Dyomics-548 |
| Dyomics-549 |
| Dyomics-549P1 |
| Dyomics-550 |
| Dyomics-554 |
| Dyomics-555 |
| Dyomics-556 |
| Dyomics-560 |
| Dyomics-590 |
| Dyomics-591 |
| Dyomics-594 |
| Dyomics-601XL |
| Dyomics-605 |
| Dyomics-610 |
| Dyomics-615 |
| Dyomics-630 |
| Dyomics-631 |
| Dyomics-632 |
| Dyomics-633 |
| Dyomics-634 |
| Dyomics-635 |
| Dyomics-636 |
| Dyomics-647 |
| Dyomics-647P1 |
| Dyomics-648 |
| Dyomics-648P1 |
| Dyomics-649 |
| Dyomics-649P1 |
| Dyomics-650 |
| Dyomics-651 |
| Dyomics-652 |
| Dyomics-654 |
| Dyomics-675 |
| Dyomics-676 |
| Dyomics-677 |
| Dyomics-678 |
| Dyomics-679P1 |
| Dyomics-680 |
| Dyomics-681 |
| Dyomics-682 |
| Dyomics-700 |
| Dyomics-701 |
| Dyomics-703 |
| Dyomics-704 |
| Dyomics-730 |
| Dyomics-731 |
| Dyomics-732 |
| Dyomics-734 |
| Dyomics-749 |
| Dyomics-749P1 |
| Dyomics-750 |
| Dyomics-751 |
| Dyomics-752 |
| Dyomics-754 |
| Dyomics-776 |
| Dyomics-777 |
| Dyomics-778 |
| Dyomics-780 |
| Dyomics-781 |
| Dyomics-782 |
| Dyomics-800 |
| Dyomics-831 |
| eFluor 450 |
| Eosin |
| FITC |
| Fluorescein |
| HiLyte Fluor 405 |
| HiLyte Fluor 488 |
| HiLyte Fluor 532 |
| HiLyte Fluor 555 |
| HiLyte Fluor 594 |
| HiLyte Fluor 647 |
| HiLyte Fluor 680 |
| HiLyte Fluor 750 |
| IRDye 680LT |
| IRDye 750 |
| IRDye 800CW |
| JOE |
| LightCycler 640R |
| LightCycler Red 610 |
| LightCycler Red 640 |
| LightCycler Red 670 |
| LightCycler Red 705 |
| Lissamine Rhodamine B |
| Napthofluorescein |
| Oregon Green 488 |
| Oregon Green 514 |
| Pacific Blue |
| Pacific Green |
| Pacific Orange |
| PET |
| PF350 |
| PF405 |
| PF415 |
| PF488 |
| PF505 |
| PF532 |
| PF546 |
| PF555P |
| PF568 |
| PF594 |
| PF610 |
| PF633P |
| PF647P |
| Quasar 570 |
| Quasar 670 |
| Quasar 705 |
| Rhoadmine 123 |
| Rhodamine 6G |
| Rhodamine B |
| Rhodamine Green |
| Rhodamine Green-X |
| Rhodamine Red |
| ROX |
| Seta 375 |
| Seta 470 |
| Seta 555 |
| Seta 632 |
| Seta 633 |
| Seta 650 |
| Seta 660 |
| Seta 670 |
| Seta 680 |
| Seta 700 |
| Seta 750 |
| Seta 780 |
| Seta APC-780 |
| Seta PerCP-680 |
| Seta R-PE-670 |
| Seta646 |
| SeTau 380 |
| SeTau 405 |
| SeTau 425 |
| SeTau 647 |
| Square 635 |
| Square 650 |
| Square 660 |
| Square 672 |
| Square 680 |
| Sulforhodamine 101 |
| TAMRA |
| TET |
| Texas Red |
| TMR |
| TRITC |
| Yakima Yellow |
| Zenon |
| Zy3 |

TABLE FL-1-continued

Exemplary fluorophores.
Fluorophores

Zy5
Zy5.5
Zy7

In certain embodiments, the luminescent marker may be (Dye 101) or (Dye 102), of formulae:

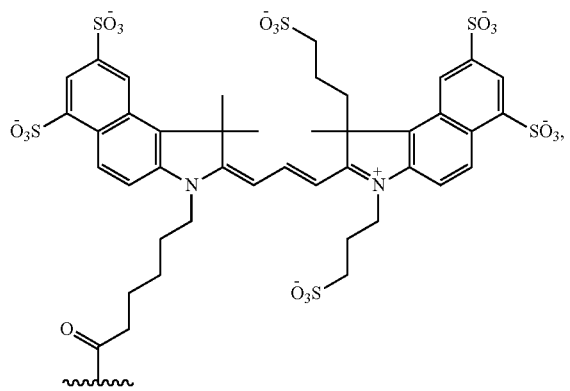

(Dye 101)

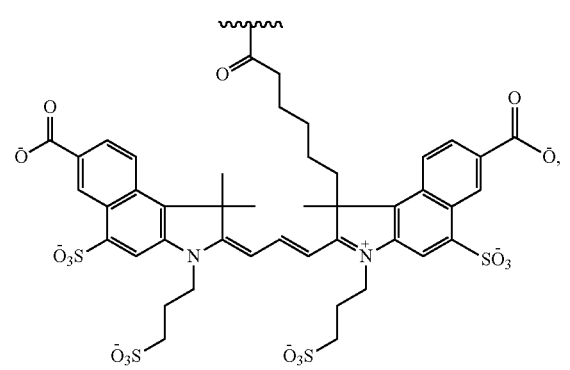

(Dye 102)

or an analog thereof. In some embodiments, each sulfonate or carboxylate is independently optionally protonated. In some embodiments, the dyes above are attached to the linker or nucleotide by formation of an amide bond at the indicated point of attachment.

In certain embodiments, at least one type, at least two types, at least three types, or at least four of the types of luminescently labeled nucleotides comprise a luminescent marker selected from the group consisting of 6-TAMRA, 5/6-Carboxyrhodamine 6G, Alex Fluor 546, Alexa Fluor 555, Alexa Fluor 568, Alexa Fluor 610, Alexa Fluor 647, Aberrior Star 635, ATTO 647N, ATTO Rho 14, Chromis 630, Chromis 654A, Chromeo 642, CF514, CF532, CF543, CF546, CF546, CF555, CF568, CF633, CF640R, CF660C, CF660R, CF680R, Cy3, Cy3B, Cy3.5, Cy5, Cy5.5, Dyomics-530, Dyomics-547P1, Dyomics-549P1, Dyomics-550, Dyomics-554, Dyomics-555, Dyomics-556, Dyomics-560, Dyomics-650, Dyomics-680, DyLight 554-R1, DyLight 530-R2, DyLight 594, DyLight 635-B2, DyLight 650, DyLight 655-B4, DyLight 675-B2, DyLight 675-B4, DyLight 680, HiLyte Fluor 532, HiLyte Fluor 555, HiLyte Fluor 594, LightCycler 640R, Seta 555, Seta 670, Seta700, SeTau 647, and SeTau 665, or are of formulae (Dye 101) or (Dye 102), as described herein.

In some embodiments, at least one type, at least two types, at least three types, or at least four of the types of luminescently labeled nucleotides comprise a luminescent marker selected from the group consisting of Alexa Fluor 532, Alexa Fluor 546, Alexa Fluor 555, Alexa Fluor 594, Alexa Fluor 610, CF532, CF543, CF555, CF594, Cy3, DyLight 530-R2, DyLight 554-R1, DyLight 590-R2, DyLight 594, and DyLight 610-B1, or are of formulae (Dye 101) or (Dye 102).

In some embodiments, a first and second type of luminescently labeled nucleotide comprise a luminescent marker selected from the group consisting of Alexa Fluor 532, Alexa Fluor 546, Alexa Fluor 555, CF532, CF543, CF555, Cy3, DyLight 530-R2, and DyLight 554-R1, and a third and fourth type of luminescently labeled nucleotide comprise a luminescent label selected from the group consisting of Alexa Fluor 594, Alexa Fluor 610, CF594, DyLight 590-R2, DyLight 594, and DyLight 610-B1, or are of formulae (Dye 101) or (Dye 102).

E. Linkers

A luminescent marker may be attached to the molecule directly, e.g., by a bond, or may be attached via a linker. In certain embodiments, the linker comprises one or more phosphates. In some embodiments, a nucleoside is connected to a luminescent marker by a linker comprising one or more phosphates. In some embodiments, a nucleoside is connected to a luminescent marker by a linker comprising three or more phosphates. In some embodiments, a nucleoside is connected to a luminescent marker by a linker comprising four or more phosphates.

In certain embodiments, a linker comprises an aliphatic chain. In some embodiments a linker comprises —$(CH_2)_n$—, wherein n is an integer from 1 to 20, inclusive. In some embodiments, n is an integer from 1 to 10, inclusive. In certain embodiments, a linker comprises a heteroaliphatic chain. In some embodiments, a linker comprises a polyethylene glycol moiety. In some embodiments, a linker comprises a polypropylene glycol moiety. In some embodiments, a linker comprises —$(CH_2CH_2O)_n$—, wherein n is an integer from 1 to 20, inclusive. In some embodiments, a linker comprises —$(CH_2CH_2O)_n$—, wherein n is an integer from 1 to 10, inclusive. In certain embodiments, a linker comprises —$(CH_2CH_2O)_4$—. In certain embodiments, a linker comprises one or more arylenes. In some embodiments, a linker comprises one or more phenylenes (e.g., para-substituted phenylene). In certain embodiments, a linker comprises a chiral center. In some embodiments, a linker comprises proline, or a derivative thereof. In some embodiments, a linker comprises a proline hexamer, or a derivative thereof. In some embodiments, a linker comprises coumarin, or a derivative thereof. In some embodiments, a linker comprises naphthalene, or a derivative thereof. In some embodiments, a linker comprises anthracene, or a derivative thereof. In some embodiments, a linker comprises a polyphenylamide, or a derivative thereof. In some embodiments, a linker comprises chromanone, or a derivative thereof. In some embodiments, a linker comprises 4-aminopropargyl-L-phenylalanine, or a derivative thereof. In certain embodiments, a linker comprises a polypeptide.

In some embodiments, a linker comprises an oligonucleotide. In some embodiments, a linker comprises two annealed oligonucleotides. In some embodiments, the oligonucleotide or oligonucleotides comprise deoxyribose nucleotides, ribose nucleotide, or locked ribose nucleotides. In certain embodiments, a linker comprises a photostabilizer.

F. Sample Well Surface Preparation

In certain embodiments, a method of detecting one or luminescently labeled molecule is performed with the molecules confined in a target volume. In some embodiments, the target volume is a region within a sample well (e.g., a nanoaperture). In certain embodiments, the sample well comprises a bottom surface comprising a first material and sidewalls formed by a plurality of metal or metal oxide layers. In some embodiments, the first material is a transparent material or glass. In some embodiments, the bottom surface is flat. In some embodiments, the bottom surface is a curved well. In some embodiments, the bottom surface includes a portion of the sidewalls below the sidewalls formed by a plurality of metal or metal oxide layers. In some embodiments, the first material is fused silica or silicon dioxide. In some embodiments, the plurality of layers each comprise a metal (e.g., Al, Ti) or metal oxide (e.g., $Al_2O_3$, $TiO_2$, TiN).

G. Passivation

In some embodiments when one or more molecule or complex is immobilized on a surface, it is desirable to passivate other surfaces of the device to prevent immobilization at an undesired location. In some embodiments, the molecule or complex is immobilized on a bottom surface of a sample well and the sidewalls of the sample well are passivated. In some embodiments, the sidewalls are passivated by the steps of: depositing a metal or metal oxide barrier layer on the sidewall surfaces; and applying a coating to the barrier layer. In some embodiments, the metal oxide barrier layer comprises aluminum oxide. In some embodiments, the step of depositing comprises depositing the metal or metal oxide barrier layer on the sidewall surfaces and the bottom surface. In some embodiments, the step of depositing further comprises etching metal or metal oxide barrier layer off of the bottom surface.

In some embodiments, the barrier layer coating comprises phosphonate groups. In some embodiments, the barrier layer coating comprises phosphonate groups with an alkyl chain. In some embodiments, the barrier layer coating comprises a polymeric phosphonate. In some embodiments, the barrier layer coating comprises polyvinylphosphonic acid (PVPA). In some embodiments, the barrier layer coating comprises phosphonate groups with a substituted alkyl chain. In some embodiments, the alkyl chain comprises one or more amides. In some embodiments, the alkyl chain comprises one or more poly(ethylene glycol) chains. In some embodiments, the coating comprises phosphonate groups of formula:

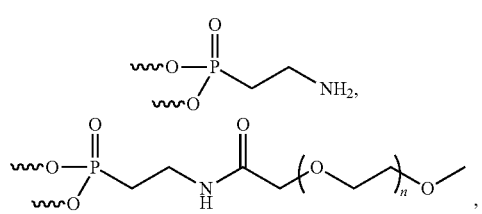

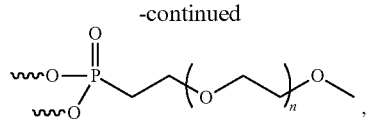

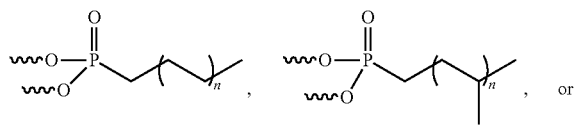

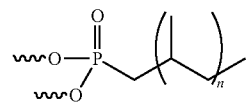

wherein n is an integer between 0 and 100, inclusive, and ⁓ is hydrogen or a point of attachment to the surface. In some embodiments n is an integer between 3 and 20, inclusive. In some embodiments, the barrier layer coating comprises a mixture of different types of phosphonate groups. In some embodiments, the barrier layer coating comprises a mixture of phosphonate groups comprising poly(ethylene glycol) chains of different PEG weight.

In certain embodiments, the barrier layer comprises nitrodopa groups. In certain embodiments, the barrier layer coating comprises groups of formula:

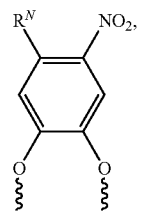

wherein $R^N$ is an optionally substituted alkyl chain and ⁓ is hydrogen or a point of attachment to the surface. In some embodiments, $R^N$ comprises a polymer. In some embodiments, $R^N$ comprises a poly(lysine) or a poly(ethylene glycol). In some embodiments, the barrier layer comprises a co-polymer of poly(lysine) comprising lysine monomers, wherein the lysine monomers independently comprise PEG, nitrodopa groups, phosphonate groups, or primary amines. In certain embodiments, the barrier layer comprises a polymer of formula (P):

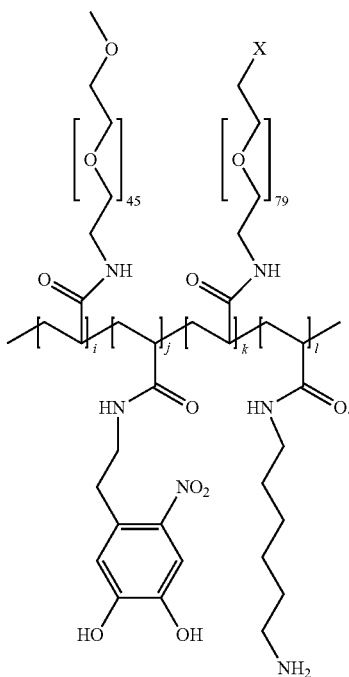

In some embodiments, X is —OMe, a biotin group, phosphonate, or silane. In some embodiments, each of i, j, k, and l is independently an integer between 0 and 100, inclusive.

H. Polymerase Immobilization

In some embodiments, when one or more molecule or complex is immobilized on a surface the surface is functionalized to allow for attachment of one or more of the molecules or complexes. In some embodiments, the functionalized surface is a bottom surface of a sample well. In certain embodiments, the functionalized surface comprises a transparent glass. In certain embodiments, the functionalized surface comprises fused silica or silicon dioxide. In some embodiments, the functionalized surface is functionalized with a silane. In some embodiments, the functionalized surface is functionalized with an ionically charged polymer. In some embodiments, the ionically charged polymer comprises poly(lysine). In some embodiments, the functionalized surface is functionalized with poly(lysine)-graft-poly(ethylene glycol). In some embodiments, the functionalized surface is functionalized with biotinylated bovine serum albumin (BSA).

In certain embodiments, the functionalized surface is functionalized with a coating comprising nitrodopa groups. In certain embodiments, the coating comprises groups of formula:

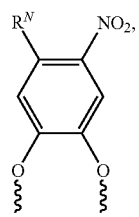

wherein $R^N$ is an optionally substituted alkyl chain and ⁓ is hydrogen or a point of attachment to the surface. In some embodiments, $R^N$ comprises a polymer. In some embodiments, $R^N$ comprises a poly(lysine) or a poly(ethylene glycol). In some embodiments, $R^N$ comprises a biotinylated poly(ethylene glycol). In some embodiments, the coating comprises a co-polymer of poly(lysine) comprising lysine monomers, wherein the lysine monomers independently comprise PEG, biotinylated PEG, nitrodopa groups, phosphonate groups, or silanes. In certain embodiments, the coating comprises a polymer of formula (P):

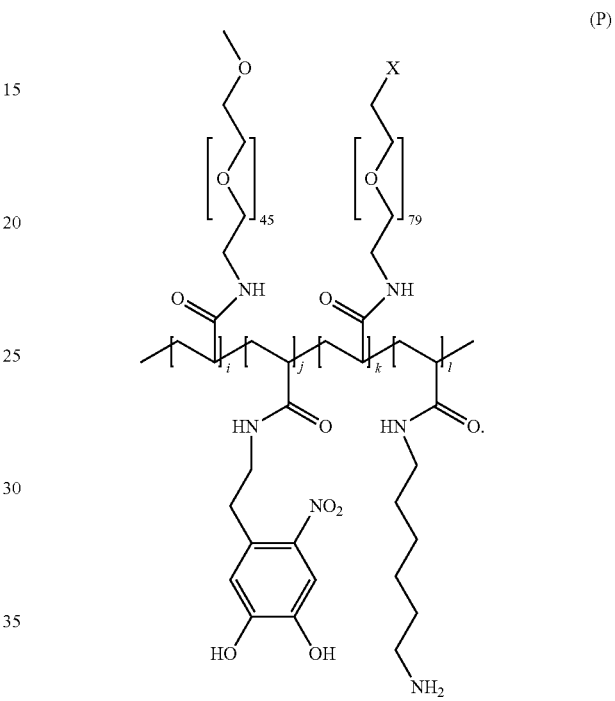

In some embodiments, X is —OMe, a biotin group, phosphonate, or silane. In some embodiments, each of i, j, k, and l is independently an integer between 0 and 100, inclusive.

In some embodiments, the functionalized surface is functionalized with a silane comprising an alkyl chain. In some embodiments, the functionalized surface is functionalized with a silane comprising an optionally substituted alkyl chain. In some embodiments, the surface is functionalized with a silane comprising a poly(ethylene glycol) chain. In some embodiments, the functionalized surface is functionalized with a silane comprising a coupling group. For example the coupling group may comprise chemical moieties, such as amine groups, carboxyl groups, hydroxyl groups, sulfhydryl groups, metals, chelators, and the like. Alternatively, they may include specific binding elements, such as biotin, avidin, streptavidin, neutravidin, lectins, SNAP-Tags™ or substrates therefore, associative or binding peptides or proteins, antibodies or antibody fragments, nucleic acids or nucleic acid analogs, or the like. Additionally, or alternatively, the coupling group may be used to couple an additional group that is used to couple or bind with the molecule of interest, which may, in some cases include both chemical functional groups and specific binding elements. By way of example, a coupling group, e.g., biotin, may be deposited upon a substrate surface and selectively activated in a given area. An intermediate binding agent, e.g., streptavidin, may then be coupled to the first coupling group. The molecule of interest, which in this particular example would be biotinylated, is then coupled to the streptavidin.

In some embodiments, the functionalized surface is functionalized with a silane comprising biotin, or an analog thereof. In some embodiments, the surface is functionalized with a silane comprising a poly(ethylene) glycol chain, wherein the poly(ethylene glycol) chain comprises biotin. In certain embodiments, the functionalized surface is functionalized with a mixture of silanes, wherein at least one type of silane comprises biotin and at least one type of silane does not comprise biotin. In some embodiments, the mixture comprises about 10 fold less, about 25 fold less, about 50 fold less, about 100 fold less, about 250 fold less, about 500 fold less, or about 1000 fold less of the biotinylated silane than the silane not comprising biotin.

FIG. 10-3 depicts a non-limiting exemplary process for preparing the sample well surface from the fabricated chip (e.g., integrated device) to initiation of a sequencing reaction. The sample well is depicted with a bottom surface (unshaded rectangle) and sidewalls (shaded vertical rectangles). The sidewalls may be comprised of multiple layers (e.g., Al, $Al_2O_3$, Ti, $TiO_2$, TiN). In step (a) the sidewalls are deposited with a barrier layer of $Al_2O_3$. The $Al_2O_3$ barrier layer is then coated, in step (b), with a PEG phosphonate groups, for example, by treating the surface with one or more PEG-phosphonic acids. In step (c), the bottom surface is functionalized, for example, with a mixture of PEG-silane and biotinylated-PEG-silane. The ovals represent individual biotin groups which may provide sites for an attachment of a single molecule or complex, such as a polymerase complex. In step (d), a polymerase complex is attached to a biotin group on the bottom surface. The polymerase may be attached by way of a binding agent, such as streptavidin, and a biotin tag on the polymerase complex. The polymerase complex may further comprise a template nucleic acid and primer (not shown). Step (e) depicts the initiation of a sequencing reaction by exposure of the immobilized polymerase complex to luminescently labeled nucleotides.

I. Polymerases

The term "polymerase," as used herein, generally refers to any enzyme (or polymerizing enzyme) capable of catalyzing a polymerization reaction. Examples of polymerases include, without limitation, a nucleic acid polymerase, a transcriptase or a ligase. A polymerase can be a polymerization enzyme.

Embodiments directed towards single molecule nucleic acid extension (e.g., for nucleic acid sequencing) may use any polymerase that is capable of synthesizing a nucleic acid complementary to a target nucleic acid molecule. In some embodiments, a polymerase may be a DNA polymerase, an RNA polymerase, a reverse transcriptase, and/or a mutant or altered form of one or more thereof.

Embodiments directed towards single molecule nucleic acid sequencing may use any polymerase that is capable of synthesizing a nucleic acid complementary to a target nucleic acid. Examples of polymerases include, but are not limited to, a DNA polymerase, an RNA polymerase, a thermostable polymerase, a wild-type polymerase, a modified polymerase, E. coli DNA polymerase I, T7 DNA polymerase, bacteriophage T4 DNA polymerase φ29 (psi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Tth polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some embodiments, the polymerase is a single subunit polymerase. Non-limiting examples of DNA polymerases and their properties are described in detail in, among other places, DNA Replication 2nd edition, Kornberg and Baker, W. H. Freeman, New York, N.Y. (1991).

Upon base pairing between a nucleobase of a target nucleic acid and the complementary dNTP, the polymerase incorporates the dNTP into the newly synthesized nucleic acid strand by forming a phosphodiester bond between the 3' hydroxyl end of the newly synthesized strand and the alpha phosphate of the dNTP. In examples in which the luminescent tag conjugated to the dNTP is a fluorophore, its presence is signaled by excitation and a pulse of emission is detected during or after the step of incorporation. For detection labels that are conjugated to the terminal (gamma) phosphate of the dNTP, incorporation of the dNTP into the newly synthesized strand results in release the beta and gamma phosphates and the detection label, which is free to diffuse in the sample well, resulting in a decrease in emission detected from the fluorophore.

In some embodiments, the polymerase is a polymerase with high processivity. However, in some embodiments, the polymerase is a polymerase with reduced processivity. Polymerase processivity generally refers to the capability of a polymerase to consecutively incorporate dNTPs into a nucleic acid template without releasing the nucleic acid template.

In some embodiments, the polymerase is a polymerase with low 5'-3' exonuclease activity and/or 3'-5' exonuclease. In some embodiments, the polymerase is modified (e.g., by amino acid substitution) to have reduced 5'-3' exonuclease activity and/or 3'-5' activity relative to a corresponding wild-type polymerase. Further non-limiting examples of DNA polymerases include 9° Nm™ DNA polymerase (New England Biolabs), and a P680G mutant of the Klenow exo-polymerase (Tuske et al. (2000) JBC 275(31):23759-23768). In some embodiments, a polymerase having reduced processivity provides increased accuracy for sequencing templates containing one or more stretches of nucleotide repeats (e.g., two or more sequential bases of the same type).

Embodiments directed toward single molecule RNA extension (e.g., for RNA sequencing) may use any reverse transcriptase that is capable of synthesizing complementary DNA (cDNA) from an RNA template. In such embodiments, a reverse transcriptase can function in a manner similar to polymerase in that cDNA can be synthesized from an RNA template via the incorporation of dNTPs to a reverse transcription primer annealed to an RNA template. The cDNA can then participate in a sequencing reaction and its sequence determined as described above and elsewhere herein. The determined sequence of the cDNA can then be used, via sequence complementarity, to determine the sequence of the original RNA template. Examples of reverse transcriptases include Moloney Murine Leukemia Virus reverse transcriptase (M-MLV), avian myeloblastosis virus (AMV) reverse transcriptase, human immunodeficiency virus reverse transcriptase (HIV-1) and telomerase reverse transcriptase.

The processivity, exonuclease activity, relative affinity for different types of nucleic acid, or other property of a nucleic acid polymerase can be increased or decreased by one of skill in the art by mutation or other modification relative to a corresponding wild-type polymerase.

J. Lifetime Measurements

Lifetime measurements may be performed using one excitation energy wavelength to excite a marker in a sample well. A combination of markers having distinct lifetimes are selected to distinguish among the individual markers based on the lifetime measurements. Additionally, the combination of markers are able to reach an excited state when illuminated by the excitation source used. Any set or number of suitable markers may be used that have distinguishable lifetimes. For example, three, four or six different markers may be used. The luminescent markers may excite at the same excitation wavelength or two or four different excitation wavelengths.

A pulsed excitation source may be one of the pulsed excitation sources using the techniques described above. In some instances, the pulsed excitation source may be a semiconductor laser diode configured to emit pulses through direct modulated electrical pumping of the laser diode. The power of the pulses is less than 20 dB of the pulse peak power at approximately 250 picoseconds after the peak. The time interval for each excitation pulse is in the range of 20-200 picoseconds. The time duration between each excitation pulse is in the range of 1-50 nanoseconds. A schematic of how example measurements may be performed is shown in FIG. 10-4, which illustrates the timing of excitation pulses 10-401 generated at regular intervals. The bottom row of FIG. 10-4 indicates what label is present when an excitation pulse 10-401 arrives. On occasion, there will be no label present. Moreover, the middle row of FIG. 10-4 illustrates the emission probability distribution 10-402 for the label that is present. Also illustrated in the middle row is a rectangle 10-403 indicating the detection of a photon from the label. As shown in FIG. 10-4, there are times when a photon is not emitted or the photon that is emitted does not get detected due to loss or detector inefficiency.

The sensor for each pixel has at least one photosensitive region per a pixel. In some embodiments, a sensor chip may include a single sensor region per pixel. The photosensitive region may have dimensions of 5 microns by 5 microns. Photons are detected within time intervals of when they reach the sensor. Increasing the number of time bins may improve resolution of the recorded histogram of photons collected over a series of time bins and improve differentiation among different luminescent markers. In some embodiments, focusing elements may be integrated with the sensor in order to improve collection of photons emitted by a marker in an associated sample well. Such focusing elements may include a Fresnel lens 10-500 as shown in FIG. 10-5. When the sensor is configured to detect a particular wavelength, the four luminescent markers may emit luminescence similar to the particular wavelength. Alternatively, the four luminescent markers may emit luminescence at different wavelengths.

In some embodiments, a sample object may be labeled with one of a plurality of different types of markers, each associated with a mutually exclusive set of sample objects. Each of the plurality of markers emits emission energy with a different lifetime. When the sensor is configured to detect a particular wavelength, the plurality markers may emit emission energy similar to the particular wavelength. Alternatively the plurality of markers may emit emission energy at different wavelengths. Techniques described herein for determining a lifetime for a marker may be used. In response to a pulse of excitation energy from the excitations source, one of the plurality of markers tagged to the sample may emit a photon. The time of the photon after the excitation pulse is recorded. Repeated pulses of excitation energy may produce multiple photon emission events which are then used to determine a lifetime for the marker. The determined lifetime may then be used to identify the marker in the sample well from among the plurality of markers.

An example set of four luminescent markers that are distinguishable based on lifetime measurements are ATRho14, Cy5, AT647N, and CF633 as shown by the plot in FIG. 10-6. These four markers have varying lifetimes and produce distinguishing histograms when at least four time bins are used. FIG. 10-7 outlines a signal profile for each of these markers across 16 time bins. The signal profile is normalized for each marker. The time bins vary in time interval in order to provide a unique signal profile for each of the markers. As illustrated in FIG. 10-7, a sensor having 16 time bins defined by time boundaries with variable spacing can be used to distinguish among ATTORho14, Cy5, ATTO647N, and CF633 by the distribution of photon counts across one or more of the 16 time bins. For example, the sensor detects 11% of total light detected by marker ATTORho14 between time boundaries 0.692 ns and 0.792 ns. As another example, the sensor detects 10% of total light detected from marker CF633 between time boundaries 1.991 ns and 2.507 ns. In this manner, each marker may be distinguished by the total amount of light in one or more time bins. FIGS. 10-8 and 10-9 illustrates signal profiles, both continuous and discrete, respectively, of another exemplary set of markers, ATTO Rho14, D650, ST647, and CF633, that are distinguishable based on lifetime measurements. Other sets of markers include ATTO Rho14, C647, ST647, CF633; Alexa Fluor647, B630, C640R, CF633; and ATTO Rho14, ATTO 647N, AlexaFluor647, CF633.

K. Spectral-Lifetime Measurements

Lifetime measurements may be combined with spectral measurements of one or more luminescent markers. Spectral measurements may depend on the wavelength of emission energy for individual markers and are captured using at least two sensor regions per pixel. The sensor is configured to detect spectral properties of the emission energy emitted from a sample well. An exemplary structure of the integrated device includes pixels that each have a sensor with two distinct regions, each region configured to detect a different wavelength. Some markers may have spectra that substantially overlap and/or have peak emission wavelengths that differ by approximately 5 nm or less, for example, and are difficult to distinguish based on spectral detection techniques alone. However, these markers may have varying lifetimes, and techniques for performing lifetime measurements may be used to distinguish among the markers.

Combining both lifetime measurements with spectral measurements may be performed using one excitation energy wavelength to excite a marker in a sample well, although more than one excitation energy wavelengths may be used, in some embodiments. A combination of markers is selected having at least two distinct emission wavelengths where the markers emitting at a wavelength have distinct lifetimes are selected to distinguish among the individual markers based on the lifetime and spectral measurements. Additionally, the combination of markers is selected to be able to reach an excited state when illuminated by the excitation source used. Any set or number of suitable markers may be used that have different emission wavelengths and/or different lifetimes.

The excitation source is a pulsed excitation source, and may be one of the excitation sources using the techniques described above. In some instances, the pulsed excitation source may be a semiconductor laser diode configured to emit pulses through direct modulated electrical pumping of the laser diode. The power of the pulses are less than 20 dB the peak power after 250 picoseconds after the peak. The time duration for each excitation pulse is in the range of 20-200 picoseconds. The time interval between each excitation pulse is in the range of 1-50 nanoseconds. A schematic of how example measurements may be performed is shown in FIG. 10-10. In some embodiments, the excitation source provides excitation energy having a wavelength of approximately 640 nm. In some embodiments, the excitation source provides excitation energy having a wavelength in the range of approximately 515 nm to 535 nm.

The sensor is configured to detect both temporal and spectral properties of the emission energy from a plurality of markers. The sensor for each pixel has at least two photosensitive regions per pixel. In some embodiments there are two photosensitive regions per a pixel. In other embodiments, there are four photosensitive regions per a pixel. Each photosensitive region is configured to detect a different wavelength or range of wavelengths. Photons are detected within time intervals of when they reach the sensor. Increasing the number of time bins may improve resolution of the recorded histogram of photons collected over a series of time bins and improve differentiation among different luminescent markers by their individual lifetimes. In some embodiments, there are two time bins per a region of the sensor. In other embodiments, there are four time bins per a region of the sensor.

In some embodiments, a sensor includes two sub-sensors that are used to detect four different markers. A first sub-sensor may be associated with the first emission wavelength emitted by two of the markers. The first sub-sensor may also be associated with two distinct lifetimes from the two markers that emit at the first emission wavelength. A second sub-sensor may be associated with the second wavelength emitted by the other two markers. The second sub-sensor may also be associated with two distinct lifetimes from the two markers that emit at the second emission wavelength. Differentiation among the four luminescent markers may occur based on a combination of detected wavelength and detected lifetime. Each of the two sub-sensors may detect a single photon of the emission energy emitted from the marker.

An example set of four luminescent markers that are distinguishable based on lifetime measurements are ATTO Rho14, AS635, Alexa Fluor647, and ATTO 647N. These four markers have two that emit at one similar wavelength and another similar wavelength. Within each pair of markers that emit at a similar wavelength, the pair of markers have different lifetimes and produce distinguishing histograms when at least four time bins are used. In this example, ATTO Rho14 and AS635 emit similar luminescence wavelengths and have distinct lifetimes. Alexa Fluor 647 and ATTO 647N emit similar luminescence wavelengths, different from the wavelengths emitted by ATTO Rho 14 and AS635, and have distinct lifetimes. FIG. 10-11 shows a plot lifetime as a function of emission wavelength for this set of markers to illustrate how each of these markers is distinguishable based on a combination of lifetime and emission wavelength. As shown in FIG. 10-11, ATTO Rho14 may emit near 645 nm, AS635 may emit near 653 nm, Alexa Fluor 647 may emit near 665 nm, and ATTO Fluor 647N may emit near 669 nm. AS635 and ATTO 647N have similar lifetimes at approximately 1.2 ns, and ATTO Rho14 and Alexa Fluor 647 have lower lifetimes than both AS635 and ATTO 647. These markers can be distinguished based on their characteristic emission wavelength and emission lifetime. For example, ATTO 647N and Alexa Fluor 647 have similar peak emission wavelengths, but have distinguishable lifetimes. AS635 and ATTO 647N have similar lifetimes, but have substantially different peak emission wavelengths.

The markers may excite at the same excitation wavelength or two or more different excitation wavelengths. When the sensor is configured to detect two wavelengths of emission energy, two of the four markers may emit at a first wavelength while the other two markers may emit at a second wavelength. Alternatively, when the sensor is configured to detect four wavelengths of emission, each marker may emit at a different wavelength and/or may have different emission probability densities and lifetimes. FIG. 10-12 shows a plot of power as a function of wavelength for ATT Rho14, Alexa Fluor 647, and ATT) 647N.

FIG. 10-13 shows plots of fluorescence signal over time for each one of these markers when present in a sample well with a diameter of 135 nm to illustrate the different time decay, and thus, lifetimes, for these markers.

FIG. 10-14 illustrates the signal profile for these markers across four sensor regions and each region captures four time bins. The signal profiles are normalized and are used to distinguish among the different markers by the relative number of photons captured by a photosensitive region for each of the four time bins. Light of a first emission wavelength, emitted from a first marker (Alexa Fluor 647), is directed towards a first sensor region. However, the directionality of the light is not perfect and some of the light is detected by a second sensor region, a third sensor region and a fourth sensor region. Thus, light emitted from the first marker is associated with a first sensor detector signal, as illustrated in the middle schematic of FIG. 10-14 by the statistics for percentage of total light detected by the four sensor regions over four time bins. In the second time bin between 1.184 ns and 2.069 ns, the first sensor region detects 4.2% of the total detected light from the first marker, the second sensor region detects 11.7% of the total detected light from the first marker, the third sensor region detects 18.6% of the total detected light from the first marker, and the fourth sensor region detects 14.6% of the total detected light from the first marker. This detected sensor pattern for one or more time bins constitutes a first detection signal associated with the first marker. FIG. 10-14 shows sensor and time bin patterns for ATRho14 and ATTO647N markers, which results in distinguishable detection signals among at least these three markers. For example, the second sensor detects 12.3% of the total light from marker ATTORho14 in the first time bin between 0.25 ns and 1.184 ns. In this manner, each marker may be distinguished based on its emission spectra and lifetime.

Other sets of four fluorophores for such spectral-lifetime measurements are ATRho14, D650, ST647, CF633; ATTO Rho14, C647, ST647, CF633; Alexa Fluor 647, B630, C640R, CF633; and ATTO Rho 14, ATTO 647N, Alexa Fluor 647, CF633. FIG. 10-15 shows a plot of the signal profile of intensity over time for ATRho14, D650, ST647, and C633. FIG. 10-16 illustrates the signal profile for ATRho14.

L. Lifetime-Excitation Energy Measurements

Lifetime measurements combined with using at least two excitation energy wavelengths may be used to distinguish among multiple markers. Some markers may excite when one excitation wavelength is used and not another. A combination of markers having distinct lifetimes is selected for each excitation wavelength to distinguish among the individual markers based on the lifetime measurements. In this embodiment, a sensor chip may be configured to have each pixel with a sensor having one region and the instrument may be configured to provide at least two excitation energy wavelengths, such as by electrically modulated pulsed diode lasers with temporal interleaving.

The markers may excite at different excitation wavelengths. When the light source is configured to deliver two wavelengths of excitation energy, some markers may excite at a first wavelength of excitation and not excite at a second wavelength of excitation, while the other markers excite at a second wavelength of excitation and not substantially excite as a first wavelength of excitation. In some embodiments, two markers excite at the first excitation wavelength and do not substantially excite at the second excitation wavelength, but emit at different emission probability densities and lifetimes. Two different markers excite at the second excitation wavelength and do not substantially excite at the first excitation wavelength, but have different emission probability densities and lifetimes.

The excitation source is a combination of at least two excitation energies. The excitation source is a pulsed excitation source and may be one or more of the excitation sources using the techniques described above. In some instances, the pulsed excitation source may be two semiconductor laser diode configured to emit pulses through direct modulated electrical pumping of the laser diode. The power of the pulses are 20 dB less than the pulse peak power at 250 picoseconds after the peak. The time interval for each excitation pulse is in the range of 20-200 picoseconds. The time interval between each excitation pulse is in the range of 1-50 nanoseconds. One excitation wavelength is emitted per a pulse and by knowing the excitation wavelength a subset of markers with distinct lifetimes is uniquely identified. In some embodiments, pulses of excitation alternate among the different wavelengths. For example, when two excitation wavelengths are used subsequent pulses alternate between one wavelength and the other wavelength. A schematic of how example measurements may be performed is shown in FIG. 10-17. Any suitable technique for combining multiple excitation sources and interleaving pulses having different wavelengths may be used.

The sensor for each pixel has at least one photosensitive region per a pixel. The photosensitive region may have dimensions of 5 microns by 5 microns. Photons are detected within time intervals of when they reach the sensor. Increasing the number of time bins may improve resolution of the recorded histogram of photons collected over a series of time bins and improve differentiation among different luminescent markers. The sensor has at least two time bins. In some embodiments, the sensor may have four time bins to identify the lifetime of emission energy from a marker.

An example set of four luminescent markers that are distinguishable based on lifetime measurements are Alexa Fluor 546, Cy3B, Alexa Fluor 647, and ATTO 647N. As shown in FIG. 10-18, Alexa Fluor 546 and Cy3B excite at one wavelength, such as 532 nm, and have distinct lifetimes. Alexa Fluor 647 and ATTO 647N excite at another wavelength, 640 nm, and have distinct lifetimes as shown in FIG. 10-19. For example, curves for ATTO 647N and Alexa Fluor 647 are shown in FIG. 10-19 that illustrate these two markers having different lifetimes. Distinguishable normalized signal profiles across 16 time bins for ATTO647N and CF633, which are both excited at 640 nm, are shown in FIG. 10-20. For example, the sensor detects 12% of total light detected from marker ATTO 647N between time boundaries 0.629 ns and 0.997 ns. By detecting a photon after a known excitation wavelength, one of these two pairs of markers may be determined based on the previous excitation wavelength and each marker for a pair is identified based on lifetime measurements.

M. Spectral Measurements

One or more sensors are configured to detect spectral properties by including one or more layers of the assay chip or sensor chip configured to sort the wavelengths before they reach the sensor. One or more layers may include at least one structural component configured to spectrally sort emission energy emitted from a sample well. The at least one structural component may include an offset Fresnel lens, a blazed phase grating, or any other suitable structure configured to provide desired directivity for spectrally distribution emission energy. A pixel of a sensor chip may include multiple sub-sensors configured to detect a spectral distribution of emission energy directed from a corresponding sample well on an assay chip. The configuration of the sensor chip and the multiple sub-sensors on the sensor chip may be sized, shaped, and arranged to sufficiently distinguish among different markers used to label a sample. Differentiation among luminescent markers may occur based on the detected wavelength.

In some embodiments, the sensor may be segmented into four sub-sensors to detect the four different luminescent markers. The sensor may be sized and positioned in any suitable way to capture the emitted emission energy from the sample well.

In some embodiments, each sub-sensor is associated with a different luminescence wavelength. Light of a first luminescence wavelength, emitted from a first luminescent marker (e.g., Alexa Fluor 555), is directed towards a first sub-sensor. However, the directionality of the light is not perfect and some of the light is detected by a second sub-sensor, a third sub-sensor and a fourth sub-sensor. Thus, light emitted from the first luminescent marker is associated with a first sensor detector signal, as illustrated in FIG. 10-21. When photons are collected during the integration time of the sensors, the first sub-sensor detects 42% of the total light detected from the first luminescent marker, the second sub-sensor detects 39% of the total light detected from the first luminescent marker, the third sub-sensor detects 15% of the total light detected from the first luminescent marker, and the fourth sub-sensor detects 4% of the total light detected from the first luminescent marker. This detected sub-sensor pattern constitutes a first detection signal associated with the first luminescent marker. Different sub-sensor patterns are associated with different luminescence wavelengths from different luminescent markers which results in distinguishable detection signals, as illustrated in FIG. 10-21.

Similarly, the second sub-sensor is associated with a second luminescence wavelength, the third sub-sensor is associated with a third luminescence wavelength, and the fourth sub-sensor is associated with a fourth luminescence wavelength. In this manner, exemplary markers that are distinguishable based om emission energy are Alexa Fluor 555, Alexa Fluor 568, Alexa Fluor 647, and Alexa Fluor 660, which have emission spectra shown in FIG. 10-22.

VII. Computing Device

FIG. 10-23 illustrates an example of a suitable computing system environment 1000 on which embodiments may be implemented. For example, computing device 2-130 of FIG. 2-1 may be implemented according to the computing system environment 1000. Additionally, the computing system environment 1000 may act as a control system that is programmed to control the instrument to perform an assay. For example, the control system may control the excitation source to emit and direct light towards the sample wells of the assay chip; control the sensors to allow detection of emission light from one or more samples in the sample wells; and analyze signals from the sensors to identify, e.g., by analyzing the spatial distribution of the emission energy, the sample present in a sample well. The computing system environment 1000 is only one example of a suitable computing environment and is not intended to suggest any limitation as to the scope of use or functionality of the invention. Neither should the computing environment 1000 be interpreted as having any dependency or requirement relating to any one or combination of components illustrated in the exemplary operating environment 1000.

Embodiments are operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 10-23, an exemplary system for implementing the invention includes a general purpose computing device in the form of a computer 1010. Components of computer 1010 may include, but are not limited to, a processing unit 1020, a system memory 1030, and a system bus 1021 that couples various system components including the system memory to the processing unit 1020. The system bus 1021 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 1010 typically includes a variety of computer readable media. Computer readable media can be any available media that can be accessed by computer 1010 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 1010. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 1030 includes computer storage media in the form of volatile and/or nonvolatile memory such as read only memory (ROM) 1031 and random access memory (RAM) 1032. A basic input/output system 1033 (BIOS), containing the basic routines that help to transfer information between elements within computer 1010, such as during start-up, is typically stored in ROM 1031. RAM 1032 typically contains data and/or program modules that are immediately accessible to and/or presently being operated on by processing unit 1020. By way of example, and not limitation, FIG. 10-23 illustrates operating system 1034, application programs 1035, other program modules 1036, and program data 1037.

The computer 1010 may also include other removable/non-removable, volatile/nonvolatile computer storage media. By way of example only, FIG. 10-23 illustrates a hard disk drive 1041 that reads from or writes to non-removable, nonvolatile magnetic media, a magnetic disk drive 1051 that reads from or writes to a removable, nonvolatile magnetic disk 1052, and an optical disk drive 1055 that reads from or writes to a removable, nonvolatile optical disk 1056 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1041 is typically connected to the system bus 1021 through an non-removable memory interface such as interface 1040, and magnetic disk drive 1051 and optical disk drive 1055 are typically connected to the system bus 1021 by a removable memory interface, such as interface 1050.

The drives and their associated computer storage media discussed above and illustrated in FIG. 10, provide storage of computer readable instructions, data structures, program modules and other data for the computer 1010. In FIG. 10-23, for example, hard disk drive 1041 is illustrated as storing operating system 1044, application programs 1045, other program modules 1046, and program data 1047. Note that these components can either be the same as or different from operating system 1034, application programs 1035, other program modules 1036, and program data 1037. Operating system 1044, application programs 1045, other program modules 1046, and program data 1047 are given different numbers here to illustrate that, at a minimum, they are different copies. A user may enter commands and information into the computer 1010 through input devices such as a keyboard 1062 and pointing device 1061, commonly referred to as a mouse, trackball or touch pad. Other input devices (not shown) may include a microphone, joystick, game pad, satellite dish, scanner, or the like. These and other input devices are often connected to the processing unit 1020 through a user input interface 1060 that is coupled to the system bus, but may be connected by other interface and bus structures, such as a parallel port, game port or a universal serial bus (USB). A monitor 1091 or other type of display device is also connected to the system bus 1021 via an interface, such as a video interface 1090. In addition to the monitor, computers may also include other peripheral output devices such as speakers 1097 and printer 1096, which may be connected through a output peripheral interface 1095.

The computer 1010 may operate in a networked environment using logical connections to one or more remote computers, such as a remote computer 1080. The remote computer 1080 may be a personal computer, a server, a router, a network PC, a peer device or other common network node, and typically includes many or all of the elements described above relative to the computer 1010, although only a memory storage device 1081 has been illustrated in FIG. 10-23. The logical connections depicted in FIG. 10-23 include a local area network (LAN) 1071 and a wide area network (WAN) 1073, but may also include other networks. Such networking environments are commonplace in offices, enterprise-wide computer networks, intranets and the Internet.

When used in a LAN networking environment, the computer 1010 is connected to the LAN 1071 through a network interface or adapter 1070. When used in a WAN networking environment, the computer 1010 typically includes a modem 1072 or other means for establishing communications over the WAN 1073, such as the Internet. The modem 1072, which may be internal or external, may be connected to the system bus 1021 via the user input interface 1060, or other appropriate mechanism. In a networked environment, program modules depicted relative to the computer 1010, or portions thereof, may be stored in the remote memory storage device. By way of example, and not limitation, FIG. 10-23 illustrates remote application programs 1085 as residing on memory device 1081. It will be appreciated that the network connections shown are exemplary and other means of establishing a communications link between the computers may be used.

IX. Fabrication Steps

The above integrated device may be fabricated in any suitable way. What follows is a description of the fabrication of various components of the integrated device, which may be combined in any way with techniques known in the art, to create a suitable integrated device.

A. Nanoaperture Fabrication Process

A sample well (e.g., nanoaperature) may be fabricated in any suitable way. In some embodiments, a sample well may be fabricated using standard photolithography processes and etching techniques. A sample well may be formed in a layer having a metal (e.g., Al, TiN) or any suitable material compatible with photolithography processing. FIG. 11-1 illustrates an exemplary method for fabricating a sample well of an integrated device. Layer 11-112 forms a sample well and may include a metal such as Al or TiN. Layer 11-110 may act as a dielectric layer and may be formed from any suitable dielectric substrate, such as $SiO_2$ or silicon nitride. One step of the method includes depositing layer 11-112 directly on substrate 11-110. In some embodiments, additional layers may be deposited between layer 11-112 and layer 11-110. Layer 11-112 may be deposited at any suitable thickness, and in some embodiments, the thickness may determine the height of the resulting sample well. The thickness of layer 11-112 may be approximately 50 nm, approximately 100 nm, or approximately 150 nm. An anti-reflection coating (ARC) 11-122 is then deposited on top of layer 11-112. Etch mask 11-120 (e.g., photoresist etch mask) is deposited on ARC 11-122. Conventional photolithographic techniques are used to pattern a hole in etch mask 11-120 and ARC 11-122. The hole patterned by etch mask 11-120 may have a diameter of approximately 50 nm, approximately 100 nm, or approximately 150 nm. The hole pattern is then transferred to underlying layer 11-112 using an etch, for example, reactive ion etching techniques, to form the sample well. Etching may stop at the surface of layer 11-110, or etching may create a divot in layer 11-110 under the hole in layer 11-112. Conventional techniques are used to strip etch mask 11-120 and ARC 11-122 off of layer 11-112. The sample well may have a diameter of t approximately 50 nm, approximately 100 nm, or approximately 150 nm.

Alternatively, a sample well may be fabricated using standard photolithography processes and lift-off techniques. FIG. 11-2 illustrates an exemplary method of forming a sample well using lift-off techniques. Sample well is formed in layer 11-212, which may include a metal (e.g., Al, Au, Cr). Layer 11-212 is formed over substrate layer 11-210, which may include any suitable material such as a dielectric (e.g., $SiO_2$). Deposition of layer 11-212 may occur separately from and after the photolithographic process. The first step in the lift-off fabrication process shown in FIG. 11-2 may involve depositing anti-reflection coating (ARC) 11-222 on substrate 11-210 followed by photoresist etch mask 11-220 directly on top of substrate 11-210. Conventional photolithographic techniques are used to pattern the photoresist such that a pillar 11-230 of resist is left behind. The pillar may have any suitable size and shape that may correspond to a resulting sample well. The pillar may have a diameter of approximately 50 nm, approximately 100 nm, or approximately 150 nm. Such techniques may include dissolving the resist and the ARC layer around the pillar off of the substrate. The following step may involve depositing layer 11-212 directly on top of the pillar of resist and the substrate, creating a capped pillar. In other embodiments, additional layers may be deposited before or after deposition of layer 11-212. As a non-limiting example, TiN may be deposited on layer 11-212 formed of Al, optionally followed by a deposition of $Al_2O_3$. Layer 11-212 may be deposited at any suitable thickness, and in some embodiments may have a thickness of approximately 50 nm, approximately 100 nm, or approximately 150 nm. To form the sample well, the capped pillar may be stripped by a solvent in the case that photoresist is used or by selective etching in the case that silicon dioxide or silicon nitride hard etch masks are used. The sample well may have a diameter of t approximately 50 nm, approximately 100 nm, or approximately 150 nm.

Alternatively, a sample well may be fabricated using standard photolithography processes and an alternate lift-off technique. FIG. 11-3 illustrates an exemplary embodiment of forming a sample well of an integrated device. A hard etch mask layer 11-314 is deposited on substrate 11-310. Hard etch mask layer 11-314 may include Ti or any other suitable material. Substrate 11-310 may include a dielectric (e.g., $SiO_2$) or any other suitable material. A layer of ARC 11-322 is then deposited onto the hard etch mask layer 11-314 followed by photoresist layer 11-320. Conventional photolithographic techniques are used to pattern the photoresist such that a pillar 11-320 of resist is formed. This photoresist pillar pattern is used as an etch mask for etching the ARC layer 11-322 and hard etch mask layer 11-314. Photoresist layer 11-320 and ARC 11-322 is then stripped, and pillar 11-330 of hard etch mask is left behind. Conventional techniques may be used to dissolve the remaining photoresist and the ARC layer off the pillar. The following step may involve depositing layer 11-312 directly on top of pillar 11-330 creating a capped pillar. To form the sample well, the capped pillar is stripped by a hydrogen peroxide etch, or other suitable etch, which erodes layer 11-314, "lifts off" the cap and results in a sample well in layer 11-312.

In some embodiments, the sample well may be fabricated to attenuate plasmon transmission through the sample well in any suitable way. For example, the sample well may be fabricated in a multi-layered stack. The multi-layered stack may include, but is not limited to, a metal layer deposited on a substrate, an absorbing layer and/or a surface layer. The surface layer may be a passivation layer. The multi-layer stack may be fabricated in any suitable way. Conventional patterning and etching techniques may be used. A metal layer may be deposited onto a substrate. Alternatively, an absorbing layer may be deposited onto the metal layer. Alternatively, a surface passivation layer may be deposited onto the absorbing layer/metal layer stack. A photoresist and anti-reflection layer may be deposited onto the top layer of the multilayer stack. The photoresist layer may be patterned with the dimensions of the sample well. The multi-layer stack may be directly etched to form the sample well.

The absorbing layers may include any suitable absorbing materials. Non-limiting examples include silicon nitride, TiN, aSi, TaN, Ge and/or Cr. Variants of the named materials are also possible, such as $Si_3N_4$. The metal layer and the surface layer may be made of any suitable materials. For example, Al, AlSi, or AlCu may be used for the metal layer. The surface layer may be made of Al or $Al_2O_3$, for example. The sample well in the multilayer stack may be fabricating using the processes described above.

Additionally and/or alternatively, a reflective layer may be deposited directly on top of the substrate before depositing the multi-layered stack to control the focus of the light beam during photolithography. A reflective layer may be deposited directly on top of the substrate and patterned with the dimensions of the sample well. Optionally, a layer of anti-reflection coating followed by a layer of photoresist may be deposited on top of the patterned reflective coating layer and patterned to leave a pillar of ARC and photoresist at a location on the substrate. A multilayer stack may then be deposited on top of the pillar, reflective layer, and substrate. The capped pillar may be removed using a lift-off process, as described above, forming a sample well at the location of the substrate where the pillar had been.

Similarly, a Ti pillar may be used to create the sample well. The first step may involve depositing a layer of Ti on the substrate, followed by a layer of anti-reflection coating and a layer of photoresist. The Ti layer may be patterned and etched to form a Ti pillar. The multilayer stack may be deposited on top of the Ti pillar and substrate. Finally, the Ti pillar may be removed forming a sample well at a location of the substrate corresponding to where the Ti pillar had been.

Any suitable deposition methods may be used. For example, PVD, CVD, sputtering, ALD, e-beam deposition and/or thermal evaporation may be used to deposit one or more layers. The deposition environment may be controlled to prevent oxidation of the layers in between depositions. For example, the environment may be kept at a high vacuum and/or low-oxygen state during and between depositions of one or more layers.

B. Concentric Grating (Bullseye) Fabrication Process

A concentric grating, or bullseye, may be fabricated in any suitable way. In some embodiments, a concentric grating may be fabricated using standard photolithography processes and etching techniques. Any suitable dielectric material, such as $SiO_2$ or silicon nitride, may be used to form the concentric grating. In the embodiment illustrated in FIG. 11-4, a $SiO_2$ layer 11-1010 is used to make the concentric grating. The first step in the fabrication process may involve depositing a hard etch mask 11-1014 directly on top of the $SiO_2$ layer. The next step (act 11-1001) in the fabrication process may involve depositing a photoresist layer 11-1020 directly on top of an anti-reflection coating layer 11-1022 onto the hard etch mask. Conventional photolithographic techniques are used to create (act 11-1003 and act 11-1005) the bullseye pattern in the hard etch mask. The bullseye pattern is then transferred (11-1007) to the underlying $SiO_2$ layer using etching, for example reactive ion etching techniques to form the concentric grating. The thickness of the concentric grating can be any suitable thickness. In the embodiment illustrated in FIG. 11-4, the etch depth is approximately 80 nm. Conventional techniques are used to strip (act 11-1009) the resist and etch mask residues and clean the surface of the concentric grating. The nanoaperture in layer 11-1012 may be fabricated (act 11-1011) directly on top of the concentric grating using the lift-off or etch processes. In other embodiments, other layers may be deposited between the concentric grating and the nanoaperture.

Alternatively, in some embodiments, the nanoaperture may be positioned central to the concentric grating. This precise alignment of the nanoaperture may be achieved in any suitable way. In the embodiment illustrated in FIG. 11-5, positioning of the nanoaperture is achieved using a self-aligned fabrication process. The first step may involve forming the concentric grating according to the techniques described above. However, in FIG. 11-5, a Ti hard etch mask 11-1114 is deposited (act 11-1101) on top of the $SiO_2$ substrate 11-1110. The bullseye pattern is transferred to the Ti layer using etching, for example reactive ion etching (act 11-1103 and act 11-1105). A layer of resist 11-1120 and a layer of anti-reflection coating 11-1122 are deposited over the two center gaps in the Ti layer to cover the gaps and the center Ti pillar. The bullseye pattern is then transferred to the $SiO_2$ substrate using conventional etching techniques to form the concentric grating (act 11-1107). The Ti layer is then removed using an isotropic wet etch (act 11-1109), for example, using peroxide, but leaving the center Ti pillar 11-1116 in place. The layer of resist is then stripped using conventional techniques. The metal nanoaperture layer is then deposited (act 11-1111) on top of the concentric grating and the Ti pillar. Lastly, the metal-capped Ti pillar is removed using a lift-off process leaving a nanoaperture precisely centered relative to the concentric grating.

The precise alignment of the nanoaperture may be achieved in various other ways. In the embodiment illustrated in FIG. 11-6, positioning of the nanoaperture is achieved using an alternate self-aligned fabrication process. The first step (11-1201) may involve depositing the Al nanoaperture layer 11-1212 directly on top of the $SiO_2$ concentric grating substrate 11-1210. A hard etch mask 11-1214 may then be deposited on top of the Al layer. In the embodiment illustrated in FIG. 11-6, Ti is used but any material compatible with photolithographic processes may be used. The bullseye pattern is transferred (act 11-1203 and

11-1205) to the Ti and Al layers using conventional etching techniques. A layer of resist 11-1220 and a layer of anti-reflection coating 11-1222 are deposited over the center gap in the Ti and Al layers to cover the position where the nanoaperture is to be formed. The bullseye pattern is then transferred (act 11-1207) to the $SiO_2$ substrate using conventional etching techniques to form the concentric grating. An additional metal layer is deposited (act 11-1209) on top of the Ti and first Al layer such that the metal fills the cavities in the $SiO_2$ layer and covers the Ti layer and the resist layer. In the embodiment illustrated in FIG. 11-6, Al is used as the additional metal layer but other suitable metals compatible with photolithographic processes may be used. Lastly, the metal-capped resist pillar 11-1230 is removed (act 11-1211) using a lift-off process leaving a nanoaperture precisely centered relative to the concentric grating.

C. Lens Fabrication Process: Refractive Lens

A refractive lens array may be created in any suitable way to improve efficiency of focusing of excitation into and collection of emission light from the nanoaperture. In some embodiments, a refractive lens array may be a "gapless" array to minimize "dead zones" on the lens array. In the embodiment illustrated in FIG. 11-7, a refractive microlens array is shown with no gaps between individual lenses. In some embodiments, fabricating a "gapless" array may involve two etching steps. A first etch (act 11-1801) may establish the depth of the microlens topography. A second etch (act 11-1803) may follow the first etch to eliminate the planar gaps between the individual microlenses such that one lens stops at the edge where another lens begins. The sum of the first and second etches defines the focal length. In the embodiment illustrated in FIG. 11-8, a top view of a microlens array is shown after the first HF etch (1), after the second HF etch (2), after the microlens array is coated with a higher refractive index material silicon nitride (3), and after the high refractive index material is polished and planarized (4).

Each refractive lens in the refractive lens array may be fabricated in any suitable way. An example refractive lens array is illustrated in FIG. 11-9 where a nanoaperture layer 11-2007 is fabricated on top of a transparent spacer layer 11-2001, which is on top of a dielectric lens layer 11-2003, which is on top of a substrate 11-2005. In some embodiments, a refractive lens may be fabricated using standard photolithography processes and etching techniques. Any suitable dielectric material, such as $SiO_2$ or silicon nitride, may be used to form the refractive lens. In the embodiment illustrated in FIG. 11-10, silicon nitride is used to fill in the $SiO_2$ substrate topography. The first step 11-2101 in the fabrication process may involve depositing a hard etch mask directly on top of a $SiO_2$ substrate 11-2110. Any suitable metal may be used for the hard etch mask 11-2114 that does not dissolve during the same etching process used for the $SiO_2$ layer. For example, Cr is used in FIG. 11-10, but other metals are possible. The next step may involve applying a photoresist layer 11-2120 on top of the Cr hard etch mask. Conventional photolithographic techniques are used to create a circular pattern in the hard etch mask. The circular pattern is then transferred to the underlying Cr layer using conventional etching techniques, such as reactive ion etching techniques, for example. The $SiO_2$ layer is etched using any suitable selective etching technique which can etch the $SiO_2$ but not the hard etch mask. For example, an isotropic wet etch using HF is used to create a concave surface in the $SiO_2$ layer. The Cr layer is then removed using conventional etching techniques. Optionally, a second wet etch using HF is performed to eliminate the gaps between lenses. To create the refractive lens, the cavity in the $SiO_2$ layer is filled with a high refractive index material layer 11-2118, such as silicon nitride. Finally, the top surface of the lens is planarized with conventional techniques, such as chemical mechanical polishing, for example. A spacer layer 11-2124 may be deposited on top of the silicon nitride layer. For example, a spacer layer made of ORMOCER™ may be spun-coat on top of the silicon nitride layer. Alternatively, a layer of $SiO_2$ may be deposited. The nanoaperture may be fabricated directly on top of the refractive lens. In other embodiments, other layers may be deposited between the refractive lens and the nanoaperture.

Alternatively, each refractive lens may include an anti-reflection layer to further improve optical efficiency. In some embodiments, an anti-reflection layer may coat a bottom, top, or all sides of a lens. First, a $SiO_2$ cavity 11-2210 is etched (act 11-2201) into a $SiO_2$ layer. In the embodiment illustrated in FIG. 11-11, an anti-reflection layer 11-2222 is deposited (act 11-2203) on the etched $SiO_2$ cavity 11-2210 before the cavity is filled (act 11-2205) with a silicon nitride layer 11-2218. The silicon nitride layer is polished (act 11-2207) via CMP and a second antireflection layer 11-2226 is deposited (act 11-2209) on top of the polished silicon nitride layer. Additional layers may be deposited on top of the antireflection layer, such as the spacer layer described above and shown as layer 11-2224 in FIG. 11-11. The anti-reflection layers may have the following parameters: index of refraction, $n_C=\text{sqrt}(n_{oxide}, n_{nitride})=\text{sqrt}(1.46*1.91)= 1.67$; range of refractive index from 1.67 to 1.75; and, thickness $t=\lambda/(4*n_C)=675 \text{ nm}/(1.670*4)=101.1$ nm. The anti-reflection layer may be deposited in any suitable way. For example, PECVD may be used. Alternatively, LPCVD may be used.

D. Lens Fabrication Process: Fresnel Lens

A diffractive optical element (DOE) may have any suitable shape and may be fabricated in any suitable way to improve the focusing of luminescence on the CMOS sensors and the sorting of the luminescence photons. In some embodiments, the DOE may include a section of a Fresnel lens. As illustrated in FIGS. 11-12 to 11-19, the DOE 11-2301 is characterized as a square section offset from the center of a Fresnel lens. As illustrated in FIG. 11-13, the DOE may comprise two unit cell layers where the first layer 11-2401 contains "small" features and the second layer 11-2403 contains "large" features. The unit cell layers may have any suitable pitch, and may further have varying pitch according to the optical design of the Fresnel lens. As illustrated in the example in FIG. 11-13, the small DOE layer has a pitch of 220 nm and the large DOE layer has a pitch of 440 nm. The large DOE layer may be overlaid onto the small DOE layer (or vice versa) to create a multilevel diffractive optic. FIG. 11-13 illustrates an example of an offset Fresnel array 11-2405 where large fiducial markers surround the offset Fresnel lens. Additionally, the offset Fresnel array may be positioned on top of the sensor to provide focusing and spectral separation of luminescence into the sensor.

Alternatively, a diffractive optical element (DOE) may be embedded underneath the nanoaperture to improve the focusing of the excitation energy into and collection of luminescence from the nanoaperture. In some embodiments, the embedded Fresnel lens positioned underneath the nanoaperture and the offset Fresnel lens positioned over the sensor may have a tiered structure with a variable period and variable step size. In other embodiments, only the offset Fresnel lens positioned over the sensor may have a variable period and variable step size. These diffractive lenses may be fabricated using standard photolithography processes and etching techniques. As illustrated in FIG. 11-14, the diffractive lens pattern 11-2501 is characterized as having a tiered structure comprising large steps (large pattern) and small steps (small pattern) on each larger step, both having a decreasing period when viewed from left to right. The fabrication process for the variable-period stepped diffractive lens may involve etching the large steps first, followed by etching the small steps as illustrated in FIG. 11-16, which may protect the corners of the large steps during the second etch. An alternate approach is to etch the small steps first on a flat substrate, followed by etching the large steps, as illustrated in FIG. 11-15. Any suitable dielectric material, such as $SiO_2$ or silicon nitride, $TiO_2$ or $Ta_2O_5$, may be used to form the fill-in layer for the diffractive lens and the tiered layer. In the embodiment illustrated in FIG. 11-15, silicon nitride is used to make the fill-in layer and $SiO_2$ is used to make the tiered layer.

The first step in the fabrication process of the tiered $SiO_2$ layer may involve depositing a hard etch mask 11-2614 directly on top of a $SiO_2$ layer 11-2610 followed by an anti-reflection layer 11-2622 followed by a photoresist layer 11-2620. Any suitable material may be used for the hard etch mask. For example, a-Si may be used for the hard etch mask shown in FIG. 11-15, but other materials are possible. The next step may involve applying an ARC and/or a photoresist layer on top of the a-Si hard etch mask. Conventional photolithographic techniques may be used to create the variable-period large binary pattern. The patterns are transferred to the underlying Si layer using conventional etching techniques, such as reactive ion etching techniques, for example.

The etch depth of a large diffractive lens step can be any suitable depth that accomplishes the desired focal length. In the embodiment illustrated in FIG. 11-16, this etch depth into the $SiO_2$ layer is approximately 684 nm for the large step. Conventional techniques are then used to strip (act 11-2605) the resist and etch mask residues and clean the surface of the $SiO_2$ layer. The next step may involve etching the small steps on each large step. In the embodiment illustrated in FIG. 11-16, each large steps comprises four smaller steps.

A second Si hard etch mask 11-2644 is then deposited on the patterned $SiO_2$ layer 11-2610. An ARC layer 11-2642 is then deposited on top of the Si layer 11-2610 followed by a photoresist etch mask layer 11-2640. The second variable-period small binary pattern is transferred to the photoresist and/or the ARC layer. In the embodiment illustrated in FIG. 11-16, the fabrication steps are similar to that described in FIG. 11-15, however, two small steps are etched per large step leaving four steps in total. In other embodiments, any number of steps may be used. The small steps are then etched into the $SiO_2$ layer 11-2710. The thickness of a small diffractive lens step can be any suitable thickness. In the embodiment illustrated in FIG. 11-16, the etch depth into the $SiO_2$ layer is approximately 342 nm for the small step. Conventional techniques are then used to strip the resist and clean the surface of the $SiO_2$ layer.

Additional stages in the fabrication process following creation of the tiered $SiO_2$ layer 11-2810 may involve filling the cavities with any suitable high index lens material 11-2818, such as silicon nitride, for example, to create an "embedded Fresnel lens", as illustrated in FIGS. 11-17 to 11-18. The tiered structure used for the "embedded Fresnel lens" may have approximately the same and/or smaller size features as the tiered structure used for the offset Fresnel lens. Any method of depositing the silicon nitride may be used such as PECVD, for example. Optionally, the silicon nitride layer may be uniformly polished down until the top step of the $SiO_2$ material is exposed. Alternatively, the silicon nitride layer 11-2818 is uniformly polished but the $SiO_2$ material is not exposed. In the embodiment illustrated in FIG. 11-18, a second layer 11-2928 of $SiO_2$ is then deposited via PECVD on top of the polished silicon nitride layer 11-2918 and polished via CMP. In some embodiments, the spacer layer 11-2928 may have a thickness equal to the focal length in that spacer layer material. Additionally, other suitable transparent spacer layers may be deposited on top of the silicon nitride layer. The nanoaperture layer may then be fabricated on top of the transparent spacer layer and/or additional layers.

Alternatively, in the embodiment illustrated in FIG. 11-19, the tiered layer 11-3018 for the diffractive lens is made of silicon nitride. The silicon nitride layer 11-3018 may be deposited at any suitable thickness on top of substrate 11-3010 followed by etch mask 11-3014, ARC layer 11-3022 and photoresist layer 11-3020. In the embodiment illustrated in FIG. 11-19, the silicon nitride layer is approximately 1 um thick. The fabrication processes may be similar to the one described above in regards to creating the tiered, variable-period diffractive lens layer in $SiO_2$. Optionally, a different hard mask may be used to create the silicon nitride tiered layer. The silicon nitride tiered layer may have approximately the same and/or smaller size features as the $SiO_2$ tiered layer. After the silicon nitride tiered layer is made, the silicon nitride layer may be coated in any suitable dielectric material 11-3028. In the embodiment illustrated in FIG. 11-19, the silicon nitride layer is coated with $SiO_2$ layer 11-3028. The $SiO_2$ layer may be deposited using conventional deposition processes such as PECVD, for example. The $SiO_2$ layer may then be polished to create a flat, planar surface. The nanoaperture layer may then be fabricated on top of the $SiO_2$ layer and/or additional layers.

Certain features of the diffractive optic may require a certain degree of uniformity and/or accuracy during the fabrication process to yield a structure with the desired optical properties. For example, the etch depth of the large and small steps may require a certain degree of accuracy. In some embodiments, an etch depth within 50 or 10% of the target may be required to achieve the desired power efficiency into the focal spot nanoaperture. Additionally, the etching of the lens features may require a certain degree of uniformity. For example, etch uniformity within 5% (or 50 nm) is required to achieve the desired focal length.

Any of the lenses described above may be fabricated using any suitable deposition and etching processes to create improved optical properties. By way of example and not limitation, PECVD may be used. The deposition parameters may be tuned in any suitable way to reduce autoluminescence, reduce lens absorption of luminescence, and/or create a high index of refraction. For example, a reduced autoluminescence and lens absorption may be achieved by reducing the density of Si—Si bonds, which may form silicon nanocrystals, during deposition of silicon nitride. In some embodiments, the input gases and their ratios may be modified to reduce the density of Si—Si bonds and silicon nanocrystals. For example, $SiH_4$ and $N_2$ may be used and their ratios adjusted in any suitable way to reduce the density of Si nanocrystals. In other embodiments, $SiH_4$ and $NH_3$ may be used and their ratios adjusted in any suitable way to reduce the density of Si—Si bonds and silicon nanocrystals. For example, the ratio of $NH_3$ to $SiH_4$ may be at least 10:1. Additionally, tuning the frequencies that control the plasma during PECVD may be used to improve optical properties.

For example, the low frequency (e.g. below 0.5 MHz) to high frequency (e.g. above 10 MHz) ratio may be at least 1:1.

Additionally, the above described deposition parameters may tune the lens index of refraction to improve optical properties. In some embodiments, the index of refraction for a silicon nitride lens may be less than n=1.92 and associated with a wavelength of 633 nm for a suitable low autoluminescence effect and/or a suitable low absorption loss. The tuned qualities described above may be related to, proportional, correlated, associated with and/or dependent each other. For example, an index of refraction of n=1.92 is indicative of a low luminescence and low absorption loss which is related to a low density of Si—Si bonds and silicon nanocrystals for a lens made of silicon nitride.

X. Conclusion

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semicustom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A system including an instrument configured to interface with an assay chip, the system comprising:
    a plurality of sample wells, each of at least a portion of the plurality of sample wells configured to receive a sample;
    at least one pulsed excitation light source configured to excite the sample of the at least a portion of the plurality of sample wells;
    at least one optical element configured to direct emission energy from each sample well of the at least a portion of the plurality of sample wells; and
    a plurality of sensors, each of at least some of the plurality of sensors corresponding to a sample well of the plurality of sample wells, wherein each of at least some of the plurality of sensors is configured to detect emission energy from the sample in a respective sample well; and
    wherein each of at least some sensors of the plurality of sensors is configured to aggregate, into at least two time bins, charge carriers produced in response to the emission energy.

2. The system of claim 1, further comprising:
    an optical housing having an opening; and
    at least one alignment component configured to mechanically position the assay chip on the outside of the optical housing to overlap with the opening when the assay chip interfaces with the instrument.

3. The system of claim 2, wherein the at least one pulsed excitation light source is configured to emit excitation energy through the opening of the optical housing.

4. The system of claim 2, wherein the at least one alignment component includes a plurality of alignment components positioned around the opening.

5. The system of claim 1, wherein the sample is a biological sample.

6. The system of claim 5, wherein the biological sample comprises a protein.

7. A system including an instrument and an assay chip configured to interface with the instrument, the system comprising:
    at least one pulsed excitation light source configured to produce excitation light;
    a plurality of sample wells, each of at least some of the plurality of sample wells being configured to receive a sample, the sample to emit emission energy upon excitation by the excitation light; and
    a plurality of sensors, each of at least some of the plurality of sensors corresponding to a sample well of the plurality of sample wells, wherein each of at least some of the plurality of sensors is configured to detect emission energy from the sample in a respective sample well, wherein each of at least some sensors of the plurality of sensors is configured to aggregate, into at least two time bins, charge carriers produced in response to the emission energy.

8. The system of claim 7, further comprising at least one element configured to direct the emission energy in a particular direction, wherein the at least one element is selected from a group consisting of a refractive element, a diffractive element, a plasmonic element, and a resonator.

9. The system of claim 7, wherein the assay chip is configured to be connected to and removed from the instrument.

10. The system of claim 7, wherein the sample is a biological sample.

11. The system of claim 10, wherein the biological sample comprises a protein.

12. The system of claim 9, wherein the optical distance between a sample well of the plurality of sample wells and the corresponding sensor of the plurality of sensors is less than 30 cm.

13. The system of claim 9, wherein the optical distance between a sample well of the plurality of sample wells and the corresponding sensor of the plurality of sensors is less than 5 cm.

14. The system of claim 9, wherein the optical distance between a sample well of the plurality of sample wells and the corresponding sensor of the plurality of sensors is less than 1 cm.

* * * * *